US005863950A

United States Patent [19]
Reich et al.

[11] Patent Number: 5,863,950
[45] Date of Patent: *Jan. 26, 1999

[54] HIV PROTEASE INHIBITORS

[75] Inventors: Siegfried H. Reich; Kathleen Lewis; Michael Melnick, all of San Diego, Calif.; Mary Ann M. Fuhry, Mildenhau, U.S.; Stephen Warren Kaldor, Indianapolis, Ind.

[73] Assignee: Agouron Pharmaceuticals, Inc., San Diego, Calif.

[ * ] Notice: The term of this patent shall not extend beyond the expiration date of Pat. No. 5,714,518.

[21] Appl. No.: 325,340

[22] PCT Filed: Jan. 18, 1994

[86] PCT No.: PCT/US94/00419

§ 371 Date: Oct. 27, 1994

§ 102(e) Date: Oct. 27, 1994

[87] PCT Pub. No.: WO94/15608

PCT Pub. Date: Jul. 21, 1994

[51] Int. Cl.[6] .................. A61K 31/16; C07C 231/00; C07C 233/65

[52] U.S. Cl. .................. 514/616; 514/307; 514/311; 514/354; 514/355; 514/357; 514/374; 514/400; 514/423; 514/478; 546/143; 546/146; 546/175; 546/314; 546/315; 546/316; 546/317; 546/334; 546/336; 546/337; 548/237; 548/338.1; 548/537; 560/13; 564/156; 564/158

[58] Field of Search ................. 564/155, 158; 514/616, 307, 311, 354, 305, 357, 374, 400, 423, 478; 546/143, 146, 174, 314, 315, 316, 317, 334, 336, 337; 548/237, 338.1, 537; 560/13

[56] References Cited

U.S. PATENT DOCUMENTS 2,895,991 7/1959 Randall et al. .................. 260/558
4,299,845 11/1981 Loebenberg et al. ............ 424/324

FOREIGN PATENT DOCUMENTS

WO95/33464 12/1995 WIPO .

OTHER PUBLICATIONS

Broquet et al., "Reaction of Amines with 4,6–dimethoxy–3–(chloromethyl) Phthalide," C.R. Acad. Sc., Paris, 265(2):117–20 (1967).

Gear et al., "The Biosynthesis of Hydrastine and Beberine," Canadian Journal of Chemistry, 41: 783–803 (1963).

Akashi et al., "Syntheses of Ring–Hydroxylated Nipradiolols and Their Denitro Derivatives," Chem. Parm. Bull., 34(5):2024–2036 (1986).

Chupp et al., "Derivation of Fluorine–Containing Pyridine Dicarboxylates. II. Elaboration at the 4–Position," J. of Heterocyclic Chemistry, 26(3):645–653 (1989) and Chemical Abstract, 112(9):Abs. No. 76991 (1990).

Quelet et al., "Condensation Products of Chloroacetaldehyde Diethyl Acetal and Dichloroacetaldehyde Diethyl Acetal with Gallic Acid," Chemical Abstracts, 62:(10): Abs. No. 11731 (1965).

Occelli et al., "Synthesis of 4–Alkenyl–3,5–Dimethoxybenzoic Acids by Claisen Rearrangement," Gazzetta Chimica Italiana, 111:383–389 (1981) and Chemical Abstract, 96(17):Abs. No. 142391j (1982).

*Primary Examiner*—Shailendra Kumar
*Attorney, Agent, or Firm*—Finnegan, Henderson, Farabow, Garrett & Dunner, L.L.P.

[57] ABSTRACT

HIV protease inhibitors, obtainable by chemical synthesis, block the biological activity of the HIV protease enzyme, causing the replication of the HIV virus to terminate. These compounds, as well as pharmaceutical compositions that contain these compounds and possibly other anti-viral agents as ingredients, are thus suitable for the treatment of the HIV virus known to cause AIDS.

141 Claims, No Drawings

HIV PROTEASE INHIBITORS

This application is a 371 of PCT/US94/00419 filed Jan. 18, 1994.

This invention relates to a novel series of non-peptidic chemical compounds which have been found to be useful as HIV protease inhibitors and to the use of such compounds as anti-viral agents.

Acquired Immune Deficiency Syndrome (AIDS) is a relatively newly recognized disease or condition. AIDS causes a gradual breakdown of the body's immune system as well as progressive deterioration of the central and peripheral nervous systems. Since its initial recognition in the early 1980's, AIDS has spread rapidly and has now reached epidemic proportions within a relatively limited segment of the population. Intensive research has led to the discovery of the responsible agent, human T-lymphotropic retrovirus III (HTLV-III), now more commonly referred to as the human immunodeficiency virus or HIV.

HIV is a member of the class of viruses known as retroviruses. The retroviral genome is composed of RNA which is converted to DNA by reverse transcription. This retroviral DNA is then stably integrated into a host cell's chromosome and, employing the replicative processes of the host cells, produces new retroviral particles and advances the infection to other cells. HIV appears to have a particular affinity for the human T-4 lymphocyte cell which plays a vital role in the body's immune system. HIV infection of these white blood cells depletes this white cell population. Eventually, the immune system is rendered inoperative and ineffective against various opportunistic diseases such as, among others, pneumocystic carini pneumonia, Karposis sarcoma, and cancer of the lymph system.

Although the exact mechanism of the formation and working of the HIV virus is not understood, identification of the virus has led to some progress in controlling the disease. For example, the drug azidothymidine (AZT) has been found effective for inhibiting the reverse transcription of the retroviral genome of the HIV virus, thus giving a measure of control, though not a cure, for patients afflicted with AIDS. The search continues for drugs that can cure or at least provide an improved measure of control of the deadly HIV virus.

Retroviral replication routinely features post-tranlational processing of pre-peptides. This processing is accomplished by virally encoded HIV protease enzyme. This yields mature polypeptides that will subsequently aid in the formation and function of infectious virus. If this molecular processing is stifled, then the normal production of HIV is terminated. Therefore, inhibitors of HIV protease may function as anti-HIV viral agents.

HIV protease is one of the translated products from the HIV structural protein pol gene. This retroviral protease specifically cleaves other structural polypeptides at discrete sites to release these newly activated structural proteins and enzymes, thereby rendering the virion replication-competent. As such, inhibition of the HIV protease by potent compounds may prevent proviral integration of infected T-lymphocytes during the early phase of the HIV-1 life cycle, as well as inhibit viral proteolytic processing during its late stage. Additionally, the protease inhibitors may have the advantages of being more readily available, longer lived in virus, and less toxic than currently available drugs, possibly due to their specificity for the retroviral protease.

In accordance with this invention, there is provided a novel class of chemical compounds that have been found to inhibit and block the activity of the HIV protease, which halts the proliferation of HIV virus, pharmaceutical compositions containing these compounds, novel intermediates for these compounds, novel methods for making these compounds, and intermediates and the use of the compounds as inhibitors of the HIV.

The novel class of compounds according to this invention is represented by the formula I

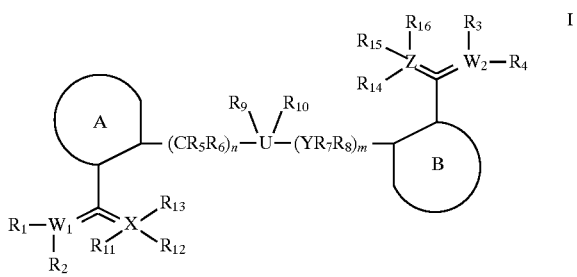

wherein:

A and B are independently selected from carbocyclic or heterocyclic, monocyclic or fused or unfused polycyclic ring systems which can be further substituted;

n=0 to 6 and m=0 to 6 with the further proviso that n and m cannot both be zero;

X, Y, Z, $W_1$ and $W_2$ are independently selected from nitrogen, oxygen, carbon, sulfur and selenium and, in the case of Y, when m is from 2 to 6, all Y's need not be the same, U is carbon, boron, selenium, sulfur or phosphorus;

$R_1$, $R_2$, $R_3$ and $R_4$ are independently selected from nothing, hydrogen, alkyl, aryl, and substituted alkyl or aryl and at least one of $R_1$ and $R_2$ can form a ring with $W_1$ and at least one of $R_3$ and $R_4$ can form a ring with $W_2$;

$R_5$, $R_6$, $R_7$ and $R_8$ are independently selected from nothing, hydrogen, halogen, hydroxy, substituted or unsubstituted alkoxy, substituted or unsubstituted aryloxy, nitrogen, alkyl, aryl, and substituted alkyl or aryl and when n is greater than 1, all $R_5$'s need not be the same and all $R_6$'s need not be the same and when m is greater than one, all $R_7$'s need not be the same and all $R_8$'s need not be the same;

$R_9$ and $R_{10}$ are independently selected from nothing, hydrogen, halogen, hydroxy, substituted or unsubstituted alkoxy, substituted or unsubstituted aryloxy, nitrogen, carbonyl oxygen, substituted or unsubstituted alkyl and substituted or unsubstituted aryl;

$R_{11}$ to $R_{16}$ are independently selected from nothing, hydrogen, halogen, hydroxy, substituted or unsubstituted alkoxy, substituted or unsubstituted aryloxy, nitrogen, substituted or unsubstituted alkyl, and substituted or unsubstituted aryl, and at least one of $R_{11}$, $R_{12}$ and $R_{13}$ can form a ring with X and at least one of $R_{14}$, $R_{15}$ and $R_{16}$ can form a ring with Z; and $W_1$ and X can be included in a ring and W and Z can be included in a ring with the proviso that $W_1$ and X can be included together in only one ring and $W_2$ and Z can be included together in only one ring;

or pharmaceutically acceptable salts thereof.

A preferred embodiment of the invention is the group of compounds represented by the formula II

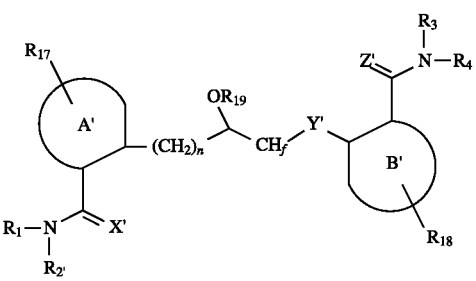

wherein:

f is 0, 1, or 2;

A' and B' are individually selected from carbocyclic or heterocyclic, aromatic, saturated or partially saturated 5, 6 or 7 member rings which can be further substituted;

n' is 0, 1 or 2;

X' and Z' are individually selected from oxygen and sulphur;

when f is 2, Y' is a substituted or unsubstituted amino group, oxygen, sulphur, or —$CH_2$—;

when f is 1, Y' is —CH=;

when f is 0, Y' is —C≡;

$R'_1$, $R'_2$, $R'_3$ and $R'_4$ are individually selected from hydrogen, alkyl, cycloalkyl, aryl, substituted alkyl, cycloalkyl or aryl, substituted oxygen, hydroxyl, substituted or unsubstituted non-cyclic amino and substituted or unsubstituted non-aryl heterocycle, wherein $R'_1$ and $R'_2$ or $R'_3$ and $R'_4$ can form a ring with the nitrogen atom to which they are attached;

$R_{17}$ and $R_{18}$ are individually selected from hydrogen, halogen, hydroxyl, substituted or unsubstituted alkoxy, mercapto, thioether, —$NR'_1R'_2$, nitro, alkyl, aryl and substituted alkyl or aryl, wherein $R_{17}$ can form a fused ring structure with A' and $R_{18}$ can form a fused ring structure with B'; and $R_{19}$ is hydrogen or a 1 to 3 carbon substituted or unsubstituted alkyl group;

or pharmaceutically acceptable salts thereof.

Typical examples of carbocyclic ring systems represented by A and B include, but are not limited to, phenyl, naphthyl, anthryl, and phenanthryl, either in their aromatic or fully or partially hydrogenated states. Typical heterocyclic ring systems represented by A and B include (1) 5-membered monocyclic ring groups such as thienyl, pyrrolyl, imidazolyl, pyrazolyl, furyl, isothiazolyl, furazanyl, isoxazolyl, thiazolyl and the like; (2) 6-membered monocyclic groups such as pyridyl, pyrazinyl, pyrimidinyl, pyridazinyl, triazinyl and the like; and (3) polycyclic heterocyclic ring groups, such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl and fully or partially hydrogenated analogs thereof.

The term "alkyl," as used herein refers to straight or branched chain groups, preferably having one to eight, more preferably one to six, carbon atoms. For example, "alkyl" may refer to methyl, ethyl, n-propyl, isopropyl, butyl, isobutyl, sec-butyl, tert-butyl, pentyl, isopentyl tert-pentyl, hexyl, isohexyl, and the like. Suitable substituents for the substituted alkyl and aryl groups used in the invention include the mercapto, thioether, nitro, amino, aryloxy, halogen, hydroxyl, and carbonyl groups as well as aryl, cycloalkyl and non-aryl heterocyclic groups.

The term "cycloalkyl" as used herein refers to groups, preferably having three to seven, more preferably, three to six carbon atoms. Suitable cycloalkyls include, but are not limited to, cyclopropyl, cyclobutyl, cyclopentyl, cyclohexyl, cycloheptyl and the like.

The term "aryl" as used herein refers to both carbocyclic and heterocyclic, substituted or unsubstituted, aromatic residues. Accordingly, the term includes the types of substituents identified hereinabove as typical carbocyclic or heterocyclic ring systems which contain the requisite unsaturation to retain their aromatic character.

The terms "alkoxy" and "aryloxy" refer to groups as defined hereinabove as alkyl or aryl groups, as the case may be, which also carry an oxygen atom interposed between them and the substrate residue to which they are attached.

The "halogen" substituent according to the present invention may be a fluoro, chloro, bromo or iodo substituent.

Some compounds of the invention possess one or more asymmetrically substituted carbon atoms and therefore exist in racemic and optically active forms. The invention is intended to encompass the racemic forms of the compounds as well as any of the optically active forms thereof.

In the syntheses of the novel HIV inhibiting compounds of this invention, a large number of novel intermediate compounds has also been prepared. These novel intermediate compounds also form part of the invention. One class of such novel intermediates are compounds of the formula III

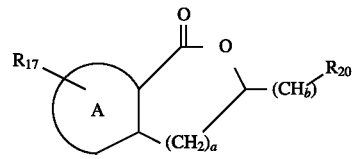

wherein:

A' is selected from carbocyclic or heterocyclic, aromatic, saturated or partially saturated 5, 6 or 7 member rings which can be further substituted;

$R_{17}$ is selected from hydrogen, halogen, hydroxyl, substituted or unsubstituted alkoxy, mercapto, thioether, —$NR'_1R'_2$, nitro, alkyl, aryl and substituted alkyl or aryl, wherein $R_{17}$ can form a fused ring structure with A';

$R'_1$ and $R'_2$ are individually selected from hydrogen, alkyl, cycloalkyl, aryl, substituted alkyl, cycloalkyl or aryl, substituted oxygen, hydroxyl, substituted or unsubstituted non-cyclic amino and substituted or unsubstituted non-aryl heterocycle, wherein $R'_1$ and $R'_2$ can form a ring with the nitrogen atom to which they are attached;

a=0, 1, or 2;

b=0, 1, or 2;

and $R_{20}$ is halogen or a group having the formula IV

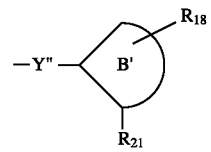

wherein:

when b is 2, Y" is a substituted or unsubstituted group, oxygen, sulphur, or —$CH_2$—;

when b is 1, Y" is —CH=;

when b is 0, Y" is —C≡;

B' is selected from carbocyclic or heterocyclic, aromatic, saturated or partially saturated 5, 6 or 7 member rings which can be further substituted;

$R_{18}$ is selected from hydrogen, halogen, hydroxyl, substituted or unsubstituted alkoxy, mercapto, thioether, $-NR'_1R'_2$, nitro, alkyl, aryl and substituted alkyl or aryl, wherein $R_{18}$ can form a fused ring structure with B';

and $R_{21}$ is (1) amino, (2) nitro or (3) a group convertible to a group of the formula V, $$Z \overset{R_3'}{=} \underset{}{N-R_4'} \qquad V$$

wherein

Z' is oxygen or sulphur; and $R'_3$ and $R'_4$ are individually selected from hydrogen, alkyl, cycloalkyl, aryl, substituted alkyl, cycloalkyl or aryl, substituted oxygen, hydroxyl, substituted or unsubstituted non-cyclic amino and substituted or unsubstituted non-aryl heterocycle, wherein $R'_3$ and $R'_4$ can form a ring with the nitrogen atom to which they are attached.

Another class of novel intermediates are compounds of the formula VI $$\text{VI}$$

wherein:

c is 0, 1, or 2;

A' is selected from carbocyclic or heterocyclic, aromatic, saturated or partially saturated 5, 6 or 7 member rings which can be further substituted;

$R_{17}$ is selected from hydrogen, halogen, hydroxyl, substituted or unsubstituted alkoxy, mercapto, thioether, $-NR'_1R'_2$, nitro, alkyl, aryl and substituted alkyl or aryl, wherein $R_{17}$ can form a fused ring structure with A';

$R'_1$ and $R'_2$ are individually selected from hydrogen, alkyl, cycloalkyl, aryl, substituted alkyl, cycloalkyl or aryl, substituted oxygen, hydroxyl, substituted or unsubstituted non-cyclic amino and substituted or unsubstituted non-aryl heterocycle, wherein $R'_1$ and $R'_2$ can form a ring with the nitrogen atom to which they are attached;

$R_{22}$ is a substituted or unsubstituted amino group or an alkoxy group;

$R_{23}$ is hydrogen, hydroxyl, a substituted or unsubstituted amino group, or a group of the formula VII $$\text{VII}$$

wherein:

d is 0, 1, or 2;

when d is 2, Y" is a substituted or unsubstituted amino group, oxygen, sulphur, or $-CH_2-$;

when d is 1, Y" is $-CH=$;

when d is 0, Y" is $-C\equiv$;

B' is selected from carbocyclic or heterocyclic, aromatic, saturated or partially saturated 5, 6 or 7 member rings which can be further substituted;

$R_{18}$ is selected from hydrogen, halogen, hydroxyl, substituted or unsubstituted alkoxy, mercapto, thioether, $-NR'_1R'_2$, nitro, alkyl, aryl and substituted alkyl or aryl, wherein $R_{18}$ can form a fused ring structure with B';

and $R_{21}$ is (1) amino, (2) nitro or (3) a group convertible to the group of the formula V, defined above, wherein Z' is oxygen or sulphur; and $R'_3$ and $R'_4$ are individually selected from hydrogen, alkyl, cycloalkyl, aryl, substituted alkyl, cycloalkyl or aryl, substituted oxygen, hydroxyl, substituted or unsubstituted non-cyclic amino and substituted or unsubstituted non-aryl heterocycle, wherein $R'_3$ and $R'_4$ can form a ring with the nitrogen atom to which they are attached.

The novel compounds of this invention can be prepared by a number of synthetic routes. A preferred synthesis comprises the following reaction sequence A in which all variable groups and substituents are as previously defined except the groups $R_{24}$ and $R'_{24}$ in compound X, which are individually selected from alkyl groups:

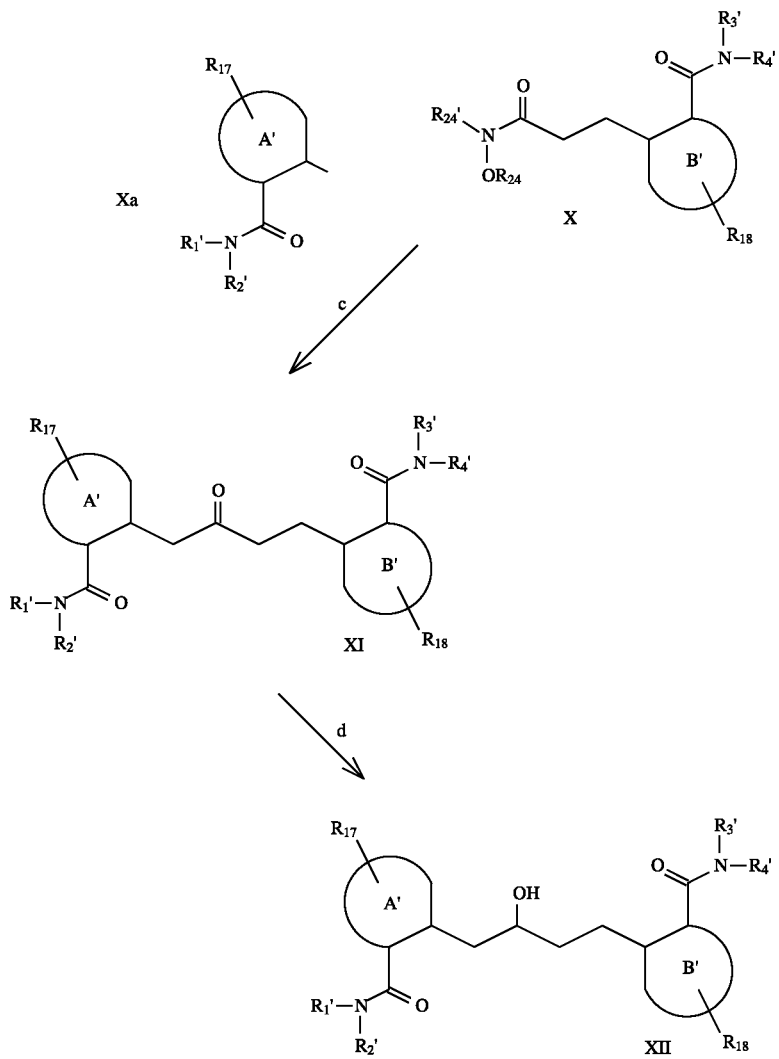

wherein:

a) the compound of the formula VIII is oxidized under conditions sufficient to obtain the compound of the formula IX;

b) the compound of the formula IX is reacted with an alkyl alkoxylamine under conditions sufficient to obtain the compound of the formula X;

c) the compound of the formula X is reacted with the compound of the formula Xa under conditions sufficient to obtain the compound of the formula XI; and d) the compound of the formula XI is reduced under conditions sufficient to obtain the compound of the formula XII.

All steps are preferably carried out in a suitable solvent.

In the first step of sequence A, compound VIII, prepared by known methods, is oxidized to the carboxylic acid IX. Oxidation can be carried out using conventional oxidizing agents such as e.g. chromium trioxide, pyridinium dichromate, under conditions conventionally known for carrying out such an oxidation, i.e. usually acid conditions and moderate temperatures.

Alternatively, the oxidation can be carried out in basic medium, which results in formation of the aldehyde corresponding to the carboxylic acid IX.

In many of the compounds of the invention, one or both of $R'_1$ and $R'_2$ are hydroxyalkyl groups. In such cases, it is highly preferred that the hydroxyl group(s) be protected from oxidation during this first step. Such protection is readily provided by reacting the hydroxyl group with conventional protecting groups such as e.g. an alkyl or aryl substituted silane, benzyl, or substituted benzyl group, prior to the oxidation step. The protecting group is readily removed as a final (additional) step in the sequence.

In the second step of this sequence, the carboxylic acid IX is reacted with a secondary amine to form the carboxylic acid amide X. Preferred secondary amines include N-alkyl-O-alkyl hydroxylamines, which are readily reacted in subsequent steps. The reaction can be carried out in the presence of a base, such as a lower alkyl tertiary amine, and a suitable coupling reagent, such as DCC, defined later herein, BOP, defined later herein, and EDC (1-(3-dimethylaminopropyl)-3-ethylcarbodiimide hydrochloride, preferably at moderate temperatures, e.g. about room temperature. The preferred secondary amine is N-methyl O-methyl hydroxylamine while the preferred base is a tertiary amine, such as triethylamine or diisopropyl ethylamine.

In the third step of this sequence, the carboxylic acid amide X is coupled with a compound of formula Xa to form the ketone of formula XI. This reaction can be carried out at low temperatures, i.e. about −60° to −85°, preferably about −78° C., in the presence of an alkyl lithium compound and an amine. When one or more of $R'_1$, $R'_2$, $R'_3$ and $R'_4$ is hydrogen, the preferred amine is tetramethyl ethylene diamine (TMEDA). When all of $R'_1$, $R'_2$, $R'_3$ and $R'_4$ are other than hydrogen, the preferred amine is a secondary dialkyl amine, such as diisopropyl amine. In each case, the preferred alkyl lithium compound is a butyl lithium, preferably s-butyl lithium.

In the fourth step of this sequence, the ketone of formula XI is reduced to the compound of formula XII. Reduction can be carried out with a reducing agent such as, e.g. $NaBH_4$ or $LiBH_4$. Reduction with $NaBH_4$ can be carried out at relatively low temperatures, i.e. about 0° C. to room temperature.

In the case where one or both of $R'_1$ and $R'_2$ is a hydroxylalkyl group, the reduction step is preferably followed by a fifth step, i.e. a deprotection step. The deprotection method to be used depends on the identity of the protecting group. In the case of the preferred alkyl or aryl silane protecting group, deprotection can be accomplished in the presence of fluoride ion, e.g., tetrabutyl ammonium fluoride. In the case of a benzyl protecting group, deprotection can be accomplished by hydrogenation over palladium.

Another useful synthesis for certain compounds according to the invention comprises the reaction sequence B in which all variable groups and substituents are as previously defined:

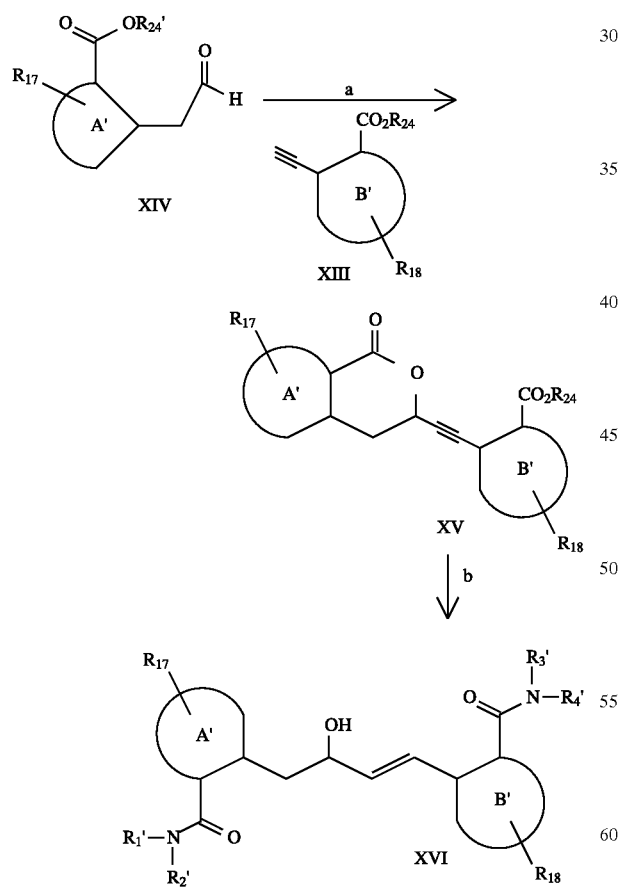

wherein:
a) the compound of the formula XIII is reacted with a compound of the formula XIV under conditions sufficient to form a compound of the formula XV; and b) sequentially reducing and reacting the compound of formula XV with at least one amine selected from $R'_1R'_2NH$ and $R'_3R'_4NH$ under conditions sufficient to form a compound of the formula XVI.

In the first step of this sequence a compound of formula XIII and a compound of formula XIV are coupled to form the lactone of formula XV, preferably in a suitable solvent. Compounds of formula XIII and XIV are readily prepared by known methods. The coupling can be carried out in the presence of lithium diisopropyl amide (LDA) at a temperature ranging from about −60° to −78° C.

The compound of formula XV is sequentially reduced and reacted with an amine of formula $NR'_1R'_2$ or $NR'_3R'_4$ to form a compound of formula XVI. Reaction with the amine and reduction can be carried out in either order, i.e. amine reaction followed by reduction or reduction followed by amine reaction. Also, reduction can be full or partial.

The reaction with the amine can be carried out by first reacting the amine with a trialkyl aluminum compound, preferably trimethyl aluminum, at relative low temperature, e.g. between about room temperature and 0° C. to form amino aluminum dialkyl. The reaction is preferably carried out in an aromatic hydrocarbon solvent.

This amino aluminum dialkyl compound is then reacted with the compound of formula XV, preferably at elevated temperatures, e.g. about 90° to 105° C., preferably for a time sufficient for the reaction to go to completion. This treatment serves both to open the lactone ring and to form an amide on both sides of the molecule.

Reduction of the triple bond either to a double bond or to complete saturation can be accomplished by use of molecular hydrogen in the presence of known hydrogenation catalysts such as Pd, Raney Nickel or Lindlar catalyst.

Still other compounds according to the invention can be prepared by the following reaction sequence C, in which Y''' is oxygen, sulfur, or —NH—, and all other variable groups and substituents are as previously defined:

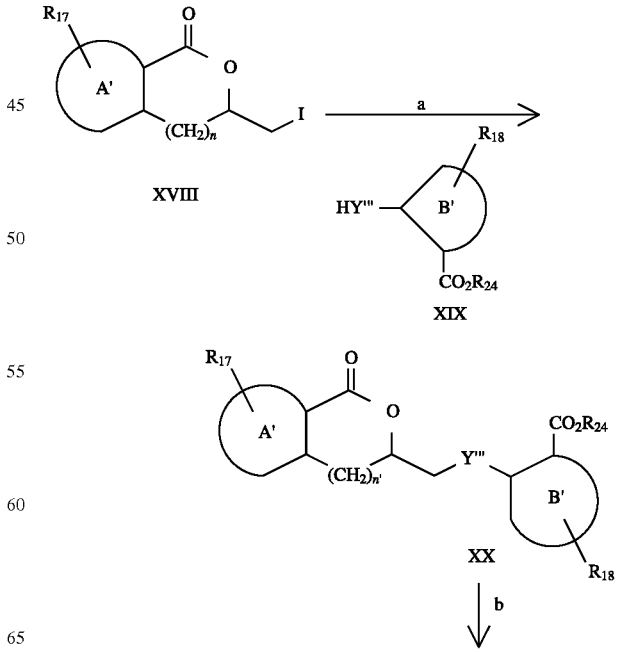

-continued

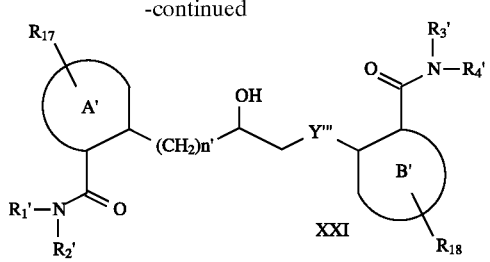

wherein:

a) the compound of the formula XVIII is reacted with the compound of the formula XIX under conditions sufficient to obtain the compound of the formula XX; and b) the compound of the formula XX is reacted with at least one amine selected from $R'_1R'_2$ NH and $R'_3R'_4$NH under conditions sufficient to obtain the compound of the formula XXI.

In the first step of this sequence, compounds XVIII and XIX are coupled (reacted) to form the lactone XX. This reaction can be carried out by bringing the two compounds together in an alcohol or ethereal solvent medium with a suitable base for a time sufficient to effect coupling. Suitable solvents for this reaction include, e.g. ethanol, tetrahydrofuran (THF) and dioxane. The reaction can be carried out at temperatures from about 0° C. to room temperature.

In the second step of this sequence, the compound of formula XX can be reacted with an aminoaluminum dialkyl whereby the lactone ring is opened and an amide is formed from the lactone carbonyl group and also on the other (ester) carbonyl group that is already present on the molecule. However, both reactions need not be effected simultaneously in all cases.

If it is desired to have

the same as

the reaction can be carried out between about 65° and 100° C. for a time sufficient to obtain the desired diamide.

Alternatively, the operation can be carried out in two steps if it is desired to have

different from

The first step is carried out at room temperature using a first aminoaluminum dialkyl whereby opening of the lactone ring occurs preferentially and the lactone carbonyl group is converted to the amide corresponding to the aminoaluminum dialkyl used in this step. In a second step, a second aminoaluminum dialkyl compound is employed, moderately elevated temperatures are used (up to about 100° C.) and the carboxylalkyl group on ring B' is converted to an amide group.

In another alternative procedure, which is particularly useful when n' is 0, the reaction can be carried out at temperatures of 0° C. or less, such as −78° C., in an ethereal solvent such as THF using an n-alkyl lithium as a base. n-Butyl lithium is the preferred base. In this case, the same amine is usually employed for both sides of the molecule so that the resultant

is the same as the resultant

Yet another synthetic route which produces intermediates for use in preparing compounds of the invention comprises reaction D, wherein all variable groups and substituents are as previously defined:

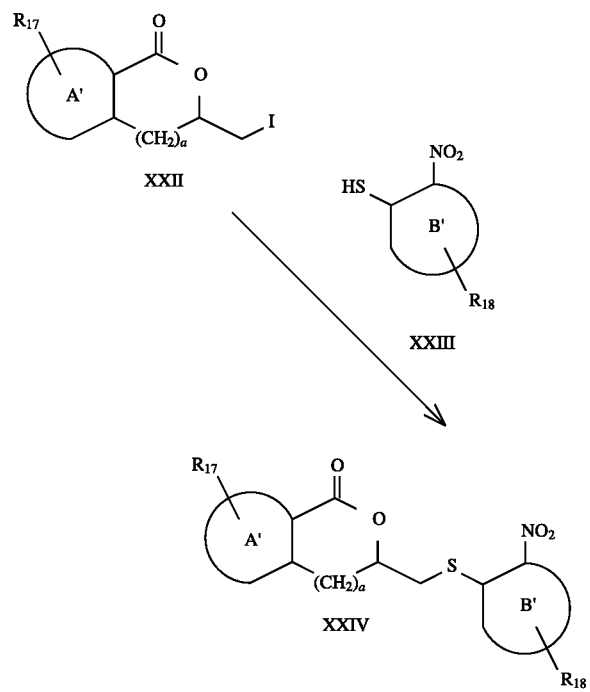

wherein the compound of the formula XXII is reacted with the compound of the formula XXIII under conditions sufficient to obtain the compound of the formula XXIV.

This reaction is essentially the same as the first step of sequence C above. Thus the compound of formula XXII and the compound of formula XXIII are coupled to form the lactone XXIV. The reaction can be carried out by bringing the two compounds together in a basic alcohol or ethereal solvent medium for a time sufficient to effect coupling. The reaction can be carried out at temperatures from about 0° C. to room temperature.

The nitro group on compound XXIV can be converted to an amide in two steps, i.e. reducing it to an amine followed by reaction with a carboxylic acid chloride of the formula $ClC(O)R'_5$, wherein $R'_5$ is individually selected from hydrogen, alkyl, cycloalkyl, aryl, alkoxy, aryloxy, substituted alkyl, cycloalkyl or aryl, and substituted or unsubstituted non-aryl heterocycle, by known methods to provide the alkyl carbonyl substituent desired on the amide.

The compound of formula XXIV, as well as its amino and amido derivatives, can be reacted to open the lactone ring and form an amide as has been taught hereinabove for other lactones.

Still other compounds of the invention can be prepared via reaction sequence E in which all variable groups and substituents are as previously defined:

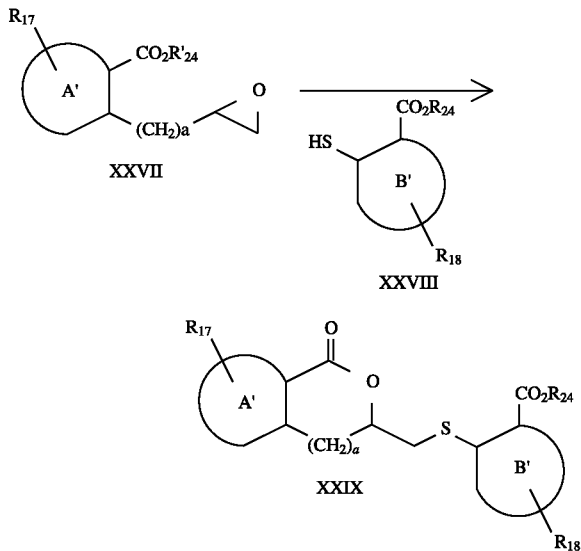

wherein the compound of the formula XXVII, wherein $R'_{24}$ is an alkyl group, is reacted with a compound of the formula XXVIII under conditions sufficient to obtain the compound of the formula XXIX.

In reaction E, a compound of XXVII is reacted with a compound of formula XXVIII to form a compound of formula XXIX. The compound of formula XXIX can be reacted to open the lactone ring and form an amide as has been taught hereinabove for other lactones.

The compounds of this invention, as indicated hereinabove, are effective in inhibiting the activity of the HIV protease, which halts the proliferation of the HIV virus. A compound according to the invention may be active per se, or it may be a precursor which is converted in vivo to an active compound. Moreover, many of the compounds of the invention contain functional groups that are capable of forming salts. It is intended that the invention also include such pharmaceutically acceptable salts, e.g. carboxylic acid salts or quaternary salts.

The compounds according to the invention, as well as the pharmaceutically acceptable salts thereof, can be incorporated into convenient dosage forms such as capsules, tablets, or injectable preparations. Solid or liquid pharmaceutically acceptable carriers can also be employed. Solid carriers can include starch, lactose, calcium sulphate dihydrate, terra alba, sucrose, talc, gelatin, agar, pectin, acacia, magnesium stearate and steric acid. Liquid carriers can include syrup, peanut oil, olive oil, saline solution and water.

The carrier or diluent can include prolonged release material, such as glyceryl monostearate or glyceryl distearate, alone or with wax. When a liquid carrier is used, the preparation may be in the form of a syrup, elixir, emulsion, soft gelatin capsule, sterile injectable liquid (e.g. solution) or a nonaqueous or aqueous liquid suspension.

The pharmaceutical preparations can be prepared following conventional techniques of the pharmaceutical chemist involving steps such as mixing, granulating, and compressing when necessary for tablet forms, or mixing, filling and dissolving the ingredient as appropriate to give the desired products for oral, parenteral, topical, intravaginal, intranasal, intrabronchial, intraocular, intraaural and rectal administration or by injection.

The compositions of the invention may further comprise one or more other compounds which are either HIV inhibitors, such as azidothymidine, or which perform a different pharmaceutically desirable function, such as, for example antibacterial, antifungal, antiparasitic, antiviral, antipsoriatic or anticoccicidal agents. Exemplary antibacterial agents include, for example, sulfonamides such as sulfamethoxazole, sulfadiazine, sulfameter or sulfadoxine.

An exemplary daily dosage unit comprises an amount up to about one gram of active compound per kilogram of the host, preferably one half gram, more preferably 100 milligrams, and most preferably, about 50 milligrams or less per kilogram of the host weight. The selected dose may be administered to a patient in recognized need of treatment, by any known method of administrating the dose including topically as, for example, an ointment or cream; orally; rectally, for example, as a suppository; parenterally by injection; or continuously by intravaginal, intranasal, intrabronchial, intraaural or intraocular infusion.

Details and specific embodiments of these syntheses will be presented in the example hereinbelow. In these examples, the structures of all new compounds were confirmed by proton magnetic resonance spectroscopy, infrared spectroscopy, and either elemental microanalysis (C, H, and N to within 0.4%) or by high resolution mass spectrometry. Proton magnetic resonance spectra were determined using a General Electric QE-300 spectrometer operating at a field strength of 300 mHz.

Most of the examples consist of a sequence of syntheses proceeding from commercially available compounds through a series of intermediates to a final product meeting the limitations of formula I or formula II. Each of these steps has actually been carried out and each such intermediate has actually been prepared. However, it must be understood that when a step in a sequence refers to a compound from an earlier step, the physical specimen of that compound that was employed in that step may not be the same physical specimen of that compound that was actually prepared in the cited earlier step. For example, in step 12b of Example 12, the reaction of compound 12a with compound 9e is described. It is believed that although the compound actually reacted with compound 12a was identical in chemical structure to the compound 9e, it is possible that the compound actually reacted with compound 12a was not the same physical specimen of compound 9e as was prepared in Example 9. If the compound actually reacted with compound 12a was not the same physical specimen as compound 9e, it is believed that the compound actually reacted was prepared in the same way as the compound 9e.

EXAMPLE 1

Preparation of

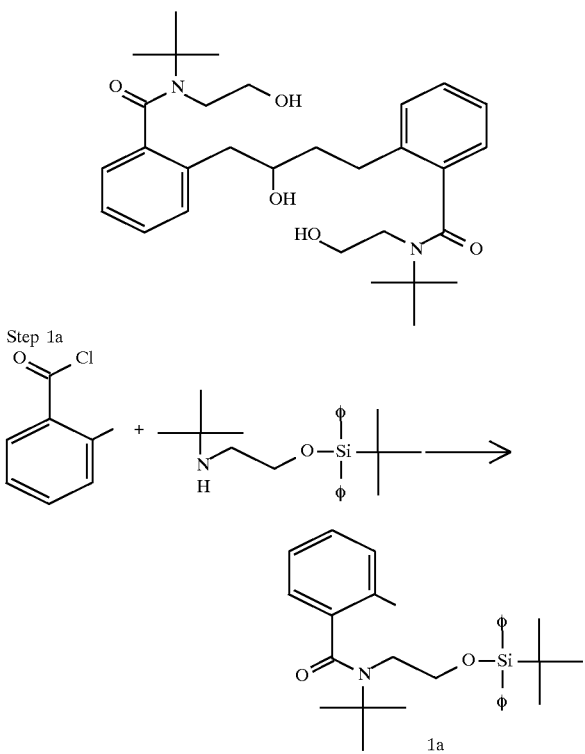

Step 1a

A reaction flask containing 25.5 gm (71.7 mmol) of silane-protected N-t-butyl ethanol amine dissolved in about 50 ml of methylene chloride, cooled to 0° C. with an ice bath, was fitted with an argon balloon and a septum. Over a five minute period, keeping the temperature no higher than 5° C., 13.1 g (13 mmol) of o-toluoyl chloride was added. The ice bath was removed and the mixture was stirred for 21 hours, at which point the reaction was quenched with 100 ml of saturated NaHCO₃, washed twice with 500 ml of H₂O and dried over Na₂SO₄. The product was treated with charcoal, filtered and concentrated under vacuum, yielding 21.6 gm of an orange oil. After Kugelrohr distillation at about 230° C. and 1.9 Torr, 12.6 gm (32% yield) of a viscous orange oil was recovered. NMR showed this material to be contaminated with residual o-toluoyl chloride so it was purified by flash chromatography on silica gel (10% ethyl acetate in hexane as eluent) to elute the acid chloride, then with neat ethyl acetate to recover the product in essentially pure form.

Step 1b

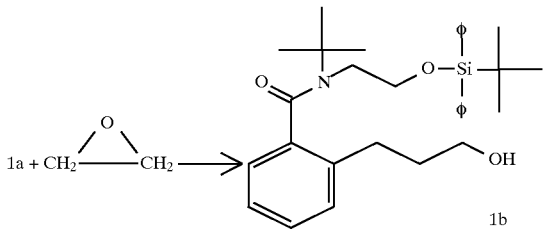

To a 250 ml round bottom flask, previously flame dried and purged with argon, was added 9.06 gm (19.12 mmol) of compound 1a, 0.29 gm (2.86 mmol) of diisopropyl amine and 100 ml of tetrahydrofuran (THF), to produce a clear, colorless solution. This solution was cooled to −78° C. in a dry ice-acetone bath and 19.1 ml of sec-butyl lithium was added via a syringe over a 15 minute period while maintaining the temperature below −70° C. This mixture (now a deep purple color) was stirred for 1.5 hour at −78° C. after which 2.53 gm (7.37 mmol) of ethylene oxide was added in a single addition. The mixture was allowed to warm to room temperature without addition of extraneous heat.

After 16 hours, the murky orange mixture was quenched with 10 ml of 0.5N HCl, then poured into about 600 ml of H₂O and extracted twice with 200 ml of ethyl acetate. The organic layers were combined, dried over Na₂SO₄, treated with charcoal and vacuum dried, yielding 9.84 gm of a viscous, peach colored oil. The oil was purified by flash chromatography on silica gel 60 using 45% ethyl acetate/ hexane eluent. Appropriate fractions were combined and concentrated under vacuum, yielding 7.08 gm of a viscous, light yellow oil.

Step 1c

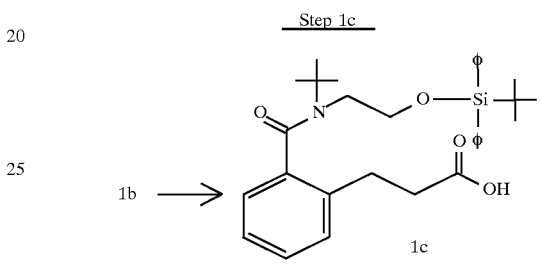

Seven (7) gm (0.0135 mmol) of 1b and 25.43 gm of pyridinium dichromate were dissolved in 50 ml of DMF and stirred under argon. After about 17 hours the solution was poured into 3 liters of H₂O and extracted twice with 500 ml of ethyl acetate. The organic phases were combined and washed with 2 liters of H₂O, filtered, treated with charcoal and concentrated under vacuum to yield 4.85 gm of a viscous brown product. This product was purified by flash chromatography using 10% methanol in methylene chloride. The appropriate fractions were combined, filtered and dried under vacuum, yielding 2.31 gm (32%) of a brown glassy product.

Step 1d

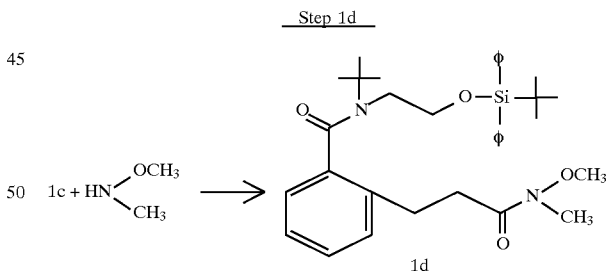

A solution of 2.31 gm (4.34 mmol) of compound 1c, 2.02 gm of benzotriazol-1-yloxyl-tris-(dimethylamino)-phosphonium-hexafluoro phosphate (BOP), 0.466 gm (4.78 mmol) of N,O-dimethyl hydroxyl-amine hydrochloride and 1.54 g of Hunig's base in 15 ml of methylene chloride was stirred in an argon atmosphere for about 2 hours. At the end of this time, the reaction mix was washed with 200 ml of H₂O, dried over Na₂SO₄, treated with charcoal, filtered and dried under vacuum, yielding 3.52 gm of a viscous brown oil. The product was purified by flash chromatography using 1 to 1 ethyl acetate/hexane. Appropriate fractions were combined, filtered and dried under vacuum, yielding 1.48 gm (59%) of a clear, colorless viscous oil.

Step 1e

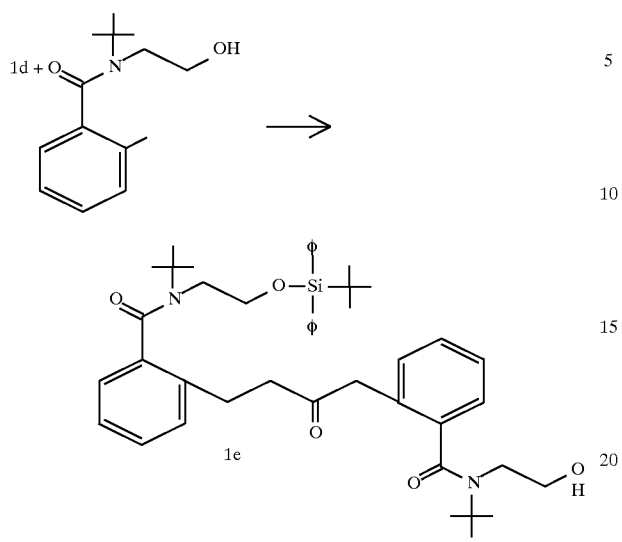

To a 25 ml round bottom flask, previously flame dried and purged with argon, was added 0.18 gm (0.765 mmol) of azeotropically dried N-t-butyl, N-hydroxyethyl-o-toluamide, 0.01 gm of diisopropylamine and 5 ml of THF, forming a clear, colorless solution. This solution was cooled to −78° C., in a dry ice-acetone bath and 1.76 ml of s-butyl lithium was syringed in over a 10 minute period. The solution was stirred at −78° C. for one hour at which time, 0.70 gm (0.696 mmol) of compound 1d in 5 ml of THF was syringed in over a 10 minute period. No color change was noted. The dry ice was allowed to evaporate and the reaction mass was allowed to return to room temperature without addition of any extraneous heat.

At room temperature, the reaction was quenched with 8 ml of 0.5N NH$_4$Cl, then poured into 25 ml of brine and 25 ml of H$_2$O, then extracted twice with 25 ml of ethyl acetate. The organic layers were combined, dried over Na$_2$SO$_4$, then treated with charcoal, filtered and concentrated under vacuum to give 455 mg of a clear "glass", sticky material suitable for further use.

Step 1f

1e →

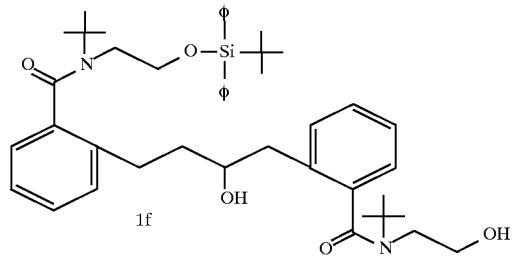

To a solution of 0.455 gm (0.607 mmol) of 1e in 5 ml of ethanol, was added 0.69 gm (1.82 mmol) of NaBH$_4$. The mixture was stirred for one hour at room temperature, then quenched with 8 ml of saturated NaHCO$_3$ solution and poured into 25 ml of saturated brine plus 15 ml of H$_2$O. This mixture was extracted twice with 25 ml of ethyl acetate. The organic layers were combined and dried over Na$_2$SO$_4$, then treated with charcoal, filtered and concentrated under vacuum, yielding 0.38 gm of white foam suitable for further use.

Step 1g

1f →

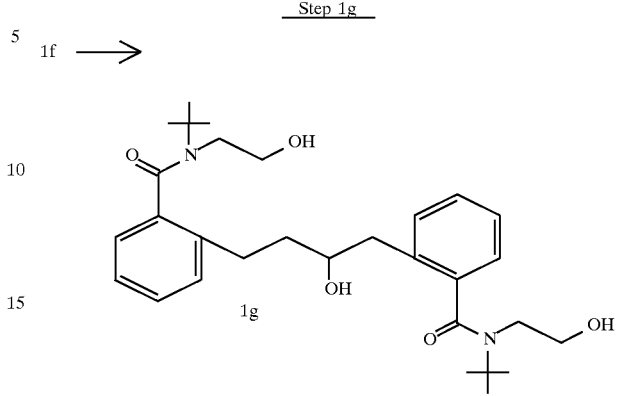

A solution of 0.38 gm (0.506 mmol) of 1f and 1.01 ml of tetrabutyl ammonium fluoride in 5 ml of THF was stirred at room temperature for 15.5 hours, then quenched with 0.8 ml of saturated NaHCO$_3$. The quenched mixture was poured into 50 ml of water and extracted with 25 ml of ethyl acetate. The organic layers were combined, dried over Na$_2$SO$_4$, treated with charcoal, filtered and dried under vacuum, yielding 338 mg of a clear viscous oil. The oil was purified by flash chromatography using ethyl acetate. Appropriate fractions were combined and concentrated under vacuum, yielding 149 mg (58%) of a white foam.

EXAMPLE 2

Preparation of

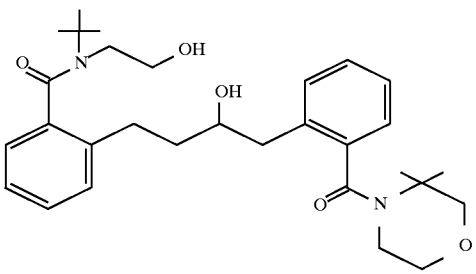

Step 2a

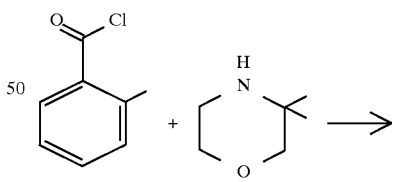

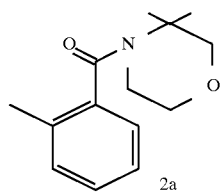

In a 25 ml 3 neck flask, previously flame dried in vacuo and purged with argon, there was prepared a solution of 1.5 gm (13.02 mmol) of 2,2-dimethyl-morpholine, and 3.95 gm of triethylamine in 10 ml of methylene chloride. This solution was cooled in an ice bath and 2.21 gm (4.32 mmol)

of 2-methyl benzoyl chloride were added over a 20 minute period. The temperature was maintained between about 5° and 10° C. Chloride salts formed and precipitated out of the solution. After addition of the 2-methyl benzoyl chloride was complete, the mixture was allowed to sit at room temperature for about 18 hours, then poured into 30 ml of $H_2O$. The chloride salts dissolved. The aqueous mixture was extracted with 10 ml of methylene chloride and the organic extract was dried over $Na_2SO_4$. The dried organic phase was filtered and concentrated under vacuum, yielding 2.47 gm of a light brown oil which slowly solidified on standing. The oil was taken up in 5 ml of ethanol, 50 ml of hexane was added and the mixture was stored in a freezer for about 72 hours. White crystals, which formed on freezing, were washed with 20 ml of cold hexane yielding 1.74 gm.

Step 2b

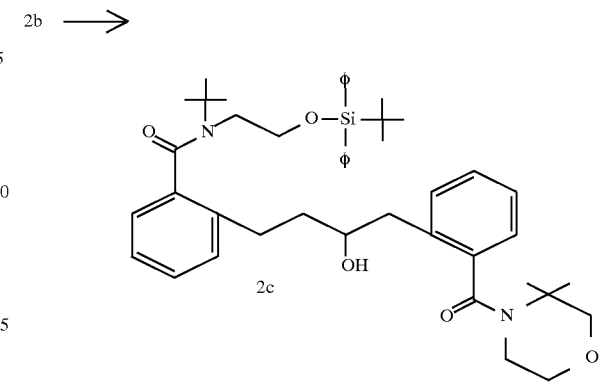

A 100 ml 3 neck round bottom flask, previously dried and purged with argon, was charged with 0.089 gm (0.383 mmol) of 2a, 0.005 gm of diisopropylethylamine and 5 ml of THF. The mixture was cooled to −78° C. in a dry ice/acetone bath and 0.35 ml of 1.2M s-butyl lithium in cyclohexane was added over about 1 minute while maintaining the temperature below −70° C. The resulting deep purple solution was stirred at −78° C. for 1 hour, whereupon a solution of 0.2 gm (0.348 mmol) of 1d in 5 ml of THF was added by syringe over a 5 minute period, maintaining the temperature below −60° C. No color change was noted. The dry ice was allowed to evaporate and the mixture warmed to room temperature without extraneous heating. After about one hour and ten minutes, the reaction was quenched with 8 ml of 0.5N $NH_4Cl$, poured into 25 ml of brine and extracted twice with 25 ml of ethyl acetate. The organic extracts were combined, dried over $Na_2SO_4$, treated with charcoal, filtered and concentrated under vacuum, yielding 0.251 gm of a clear colorless glass-like product, suitable for further use.

Step 2c

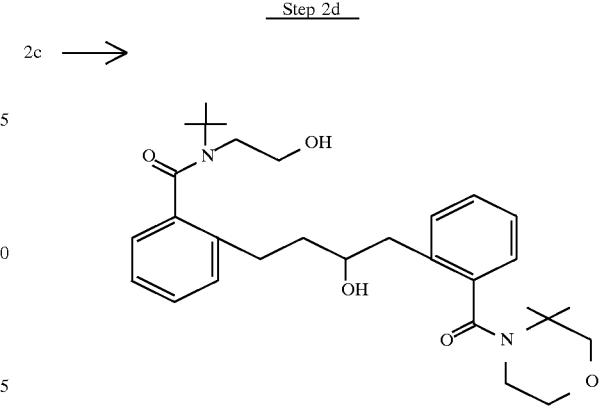

To a solution of 0.251 gm (0.336 mmol) of 2b in ethanol, was added 0.038 gm (1.008 mmol) of $NaBH_4$ in a single portion. The solution was stirred at room temperature for one hour. At the end of the hour, the mixture was quenched with 8 ml of saturated $NaHCO_3$, poured into 25 ml of brine plus about 15 ml of $H_2O$ then extracted twice with 25 ml of ethyl acetate. The organic layers were combined, dried over $Na_2SO_4$, treated with charcoal, filtered, and concentrated under vacuum, yielding 0.167 gm of a white foam suitable for further use.

Step 2d

2c →

A solution of 0.167g (0.223 mmol) of 2c, and 0.44 ml of tetrabutyl ammonium fluoride in THF was stirred at room temperature overnight. After about 15.5 hours of stirring, the solution was quenched with about 8 ml of saturated $NaHCO_3$, poured into 50 ml of water, and extracted with 25 ml of ethyl acetate. About 25 ml of brine was added to the aqueous phase, which was then extracted again with 25 ml of ethyl acetate. The extracts were combined, dried over $Na_2SO_4$, treated with charcoal, filtered, and concentrated under vacuum, yielding 1.43 gm of a crude, clear oil. This oil was purified by flash chromatography on $SiO_2$ and vacuum dried yielding 72 mg (63%) of a white foam.

EXAMPLE 3

Preparation of

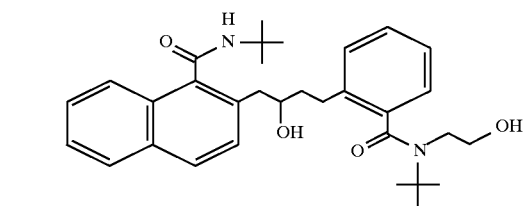

Step 3a

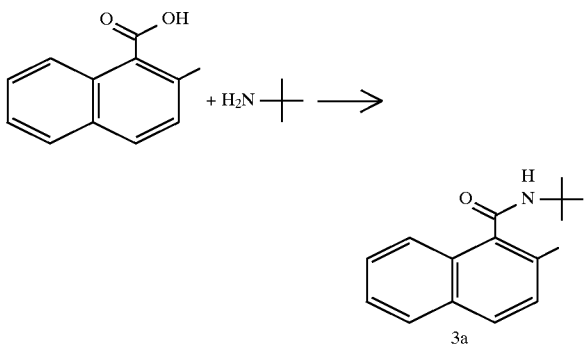

A heterogeneous mixture of 2 gm (10.75 mmol) of 2-methyl naphthoic acid in toluene was cooled to 0° C. and oxalyl chloride was added, dropwise, followed by dropwise addition of 0.236 gm of dimethylformamide (DMF). As the DMF was added, gas was vigorously evolved and the solid 2-methyl naphthoic acid began to go into solution. After 5 minutes, the reaction mixture was allowed to warm to room temperature. The solution was clear and golden with a small amount of white precipitate. After 20 minutes the precipitate had dissolved into the solution and the reaction was monitored by infrared analysis. The reaction mass was concentrated under vacuum. As the oxalyl chloride evaporated, a large amount of a white solid settled out. The solution could not be further concentrated due to the presence of the solid. The mixture was cooled to 0° C. and 1.65 gm of t-butylamine was added. A fine white precipitate settled out. The bath was then removed and after 15 minutes at room temperature the reaction mass was poured into water and extracted with ethyl acetate. The organic phases were collected, washed with brine, and dried over MgSO$_4$. The solvent was removed under vacuum. The solid was purified by column chromatography using a 2-1 hexane to ether solution as the eluant. Following chromatography the product was recrystallized from an ether/hexane mixture. Structure was confirmed by NMR. Yield was 83%.

Step 3b

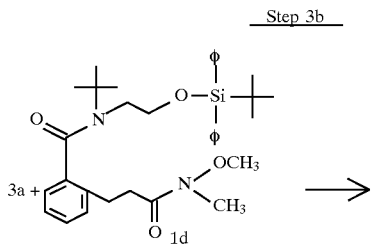

Step 3b

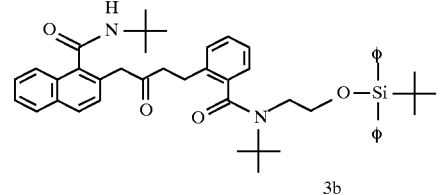

To a 25 ml round bottom flask which was previously flame dried under vacuum and purged with argon, was added 5 ml of THF and 0.9 gm (0.373 mmol) of compound 3a and 0.095 gm of tetramethyl ethylene diamine (TMEDA). This mixture was cooled to −78° C. in a dry ice-acetone bath and over a two minute period 0.313 ml of a 2.5M solution of n-butyl lithium in hexane was added, yielding a deep purple solution. This solution was stirred at −78° C. for one hour and 0.216 gm of compound 1d in 5 ml of THF was added over a three minute period. During addition the deep purple color became a little lighter. Dry ice was allowed to evaporate and the mixture warmed to room temperature without the addition of extraneous heat. After about 2 hours, the yellow reaction mass was poured into 100 ml of H$_2$O and extracted with 25 ml of ethyl acetate. Sodium chloride was added to the aqueous layer and extraction with 25 ml of ethyl acetate was repeated. The organic layers were combined, dried over Na$_2$SO$_4$, filtered and vacuum dried, yielding 265 mg of an amber colored viscous glass suitable for further use.

Step 3c

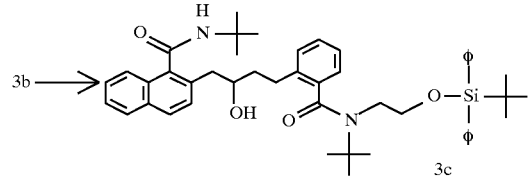

A solution was prepared of 0.265 gm (0.350 mmol) of compound 3b in 5 ml of ethanol giving a clear solution to which was added 0.04 gm of sodium borohydride in one portion. The mixture was stirred at room temperature for about 45 minutes, quenched with 2 ml of saturated NaHCO$_3$, then poured into 40 ml of brine and extracted twice with 25 ml of ethyl acetate. The organic layers were combined, dried over Na$_2$SO$_4$, filtered and concentrated under vacuum, yielding 197 mg of a white foam.

Step 3d

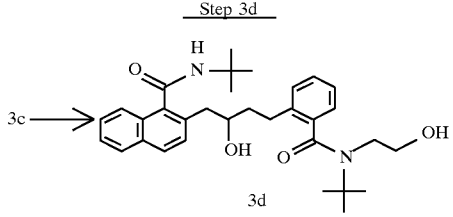

To a solution of 0.19 gm (0.2506 mmol) of compound 3c in 5 ml of THF was added, in one portion, 0.5 ml of a 1M tetrabutyl ammonium fluoride solution. The mixture was stirred for about 5.5 hours, at which point TLC indicated that all of compound 3c had disappeared. The reaction was quenched with 4 ml of saturated NaHCO$_3$ then poured into 40 ml of brine and extracted twice with 25 ml of ethyl acetate.

The organic layers were combined, dried over Na₂SO₄, filtered and concentrated under vacuum, yielding 0.222 gm of a white foam. This foam was purified by flash chromatography on silica using ethyl acetate. Appropriate fractions were combined, filtered, and vacuum dried, yielding 0.101 gm (78%) of a white foam product.

EXAMPLE 4

Preparation of

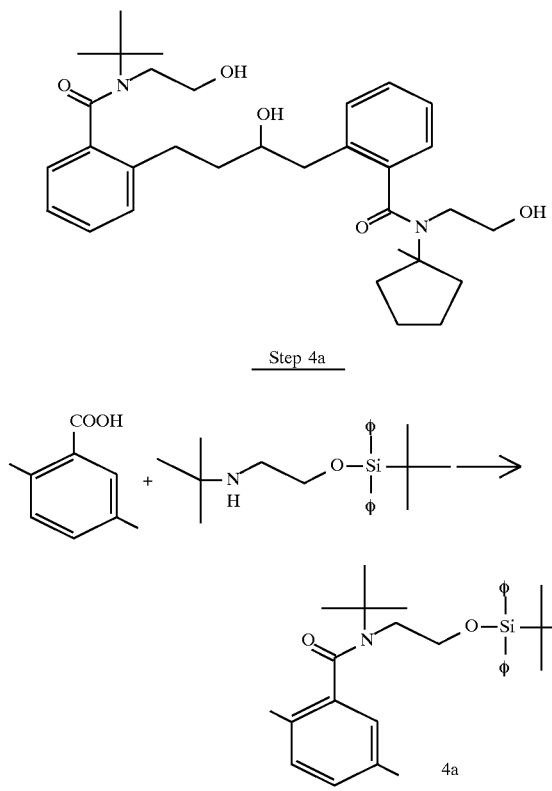

Step 4a

A suspension of 5 gm of 2,5-dimethyl benzoic acid in 50 ml of toluene was cooled in an ice bath to about 10° C. To this was added 9.3 gm of oxalyl chloride followed by the dropwise addition of 0.73 gm of DMF. Addition of the DMF caused the solution to fizzle, evolving gas. After the completion of the DMF addition, the ice bath was removed and the reaction mass was allowed to warm to room temperature. During the warm-up period all solid material went into solution, which was light and almost colorless in nature. After 40 minutes the solution was concentrated under vacuum to remove excess oxalyl chloride and toluene. To the residue was added 20 ml of THF and this solution was pipetted into an ice cooled solution of 11.8 gm (0.033 mmol) of the silyl protected N-t-butyl hydroxy-ethylamine and 3.71 gm of triethylamine in 50 ml of THF. Addition took place over a 5 minute period during which time the mixture became milky in appearance. Stirring was continued overnight. Then the mixture was poured into 1000 ml of water and extracted twice with 200 ml of ethyl acetate. The organic layers were combined, dried over Na₂SO₄, filtered and concentrated under vacuum, yielding 20.72 gm of a viscous orange oil. This oil was purified by flash chromatography using 15% ethyl acetate/hexane. Appropriate fractions were combined, filtered and vacuum dried, yielding 3.75 gm (23%) of a clear, colorless oil.

Step 4b

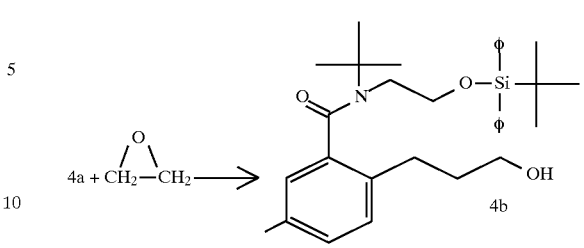

To a 100 ml round bottom flask, which was previously flame dried and vacuum purged with argon, was added 25 ml of THF, 3.75 gm (7.69 mmol) of compound 4a and 0.117 gm of diisopropyl amine yielding a clear, colorless solution. The solution was cooled in a dry ice/acetone bath to approximately −78° C. Over a 7 minute period, 7.7 ml of a 1.2M solution of s-butyl lithium in cyclohexane was added by syringe while maintaining a temperature no higher than −65° C. The resulting deep purple solution was stirred for one hour and 20 minutes at which time 1.01 gm (23.06 mmol) of ethylene oxide was added at −78° C. The dry ice was allowed to evaporate and the solution was allowed to warm to room temperature without addition of extraneous heat. After about 18 hours, the solution was quenched with 4 ml of 0.5 NHCl, poured into 300 ml of H₂O and extracted twice with 50 ml portions of ethyl acetate. The organic layers were combined, dried over Na₂SO₄, filtered and vacuum dried, yielding 3.7 gm of a viscous green oil. The oil was purified by flash chromatography using 1 to 1 ethyl acetate/hexane. Appropriate fractions were combined and vacuum dried, yielding 2.29 gm (60% yield) of a green glassy product.

Step 4c

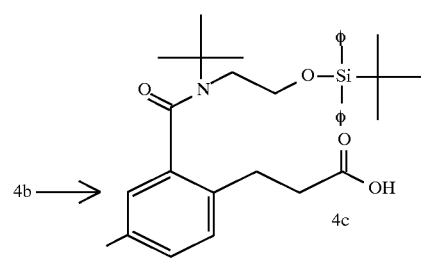

A solution of 2.29 gm (4.3 mmol) of compound 4b, and 8.1 gm of pyridinium dichromate in 20 ml of DMF was stirred at room temperature under argon for about 22 hours. At the end of this time the solution was poured into 560 ml of water and extracted twice with 75 ml of ethyl acetate. The organic layers were combined, dried over Na₂SO₄, filtered and concentrated under vacuum, yielding 1.83 gm of a brown viscous oil. The oil was purified by flash chromatography on silica gel using 10% methanol in methylene chloride. Appropriate fractions were combined and vacuum dried, yielding 635 mg (27%) of a light brown-orange oil.

Step 4d

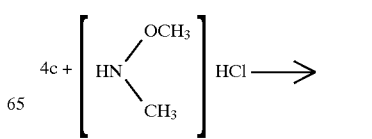

-continued

Step 4d

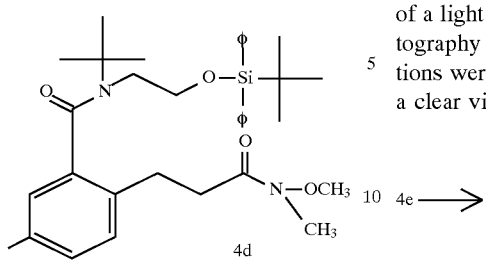

4d

A solution of 0.635 gm (0.00116 mol) of compound 4c, 0.54 gm of BOP, 0.125 gm (0.00128 mol) of N,O-dimethyl hydroxylamine hydrochloride and 0.414 gm of Hunig's base in 5 ml of methylene chloride was stirred at room temperature under argon for about 15.5 hours. A mixture of 15 ml of methylene chloride and 125 ml of $H_2O$ was added. After shaking, the organic layer was removed, dried over $Na_2SO_4$, filtered and vacuum dried, yielding 1.11 gm of a viscous khaki-colored oil.

Step 4e

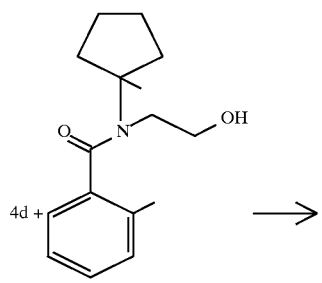

4d +  →

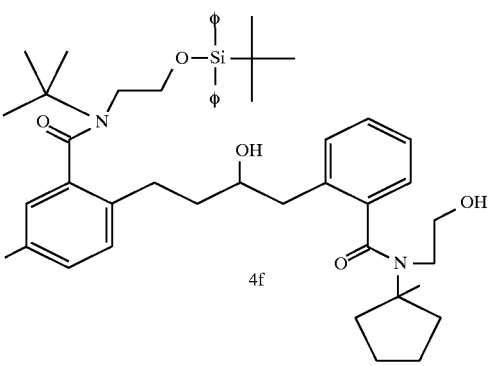

4e

To a previously flame dried and argon purged 25 ml round bottom flask was added a solution in 5 ml of THF, of compound 5b, which had previously been azeotroped twice in 2 ml of benzene. This solution was cooled to −78° C. and 0.4 ml of a 1.3M solution of s-butyl lithium in cyclohexane was added, forming a blood red solution. After stirring the solution for one hour and ten minutes, a solution of 1.26 gm (0.214 mmol) of compound 4d which had been azeotroped twice from benzene, in 5 ml of THF was added over 8 minutes. After this addition, the red color was slightly lighter. The dry ice was allowed to evaporate and the solution warmed to room temperature without addition of additional heat.

After about 16.5 hours the yellow reaction solution was quenched with 2 ml of 0.5N $NH_4Cl$ and poured into 100 ml of $H_2O$. The aqueous mass was extracted twice with 25 ml portions of ethyl acetate. The extracts were combined, dried over $Na_2SO_4$, filtered and vacuum dried, yielding 170.2 mg of a light orange oil. This oil was purified by flash chromatography using 40% ethyl acetate/hexane. Appropriate fractions were combined and vacuum dried, yielding 56 mg of a clear viscous oil.

Step 4f

4e  →

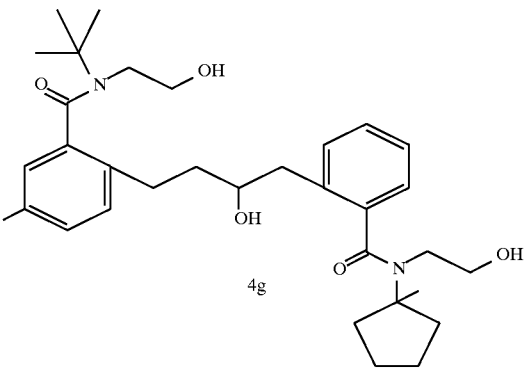

4f

To a solution of 0.056 gm (0.071 mmol) of compound 4e in 2.5 milliliters of ethanol was added, in one step, 0.008 gm of $NaBH_4$. This solution was stirred at room temperature for about 45 minutes then quenched with 4 ml of saturated $NaHCO_3$, poured into 40 ml of brine and extracted twice with 25 ml portions of ethyl acetate. The organic layers were combined, dried over $Na_2SO_4$, filtered and concentrated under vacuum, yielding 55 mg (98%) of a crude, viscous oil.

Step 4g

4f  →

4g

To a solution of 0.055 gm (0.0697 mmol) of compound 4f in 2.5 milliliters of THF was added 0.139 ml of a 1M solution of tetrabutyl ammonium fluoride in THF. This mixture was stirred for 17.5 hours, then quenched with 2 ml of saturated $NaHCO_{31}$ poured into 40 ml of brine and extracted twice with 15 ml portions of ethyl acetate.

The organic layers were combined, dried over $Na_2SO_4$, filtered and vacuum dried, yielding 61 mg of a crude oil. This oil was purified by flash chromatography using ethyl acetate. Appropriate fractions were combined, filtered and vacuum dried, yielding 24 mg (62%) of a white foam.

EXAMPLE 5

Preparation of

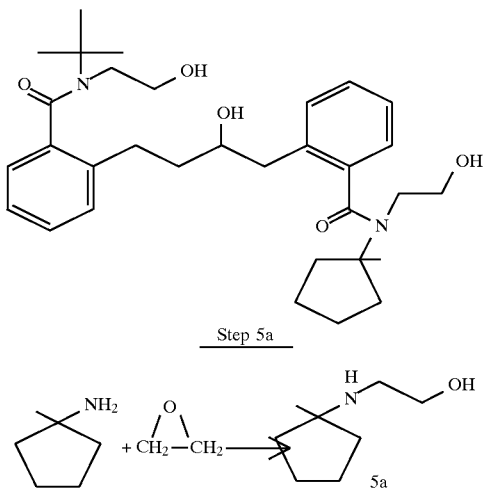

Step 5a

A suspension of 1.5 gm of Mg(ClO$_4$)$_2$ in 3 ml of THF was cooled in a dry ice/acetone bath to −78° C. and 0.345 gm (7.84 mmol) of ethylene oxide was added. In one addition 0.707 gm (7.13 mmol) 1-amino, 1-methyl cyclopentane was added. The mixture was removed from the cooling bath after this addition and the slurry was allowed to stir at room temperature for two hours and forty minutes. It was then poured into 100 ml of water and extracted twice with 50 ml of diethyl ether. The organic layers were combined, washed with 100 ml of water and dried over Na$_2$SO$_4$, filtered and concentrated under vacuum to remove residual ethylene oxide at less than 40° C. yielding a slightly viscous liquid which was subjected to Kugelrohr distillation at 150° C. and 1.8 Torr to yield 100 mg of product.

Step 5b

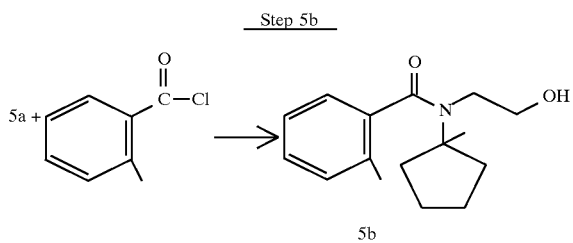

A solution of 0.221 gm of compound 5a and 0.34 gm of triethylamine in 5 ml of methylene chloride was cooled to 0° C. To this was added 0.52 gm (3.39 mmol) of 1 methyl benzoyl chloride in one portion. After this addition, a white precipitate was formed, the ice bath was removed and the solution was stirred under argon at room temperature. After about 2 hours and 50 minutes the solution was poured into 50 ml of H$_2$O and extracted with methylene chloride. The organic extracts were washed with 10% acetic acid, followed by saturated NaHCO$_3$, then dried over Na$_2$SO$_4$, filtered and vacuum dried, yielding 696 mg of an amber oil which slowly solidified on standing.

The solidified material was taken up in 12 ml of 10% aqueous methanol, 0.7 ml of 50% NaOH was added and the mass was stirred at room temperature for 35 min. The mass was poured into 50 ml of H$_2$O and extracted twice with 30 ml portions of ether. The combined extracts were dried over Na$_2$SO$_4$, filtered and vacuum dried, yielding 436 mg of an amber oil.

Step 5c

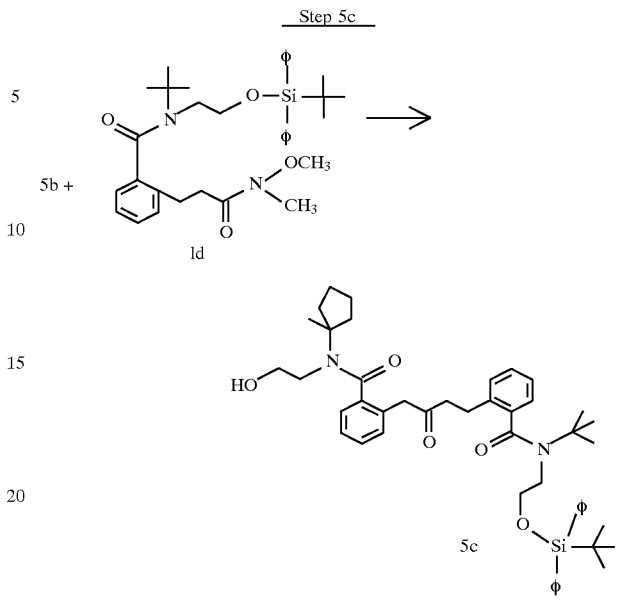

To a 25 ml round bottom flask which had been previously flame dried and vacuum purged with argon was added 0.056 gm (0.214 mmol) of compound 5b in 5 ml of THF. The mixture was cooled to −78° C. in a dry ice/acetone bath and 0.2 ml of a 1.3 M-cyclohexane solution of s-butyl lithium was added over a one minute period. The resulting blood red solution was stirred for sixty-five minutes and a solution of 0.123 gm (0.214 mmol) of compound id in 5 ml of THF was syringed in over a three minute period.

After addition of compound id, the blood red color became lighter. The dry ice was allowed to evaporate and the reaction mixture warmed to room temperature. After about 16.5 hours, the yellow reaction solution was quenched with 12 ml of 0.5N NH$_4$Cl, poured into 100 ml of H$_2$O and extracted with ethyl acetate. Sodium chloride was added to the aqueous phase and it was extracted again with 25 ml of ethyl acetate. The organic layers were combined, filtered and vacuum dried, yielding 159 mg of a light orange oil. This oil was purified by flash chromatography using 40% ethyl acetate/hexane. Appropriate fractions were combined, filtered and vacuum dried, yielding 68 mg (41%) of a clear oil.

Step 5d

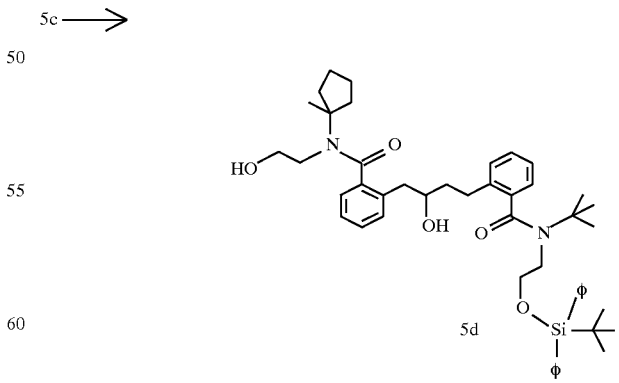

To a solution of 0.068 gm (0.088 mmol) of compound 5c in 2.5 ml of ethanol was added 0.10 gm of sodium borohydride. The mixture was stirred at room temperature for forty-five minutes, quenched with 2 ml of saturated NaHCO₃, then poured into 40 ml of saturated brine and extracted twice with 25 ml portions of ethyl acetate. The organic layers were combined: dried over Na₂SO₄, filtered and concentrated under vacuum, yielding 0.057 gm (84%) of a clear oil.

Step 5e

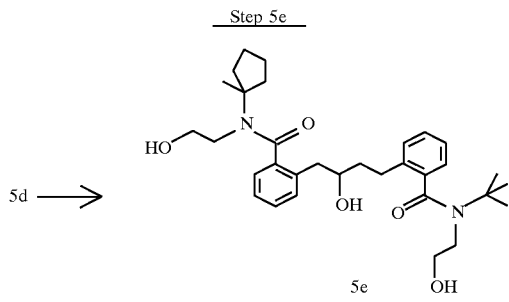

To a solution of 0.657 gm (0.073 mmol) of compound 5d in 2.5 ml of THF was added 0.146 ml of 1M solution of tetrabutyl ammonium fluoride in THF. This light yellow solution was stirred at room temperature for about 5.5 hours when TLC with ethyl acetate showed disappearance of all compound 5d. The reaction was quenched with 4 ml of saturated NaHCO₃, poured into 4 ml of a saturated sodium chloride solution and extracted twice with 25 ml of ethyl acetate. The organic layers were combined, dried over Na₂SO₄, filtered and concentrated under vacuum, yielding 72 mg of a crude viscous oil. This material was purified by flash chromatography on silica using ethyl acetate. Appropriate fractions were combined and concentrated under vacuum to yield 30.7 mg (78%) of the product as a white foam.

EXAMPLE 6

Preparation of

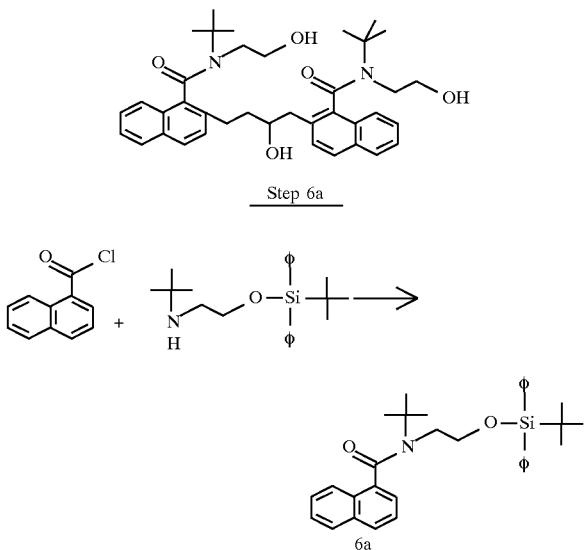

To a solution of 3.2 gm (31.5 mmol) of triethylamine and 11.2 gm (31.5 mmol) of N-(t-butyl)-N-hydroxyethyl (diphenyl, t-butyl-silyl) amine in 100 ml of THF at 0° C. was added 6.0 gm (31.5 mmol) of naphthoyl chloride. Within 5 minutes a white precipitate formed and settled out. The solution was allowed to warm to room temperature and was stirred for one hour. Monitoring by TLC indicated no residual amine was present. The reaction mix was poured into water and extracted with diethyl ether. The organic extracts were washed with brine and dried over MgSO₄.

The organic extract was filtered and solvent was removed under vacuum, yielding 17.15 gm of crude product. The crude product was purified by flash chromatography using 3 to 1 hexane/diethyl ether. 'HNMR confirmed the structure.

Step 6b

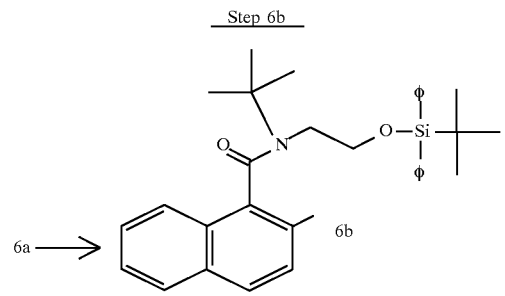

A solution of 4.5 gm (8.83 mmol) of compound 6a and 1.13 gm of TMEDA in 100 ml of THF was cooled to -78° C. in a dry/ice acetone bath. After 15 minutes 8.8 ml of a 1.1M solution of s-butyl lithium in cyclohexane was added dropwise. The clear solution became a light orange in color and was stirred at -78° C. for 1.5 hours. At this time 3.45 gm (24.3 mmol) of methyl iodide (filtered through basic alumina) was added rapidly to the solution. The reaction mass became a lighter orange in color and a white solid appeared. After 1 hour at -78° C., TLC indicated that some residual starting material remained. The reaction mixture was allowed to warm to room temperature and after 1 hour, was monitored again by TLC. At this point, no residual starting material remained. The reaction mixture was poured into diethyl ether, washed with water and then with brine, dried over MgSO₄ and filtered. The solvent was removed in vacuum yielding 17.15 gm of a light yellow oil. The oil was purified by flash chromatography using 2:1 hexane/ether. Fractions 14–25 were collected cleanly and the solvent was removed under vacuum. The structure of the product was confirmed by 'HNMR.

Step 6c

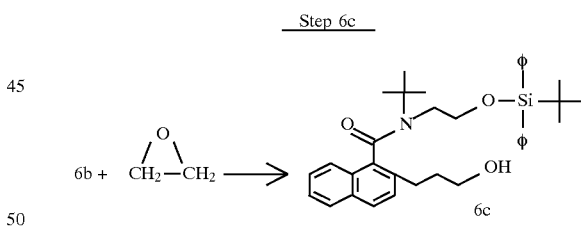

A solution of 2.36 gm (4.51 mmol) of compound 6b, 0.07 gm of diisopropylamine and 40 ml of THF was cooled to -78° C. and 4.72 ml of a 1.1M solution of s-butyl lithium in cyclohexane was slowly added. The resulting blood red solution was stirred for 1.5 hours at -78° C. at which time 0.6 gm (13.53 mmol) of ethylene oxide was added rapidly to the solution. After 15 minutes no color change was observed. The reaction was allowed to warm to 0° C. As the reaction warmed the solution became dark green and was stirred for 30 minutes at which time monitoring by TLC indicated that no residual starting material was present. The mass was poured into water, extracted with diethylether, washed with brine, dried over MgSO₄ and filtered. Solvent was removed under vacuum and the product purified by column chromatography using a 3:1 mixture of diethylether and hexane. Fractions 21–40 were collected cleanly and solvent was removed under vacuum. Yield was 3.43 gm. The structure of the product was confirmed by 'HNMR.

Step 6d

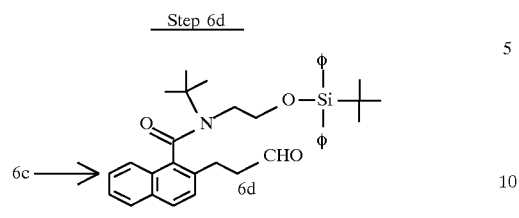

To a solution of 1.9 gm of pyridine in 30 ml of methylene chloride was added 1.2 gm of chromium trioxide at room temperature. The reddish solid partially dissolved into an orange solution with a brown solid residue. After 10 minutes a solution of 1.14 gm (2.0 mmol) of compound 6c in 6 ml of methylene chloride was added, dropwise. After 15 minutes a small amount was syringed into 1N HCL extracted with diethylether and monitored by TLC which indicated that no starting material remained. The mixture was poured into diethylether, washed twice with NaOH, then with 1N HCL, then with saturated NaHCO₃, and finally with brine. The crude product was filtered and the solvent was removed under vacuum. This crude product (1.5 gm) was purified by flash chromatography using a 2:1 ether/hexane solution as eluant. Fractions 36–45 were collected and solvent was removed under vacuum. The structure was proven by 'HNMR.

Step 6f

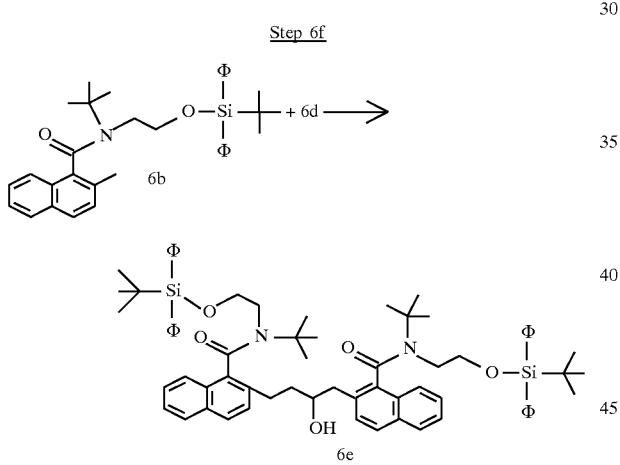

A solution of 0.176 gm (0.34 mmol) of compound 6b, 0.0052 gm of diisopropylamine and 4 ml of THF was cooled to −78° C. and 355.5 microliters of a 1.1M solution of s-butyl lithium in cyclohexane was added, dropwise. A blood red solution was produced and was allowed to stir for one hour at −78° C. At the end of this hour a solution of 0.192 gm (0.34 mmol-) of compound 6d in 1 ml of THF was added in a single addition. The blood red color turned into a light yellow. After 15 minutes, TLC indicated that most of the starting materials had been consumed. The reaction mass was poured into ether, washed with water and brine and then dried over MgSO₄. The dried mixture was filtered and solvent was removed under vacuum, yielding a clear oil. This oil was subjected to column chromatography using a 1:1 ether/hexane solution.

Fractions 23–35 were a mixture of the compound 6d and product. These were resubmitted to chromatography and purified, yielding 0.041 gm of compound 6e. Structure was confirmed by NMR.

Step 6f

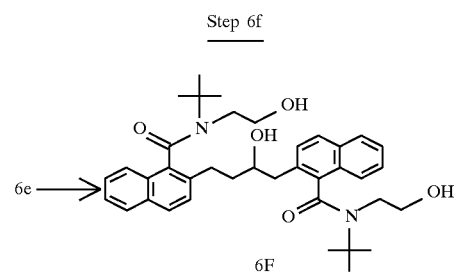

A solution of 0.15 gm (0.15 mmol) of compound 6e in 1 ml of THF was charged to a 5 ml round bottom flask and 304 microliters of a 1.0M solution of tetrabutyl ammonium fluoride was added, dropwise. The clear solution became light yellow. After 30 minutes, TLC indicated no residual starting material remained. The mixture was poured into ether, washed with water and brine and dried over MgSO₄. The organic phase was then filtered and the solvent was removed under vacuum, yielding a clear oil which was purified by flash chromatography. 'HNMR confirmed the structure.

EXAMPLE 7

Preparation of

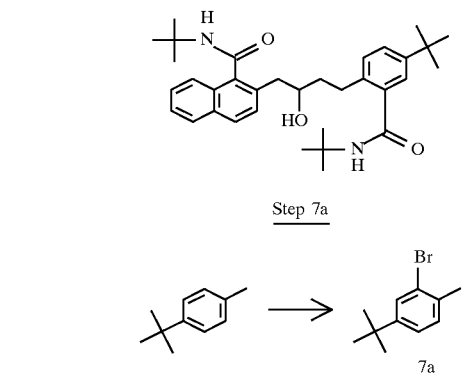

To a solution (reddish purple) of 5 gm (33.73 mmol) of p-t-butyl toluene and a catalytic amount of iodine was added 5.66 gm (35.41 mmol) of bromine. The reaction mixture turned bright red within 5 minutes, generating white smoke. The reaction was stirred for 2 hours at room temperature at which time water and ether were carefully added to the mixture. The mixture was poured into a separatory funnel with additional water and ether. The organic layer was separated, washed three times with saturated NaHCO₃ and once with brine, then dried over MgSO₄ and filtered. The solvent was removed under vacuum. The product was evaporated twice with benzene and subjected to high vacuum to remove all residual solvents. 'HNMR confirmed the product structure.

Step 7b

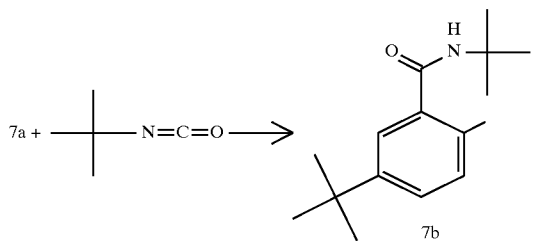

Compound 7a was brought to a gentle reflux in 25 ml of ether containing 0.2 gm of lithium wire. After 4 hours the original clear solution was murky and light yellow. The heating bath was removed and the mixture allowed to cool to room temperature whereupon 1.21 gm (14.52 mmol) of t-butyl isocyanate was added. The solution became orange and finally light yellow and refluxed slightly during the addition. After 30 minutes the reaction was monitored by TLC and no residual starting material was present. The mixture was poured into water, extracted with ether and then the organic layers were washed with brine and dried over MgSO$_4$. The extracts were filtered and the solvent was removed under vacuum. A white solid was recovered which was triturated with hexane and collected by vacuum filtration. Yield was 1.1 gm. The entire procedure was repeated with the filtrate and an additional 0.44 gm was recovered. The structure was confirmed by NMR.

Step 7c

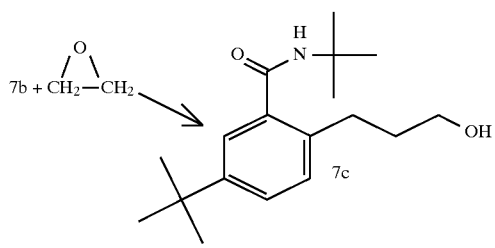

A solution of 1.45 gm (5.86 mmol) of compound 7b and 1.4 gm of TMEDA was cooled to −78° C. and 7.1 ml of a 1.69M solution of n-butyl lithium in hexane was added dropwise. A light orange color formed and disappeared into a clear solution during the addition. This color then developed into a neon orange by the time all of the n-butyl lithium had been added. The mixture was stirred at −78° C. for 1 hour. At this time 0.29 gm (6.5 mmol) of ethylene oxide was added rapidly in a single addition. No color change was observed. After 5 minutes at −78° C. the reaction mass was allowed to warm to 0° C. As the mass began to warm the color changed to bright yellow, slightly murky. Monitoring by TLC indicated that no residual starting material was present. The reaction mass was then poured into water and extracted with diethylether. The organic phases were washed with brine and dried over MgSO$_4$. The mixture was then filtered and the solvent removed under vacuum. A white solid was recovered which was triturated with hexane and collected by vacuum filtration. The structure was confirmed by 'HNMR.

Step 7d

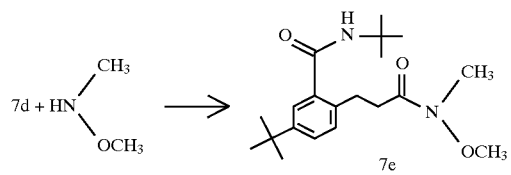

A solution of 1.21 gm (4.15 mmol) of compound 7c and 7.81 gm of pyridinium dichromate in 16 ml of DMF, was stirred at room temperature overnight. After overnight stirring the mixture was poured into water and extracted twice with ethyl acetate. The organic phases were collected, dried over MgSO$_4$ and filtered. The solvent was removed under vacuum, producing a brown oil. TLC indicated DMF was still present so the oil was dissolved in ether, washed with water and brine, and dried over MgSO$_4$ and filtered. The solvent was removed under vacuum. A white solid product was recovered, triturated with hexane and collected by vacuum filtration. The structure was confirmed by 'HNMR.

Step 7e

A solution of 0.305 gm (1 mmole) of compound 7d and 0.098 gm (1 mmole) of N,O-dimethyl hydroxylamine hydrochloride in 2 ml of DMF was cooled to 0° C. To this clear solution 0.135 gm of 1-hydroxy benzotriazole, 0.192 gm of 1-(3-dimethylaminopropyl)-3-ethylcarbodiimide (EDC) and 0.304 gm of triethylamine were added, producing a turbid solution. After sitting 5 minutes the reaction mass was allowed to warm to room temperature and stirred for three hours. After 2 additional hours TLC analysis indicated that no residual starting material was present. The mixture was then poured into ethyl acetate, washed with water, 10% citric acid, saturated sodium bicarbonate and brine and dried over MgSO$_4$. The mixture was then filtered and the solvent was removed under vacuum, producing a clear oil. This oil was purified by column chromatography using a 4:1 ether/hexane mixture. Fractions 13–31 were collected and structure was confirmed by NMR. The yield was 52%.

Step 7f

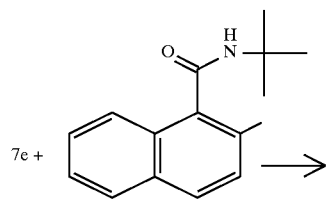

-continued

Step 7f

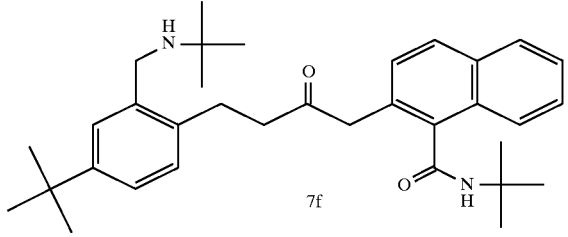

7f

A solution of 0.28 gm (1.15 mmol) of compound 3a and 0.272 gm of TMEDA in 10 ml of THF was cooled to −78° C. in a dry ice/acetone bath. After 15 minutes at −78° C., 1.4 ml of a 1.69N solution of n-butyl lithium in hexane was added dropwise. A faint purple color changed to turquoise and eventually to purple during the addition of the n-butyl lithium. The deep purple solution was stirred for one hour at −78° C. After 1 hour of stirring, a solution of 0.18 gm (0.52 mmol) of compound 7e in 4 ml of THF was added. After 20 more minutes at −78° C., TLC monitoring indicated that no residual starting material was present. The mixture was poured into water, extracted with ether, washed with brine and dried over MgSO$_4$. Solvent was removed under vacuum and the residue was purified by column chromatography using a 2:1 mixture of ether and hexane. Fractions 25–45 were collected. 'HNMR confirmed the structure. The yield was 81%.

Step 7g

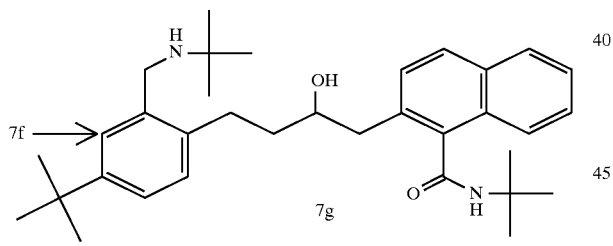

7f → 7g

A solution of 0.1 gm (0.28 mmol) of compound 7f in 1 ml of ETOH was cooled to 0° C. and 0.011 gm of sodium borohydride granules was added to the clear solution. After 30 minutes, TLC monitoring indicated that starting material was still present. The reaction was allowed to warm to room temperature and 0.015 gm of additional sodium borohydride was added. After 30 more minutes at room temperature, there appeared to be no more residual starting material present. The reaction mass was poured into saturated sodium bicarbonate, extracted with ether, washed with brine, dried over MgSO$_4$ and filtered. Solvent was removed under vacuum and the white amorphous solid which was recovered was purified by column chromatography using a 2:1 ether/hexane solution. Fractions 5–13 were collected and the structure was confirmed by NMR. Yield was 85.3%.

EXAMPLE 8

Preparation of

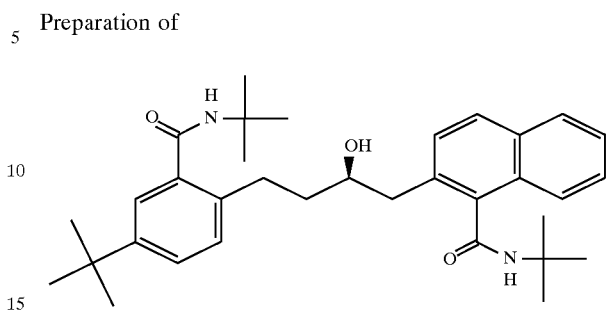

Step 8a

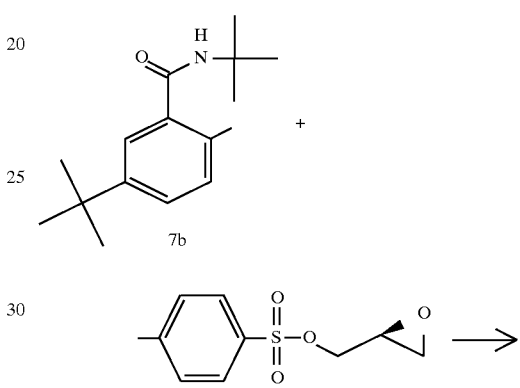

7b

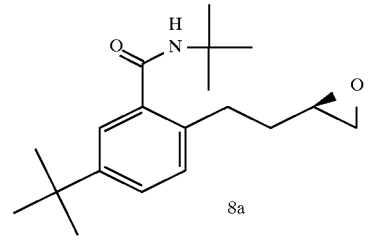

8a

A solution of 0.5 gm of compound 7b and 0.47 gm of TMEDA in 10 ml of toluene was cooled to −78° C. in a dry ice/acetone bath. The mixture was allowed to sit for 15 minutes at −78° C. and 2.38 ml of a 1.7M solution of n-butyl lithium in hexane was added dropwise. The color of the reaction mixture changed from light orange to clear and then to a bright orange color during the addition of the n-butyl lithium. The mass was stirred at −78° C. for 1 hour and a solution of 0.461 gm (2.02 mmol) of S-glycidyl tosylate in 5 ml of THF was added. The color changed immediately to a light yellow. After an additional 15 minutes at −78° C., TLC indicated only a small amount of starting material remained. The reaction was poured into water and extracted with ether, washed with brine, and dried over MgSO$_4$. The mixture was then filtered and the solvent was removed under vacuum. The yellow oil thus recovered was purified by flash chromatography using a 2:1 solution of hexane and ether. Fractions 45–75 were collected. NMR confirmed the structure of the product. The yield was 52%.

Step 8b

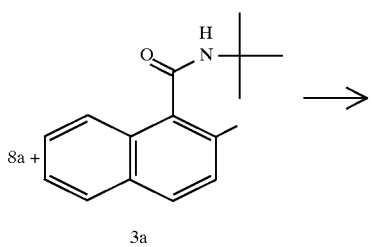

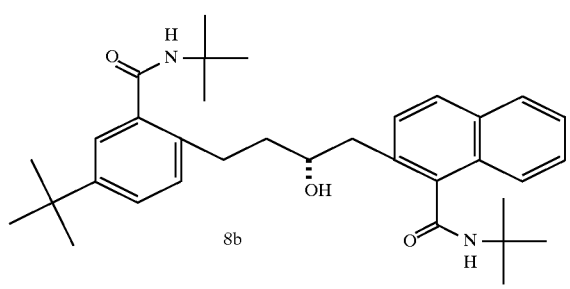

A solution of 0.3 gm (1.32 mmol) of compound 3a and 0.31 gm of TMEDA in 5 ml of THF was cooled to 0° C. After the solution had stirred at 0° C. for 15 minutes, 2.6 ml of a 1.0N solution of s-butyl lithium in cyclohexane was slowly added to it. As the butyl lithium was added, the original orange color changed to clear and then to an orange color which bright red/orange. After 1 more hour at 0° C. a solution of 0.2 gm (0.66 mmol) of compound 8a in 1.5 ml of THF was slowly added. No color change was observed. After 15 minutes, TLC indicated no residual starting material. The solution was then poured into ether, washed with water, then brine and dried over MgSO₄. The product was then filtered and the solvent was removed under vacuum, yielding a clear oil. This oil was purified by flash chromatography using a 2-1 ether to hexane mixture as the eluant. Fractions 20–30 were collected and the solvent was removed under vacuum. NMR confirmed the structure. Yield was 50%.

EXAMPLE 9

Preparation of

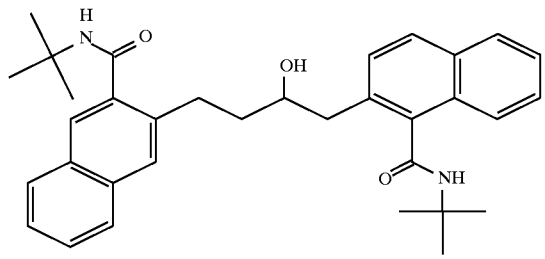

Step 9a

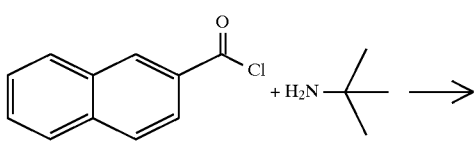

-continued
Step 9a

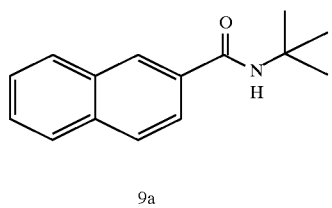

A solution of 7.96 gm of triethylamine and 5.76 gm (78.7 mmol) of t-butylamine in 140 ml of THF was cooled to 0° C. and a solution of 15 gm (78.7 mmol) of 2-naphthoyl chloride in 10 ml of THF was added. A white precipitate formed immediately. After 10 minutes the reaction mass was allowed to warm and was stirred at room temperature for two hours. TLC indicated at this point that no residual starting material was present. The mixture was poured into water, extracted with ether, washed with 10% citrate acid, saturated NaHCO₃, then with brine, and finally was dried over MgSO₄. The mixture was then filtered and the solvent was removed under vacuum. A white solid precipitated out as the solvent evaporated and 9.8 gm of product were collected by vacuum filtration.

The above procedure was repeated with the filtrate and an additional 2.2 gm of product were collected. NMR confirmed the structure. Yield was 67%.

Step 9b

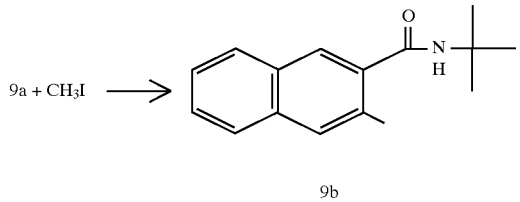

A solution of 3.5 gm (15.41 mmol) of compound 9a and 3.94 gm of TMEDA in 90 ml of THF was cooled to −78° C. in a dry ice/acetone bath. After 15 minutes at −78° C., 34 ml of a 1.0N solution of s-butyl lithium in cyclohexane was slowly added. The solution immediately turned yellow and, as the butyl lithium addition continued, turned to bright orange and finally to an opaque butterscotch color. The mixture was then stirred for 1 hour at −78° C., at which time 2.4 gm (16.94 mmol) of iodomethane was added. The solution immediately turned to a light yellow green color with a white precipitate floating in it. The reaction mass was stirred at −78° C. for another hour. Although TLC indicated that there was residual starting material still present, the mixture was poured into ether, washed with water and brine, then dried over MgSO₄. The mixture was filtered and solvent was removed under vacuum. The product was purified by flash chromatography using a 3:1 hexane/ether solution. Fractions 13–19 were collected and solvent was removed under vacuum yielding 1.35 gm of a white solid material. The procedure was repeated and an additional 0.65 gm was recovered from the second procedure. Structure of the product was confirmed by ¹HNMR.

Step 9c

9b + CH2—CH2 (epoxide, O) → 9c

[structure 9c: naphthalene with C(O)NH-tBu and CH2CH2CH2OH substituents]

A solution of 2.21 gm (9.16 mmol) of compound 9b and 2.19 gm of TMEDA in 80 ml of THF was cooled to −78° C. in a dry ice/acetone bath. After the solution had cooled for 15 minutes, 11.1 ml of a 1.69M solution of n-butyl lithium in hexane was added dropwise. The original bright purple color disappeared and then reappeared as the butyl lithium addition progressed. The reaction was stirred for another hour at −78° C. at which time 0.81 gm (18.32 mmol) of ethylene oxide was added. No color change was observed. After 10 more minutes at −78° C. the reaction mass was allowed to warm to 0° C. As it warmed, its color changed to a light orange. TLC analysis indicated that almost no residual starting material was present. The solution was then poured into water, extracted with ether, and washed with brine. The organic portion was dried over $MgSO_4$. The mixture was then filtered and solvent was removed under vacuum. Structure was confirmed by NMR.

Step 9d

9c → [structure 9d: naphthalene with C(O)NH-tBu and CH2CH2COOH substituents]

A solution of compound 9c (about 9.16 mmol) and 17.23 gm of pyridinium dichromate in 35 ml of methylene chloride was stirred at room temperature for 4 hours. TLC indicated that a small amount of aldehyde was present, so the reaction was then allowed to continue with stirring for another 16 hours At that time, TLC analysis indicated that no aldehyde was present. The mixture was poured into 350 ml of water and extracted twice with 300 ml of ether. The organic layers were combined, washed with water, dried over $MgSO_4$, and filtered. The solvent was then removed under vacuum and a white solid material precipitated out. This was triturated with benzene and 12.08 gm of product was recovered by vacuum filtration. The structure was confirmed by NMR. Yield was about 40% over two steps.

Step 9e

9d + [HN(OCH3)(CH3)]·HCl →

Step 9e (continued)

[structure 9e: naphthalene with C(O)NH-tBu and CH2CH2C(O)N(CH3)(OCH3) substituents]

A solution was prepared consisting of 0.4 gm (1.34 mmol) of compound 9d, 0.131 gm (1.34 mmol) of N,O-dimethylhydroxylamine hydrochloride, 0.405 gm of triethyl amine and 0.6 gm of BOP reagent. The solution was stirred at room temperature for 2 hours at which time TLC indicated that no residual starting material remained. The reaction was poured into ether, washed with water and 10% citric acid, saturated $NaHCO_3$ and brine, then dried over $MgSO_4$. The mixture was filtered and solvent was removed under vacuum, yielding a white oily product. This white oil was purified by flash chromatography using a 3:1 ether/hexane solution. Fractions 34–69 were collected. NR confirmed the structure of the product. The yield was 78%.

Step 9f

[structure 9b: naphthalene with C(O)NH-tBu and CH3 substituents] + 9e →

[structure 9f: bis-naphthalene linked by CH2CH2C(O)CH2 with two C(O)NH-tBu groups]

A solution of 0.148 gm (0.613 mmol) of compound 9b and 0.143 gm of TMEDA in 5 ml of THF was cooled to −78° C. in a dry ice/acetone bath. After the solution had cooled at −78° C. for 15 minutes, 0.725 ml of a 1.7M solution of n-butyl lithium in hexane was added. The resulting purple solution was stirred at −78° C. for 1 hour at which time 0.1 gm (0.292 mmol) of compound 9e in 1 ml of THF was added in a single portion. No color change was observed. The reaction mass was stirred for an additional 15 minutes at −78° C. at which time TLC analysis indicated no residual starting material was present. The mixture was then poured into ether, washed sequentially with water and brine, dried over $MgSO_4$, and filtered. Solvent was removed under vacuum. $^1H$ NMR confirmed the structure. Material was not purified further.

Step 9g

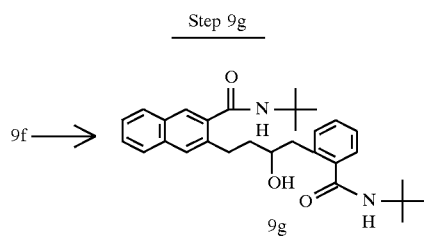

-continued

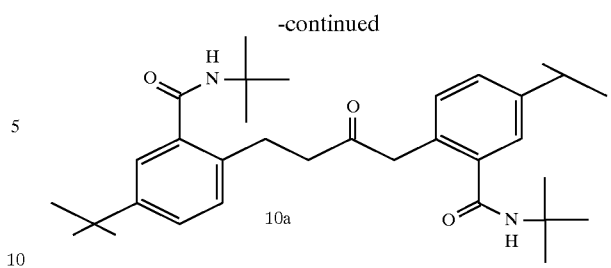

A solution was prepared of product 9f in 5 ml of ethanol and 0.017 gm (0.44 mmol) of sodium borohydride granules was added to the clear solution. After 30 minutes, TLC indicated no residual starting material remained. The reaction mixture was poured into ether, washed sequentially with saturated NaHCO₃ and brine, then dried over MgSO₄. The dried extracts was filtered and the solvent was removed under vacuum. A yellow oil/solid material was recovered and purified by flash chromatography using a 3 to 2 ether/hexane solution. Fractions 50–90 were collected. NMR confirmed structure of the product.

A solution of 0.151 gm (0.61 mmol) of compound 7b and 0.142 gm of TMEDA in 5 ml of THF was cooled to −78° C. in a dry ice/acetone bath. After the solution had cooled for 15 minutes at −78° C., 0.47 ml of a 2.6M solution of n-butyl lithium in hexane was added slowly. An orange solution resulted which was stirred at −78° C. for 1 hour. At the end of this hour 0.1 gm (0.29 mmol) of compound 7e in 1 ml of THF was added. The solution became light yellow at the end of the addition and was stirred for an additional 15 minutes at −78° C. At this time, TLC indicated no residual starting material was present. The mixture was poured into ether, washed sequentially with water and brine, dried over MgSO₄, and filtered. Solvent was removed under vacuum. The product was not further purified.

EXAMPLE 10

Preparation of

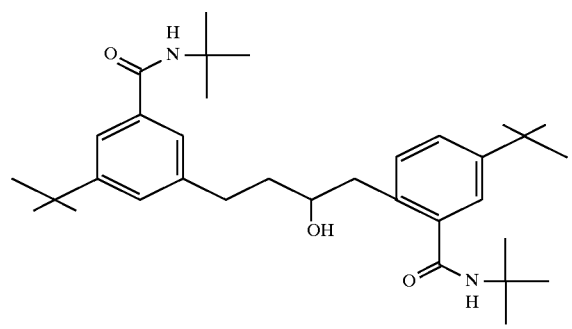

Step 10a

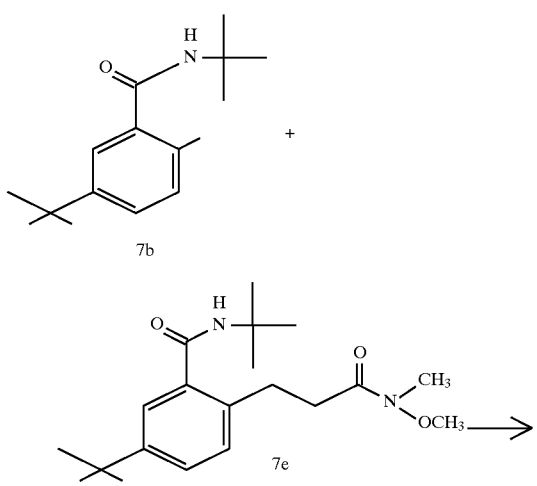

Step 10b

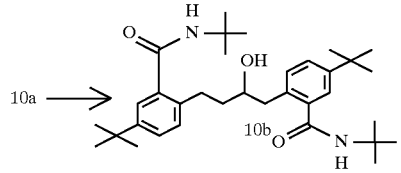

The crude product from step 10a (approximately 0.29 mmol) was dissolved in 5 ml of ethanol and 0.017 gm of sodium borohydride granules was added to the clear solution. After 30 minutes, TLC indicated no residual starting material was present. The reaction was poured into ether, washed sequentially with saturated NaHCO₃ and brine, then dried over MgSO₄. The extracts were filtered, the solvent was removed under vacuum and the residual product was purified by flash chromatography using a 1:1 ether hexane solution as the eluent. Fractions 46–72 were collected and the solvent was removed under vacuum. Yield was 55% over steps a and b and NMR confirmed the structure.

EXAMPLE 11

Preparation of

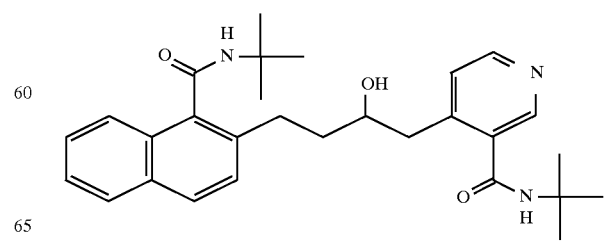

43

-continued
Step 11a

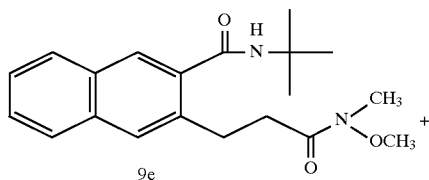

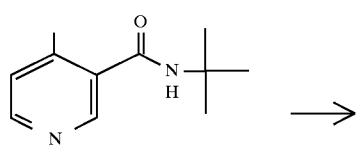

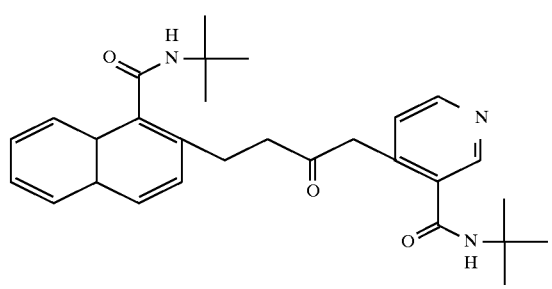

A solution of 0.12 gm (0.61 mmol) of 4-methyl-3-(t-butyl) carbamoyl-pyridine and 0.142 gm of TMEDA in 5 ml of THF was cooled to −78° C. in a dry ice/acetone bath. After the solution had cooled for 15 minutes at −78° C., 0.47 ml of a 2.6M solution of n-butyl lithium in hexane was slowly added. The solution changed to a light yellow color and was allowed to stir at −78° C. for an additional hour. At this time a solution of 0.1 gm (0.29 mmol) of compound 9e in 1 ml of THF was rapidly added. After 30 minutes and again at 1 hour, TLC analysis indicated that not all of compound 9e had been consumed. The reaction mass was then poured into ether, washed sequentially with water and brine and dried over MgSO$_4$. The mixture was filtered and the solvent was removed under vacuum, yielding an oil. The oil was purified by column chromatography and fractions 68–78 were collected cleanly. NMR confirmed the structure of these materials.

Step 11b

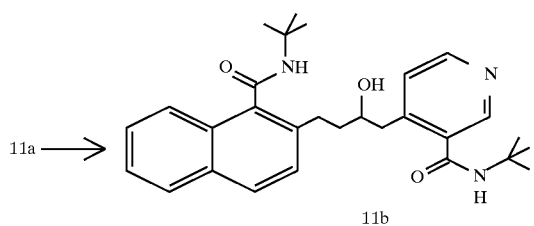

Compound 11a was reduced with sodium borohydride in the manner described in previous examples. NMR confirmed the structure.

44

EXAMPLE 12

Preparation of

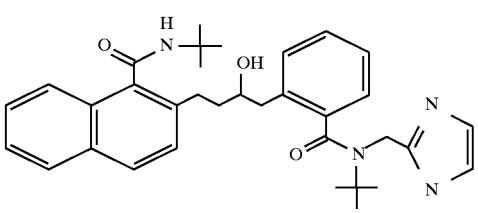

Step 12a

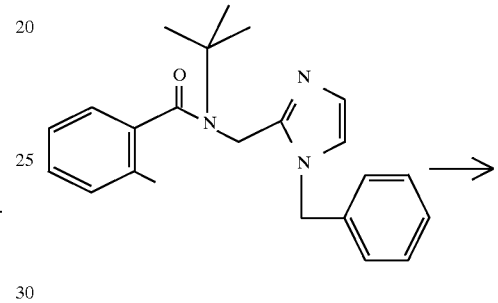

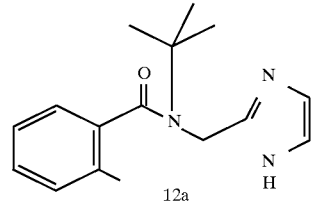

A solution of 0.21 gm (0.58 mmol) of N-(N-benzyl) imidazole, N-t-butyl-toluamide was prepared in 2 ml of ethanol. To this solution was added 0.062 gm of palladium black followed by 0.36 gm of ammonium formate. Within 5 minutes, the black solution began to bubble. After 1 hour, TLC indicated that no reaction had taken place as yet. The reaction mixture was warmed to 70° C. and, after 1 hour at that temperature, TLC indicated that no residual starting material was present. An additional 0.36 gm of ammonium formate was added and the reaction left at 70° C. overnight. The mass was filtered over Celite™ and washed with ethyl acetate and methanol. Solvent was removed under vacuum, producing a white solid. The structure was confirmed by NMR. Yield was 95%.

Step 12b

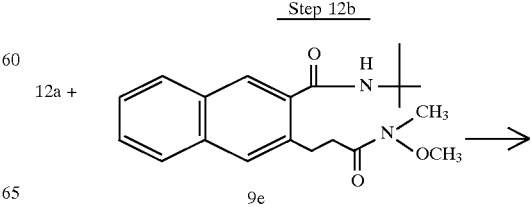

-continued

Step 12b

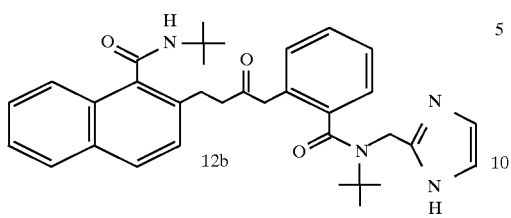

A solution of 0.15 gm (0.55 mmol) of compound 12a and 0.03 gm (0.33 mmol) of diisopropylamine in 5 ml of THF was cooled to −78° C. in a dry ice acetone bath. After the solution had sat at −78° C. for 15 minutes, 1.57 ml of a 0.91M solution of s-butyl lithium in cyclohexane was slowly added. A bright blood red color developed and the solution was stirred for 20 additional minutes at −78° C. At this point, a solution of 0.095 gm (0.275 mmol) of compound 9e in 1 ml of THF was quickly added. The color faded to a burgundy red color. TLC indicated almost no residual starting material to be present. The reaction mass was quenched with 1 ml of water, poured into additional water and extracted with 15 ml of ether. The organic phase was washed with 15 ml of brine, dried over $MgSO_4$ and filtered. The solvent was removed under vacuum. The residue was purified by flash chromatography using a 3 to 1 solution of ethyl acetate and hexane as the eluent. Fractions 21–49 were collected and solvent was removed under vacuum. NMR confirmed the structure. Further workup was not carried out at this point.

Step 12c

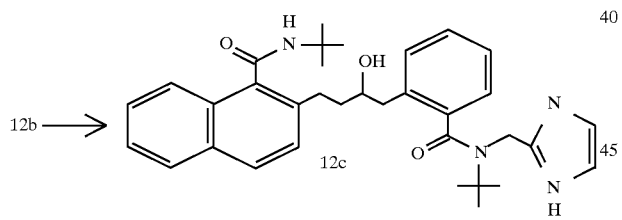

A solution of 0.11 gm (0.2 mmol) of crude compound 12b in ethanol was prepared and 0.012 gm of sodium borohydride granules was added to the clear solution. After 30 minutes, TLC indicated that no residual starting material was present. The reaction mixture was quenched with 10 drops of saturated $NaHCO_3$ and the mixture was poured into 10 ml of saturated $NaHCO_3$ and extracted with 15 ml of ethyl acetate. The organic layers were washed with brine and dried over $MgSO_4$. The mixture was filtered and the solvent was removed under vacuum. The residue was purified by flash chromatography using ether as the eluent until the first spot came off and then using ethyl acetate. Fractions 81–102 were collected cleanly. NMR confirmed the structure.

EXAMPLE 13

Preparation of

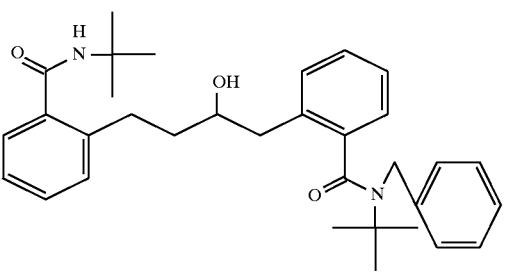

Step 13a

To a solution of 3.27 gm of triethylamine and 5.28 gm of N-(t-butyl) benzylamine in 40 ml THF at 0° C. was added 5.0 gm (33.34 mmol) of O-toluoyl chloride, dropwise, at 0° C. Within 5 minutes, a white precipitate came out of the solution and after an additional 15 minutes the cooling bath was removed and the reaction mixture was stirred for 2 hours. At this time, TLC indicated that no residual starting material was present. The mixture was poured into water and extracted with ether. The organic phase was washed sequentially with saturated $NaHCO_3$, 10% citric acid and brine, and dried over $MgSO_4$. The mixture was filtered and the solvent was removed under vacuum yielding a yellow oil. This oil was purified by flash chromatography. The material was collected and the solvent was removed under vacuum. The clear oil crystallized into a white solid when hexane was added and was collected by filtration. NMR confirms the structure. Yield was 73.5%.

Step 13b

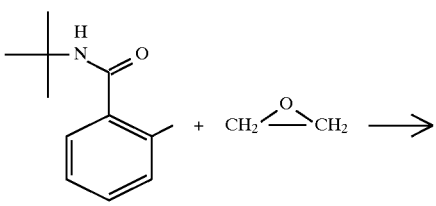

Step 13b

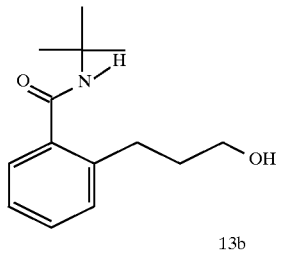

13b

N-(t-butyl)-toluamide (7.58 gm, 39.6 mmol) was dissolved in 400 ml of THF and 9.96 gm (81.2 mmol) of TMEDA was added. The mixture was cooled to −78° C. and 31.2 ml of 2.6M n-butyl lithium in hexane was added dropwise. After 1 hour, a solution of 1.92 gm (43.6 mmol) of ethylene oxide was added as a 10% solution in THF. After 15 minutes the solution was warmed to 0° C. A precipitate formed and the reaction mixture turned murky orange. After another 30 minutes, TLC indicated presence of product plus starting material. Recrystallization from ether/hexane yielded 3.49 gm of pure product. Flash chromatography of the remainder with 2:1 ether/hexane, yielded another 2.96 gm of pure product. Total yield was 6.45 gm (69%).

Step 13c

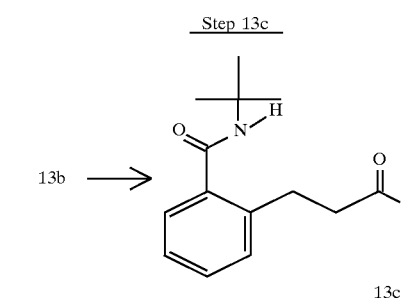

13c

A solution of 3.49 gm (14.8 mmol) of compound 13b in 60 ml of DMF was prepared and 27.9 gm of pyridinium dichromate was added. The solution turned a dark brown/orange color and was stirred overnight at room temperature. The mixture was poured into H₂O and extracted once with 150 ml of ether and once with 50 ml of ether, then dried over MgSO₄. Solvent was removed under vacuum, yielding a clear, colorless oil, which turned solid after standing. Recrystallization in pure ether yielded white crystals. The product was filtered and washed with hexane. Two crops yielded 1.48 gm (40%) of white powder.

Step 13d

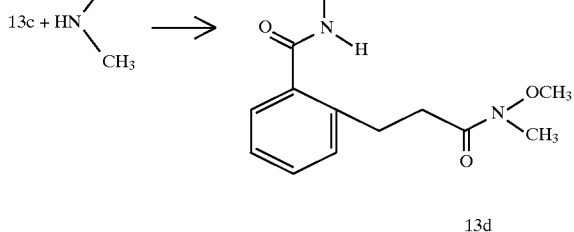

13d

A solution of 0.8 gm (3.21 mmol) of compound 13c in 40 ml of methylene chloride was prepared. To this solution was added 0.313 gm (3.21 mmol) of N,O-dimethylhydroxyl amine hydrochloride and 1.34 ml of triethylamine. When the amine hydrochloride was completely dissolved, 1.42 gm of BOP reagent was added and the clear solution was stirred for 2 hours at room temperature. TLC indicated that no starting material remained. The reaction mixture was poured into ether and washed with 10% citric acid solution, H₂O, saturated NaHCO₃ and brine, then dried over MgSO₄. Flash chromatography in 2:1:1 methylene chloride/ethyl acetate/hexane yielded 0.539 (57%) of white powder.

Step 13e

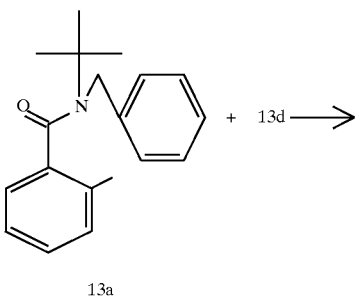

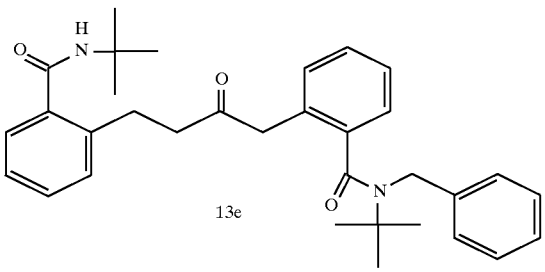

13e

A solution of 0.2 gm (0.7 mmol) of compound 13a and 0.02 gm of diisopropylamine in 5 ml of THF was cooled to −78° C. in a dry ice/acetone bath. After the solution had cooled at −78° C. for 15 minutes, 1 ml of 0.92M s-butyl lithium was slowly added, producing a bright purple color.. A solution of 0.1 gm (0.342 mmol) of compound 13d in 1 ml of THF was added within 10 seconds following the addition of the butyl lithium solution and before the color changed. The addition caused the solution to turn a slight peach color. After 5 minutes, TLC indicated that residual starting materials were still present but the color had all disappeared. The reaction was quenched with 1 ml of water, then poured into 20 ml of water and extracted with ether. The organic extract was washed with 20 ml of brine, dried over MgSO₄ and filtered. The solvent was removed under vacuum and the clear residue (280 mg) was purified by column chromatography using a 2 to 1 ether/hexane solution. The product was collected cleanly and NMR confirmed the structure. Yield was about 29%.

Step 13f

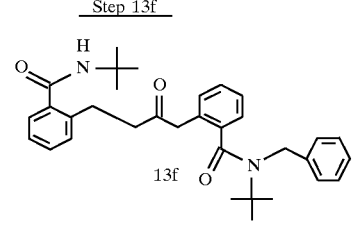

13f

A solution of 0.05 gm (0.10 mmol) of compound 13e in 3 ml of ethanol was prepared and 0.0057 gm of NaBH₄ granules was added to the clear solution. After stirring for 30 minutes, TLC indicated that some residual starting material was still present. Another equivalent of NaBH₄ was added and the reaction was stirred for an additional 45 minutes. No residual starting material was found at this point. The reaction was quenched with 10 drops of saturated NaHCO₃, poured into 10 ml of saturated NaHCO₃ and extracted with 15 ml of ether. The extracts were washed with brine, dried over MgSO₄ and filtered. Solvent was removed under vacuum and the residue was purified by column chromatography using a 3 to 1 ether/hexane solution. Fractions 21–45 were collected cleanly. NMR confirmed the structure. Yield was about 90%.

EXAMPLE 14

Preparation of

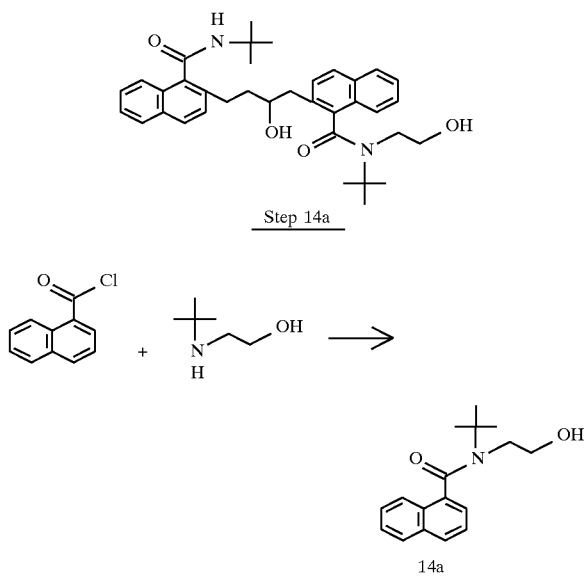

A solution of 3.07 gm (26.23 mmol) of N-t-butyl amine and 7.96 gm of triethylamine in 60 ml of methylene chloride was cooled to 0° C. and 10 gm (52.46 mmol) of naphthoyl chloride was slowly added. The reaction mixture was allowed to warm slowly to room temperature. After 1 hour at room temperature, TLC indicated that residual starting N-t-butyl ethanol amine was still present so the reaction was allowed to sit overnight. The mixture was then poured into ether, washed sequentially with water, 10% citric acid, saturated NaHCO₃ and brine. The organic layers were dried over MgSO₄ and filtered. The solvent was removed under vacuum yielding a yellow oil. The yellow oil was dissolved in a 9 to 1 methanol/water solution and 5 ml of a 45% KOH solution was added. The solution immediately became turbid with a white solid, which settled to yield a clear solution. After 5 minutes, TLC indicated that no residual starting material was present. The reaction was poured into water and extracted twice with ether. The organic extract was dried over MgSO₄ and filtered. The solvent was evaporated under vacuum. The yellow oil solidified upon standing, was triturated with hexanes and collected by filtration. NMR confirmed the structure. The yield was 64%.

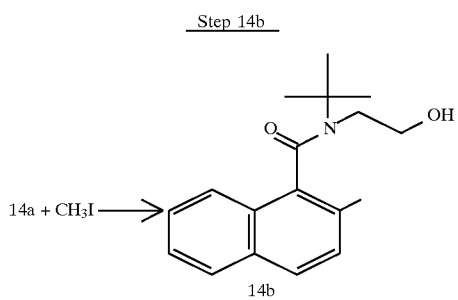

A solution of 2.5 gm (9.2 mmol) of compound 14a and 2.36 gm of TMEDA in 50 ml of THF was cooled to −78° C. in a dry ice/acetone bath. After the mixture had stirred for 15 minutes at −78° C., 20.27 ml of a 1.0M solution of s-butyl lithium in cyclohexane was added, dropwise. The color changed to yellow and then to green and then to a dark green during this addition. The solution was stirred at −78° C. for 1 hour after which 1.3 gm (9.2 mmol) of iodomethane was added in one portion. The reaction mix became yellow with a white precipitate. After 15 minutes TLC indicated that almost no residual starting material was present. The mixture was poured into an ether and water mixture. The organic phase was washed sequentially with water and brine and then dried over MgSO₄. The mixture was then filtered and solvent was removed under vacuum, yielding an orange oil. This oil was purified by flash chromatography using a 2 to 1 ether/hexane solution. Fractions 28–46 were collected cleanly. Structure was confirmed by NMR. Yield was approximately 45%.

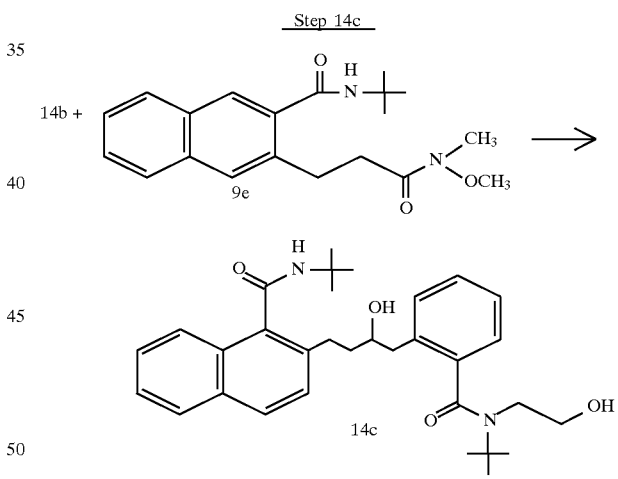

A solution of 0.17 gm (0.595 mmol) of compound 14b and 0.0176 gm of diisopropylamine in 5 ml of THF was cooled to −78° C. After the mixture had cooled for 15 minutes at −78° C., 1.33 ml of a 1.0M solution of s-butyl lithium in cyclohexane was slowly added. No color change was apparent at this point, so another 0.4 ml of the solution was added and a blood red color was noted. When the entire amount of the s-butyl lithium had been added the reaction mixture was stirred for an additional 15 minutes at −78° C. At this point, a solution of 0.10 gm (0.29 mmol) of compound 9e in 1 ml of THF was added quickly. No color change was observed. After 15 minutes TLC indicated that no residual starting material was present and 1 ml of water was added to quench the reaction. The mixture was poured into ether and the organic layers were washed sequentially with water and brine, then dried over MgSO₄. The mix was then filtered and the solvent was removed under vacuum. The residue was dissolved in 5 ml of ethanol and 0.017 gm of NaBH₄ crystals were added. A white precipitate formed in the solution and slowly dissolved, yielding again a clear solution. This solution was poured into saturated NaHCO₃ and extracted with ether. The organic extract was washed in brine then dried over MgSO₄ and filtered. The solvent was then removed under vacuum. The clear oil was purified by column chromatography. The structure was confirmed by 'HNMR.

EXAMPLE 15

Preparation of

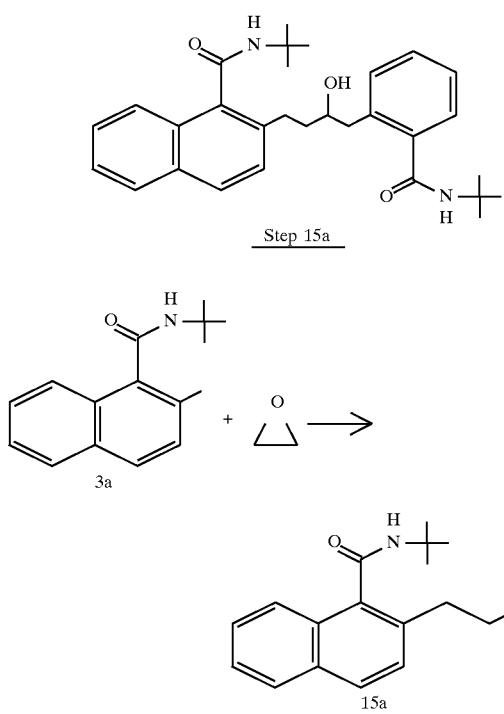

Step 15a

A solution of 0.8 gm (3.317 mmol) of compound 3a and 0.79 gm of TMEDA and 27 ml of THF was cooled to -78° C. in a dry ice/acetone bath. After the solution had cooled for 15 minutes at -78° C., 4.02 ml of a 1.69M solution of n-butyl lithium in hexane was added dropwise to the solution. A deep purple color resulted. The solution was then stirred at -78° C. for 1.5 hours. At this point, a solution of 0.292 gm (6.64 mmol) of ethylene oxide in THF (10% in THF) was added. After 15 minutes, TLC indicated that there was residual starting material. Accordingly, another equivalent of ethylene oxide was added. The reaction was monitored again and starting material was still seen so yet another 5 equivalents of ethylene oxide was added. The reaction was then allowed to warm to 0° C. and the purple color changed to a light green. The reaction mixture was poured into water, extracted with ether, washed with brine, dried over MgSO₄ and filtered. Solvent was removed under vacuum, yielding a yellow oil. The yellow oil was purified by flash chromatography using a 2 to 1 ether/hexane solution. Fractions 6–11 were collected cleanly and the solvent was removed under vacuum. Structure was confirmed by NMR. Yield was 42%.

Step 15b

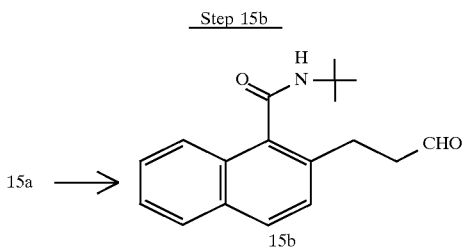

To a solution of 0.83 gm of pyridine and 15 ml of methylene chloride there was added 0.526 gm of chromium trioxide. The solid partially dissolved into an orange solution with a brown solid settling out. After 60 minutes, a solution of 0.25 gm of compound 15a in 4 ml of methylene chloride was added, dropwise. After 15 minutes, TLC indicated that no residual starting material was present. The mixture was poured into ether, washed twice with 1N NaOH, then sequentially with 1N HCl, saturated NaHCO₃ and brine, then dried over MgSO₄. The mixture was filtered and the solvent was removed in vacuum yielding a solid product which was then recrystallized from ether and hexane. The structure was confirmed by NMR. Yield was 72.5%.

Step 15c

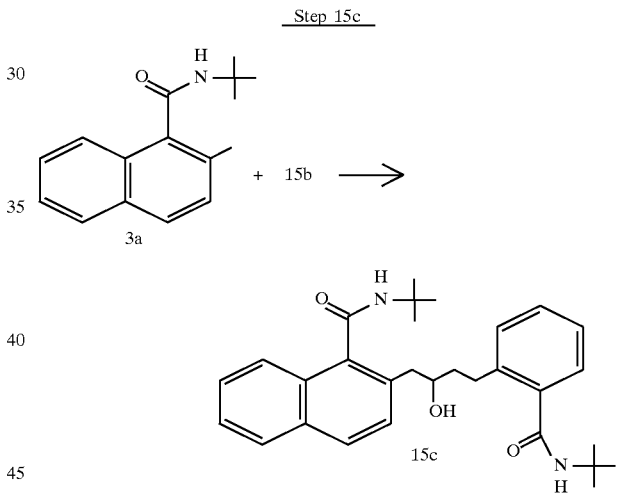

A solution of 0.136 gm (0.565 mmol) of compound 3a and 0.132 gm of TMEDA in 10 ml THF was cooled to -78° C. in a dry ice/acetone bath. After the solution had stirred for 15 minutes at -78° C., 0.34 ml of a 1.69M solution of n-butyl lithium in hexane was added. A purple color developed and the solution stirred at -78° C. for 45 minutes. At this time, a solution of 0.08 gms (0.283 mmol) of compound 15b in 2 ml of THF was added. The solution was stirred for an additional 15 minutes at which time some residual starting aldehyde persisted. The reaction was allowed to warm to 0° C. and TLC did not indicate whether residual aldehyde still remained. The reaction mixture was allowed to warm to room temperature. After 10 minutes it was poured into water and extracted with ether. The extracts were washed with brine and dried over MgSO₄. The mixture was then filtered and the solvent was removed under vacuum and a yellow oil was recovered. This oil was purified by flash chromatography and the desired material was confirmed by NMR.

EXAMPLE 16

Preparation of

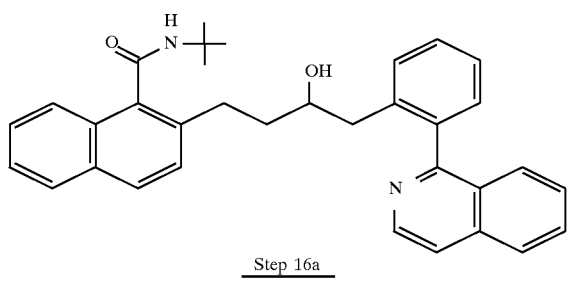

Step 16a

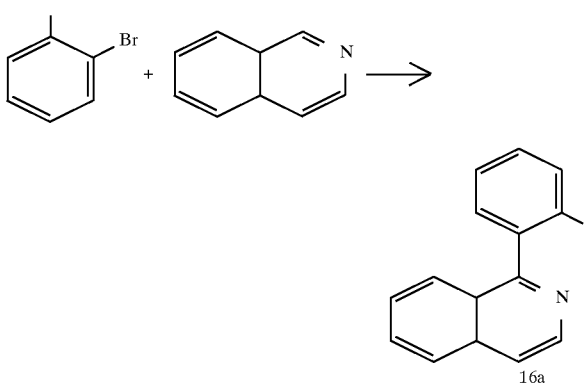

A solution was prepared of 21.37 gm (0.125 mol) of O-bromotoluene in 100 ml of ether. The solution was stirred and 1.75 gm of lithium wire was added. The mixture was allowed to stir at room temperature. As the lithium dissolved, the solution began to reflux spontaneously. After 1 hour the mixture was murky and brown with a white precipitate. The reaction was then allowed to stir for an additional 3 hours at which time 32.25 gm (0.25 mmol) of isoquinoline and 100 ml of toluene were added through the condenser. As the isoquinoline addition proceeded the solution turned blood red with a yellow precipitate and refluxed spontaneously. The mixture was no longer exothermic after about one-half of the isoquinoline had been added. When the addition was completed the condenser was replaced with a short path distillation apparatus, the reaction mass was concentrated down to 115 ml and reflux was continued for about 2.5 hours. At this time, TLC indicated that no bromotoluene material remained. The reaction was quenched with water and poured into additional water. Organic materials were extracted with ethyl acetate and washed with saturated NaHCO$_3$ and brine. A brown oil (49.01 gm) was collected, dried over MgSO$_4$ and purified by fractional distillation. The desired product distilled at 115°–120° C. Yield was 13.5 gm.

Step 16b

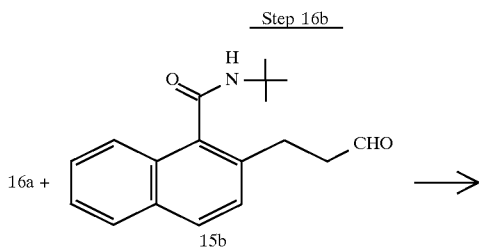

-continued
Step 16b

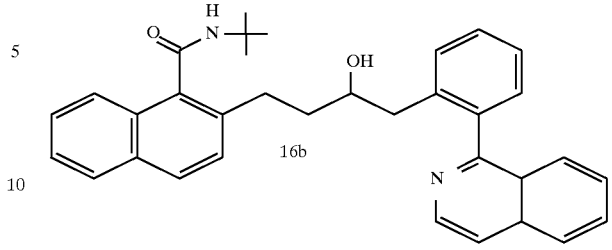

A solution of 0.465 gm of TMEDA in 20 ml of THF was cooled to −78° C. After 10 minutes 2.35 ml of a 1.7M solution of n-butyl lithium in hexane was added. The clear solution which resulted was stirred at −78° C. for 30 minutes at which time a solution of 0.85 gm (3.87 mmol) of compound 16a and 5 ml THF was added, dropwise. The solution gradually turned dark green and was allowed to warm to about −30° C. and stirred at that temperature for about an hour.

At the end of this one hour period, a solution of 0.30 gm (1.29 mmol) of compound 15b in 3 ml of THF was rapidly added. The solution immediately turned black and stirring was continued at −30° C. for another hour. The mixture was warmed to room temperature and stirring was continued for another hour. TLC indicated the presence of residual starting material so the mass was allowed to stir overnight at room temperature.

The reaction mass was poured into ether, washed sequentially with water and brine, then extracted with 1N HCl. The organic layer was separated, and the aqueous layer made basic (pH8) with saturated NaHCO and extracted with ether. The second organic layer was dried over MgSO$_4$ and filtered. The solvent was removed under vacuum. The organic layer was purified by flash chromatography using 5:1 ether/hexane eluent. The more polar material was collected (0.05g) and the desired material confirmed by NMR.

EXAMPLE 17

Preparation of

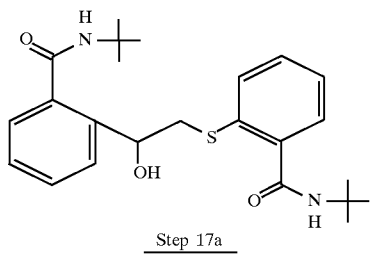

Step 17a

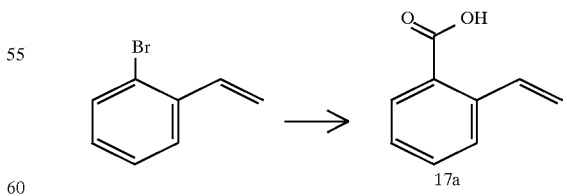

Mg turnings (1.75g, 0.072 g atom) were placed in an oven dried 250 ml 3 neck flask with condenser and addition funnel (all assembled hot). The entire apparatus was evacuated and filled with argon. The flask was charged with 10 ml of anhydrous THF and the addition funnel was charged with 8.0 gm (43.7 mmol) of 1-bromostyrene in 50 ml of anhydrous THF. Five (5) ml of the 1-bromostyrene solution was added to the Mg turnings and the mixture was heated to 65°–70° C. and the remainder of the solution was added over 1 hour. The mixture was heated an additional 30 min., then cooled to room temperature over 1 hour, then poured over crushed dry ice and the dry ice was allowed to evaporate. The mixture was made strongly acidic with 150 ml of 10% HCl solution. The organic phase was separated and the aqueous phase was extracted three times with ether. The combined organic phase was poured into 150 ml of 20% KOH solution, the solution was separated and the basic phase was filtered to remove polymer. The basic phase was then acidified with 10% HCl solution and extracted three times with 100 ml portions of ether. The extracts were combined, washed with 100 ml of brine and dried over $Na_2SO_4$. The solution was filtered and concentrated to a white solid which was recrystallized from chloroform/hexane solution to yield 6.44 g (66%) of 1-vinylbenzoic acid in two crops.

Step 17b

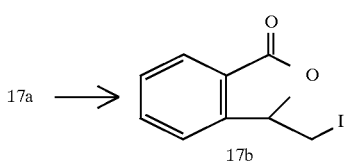

Iodine (4.12 g, 16.22 mmol) was added in a single portion to a degassed solution of 1.20 gm (8.11 mmol) of compound 17a in 12 ml of acetonitrile. The solution was stirred for 1 hour, then poured into 50 ml of saturated sodium thiosulfate solution. The solution was extracted three times with 50 ml portions of ethyl acetate. The combined organic phases were washed sequentially with 40 ml portions $H_2O$, saturated $NaHCO_3$ solution and saturated sodium thiosulfate solution then dried over $MgSO_4$. The solution was filtered and concentrated to a yellow solid (1.87 g, 84% yield) which was recrystallized from ethanol.

Step 17c

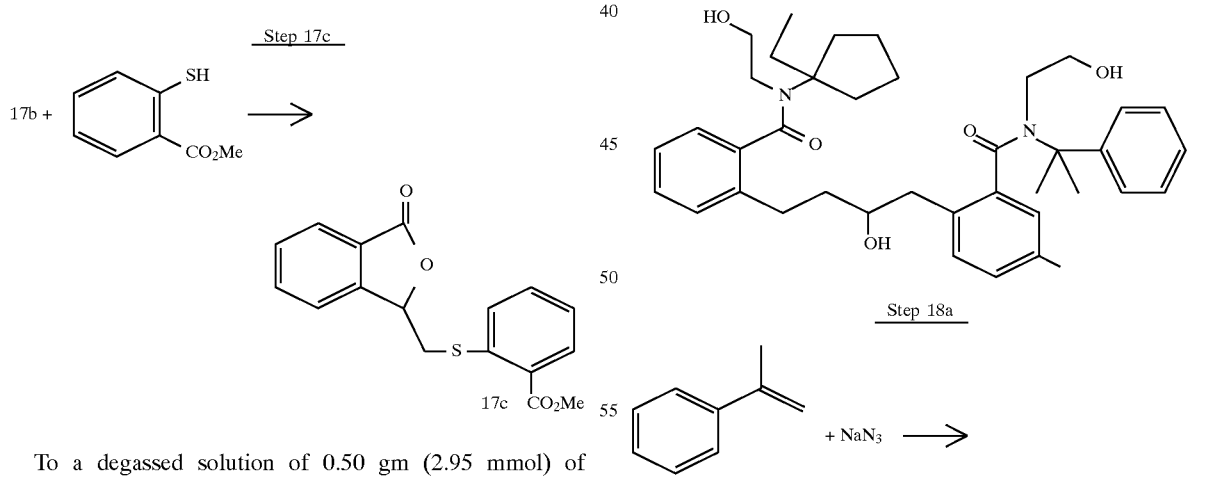

To a degassed solution of 0.50 gm (2.95 mmol) of 1-mercapto methyl benzoate in 12 ml of ethanol was added, dropwise, 0.14 g, (2.95 mmol) of KOH in 1.5 ml of $H_2O$. The resultant yellow solution was stirred for 10 minutes at room temperature. The solution was cooled to 0° C. and 0.80 g, (2.92 mmol) of compound 17b in 10 ml ethanol was added over 30 minutes. The reaction mixture was stirred for 19 hours at room temperature. The resultant yellow solution was poured into 40 ml of $H_2O$ and extracted three times with 40 ml portions of $CH_2Cl_2$. The combined extracts were washed with 30 ml portions of $H_2O$ and brine and dried over $MgSO_4$. The solution was filtered and concentrated to a yellow oil which was purified by flash chromatography (10 g silica; 25% ethyl acetate/hexane) to yield 370 mg (40% yield) of product as a white solid.

Step 17d

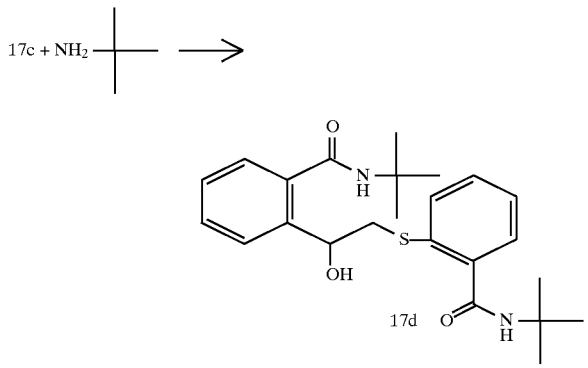

To a solution of 0.16 ml (1.50 mmol) of t-butylamine in 2 ml of anhydrous THF, cooled to 0° C., was added 0.94 ml of 1.6M m-butyl lithium in THF. The solution was stirred for 15 minutes and a solution of 157 mg, (0.50 mmol) of compound 17c in 2 ml THF was added, dropwise, at 0° C. The mixture was stirred for 2.5 hours at room temperature and was quenched with 10 ml of dilute $NH_4Cl$ solution. The mixture was extracted three times with 10 ml portions of ethyl acetate, the combined organic phase was washed with 15 ml of $H_2O$ and brine and dried over $MgSO_4$. The solution was filtered, concentrated and the residue was purified by flash chromatography (25g silica; 5–10% ethyl acetate/$CH_2Cl_2$) to yield 17 mg (10% yield) of product as a white solid.

EXAMPLE 18

Preparation of

Step 18a

A mixture of 59.09 gm (0.5 mole) of α-methylstyrene and 65 gm (1.0 mole) of sodium azide in 500 ml of chloroform was cooled in an ice/water mix to about 0° C. A solution of 193 ml trifluoro acetic acid in 500 ml of chloroform was added over one hour. With the temperature remaining below 5° C. a very thick white slurry formed during the addition. After the addition, the reaction vessel was removed from the ice bath and allowed to stir at room temperature for about 19 hours. At this point, 300 ml of NH₄OH in 250 ml of water was added. After shaking, the organic layer was removed and dried over Na₂SO₄. The solvent was removed under vacuum yielding 76.05 gm (94%) of a clear liquid. IR confirms the product to be the desired azide.

Step 18b

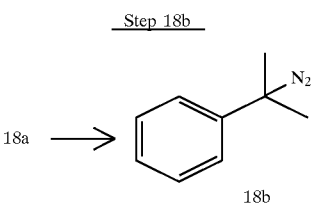

A 2 liter 3 neck round bottom flask which had previously been flame dried and purged with argon was added 30.43 gm of LiAlH₄ and 100 ml of ether. The mixture was cooled with stirring in the ice bath and 76.05 gm of compound 18a was added over a one hour period with stirring. Stirring was continued in the ice bath for about 2.5 hours after which the ice was allowed to melt overnight and the reaction mixture warmed to room temperature. After 16 hours, cooling was resumed in the ice bath and the mixture was quenched with 250 ml of 25% NaOH over a one hour period. The ether layer was removed. To the aluminum salts remaining in the water layer another 400 ml of water was added, followed by extraction with 200 ml of ether. The ether layers were combined, dried with Na₂SO₄, and the solvents were removed by vacuum at 30° C. following which the product was distilled at 60° C. and 3.2 Torr, yielding 46.82 gm (74%) of the desired amine.

Step 18c

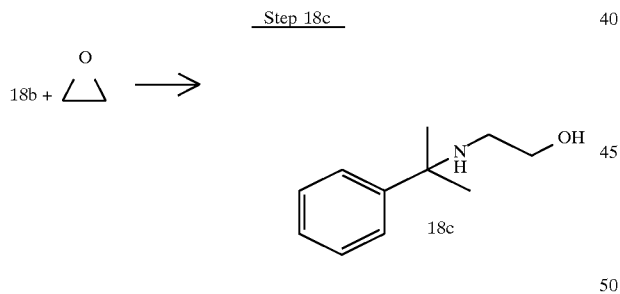

To a 100 ml round bottom flask, which had been flame dried and purged with argon, was added 25 ml of THF and the flask and contents were cooled to -780 in a dry ice acetone bath and 4.84 gm (0.11 mole) of ethylene oxide was added followed by 10.64 gm of LiClO₄. The flask and contents were switched to an ice/water bath and allowed to stir for 5 to 10 minutes and 13.52 gm (0.1 mole) of compound 18b in CH₃CN was added over a two minute period. During the addition everything went into solution. Following the addition the ice bath was removed and the mixture was allowed to stir at room temperature for three hours. The mixture was then poured into 200 ml of brine and extracted twice with 50 ml portions of ether. The combined ether layers were dried, filtered and the solvent was removed under vacuum. The resulting oily residue was distilled at about 180° C. and 2 ml of Hg, yielding 10.8 gm (60%) of product as a clear, colorless oil.

Step 18d

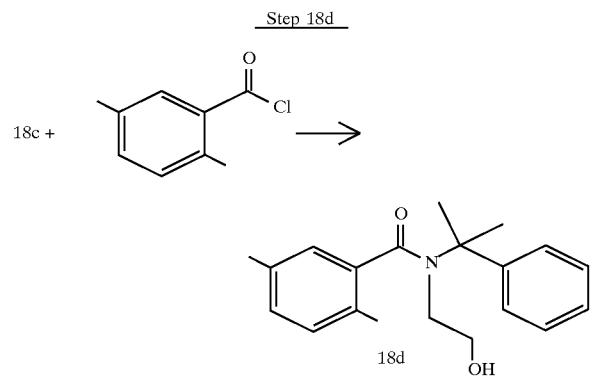

To a 100 ml flame dried and argon purged round bottom flask was added 0.153 gm of 4-dimethylamino pyridine (DMAP), 13 ml of pyridine and 1.5 gm (8.37 mmol) of compound 18c yielding a clear, colorless solution. This solution was cooled to 0° C. and over a 5 minute period 5.64 gm (33.5 mmol) of 2,5-dimethyl benzoyl chloride was added. The resulting yellow solution was placed in a 100° C. oil bath and allowed to stir overnight. The mixture was then poured into 150 ml of 2N HCl and extracted twice with 50 ml portions of ether. The combined extracts were washed again with 50 ml of water then dried over Na₂SO₄, filtered and the solvent was removed under vacuum yielding an orange oil. This oil was dissolved in 50 ml of 10% aqueous methanol and 5 ml of 50% NaOH was added. After 35 minutes the mixture was poured into 500 ml of water and extracted with first 100 ml of ether and then with 100 ml of methylene chloride. The organic layers were combined and dried over Na₂SO₄. The solvent was removed under vacuum, yielding 2.23 gm of a light, yellow oil. This was taken up in 15 ml of ethyl acetate, 50 ml of hexane was added and the product was placed in a freezer for 2 hours. The resulting light yellow solid was filtered off, washed with 20 ml of a 1:1 hexane/ethyl acetate mixture, followed by 40 ml of hexane, yielding 395 mg of pure product.

Step 18e

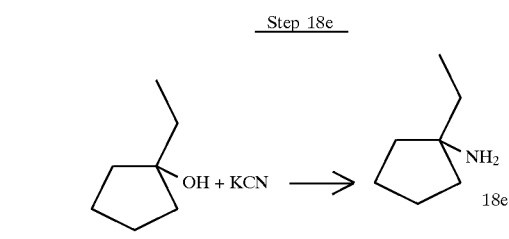

To a solution of 10 gm of 1 ethyl-1-cyclopentanol, 6.9 g of KCN and 13 ml of glacial acetic acid heated to 50° C. was added 25 gm of H₂SO₄ in acetic acid dropwise over 2 hours. The reaction mixture was then heated to 70° C. for 4 hours. The product was poured into about 150 ml of ice. When the ice melted, the mixture was extracted three times with 75 ml portions of ether. The organic layers were combined and washed three times with 100 ml portions of water. The combined washings were then extracted once with 50 ml of ethyl acetate, dried over MgSO₄, filtered and the solvent was removed under vacuum, yielding about 15 gm of an orange oil. This material was refluxed in 20 ml of concentrated HCl for about 4 hours. TLC indicated that all starting material had been used up. The mixture was cooled, the residual HCl was removed under vacuum taking the material to nearly a dry state. The crude brown solid was slurried in acetone and ether, yielding a white solid which was filtered and dried. This white solid was dissolved in KOH solution and extracted with ether. The ether was removed and a brown oil was recovered. This oil was distilled at atmospheric pressure yielding 3.3 gm (33%) of colorless liquid.

Step 18f

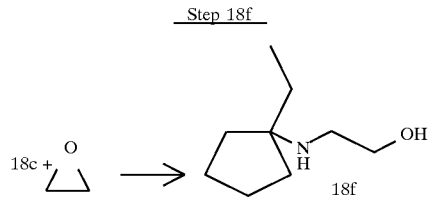

To a solution of 0.99 gm (0.022 mmol) of ethylene oxide in 6 ml of $CH_3CN$ cooled to 0° C. was added 2.13 gm of $LiClO_4$. To this was added 2.3 gm (0.020 mmol) of compound 18e dissolved in 3 ml of $CH_3CN$ and the mass was allowed to stir at room temperature for about 2 hours. At this time the reaction mixture was concentrated under vacuum and the residue was dissolved in 10 ml of water and saturated sodium chloride solution. It was then extracted with three 25 ml portions of 10% ethyl acetate in ether. The organic phases were combined, dried over $Na_2SO_4$, and solvent was removed under vacuum, yielding a colorless liquid. The liquid was distilled under high vacuum at about 70°–72° C. yielding 1.4 gm 45%) of a colorless, viscous liquid.

Step 18a

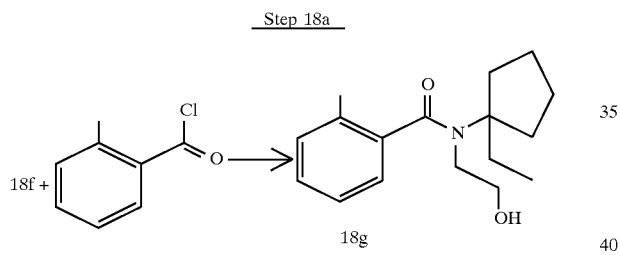

To a solution of 2.1 gm (0.013 mmol) of compound 18f in pyridine was added, dropwise, 8.3 gm (0.054 mmol) of toluoyl chloride and 0.16 gm of DMAP. The mixture was heated to reflux for about 22 hours at 120° C. The reaction mixture was then cooled and poured into 200 ml of water which was acidified with concentrated HCl to a pH of about 1 to 2. It was then extracted with three 20 ml portions of ether and the combined organics layers were washed with water, 5% HCL water and brine, dried over $MgSO_4$, filtered, and the solvent removed under vacuum, yielding a brownish orange oil. This oil was dissolved in 35 ml of 10% aqueous methanol and 1.7 ml of 45% KOH solution was added dropwise. The mixture was allowed to sit at room temperature for two hours, then was concentrated and the residue was dissolved in 50 ml of water and extracted three times with 50 ml portions of ether. The combined organic phases were washed with 50 ml of water, dried over $MgSO_4$, filtered and concentrated to a yellowish orange oil. Flash chromatography using a 50% ethyl acetate/hexane solution yielded 1.44 gm of a slightly yellow solid.

Step 18h

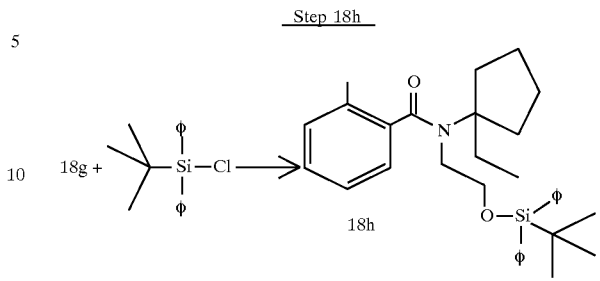

To a solution of 2.13 gm (7.75 mmol) of compound 18g and 1.16 gm of imidazole in 15 ml of DMF was added 2.34 gm (8.52 mmol) of t-butyldiphenylsilyl chloride. The mixture was allowed to stir at room temperature for about 22 hours after which it was poured into 150 ml of water and extracted three times with 50 ml portions of ether. The combined organic layers were washed twice with 60 ml portions of water, then with brine, then dried over $M_gSO_4$, and filtered. The solvent was removed, yielding a slightly yellow oil. The product was purified by flash chromatography using 20% ethyl acetate/hexane mixture. The appropriate fractions were collected as a colorless viscous oil which crystallized on the vacuum pump, yielding 3.7 gm (93%) of product.

Step 18i

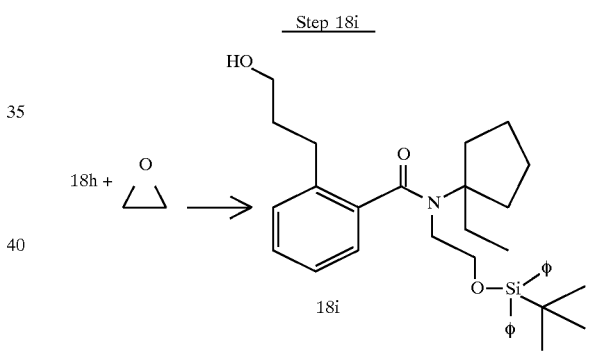

To a solution of 3.6 gm (7.01 mmol) of compound 18h and 0.11 gm of diisopropyl amide in 33 ml of THF cooled to −78° C. in a dry ice/acetone bath was added 6.2 ml of s-butyl lithium dropwise over 10 to 15 minutes. The mixture was then stirred at −78° C. for 1.5 hours and 0.93 gm of ethylene oxide in 3 ml of THF was added. The mixture was stirred while warming up slowly for about 1 hour, then was quenched with dilute $NH_4Cl$ and extracted three times with 30 ml portions of ethyl acetate. The combined organic layers were washed with 30 ml of 10% citric acid solution, then twice with 30 ml portions of water, and then with 30 ml of brine. After drying over $MgSO_4$, the product was filtered and solvent removed under vacuum yielding a brown viscous glassy material. The glassy material was purified by flash chromatography using 50% ethyl acetate/hexane yielding 780 mg (20%) of product.

Step 18j

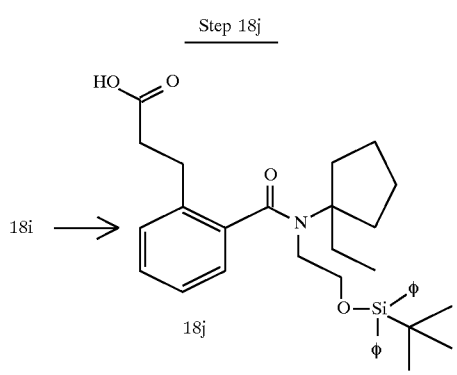

To a solution of 530 mg of compound 18i in 7 ml of acetone cooled to 0° C. was added 0.99 ml of Jones reagent dropwise. The mixture was stirred at room temperature for about 30 minutes then cooled to 0° C. and quenched with 1 ml of isopropyl alcohol. Acetone was decanted and the chromium salts were washed twice with 25 ml portions of acetone. The combined washings were concentrated to a viscous oil which was dissolved in 50 ml of ether and washed twice with 25 ml portions of water. The chromium salts were then dissolved in 5 ml of water and washed with 20 ml of ether. The combined ether extracts were dried over $MgSO_4$. The solution was then filtered and concentrated under vacuum to a viscous slightly yellow oil which was used as is in the next step. The yield was 534 mg.

Step 18k

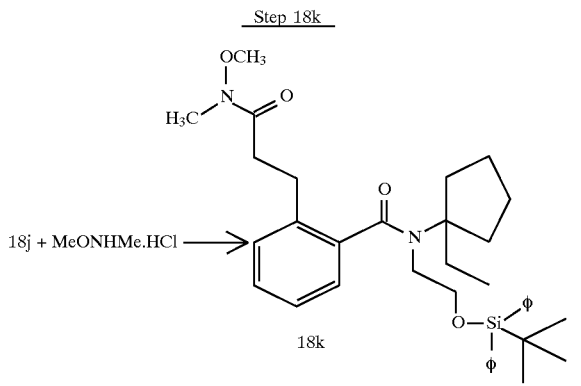

To a solution of 534 mg (0.95 mmol) of compound 18j, 106 mg (1.08 mmol) of N, o-dimethylaminehydrochloride and 0.45 ml of Honigs base in 6 ml of methylene chloride cooled to 0° C. was added 455 mg of BOP reagent. The mixture was stirred at room temperature for 6 hours and then diluted with 50 ml of methylene chloride and washed with 50 ml portions of water, 10% citric acid and saturated $NAHCO_3$, then dried over $MgSO_4$ and filtered. The solvent was removed, yielding a yellow viscous oil. This oil was purified by flash chromatography using 50% ethyl acetate/hexane. The appropriate fractions were combined yielding 408 mg (71%) of a yellow viscous oil.

Step 18l

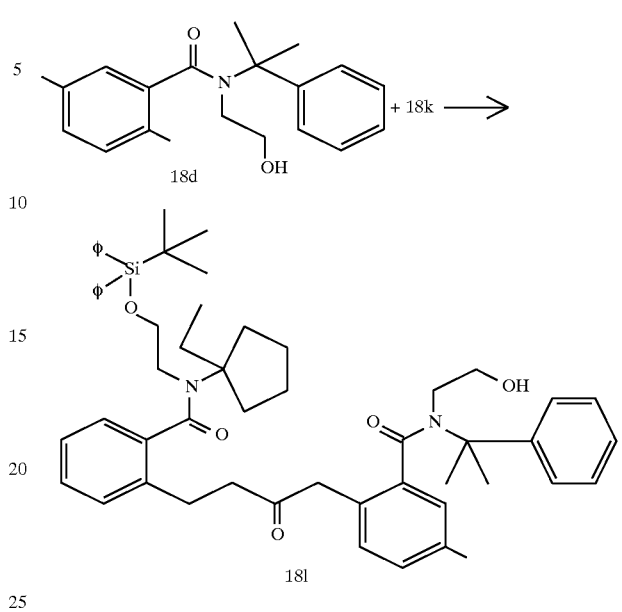

To a 25 ml round bottom flask which had been flame-dried and purged with argon, was charged 102 mg of compound 18d, 7 mg of diisopropylamide, 4 ml of THF and the mixture was cooled to −78° C. Over a five minute period, 0.56 gm of a 1.29 molar solution of s-butyl lithium in cyclohexane was added yielding a deep crimson solution. The solution was stirred for one hour and 202 mg of compound 18k and 5 ml of THF were added over a five minute period. The dry ice was allowed to evaporate and the solution warmed to room temperature. After 18.5 hours, the reaction was quenched with 4 ml of 0.5N $NH_4Cl$, then poured into 60 ml of brine and extracted with two 20 ml portions of ethyl acetate. The combined organics were then dried over $Na_2SO_4$, filtered, and the solvent removed, yielding 0.242 mg (85%) of a white foam.

Step 18m

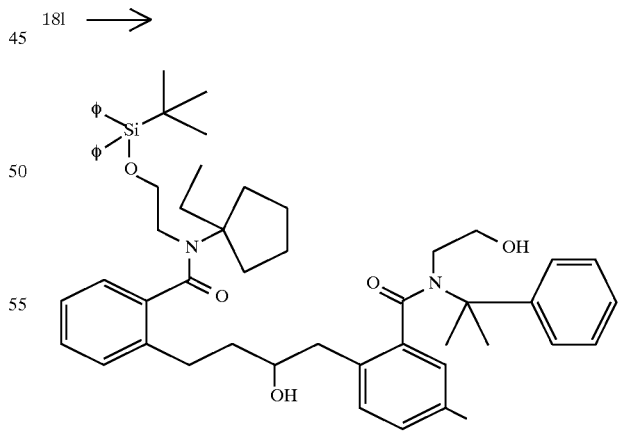

To 242 mg of compound 18l and ethanol was added 32 mg of $NaBH_4$. The mixture was stirred at room temperature for about 35 minutes then poured into 100 ml of brine and extracted twice with 25 ml portions of ethyl acetate. The extracts were combined, dried over $Na_2SO_4$, filtered and the solvent removed to yield 161 mg (66%) of a white foam.

Step 18n

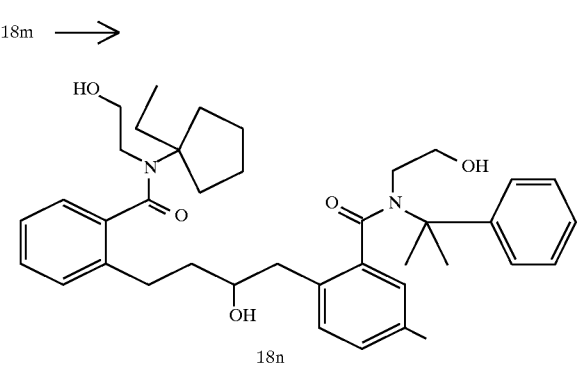

To a solution of 161 mg of compound 18m and 5 ml of THF was added 0.56 ml of a one molar solution of tetrabutyl ammonium fluoride in THF. After 30 minutes the mixture was poured into 100 ml of water and extracted with two 25 ml portions of ethyl acetate. The ethyl acetate layers were then dried over MgSO$_4$. The solvent was removed, yielding 149 mg of a crude product. This product was purified by flash chromatography using ethyl acetate. The appropriate fractions were combined, filtered and the solvent removed yielding 43 mg (37%) of the pure product as a white foam.

EXAMPLE 19

Preparation of

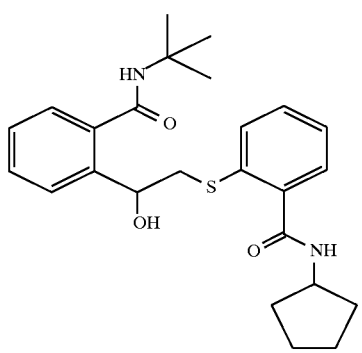

Step 19a

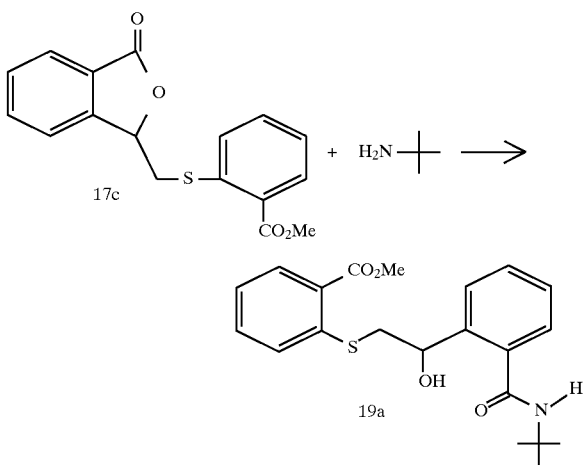

To a solution of 0.40 ml (3.82 mmol) of t-butylamine in 10 ml of CH$_2$Cl$_2$, cooled to 0° C., was added 3.82 ml of a 2.0M solution of trimethyl aluminum in toluene, dropwise, over 5 minutes. The solution was stirred for 45 minutes at room temperature and 400 mg (1.27 mmol) of compound 17c in 5 ml of CH$_2$Cl$_2$ was added, dropwise. The reaction mixture was heated to 40° C. for 21 hours, then cooled and carefully quenched by dropwise addition of 15 ml of saturated NH$_4$Cl solution. The mixture was extracted three times with 25 ml portions of CH$_2$Cl$_2$ and the organic extracts were washed with 20 ml of H$_2$O. The solution was dried over MgSO$_4$, filtered and concentrated to a yellow viscous oil which was purified by flash chromatography (80 g silica gel; 20–40% ethyl acetate/hexane) to yield 350 mg (71% yield) of a colorless glassy material.

Step 19b

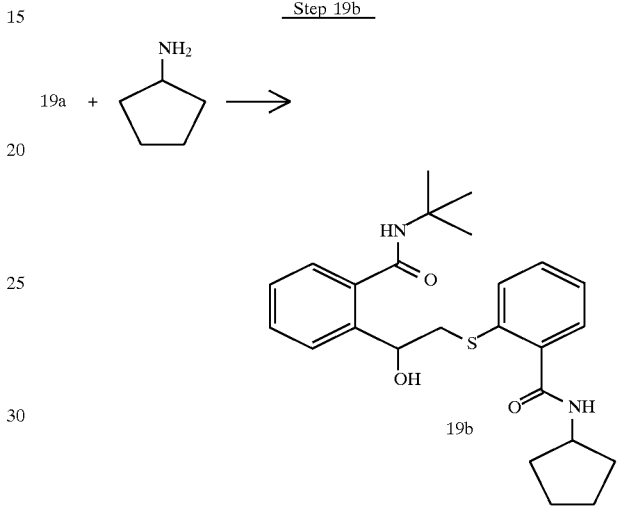

To a solution of 65 μl (0.65 mmol) of cyclopentylamine in 2 ml of dichloroethane, cooled to 0° C., was added 0.33. ml of a 2.0M solution (0.65 mmol) of trimethyl aluminum in toluene, dropwise, over 5 minutes. The solution was stirred for 45 minutes at room temperature and 50 mg (0.13 mmol) of compound 19a in 2 ml of dichloroethane was added, dropwise. The reaction mixture was heated to 65° C. for 20 hours, cooled to room temperature and carefully quenched with saturated NH$_4$Cl solution. The crude mixture was extracted three times with 10 ml portions of ethyl acetate and the combined organic extracts were dried over MgSO$_4$. The solution was filtered and concentrated to a yellow viscous oil which was purified by flash chromatography (20 g silica: 25–35% ethyl acetate/hexane) to yield 25 mg (44% yield) of the desired product as a white solid.

EXAMPLE 20

Preparation of

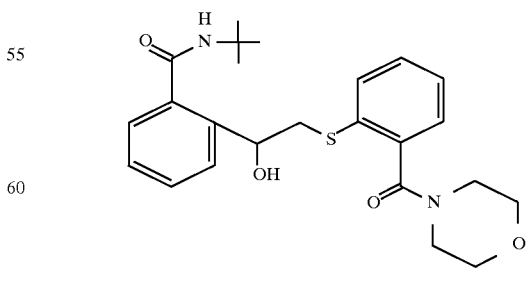

To a solution of 81 μl, (0.93 mmol) of morpholine in 2 ml of dichloroethane, cooled to 0° C., was added 0.47 ml of a 2.0M solution of trimethylaluminum (0.93 mmol) in toluene, dropwise, over 5 minutes. The solution was stirred for 45 minutes at room temperature and 60 mg (0.16 mmol) of compound 17c in 2 ml of dichloroethane was added, dropwise. The reaction mixture was heated to 65° C. for 3 hours, cooled to room temperature and carefully quenched with saturated NH$_4$Cl solution. The crude mixture was extracted three times with 10 ml portions of ethyl acetate and the combined extracts were dried over MgSO$_4$. The solution was filtered and concentrated under vacuum to a viscous oil which was purified by flash chromatography (15 g silica; 30–50% ethyl acetate/hexane) to yield 45 mg (65% yield) of the product as a white solid.

EXAMPLE 21

Preparation of

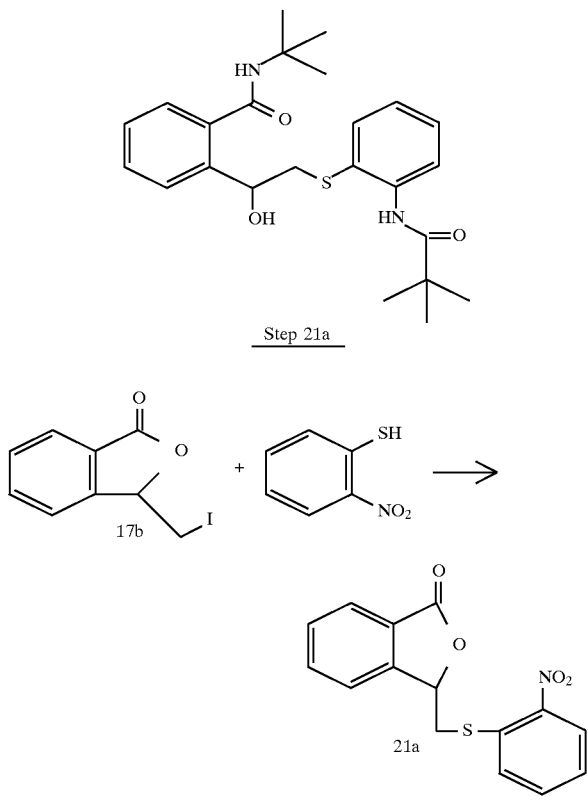

Step 21a

To a degassed solution of 0.65g, (4.22 mmol) of 1-mercaptonitrobenzene in 15 ml of ethanol was added, dropwise, 0.28g (4.2 mmol) of KOH in 1.5 ml H$_2$O. The resultant brown solution was stirred for 10–15 minutes at room temperature. The solution was cooled to 0° C. and 1.10 g (4.02 mmol) of compound 17b in 10 ml of THF was added, dropwise. The mixture was stirred at room temperature for 21 hours, then poured into 70 ml of H$_2$O and the solution was extracted three times with 50 ml portions CH$_2$Cl$_2$. The combined organic phases were washed with 50 ml of H$_2$O and brine and dried over MgSO$_4$. The solution was then filtered and concentrated under vacuum. The residue was purified by flash chromatography (125 g silica gel; 1% ethyl acetate/chloroform) to yield 0.58g (48% yield) of yellow solid.

Step 21b

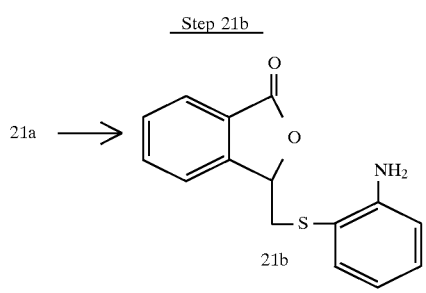

A mixture of 200 mg, (0.67 mmol) of compound 21a and 368 mg (0.73 mmol) of Fe$_3$(CO)$_{12}$ in 40 ml of benzene and 0.15 ml of MeOH was heated to reflux for 5.5 hours. The reaction mixture was then cooled and filtered through Celite and the filter pad was washed with 50 ml of benzene/MeOH. The solution was concentrated under vacuum and the orange residue was purified by flash chromatography (40 g silica: 0.25–0.5% ethyl acetate/CH$_2$Cl$_2$). The product (149 mg, 81% yield) was isolated as a colorless, viscous oil.

Step 21c

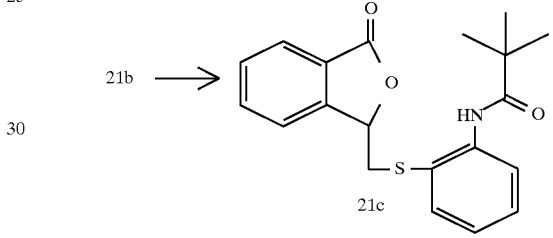

To a solution of 149 mg (0.55 mmol) of aniline 21b in 5 ml CH$_2$Cl$_2$ cooled to 0° C., was added 74 μl, (0.61 mmol) of pivaloyl chloride, followed by 98 μl (1.21 mmol) of pyridine. The reaction was stirred for 20 hours at room temperature and then poured into 20 ml of H$_2$O. The mixture was separated and the aqueous phase was extracted once with a 20 ml portion of CH$_2$Cl$_2$. The combined organic phases were washed with 20 ml portions of 5% KHSO$_4$ and saturated NaHCO$_3$ solution and dried over MgSO$_4$. The solution was then filtered and concentrated to a slightly yellow oil which was purified by flash chromatography (30 g silica; 20% ethyl acetate/hexane) to yield 174 mg (89% yield) of product as a colorless viscous oil.

Step 21d

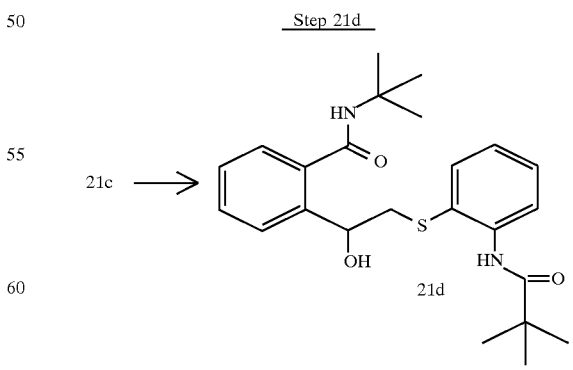

To a solution of 96 μl (0.92 mmol) of t-butylamine in 2 ml of dichloroethane, cooled to 0° C., was added 0.46 ml of a 2.0M solution of trimethyl aluminum (0.92 mmol) in toluene, dropwise, over 5 minutes and the solution was then stirred for 45 minutes at room temperature. A solution of 65 mg (0.18 mmol) of compound 21c in 2 ml of dichloroethane was added, dropwise, and the mixture was heated to 65° C. for 18 hours. The reaction mixture was then cooled and quenched with 10 ml of saturated NH₄Cl solution. The mixture was extracted with three 10 ml portions of ethyl acetate and the combined organic phases were dried over MgSO₄. The solution was filtered and concentrated and the residue purified by flash chromatography (15g silica; 1.5–3% ethyl acetate/CH₂Cl₂) to yield 40 mg (51% yield) of the product as a white solid.

EXAMPLE 22

Preparation of

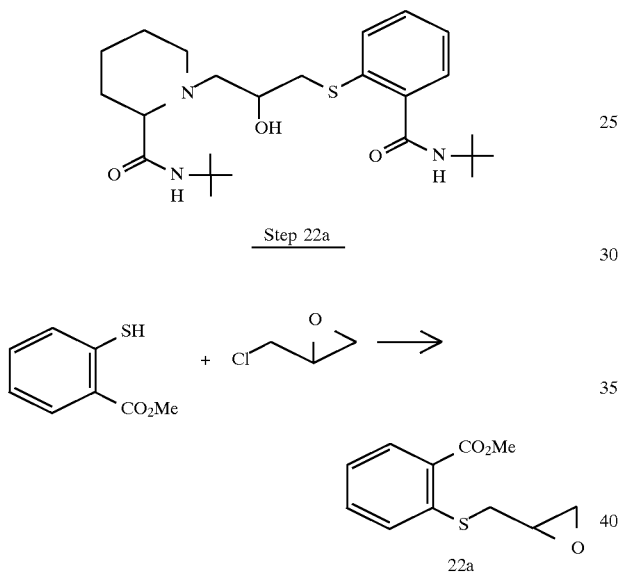

Step 22a

A solution of 3.0 g (0.018 mol) of 1-mercapto-methyl-benzoate and 1.19 g of KOH in 27 ml of 50% aqueous ethanol was added to 4.18 ml (0.054 mol) of epichlorohydrin at 0° C. The reaction mixture was allowed to warm to room temperature upon completion of the addition and the mixture was stirred for 3 hours, then poured into 100 ml of H₂O. The aqueous phase was extracted three times with 50 ml portions of ethyl acetate. The combined organic phases were washed with 50 ml portions of H₂O and brine and dried over Na₂SO₄. The solution was filtered and concentrated to a tan oil which was purified by kugelrohr distillation (155°–160° C. 0.5 torr). The product was isolated as a slightly yellow liquid (2.3 g, 57% yield) which solidified in the refrigerator.

Step 22b

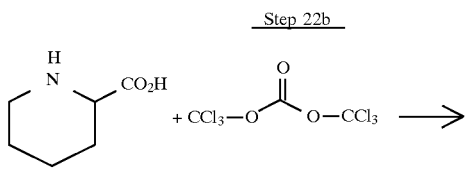

-continued

Step 22b

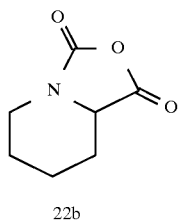

To a suspension of 90 mg (0.79 mmol) of pipecolinic acid in 2 ml of THF was added a solution of 83 mg (0.28 mmol) of triphosgene in 1 ml of THF. The mixture was heated to 40° C. for 20 hours. The now milky suspension was cooled and filtered and the solid was washed with 10 ml of ether. The filtrate was concentrated to a yellow solid (69 mg, 60% yield). No further work-up was carried out on the product.

Step 22c

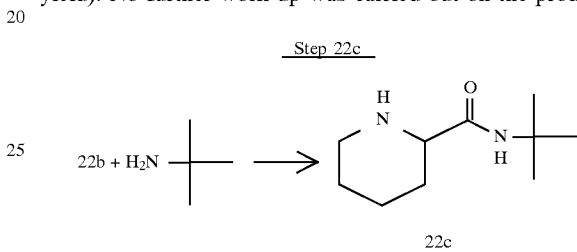

To a solution of 69 mg (0.44 mmol) of compound 22b in 1.5 ml of THF, cooled to 0° C., was added a solution of 139 μl (1.33 mmol) of t-butylamine in 0.5 ml of CHCl₃. The mixture was stirred for 1 hour at 0° C. and 2 hours at room temperature. The mixture was concentrated to a brownish oil under vacuum. This oil was purified by flash chromatography (20 g silica gel, 2.5% MeOH saturated with NH₃/CH₂Cl₂) to yield 41 mg (51% yield) of the product as a colorless solid.

Step 22d

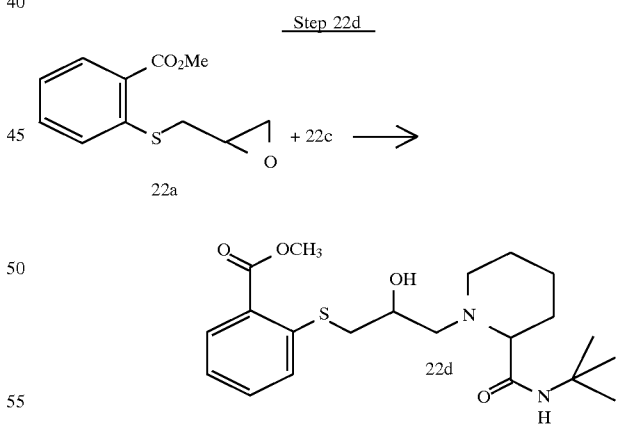

A solution of 650 mg (2.90 mmol) of compound 22a and 587 mg (3.19 mmol) of compound 22c in 27 ml of ethanol was heated to 70° C. for 19 hours. The mixture was concentrated under vacuum to a tan viscous oil which was purified by flash chromatography (175 g silica, 40–50% ethyl acetate/hexane containing a trace of MeOH saturated with NH₃) to give the product as two diastereomers. The less polar product was 497 mg of a white solid. The more polar product was 520 mg of a white foam. Total yield was 1.017 gm (89% yield).

Step 22e

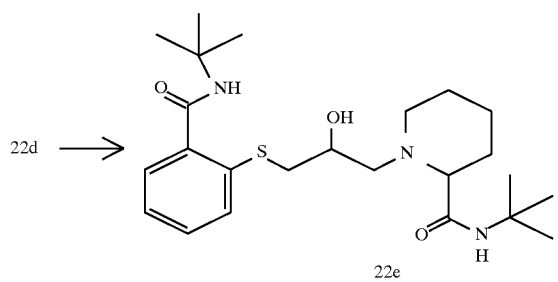

To a 2M solution of 0.62 ml (1.23 mmol) of trimethylaluminum in 4 ml of dichloroethane, cooled to 0° C., was added 130 microliters (1.23 mmol) of t-butylamine, dropwise. The solution was stirred at room temperature for 45 minutes. A solution of 100 mg (0.25 mmol) of the less polar isomer of compound 22d in 2 ml of dichloroethane was added, dropwise, and the mixture was heated to 65° C. for 26 hours. The reaction mixture was cooled and quenched with 10 ml of saturated $NH_4Cl$ solution. The mixture was then extracted with three 15 ml portions of ethyl acetate and the combined organic phases were dried over $MgSO_4$. The solution was filtered and concentrated under vacuum to a yellow oil which was purified by flash chromatography (20 g silica, 10% ethyl acetate/$CH_2Cl_2$ containing a trace of MeOH saturated with $NH_3$) to yield 80 mg (71% yield) of the product as a white solid.

To 0.47 ml of a 2.0 M solution of trimethylaluminum in 4 ml of dichloroethane, cooled to 0° C., 154 microliters (1.47 mmol) of t-butylamine was added, dropwise, and the solution was stirred at room temperature for 45 minutes. A solution of 100 mg (0.25 mmol) of the more polar isomer of compound 22d in 2 ml of dichloroethane was added, dropwise, and the reaction mixture was heated to 70° C. for 20 hours. The reaction mixture was cooled and quenched with 10 ml of saturated $NH_4Cl$ solution and then extracted with three 15 ml portions of ethyl acetate. The combined organic phases were dried over $MgSO_4$. The solution was filtered and concentrated under vacuum to a yellow solid which was purified by trituration with ether to yield 75 mg (67% yield) of product as a tan solid.

EXAMPLE 23

Preparation of

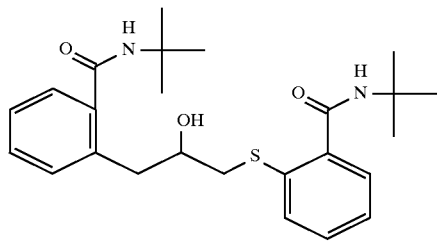

Step 23a

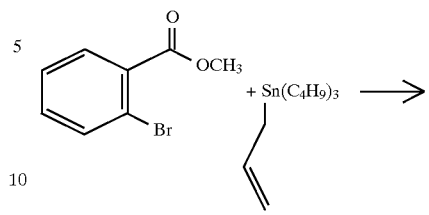

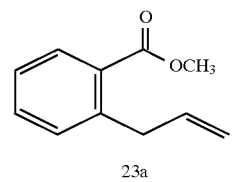

A solution of 6.0 ml (41.71 mmol) of 1-bromo methyl-benzoate and 16 ml (51.61 mmol) of tributylpropenyl tin in 15 ml of benzene was heated to 100° C. and allowed to sit at that temperature overnight in a sealed tube. In the morning the solution was filtered twice through a silica gel plug with hexane, then combined with an equal amount of the product of another run of the same reaction. The combined masses totaled 50.5 g. A portion of this product (10 g) was fractionally distilled at 2 mm and 4 fractions were collected. The distilled products were combined and purified by flash chromatography using a 5% ether/hexane to 10% ether/hexane gradient. Yield was 5.1 gm.

Step 23b

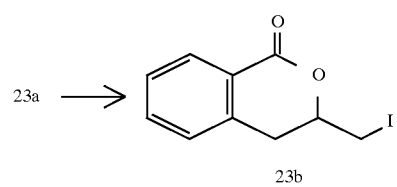

To a mixture of 1.1 gm (6.28 mmol) of compound 23a and 20 ml of acetonitrile at room temperature was added 3.0 g (12.13 mmol) of iodine. Reaction was completed in 45 minutes and the reaction mixture was poured into saturated sodium $NaHSO_3$, extracted twice with ethyl acetate, washed again with sodium $NaHSO_3$ and dried over $MgSO_4$. Concentration under vacuum yield 1.7 g of amber oil (94%). Structure was confirmed by NMR.

Step 23c

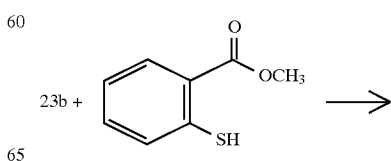

-continued

Step 23c

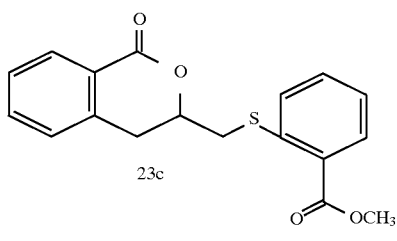

23c

To a solution of 0.8 ml (5.8 mmol) of 1-mercapto-methyl benzoate and 12 ml of ethanol at 0° C. was added to 2 ml of 1N KOH in water. The solution turned yellow. After 20 minutes of stirring, a solution of 1.7 g (5.8 mmol) of compound 23b in 6 ml of ethanol was added, dropwise, over 15 minutes. The reaction mixture was stirred for an additional 15 minutes and then warmed to room temperature. After 2 hours, TLC indicated that residual starting material remained. The mixture was stored in the freezer over a weekend and then allowed to run for 1 hour more at room temperature. When no further change was indicated by TLC, the reaction mixture was poured into 0.5N HCl and extracted twice with ethyl acetate, dried over $MgSO_4$ and concentrated under vacuum. The yield was 2.25 g of a yellow oil. This oil was purified by flash chromatography (20% ethyl acetate/hexane) yielding 1.14 g of sticky oil which was vacuum pumped overnight. The structure was confirmed by NMR.

Step 23d

23c →
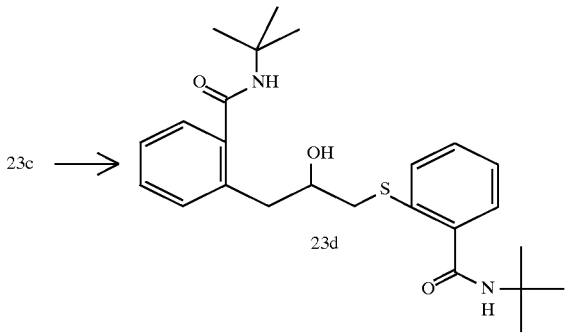

23d

To a solution of 0.6 ml of trimethyl aluminum and 2 ml of benzene at −10° C. was added 0.13 ml (1.24 mmol) of s-butylamine. The solution was warmed to room temperature and stirred for 45 minutes. The solution was then cooled to 0° C. and a solution of 0.08 g of compound 23c in 1 ml of benzene was added. The solution was warmed to room temperature then heated to reflux. The reaction was complete after about 2 hours and 15 minutes. The reaction mixture was poured into 0.5N HCl, extracted twice with ethyl acetate and dried over $MgSO_4$ and concentrated under vacuum. Purification by flash chromatography (50% ethyl acetate/methylene chloride) yielded 0.79 g (73%) of a white solid. Structure was confirmed by NMR.

EXAMPLE 24

Preparation of

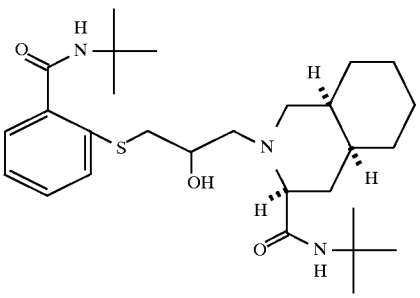

Step 24a

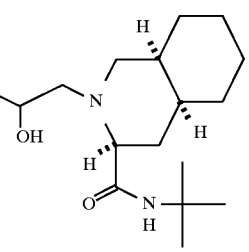

↓

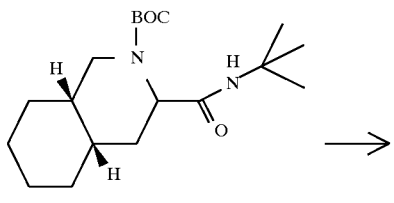

24a

To a solution of 150 mg (0.44 mmol) of BOC protected decahydro isoquinoline in 3 ml of $CH_2Cl_2$, cooled to 0° C., was added 0.5 ml of trifluoroacetic acid. The mixture was stirred at room temperature for 65 minutes and then the reaction mixture was concentrated under vacuum to an oil which was redissolved in 25 ml $CH_2Cl_2$. The solution was washed with 25 ml of saturated $NaHCO_3$, the aqueous phase was back extracted with two 10 ml portions of $CH_2Cl_2$ and the combined organic phases were dried over $MgSO_4$. The solution was filtered and concentrated under vacuum to a colorless viscous oil which slowly solidified to 100 mg (104% yield) of white solid which was used as is in the next step.

Step 24b

24a + 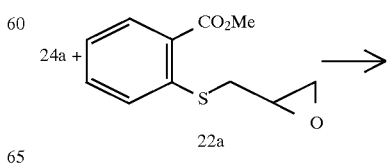 →

22a

-continued

Step 24b

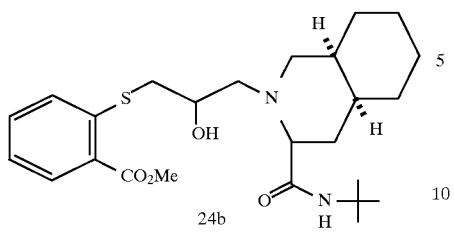

24b

A solution of 100 mg (0.42 mmol) of compound 24a and 104 mg (0.46 mmol) of compound 22a in 4.5 ml ethanol was heated to 60° C. for 23 hours. The reaction mixture was cooled and concentrated under vacuum to a tan oil which was purified by flash chromatography (50 g silica, 30–50% ethyl acetate/hexane) to yield the product as two diastereomers. The less polar diastereomers (90 mg) was a white solid, the more polar diastereomer (100 mg) was a colorless glass. Total yield was 190 mg (98%).

Step 24c

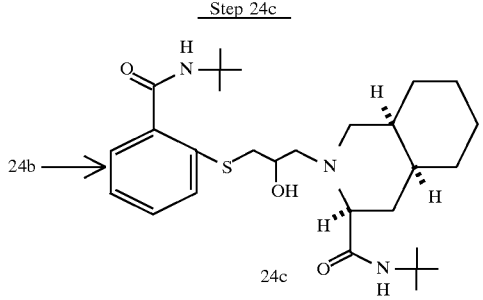

24c t-Butyl amine (86 μl, 0.76 mmol) was added dropwise to 0.38 ml of a 2.0M solution of trimethylaluminum in 3 ml of dichloroethane, cooled to 0° C. The mixture was stirred at -room temperature for 45 minutes and a solution of 70 mg (0.1–5 mmol) of the more polar isomer of compound 24b in 1 ml of dichloroethane was added, dropwise. The mixture was heated for 25 hours at 65° C., cooled and quenched with 10 ml of saturated NH$_4$Cl solution. The mixture was extracted with three 15 ml portions of ethyl acetate and the combined organic phase was dried over MgSO$_4$. The solution was filtered and concentrated under vacuum to a viscous yellow oil which was purified by flash chromatography (20 g silica, 8–10% ethyl acetate/CH$_2$Cl$_2$ containing a trace of MeOH saturated with NH$_3$) to yield 28 mg (36%) of product as a white solid along with 23 mg of recovered starting material.

T-butyl amine (100 μl, 0.91 mmol) was added dropwise to 0.46 ml of a 2.0M solution of trimethylaluminum in 4 ml of dichloroethane, cooled to 0° C. The mixture was stirred at room temperature for 45 minutes and a solution of 60 mg (0.13 mmol) of the less polar isomer of compound 24b in 1 ml of dichloroethane was added, dropwise. The mixture was heated for 17 hours at 65° C., cooled and quenched with 10 ml of saturated NH$_4$Cl solution. The mixture was extracted with three 15 ml portions of ethyl acetate and the combined organic phase was dried over MgSO$_4$. The organic phase was filtered and concentrated under vacuum to a viscous yellow oil which was purified by flash chromatography (20 g silica, 8–10% ethyl acetate/CH$_2$Cl$_2$ containing a trace of MeOH saturated with NH$_3$) to yield 30 mg (46%) of product as a white solid after trituration with ethyl ether.

EXAMPLE 25

Preparation of

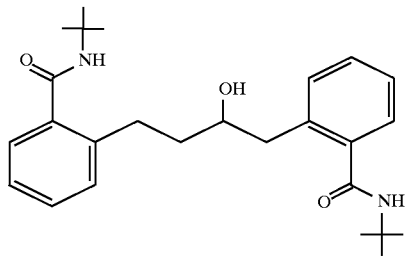

Step 25a

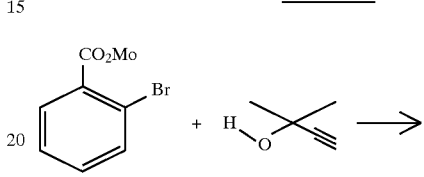

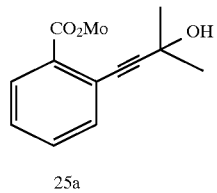

25a

A mixture of 4.0 g (18.61 mmol) of 1-bromomethylbenzoate, 2.2 ml (22.34 mmol) of 2-methyl-3-butyne-2-ol, palladium catalyst (6.1 mg), cuprous iodide (6.2 mg), and triphenylphosphine (12.3 mg) in 19 ml of triethyl amine was heated to reflux for 5 hours during which time the reaction mixture went from a yellow solution to brown with a thick precipitate. The mixture was cooled and filtered and the solid was washed with 50 ml of ether. The filtrate was concentrated under vacuum to an orange oil which was purified by flash chromatography (200 g silica, 25–35% ethyl acetate/hexane) to yield 2.97 g (73%) of product as a yellow viscous liquid.

Step 25b

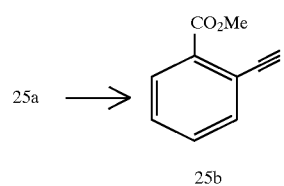

25b

To a solution of 2.97 gm (13.62 mmol) of compound 25a in 25 ml of toluene, was added 0.033 gm (1.10 mol) of an 80% dispersion of sodium hydride in mineral oil. The mixture was heated to reflux during which time the toluene was allowed to distill off. The reaction was cooled when the still head temperature reached 105° C. The solution was filtered and the solid washed with 20 ml of toluene. The filtrate was concentrated under vacuum, and the residue was dissolved in 100 ml of CH$_2$Cl$_2$. The organic solution was washed with 50 ml portions of dilute NaHCO solution and H$_2$O. The organic phase was dried over MgSO$_4$, filtered and concentrated to a brown oil. The product was isolated by kugelrohr distillation (80°–85° C., 0.5 torr) to yield 1.10 g (50%) of product as a yellow-orange liquid.

Step 25c

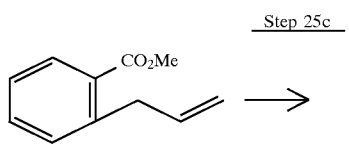

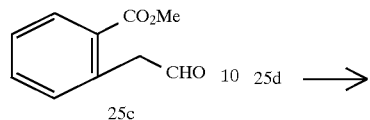

To a solution of 2.50 g (14.19 mmol) of 2-propenyl-methylbenzoate in 50 ml of dioxane and 16 ml H$_2$O was added 1.44 ml of a 2.5% solution of osmium tetraoxide in t-butyl alcohol. The mixture was stirred for 15 minutes during which time it turned from colorless to brown. NaIO$_4$ (6.07 g, 28.38 mmol) was added in small portions over 30 minutes and the mixture was stirred at room temperature for 2.5 hours during which time a thick white precipitate formed. The reaction mixture was poured into 75 ml of H$_2$O, extracted with three 60 ml portions of ethyl ether, and the combined organic phase was washed with 100 ml of H$_2$O and brine and dried over MgSO$_4$. The solution was filtered and concentrated under vacuum to a tan oil which was purified by flash chromatography (100 g silica, 30% ethyl ether/hexane) to yield 1.25 g (50%) of product as a light yellow liquid.

Step 25d

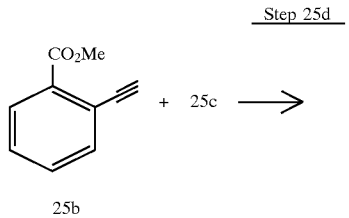

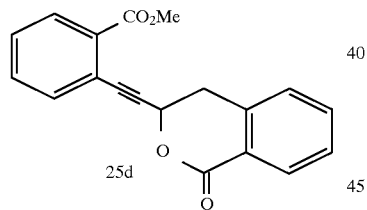

To a solution of 146 microliters of diisopropyl amine (1.04 mmol) in 9 ml of anhydrous THF cooled to −78° C. was added 0.59 ml of a 1.6M solution of n-butyl lithium, dropwise. The mixture was warmed to 0° C. for 20 minutes then cooled back to −78° C. A solution of 151 mg (0.94 mmol) of compound 25b in 1 ml of THF was added dropwise over 5 minutes, producing a yellow solution. The mixture was stirred at −78° C. for 45 minutes and a solution of 140 mg (0.79 mmol) of compound 25c in 1 ml of THF was added dropwise over 5 minutes. The mixture was stirred for 1.5 hours at −78° C., warmed to room temperature for 1.5 hours and then quenched with 10 ml of dilute NH$_4$Cl solution.

The mixture was diluted with 20 ml of H$_2$O and extracted with three 25 ml portions of ether. The organic phase was washed with 25 ml portions of 10% citric acid, H$_2$O, and brine and dried over MgSO . The solution was filtered and concentrated under vacuum to a brown oil. The residue was purified by flash chromatography (50 g silica, 20–30% ethyl acetate/hexane) to yield 52 mg (22%) of product as a yellow white solid. A sample was recrystallized from ether/hexane.

Step 25e

25d →

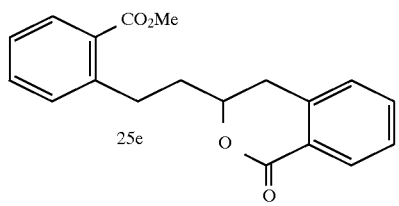

A suspension of 120 mg (0.39 mmol) of compound 25d and 5% palladium on carbon (96 mg) in 12 ml of ethyl acetate was stirred under an atmosphere of H$_2$ for 1.5 hours. The mixture was filtered through a pad of Celite which was washed with 25 ml of ethyl acetate and the solution was concentrated to a yellow viscous oil. The material was purified by flash chromatography (50 g of silica, 25–35% ethyl ether/hexane) to yield 109 mg (89%) of product as a colorless viscous oil.

Step 25f

25e →

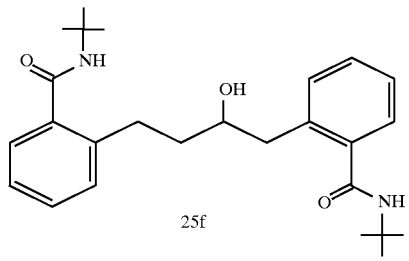

To a solution of 0.27 ml (2.58 mmol) of t-butyl amine in 6 ml of toluene at 0° C. was added 1.28 ml of a 2M solution of trimethylaluminum in toluene, dropwise over 5 minutes. The mixture was stirred for 45 minutes at room temperature and a solution of 85 mg (0.26 mmol) of compound 25e in 0.5 ml toluene was added dropwise. The solution was heated to 100° C. for 5 hours, cooled and quenched with saturated NH$_4$Cl solution. The aqueous phase was extracted three times with 20 ml portions of ethyl acetate. The combined organic phase was dried over MgSO$_4$, filtered and concentrated to a viscous yellow oil. The residue was purified by flash chromatography (40 g silica, 20–40% ethyl acetate/hexane) to yield 91 mg (83%) of product as a colorless viscous oil.

EXAMPLE 26

Preparation of

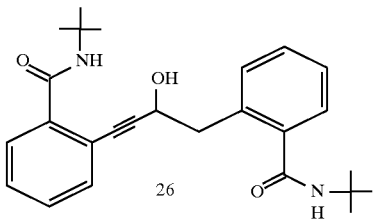

To a solution of 0.24 ml (2.3 mmol) of t-butyl amine (0.24 ml, 2.3 mmol) in 4 ml toluene at 0° C. was added 1.4 ml of a 2.0M solution of trimethylaluminum in toluene, dropwise over 5 minutes. The mixture was stirred for 45 minutes at room temperature and a solution of 70 mg (0.23 mmol) of compound 25d in 2 ml toluene was added, dropwise. The solution was heated to 70° C. for 24 hours, cooled and quenched with saturated $NH_4Cl$ solution. The aqueous phase was extracted three times with 20 ml portions of ethyl acetate. The combined organic phase was dried over $MgSO_4$, filtered and concentrated to a viscous orange oil. The residue was purified by flash chromatography (20 g silica, 20–40% ethyl acetate/hexane) to yield 31 mg (32%) of product 26 as a colorless glass.

EXAMPLE 27

Preparation of

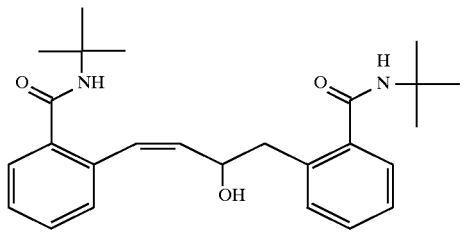

A suspension of 20 mg (0.0489 mmol) of compound 26, 20 μl of quinoline and Lindlar catalyst (6.0 mg) in 3 ml of ethyl acetate was stirred under an atmosphere of $H_2$ for 4 hours. The mixture was then filtered through Celite and the filter pad washed with 20 ml ethyl acetate. The solution was concentrated under vacuum and purified by flash chromatography (15 g silica, 25–40% ethyl acetate/hexane) to yield 17 mg (84%) of the cis isomer of the product 27 as a white solid.

EXAMPLE 28

Preparation of

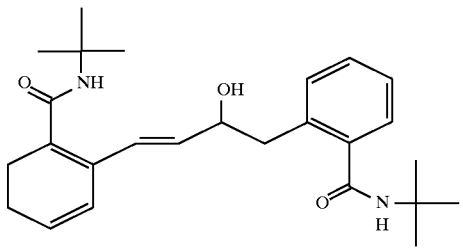

-continued

Step 28a

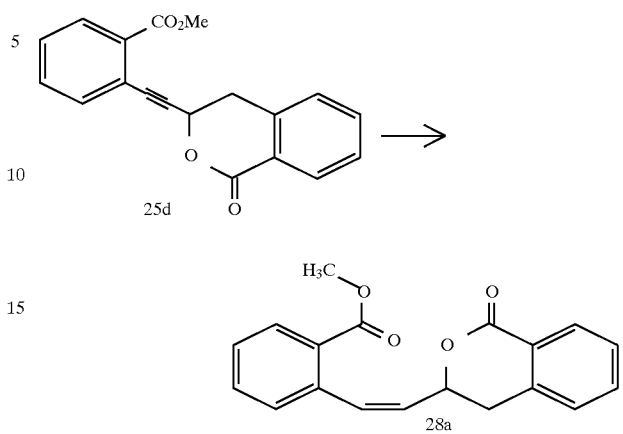

A suspension of 236 mg (0.77 mmol) of compound 25d, quinoline (60 μl), and Lindlar catalyst (55 mg) in 15 ml of ethyl acetate was stirred under an atmosphere of $H_2$ for 1 hour. The mixture was filtered through Celite and the filter pad washed with 50 ml ethyl acetate. The solution was concentrated to a yellow oil which was purified by flash chromatography (75 g of silica gel, 15–30% ethyl acetate/hexane) to yield a white solid which was triturated with ethyl ether/hexane (to remove traces of quinoline) to yield 208 mg (87%) of product 28a as a white solid.

Step 28b

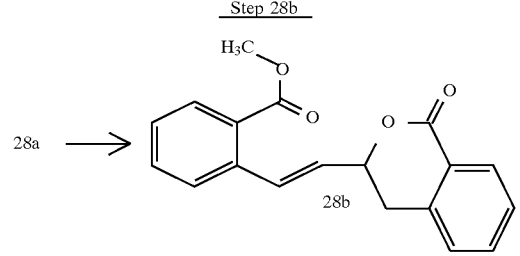

A solution of 150 mg (0.49 mmol) of compound 28a, 6.5 mg of AIBN, and 80 microliters of thiophenol in 12 ml of benzene was heated to reflux for 4 hours. After 2.5 hours, another portion of AIBN (6 mg) was added. The solution was cooled and concentrated. The residue was purified by flash chromatography (80 g silica, 10–30% ethyl acetate/hexane) to yield 112 mg (77%) of product as a white solid.

Step 28c

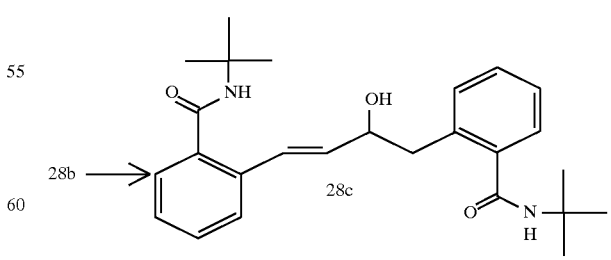

To a solution of 0.17 ml (1.6 mmol) of t-butyl amine in 3 ml of toluene at 0° C. was added 0.81 ml of a 2.0M solution of trimethylaluminum (1.6 mmol), dropwise over 5 minutes. The mixture was stirred for 45 minutes at room temperature and 50 mg (0.16 mmol) of compound 28b in 1 ml of toluene was added dropwise. The solution was heated to 70° C. for 5 hours, cooled and quenched with saturated NH₄Cl solution. The aqueous phase was extracted three times with 20 ml portions of ethyl acetate. The combined organic phase was dried over MgSO₄, filtered and concentrated to a viscous orange oil. The residue was purified by flash chromatography (15 g of silica, 20–45% ethyl acetate/hexane) to yield 33 mg (48%) of product as a white solid.

EXAMPLE 29

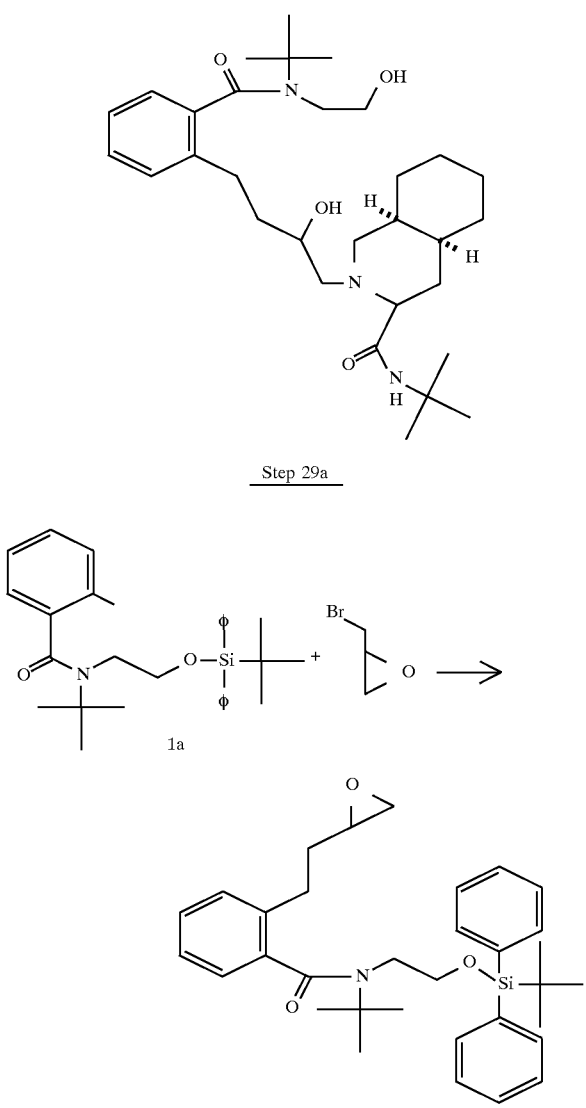

A solution of 285 mg (0.6 mmol) of compound 1a and 13 microliters of diisopropyl amine in 8.5 ml of anhydrous THF was cooled to −78° C. and 0.53 ml of a 1.3M solution of s-butyllithium in THF was added slowly over 10 minutes. The resultant purple solution was stirred at −78° C. for 1 hour and 0.14 ml (1.69 mmol) of epibromohydrin was added dropwise. The reaction mixture was stirred an additional 1 hour at −78° C., then allowed to warm to room temperature. Total reaction time was 4.5 hours after which the reaction mixture was quenched by pouring into 30 ml of dilute NH₄Cl solution. The aqueous phase was extracted with three 20 ml portions of ether. The combined organic phase was washed with 20 ml H₂O and dried over MgSO₄. The solution was filtered and concentrated under vacuum to a nearly colorless oil which was purified by flash chromatography (60 g of silica, 25–50% ethyl ether/hexane) to yield 180 mg (57%) of product as a colorless viscous oil.

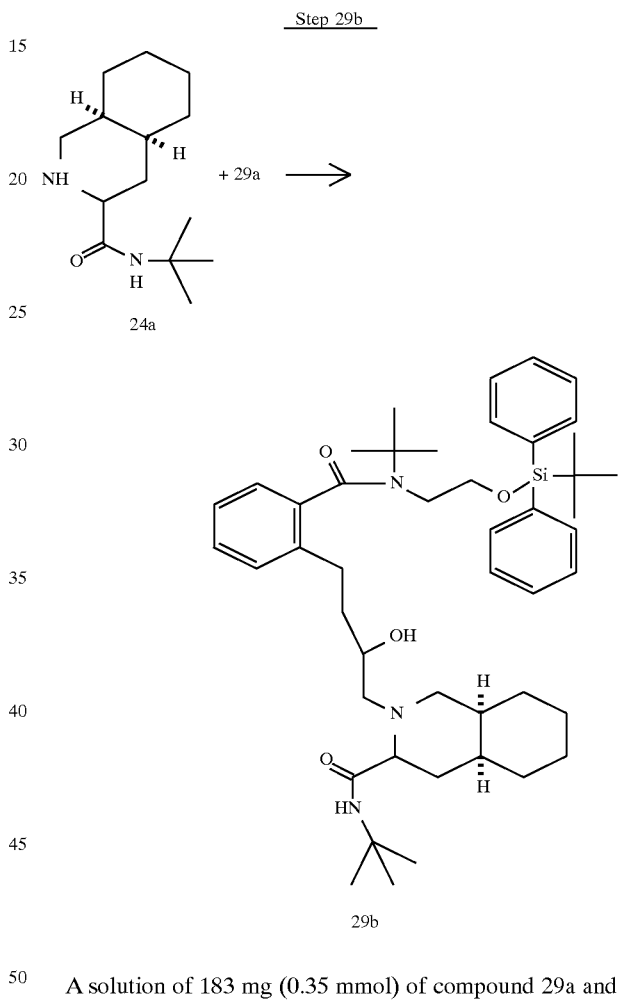

A solution of 183 mg (0.35 mmol) of compound 29a and 75 mg (0.32 mmol) of compound 24a (decahydro isoquinoline) in 4 ml of ethanol was heated to 60° C. for 29 hours. The mixture was then cooled and concentrated under vacuum to a colorless foam. The foam was purified by flash chromatography (50 g silica, 15–40% ethyl acetate/hexane) to yield the product as two separable diastereomers. The less polar product (110 mg) was a colorless, viscous oil. The more polar product (108 mg) was also a colorless, viscous oil. Total yield was 219 mg (91%).

Step 29c

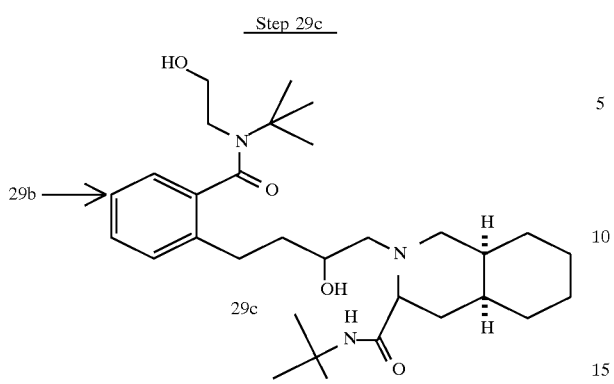

To a solution of 90 mg (0.12 mmol) of the less polar isomer of compound 29b in 3 ml THF was added 0.23 ml of a 1.0M solution of tetrabutylammonium fluoride in THF and the reaction mixture was stirred at room temperature for 45 minutes. The reaction mixture was then diluted with 25 ml of $CH_2Cl_2$. The organic phase was washed with 15 ml portions of $H_2O$, saturated $NaHCO_3$, and brine, then dried over $MgSO_4$. The solution was filtered and concentrated under vacuum to a white foam which was purified by flash chromatography (15 g silica, 2% MeOH/$CH_2Cl_2$ containing a trace of MeOH saturated with $NH_3$) to yield 49 mg (79%) of the product as a white stiff foam.

EXAMPLE 30

Preparation of

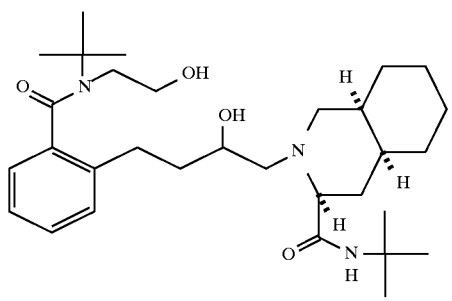

To a solution of 90 mg (0.12 mmol) of the more polar isomer of compound 29c in 3 ml THF was added 0.23 ml of 1.0M tetrabutylammonium fluoride in THF and the reaction mixture was stirred at room temperature for 35 minutes, then diluted with 25 ml of $CH_2Cl_2$. The organic phase was washed with 15 ml portions of $H_2O$, saturated $NaHCO_3$, and brine, then dried over $MgSO_4$. The solution was filtered and concentrated under vacuum to a white foam which was purified by flash chromatography (10 g of silica, 2% MeOH/$CH_2Cl_2$ containing a trace of MeOH saturated with $NH_3$) to yield 38 mg (61%) of the product as a white stiff foam.

EXAMPLE 31

Preparation of

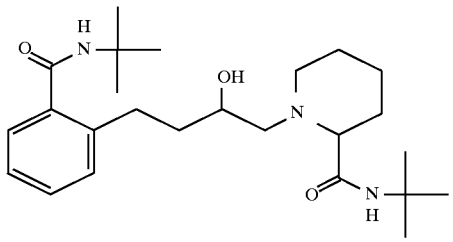

Step 31a

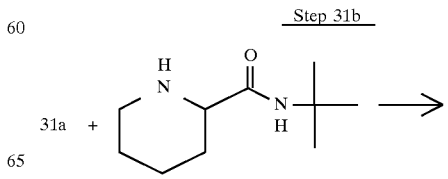

A flame dried 100 ml 3-neck flask was purged with argon, and charged with 2.0 gm (10.4 mmol) of N-t-butyl toluamide, 3.47 ml of TMEDA and 25 ml of THF. The mixture was cooled in a dry ice/acetone bath and 14.4 ml of a 1.6M solution of n-butyl lithium in hexane was added over a 20 minute period while maintaining the temperature below −65° C. After an additional hour of stirring at the dry ice/acetone temperature, the now deep orange solution was cannulated over 5 minutes into a solution of 15 ml of 5.7 gm of epibromohydrin in 15 ml of THF. A clear, light orange solution resulted. The reaction flask was transferred to a glycol/dry ice bath (−12: −15° C.) and stirred for about 70 minutes. At this time, the reaction was quenched with about 9 ml of 0.5N $NH_4Cl$, then poured into 150 ml brine, extracted twice with 50 ml portions of ethyl acetate and dried over $Na_2SO_4$. After filtering and vacuum removal of solvent, 7.38 gm of waxy, orange solid was recovered. This solid was purified by flash chromatography using 20% THF in hexane. Appropriate fractions were combined and filtered and solvent was removed by vacuum, yielding 685 mg (32%) of product.

Step 31b

-continued

Step 31b

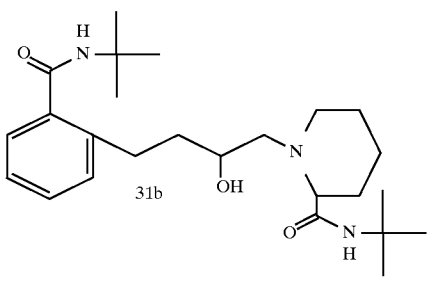

A solution of 75 mg (0.3 mmol) of compound 31a and 62 mg (0.33 mmol) of compound 22c in 4 ml of ethanol was heated to reflux for 24 hours. The reaction mixture was cooled and concentrated under vacuum to a yellow foam. The residue was purified by flash chromatography (15 g silica, 40–50% ethyl acetate/hexane containing 1.5% MeOH saturated with NH$_3$) to yield the product as two diastereomers. The less polar isomer, not pure by TLC, was rechromatographed (10 g silica, 40–50% ethyl acetate/hexane containing 0.5% MeOH saturated with NH$_3$) to yield 20 mg as a white solid. The more polar isomer was pure after the first chromatography (35 mg as a white solid). Total yield 55 mg (43%).

EXAMPLE 32

Preparation of

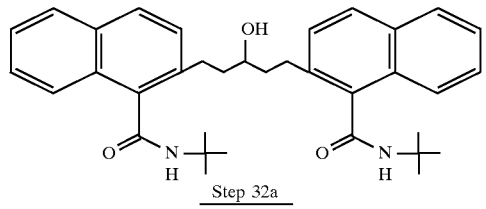

Step 32a

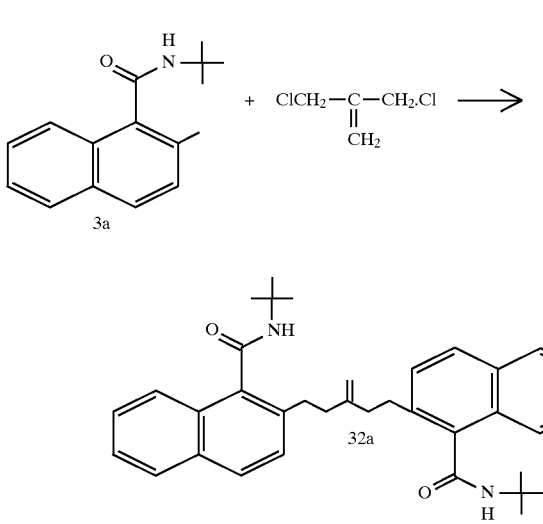

To a solution of 600 mg (2.49 mmol) of compound 3a and 0.75 ml of tetramethylethylenediamine in 15 ml of anhydrous THF, cooled to −78° C., was added 3.11 ml of a 1.6M solution of n-BuLi in hexane, dropwise, over 10 minutes. The solution was stirred at −78° C. for 45 minutes and 0.14 ml (1.25 mmol) of 1,3-dichloroisobutene was added, dropwise. The mixture was allowed to warm to −30° C., then poured into 30 ml of dilute NH$_4$Cl solution. The aqueous phase was extracted with three 25 ml portions of ethyl acetate. The combined organic phase was washed with 30 ml portions of 10% citric acid solution, H$_2$O, and brine, then dried over MgSO$_4$. The solution was filtered and concentrated to a yellowish white solid which was purified by flash chromatography (100 g of silica, 1.5–10% ethyl acetate/CH$_2$Cl$_2$) to yield 370 mg (56%) of product as a white solid.

Step 32b

32a →

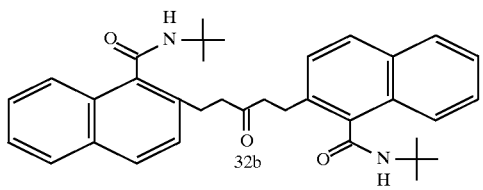

To a solution of 60 mg (0.11 mmol) of compound 32a in 2 ml dioxane and 0.5 ml H$_2$O, was added one drop of 2.5% OsO$_4$ solution in t-butyl alcohol. The mixture was stirred for 15 minutes and 48 mg (0.22 mmol) of NaIO$_4$ was added in one portion. The mixture was stirred at room temperature for 20 hours, then poured into 15 ml of H$_2$O and the aqueous mixture was extracted with three 15 ml portions of ether. The combined organic phase was washed with 10 ml portions of H$_2$O and brine, then dried over MgSO$_4$. The solution was filtered and concentrated to a viscous yellow oil which was purified by flash chromatography (10 g silica, 30–40% ethyl acetate/hexane) to yield 40 mg (67%) of product as a white solid.

Step 32c

32b →

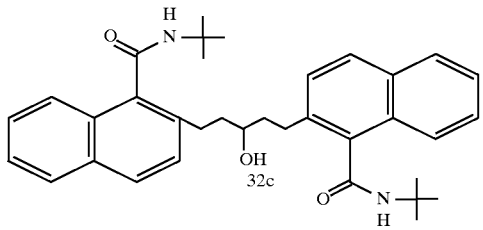

To a solution of 35 mg (0.065 mmol) of compound 32b in 2 ml of MeOH was added 3 mg (0.078 mmol) of NaBH$_4$ in one portion. The reaction was stirred for 15 minutes at room temperature, then poured into 10 ml of saturated NaHCO$_3$ solution. The aqueous phase was extracted with two 15 ml portions of ethyl acetate, the combined organic phase was washed with 10 ml of H$_2$O and dried over MgSO$_4$. The organic phase was then filtered and concentrated to a white foam which was purified by flash chromatography (10 g of silica, 30–40% ethyl acetate/hexane) to yield 29 mg (83%) of product as a white solid.

EXAMPLE 33

Preparation of

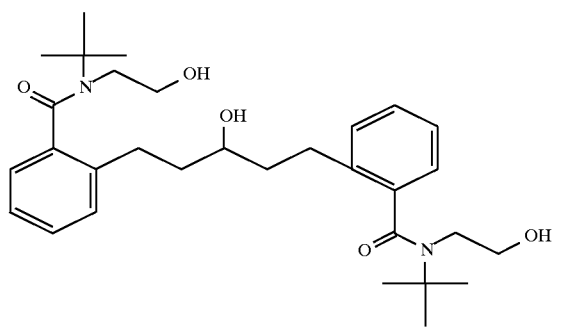

Step 33a

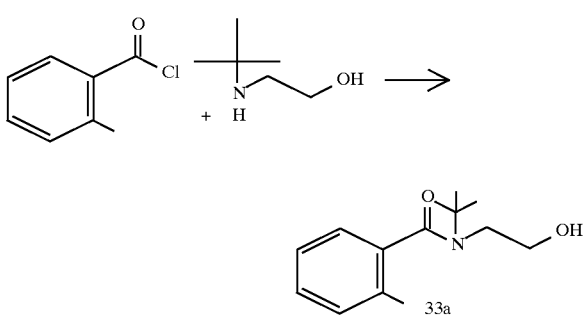

To a solution of 4.97 gm (0.043 mole) of hydroxyethyl-t-butyl amine and 18 ml of trimethyl amine in 100 ml of $CH_2Cl_2$, cooled to 0° C., was added 11 ml (0.085 mole) of o-toluoyl chloride, dropwise. The reaction mixture was allowed to warm to room temperature and was stirred for 24 hours. The reaction was then quenched by pouring the reaction mixture into 100 ml of $H_2O$ and extracted once with 100 ml of $CH_2Cl_2$. The organic phase was washed with 100 ml portions of $H_2O$, 10% citric acid, $H_2O$, and saturated $NaHCO_3$, then dried over $MgSO_4$. The dried solution was filtered and concentrated under vacuum to a viscous yellow oil which was dissolved in 100 ml of 90% aqueous methanol. To this solution was added 5.5 ml of 45% KOH and the mixture was kept at room temperature for 45 minutes. It was then concentrated under vacuum, diluted with 100 ml of $H_2O$ and extracted three times with 100 ml portions of diethyl ether. The combined organic phases were dried over $MgSO_4$, then filtered and concentrated under vacuum to a light yellow oil. This oil was dissolved in a 30% ethyl acetate/hexane mixture. The product was crystallized from this solution in two crops to yield 6.5 gm (64% yield).

Step 33b

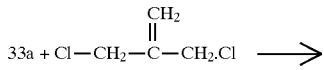

-continued
Step 33b

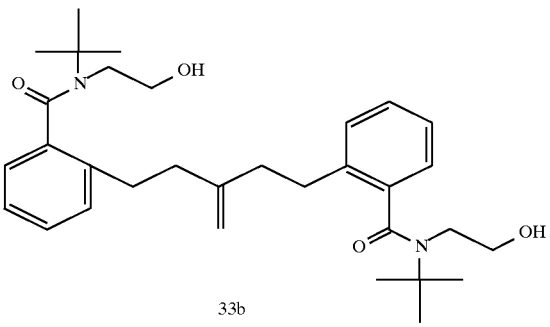

To a solution of 1.58 gm (7.21 mmol) of compound 33a and 0.15 ml of diisopropyl amine in 30 ml of anhydrous THF, cooled to −78° C., was added 14 ml of a 1.3M solution of s-BuLi (1.3M, 14 ml, 15.5 mmol) in hexane, dropwise over 5 minutes. The solution was stirred at −78° C. for 45 minutes and 0.42 ml (3.6 mmol) of 1,3-dichloroisobutene was added, dropwise. The solution was stirred at −78° C. for 1.5 hours and the reaction was then quenched by the addition of 75 ml of dilute $NH_4Cl$ solution and the aqueous phase was extracted with two 60 ml portions of ethyl acetate. The combined organic phase was washed with 50 ml portions of 10% citric acid, $H_2O$ and brine, then dried over $MgSO_4$. The solution was filtered and concentrated to a colorless foam which was purified by flash chromatography (200 g silica, 50–65% ethyl acetate/hexane) to yield 0.50 g (28%) of product as a colorless, viscous oil.

Step 33c

33b ⟶

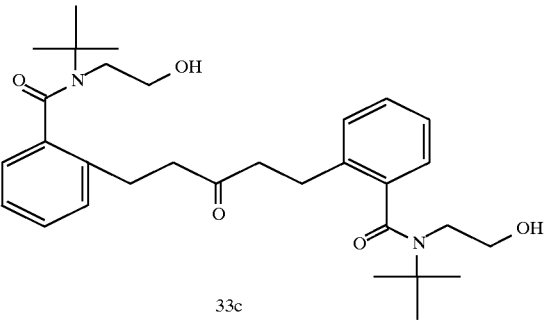

To a solution of 250 mg (0.48 mmol) of compound 33b in 10 ml of dioxane and 5 ml of $H_2O$ was added two drops of 2.5% $OsO_4$ solution in t-butyl alcohol. The mixture was stirred for 15 minutes and 308 mg (1.44 mmol) of $NaIO_4$ was added over 30 minutes and the mixture was then stirred at room temperature for 20 hours. The reaction mixture was poured into 30 ml of $H_2O$ and the aqueous mixture was extracted with three 20 ml portions of ethyl acetate. The combined organic phase was washed with 25 ml portions of $H_2O$ and brine, then dried over $MgSO_4$. The solution was filtered and concentrated to a viscous brown oil which was purified by flash chromatography (50 g silica, 1–15% ethyl acetate/ethyl ether) to yield 180 mg (71%) of product as a viscous oil.

Step 33d

33c ⟶

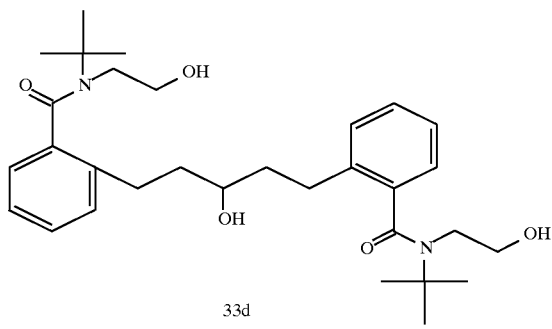

33d

To a solution of 110 mg (0.21 mmol) of compound 33c in 5 ml of methanol was added 48 mg (1.26 mmol) of NaBH$_4$ in one portion. The reaction mixture was stirred for one hour at room temperature and then poured into 15 ml of saturated NaHCO$_3$ solution. The aqueous phase was extracted three times with 15 ml portions of ethyl acetate. The combined organic phase was washed with 10 ml of water, then dried over MgSO$_4$. The organic solution was filtered and concentrated under vacuum to a white foam. This foam was purified by flash chromatography (15 g silica, 10–25% ethyl acetate/ether) to yield 70 mg (35%) of product as a stiff white foam.

EXAMPLE 34

Preparation of

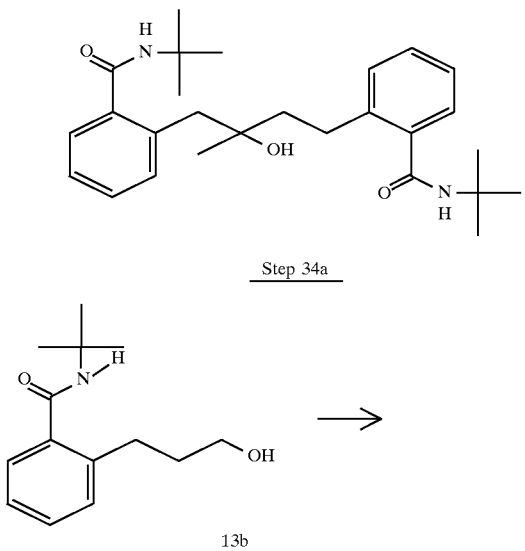

Chromium trioxide (14.4 gm, 144 mmol) was added slowly to 23.3 ml of pyridine and the mixture was diluted with 300 ml CH$_2$Cl$_2$. The alcohol 13b (6.16 gm, 26.2 mmol) was added to the chromium trioxide solution at 25° C. and the reaction was stirred for 2 hours. After dilution with ether, the reaction was washed twice with 150 ml of 1N HCl, 1N NaOH, saturated NaHCO$_3$, and brine. Drying over MgSO$_4$ and concentration afforded a yellow oil, which chromatographed on silica (1:1 ether/hexane), yielding 4 gm (65%) of aldehyde 34a as a white amorphous solid. The structure was confirmed by NMR.

Step 34b

34a ⟶

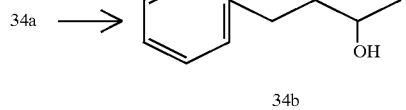

34b

To 764 mg (6.42 mmol) of methyl magnesium bromide in 10 ml of dry ether was added 500 mg (2.14 mmol) of compound 34a in 15 ml of dry ether at 0° C., resulting in a milky white solution. The ice bath was removed and the mixture was warmed to room temperature. After 1 hour at room temperature, TLC indicated that some starting material remained. Another equivalent (119 mg) of methyl magnesium bromide was added and the solution changed from milky white to clear. The reaction was quenched with ice and 1N HCl, extracted with ethyl acetate and ether, washed with brine, then dried over MgSO$_4$. Concentration under vacuum yielded 576 mg of a clear oil which was then purified by flash chromatography (SiO$_2$: 2/1 ether-hexane) yielding 358 mg (76%) of product.

The structure was confirmed by 'HNMR.

Step 34c

34b ⟶

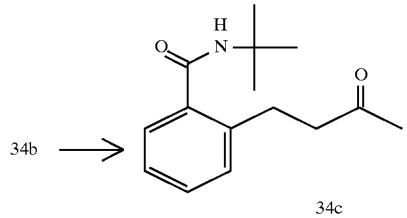

34c

CrO$_3$ (580 mg—5.8 mmol) was added to 1 mL of pyridine and a paste formed with exotherm. Three ml of CH$_2$Cl$_2$ were added and the mixture was stirred for 10 minutes more. An additional 12 ml of CH$_2$Cl$_2$ were added (total=15ml) and (360 mg, 1.4 mmol) of compound 34b in 3 ml of CH$_2$Cl$_2$ was added, dropwise. The solution turned dark. After 1 hour, TLC indicated that about 20% of the starting material remained. An additional 2 equivalents of the CrO$_3$/pyridine reagent in 3 mL of CH$_2$Cl$_2$ was added. The reaction was essentially complete after 3 more hours. The reaction mixture was diluted with ether and CH$_2$Cl$_2$ and filtered through SiO$_2$ and concentrated under vacuum to yield 309 mg of a white solid, which was purified by flash chromatography (SiO$_2$, 1:1 ether/hexane) yielding 228 mg (66%) of the product as a white solid.

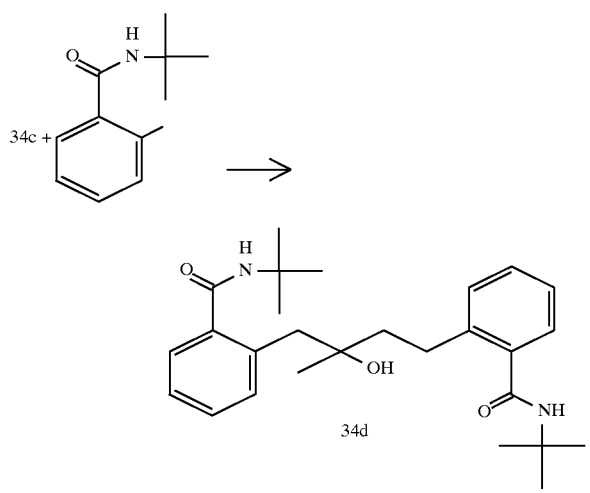

To 281 mg (1.47 mmol) of N-t-butyl toluamide, which had been pumped down on highvac equipment, was added 341 mg (2.93 mmol) of TMEDA and 8 ml of THF. The mixture was cooled to −78° C. using a dry ice/acetone bath, and s-butyl lithium (2.7 ml, 2.93 mmol) was added dropwise. The color turned to deep orange. The mixture was stirred at −78° C. for 45 minutes, at which time 165 mg (0.667 mmol) of compound 34c in 5 ml of THF was added via cannula. The color changed to light orange. The temperature was allowed to rise to −30° C. at which point the color disappeared. The reaction was quenched with 1N HCl, washed with brine, extracted with $CH_2Cl_2$ and dried over $MgSO_4$. Concentration under vacuum yielded 550 mg of clear oil. The oil was purified by flash chromatography using initially 1:1 ether/hexane, changing to 2:1 ether/hexane solvent, yielding 41 mg of product (14% yield).

EXAMPLE 35

Preparation of

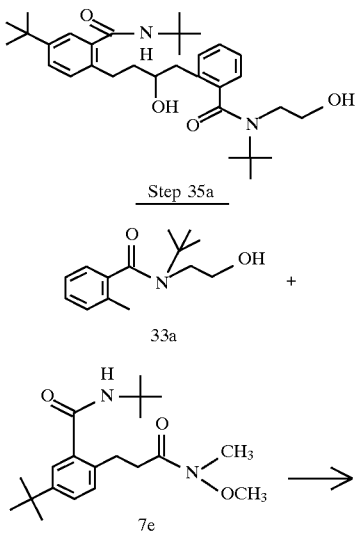

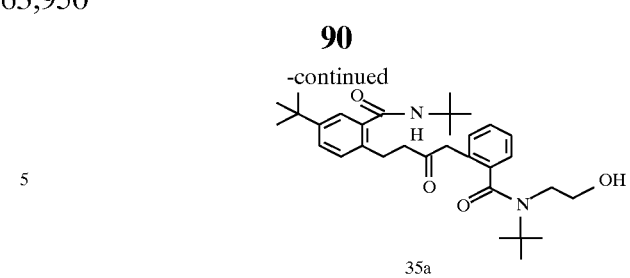

s-Butyl lithium (1.34 ml, 1.34 mmol) was added to a solution of 0.158 gm (0.67 mmol) of compound 33a and 28 μl of diisopropyl amine in THF at −78° C. A red color started to develop after about 70 μl of s-butyl lithium had been added. After all of the s-BuLi was added, solution became deep blue. The mixture was stirred at −78° C. for 1 hour, then 0.117 gm (0.335 mmole) of compound 7e in 1 ml of THF was added, dropwise. After about 30 minutes the solution became less colored (deep blue changed to very light blue). The reaction mixture was quenched 40 minutes later. The product was purified by flash chromatography. The chromatography was carried out twice; first with 70:30 methylene chloride/ethyl acetate, then with 80:20 methylene chloride/acetone. The yield was 87 mg (50%) of product.

Step 35b

35a →

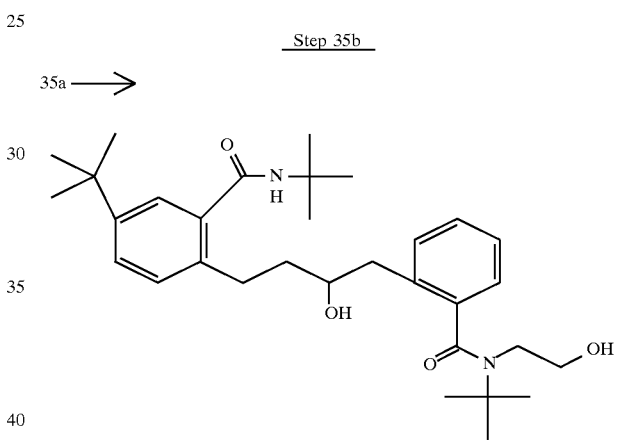

$NaBH_4$ (13.5 mg, 0.3 mmol) was added to a solution of 0.8 gm(0.15 mmol) of compound 35a in 2 ml of EtOH at room temperature and the solution was stirred for 0.5 hour. TLC analysis showed reaction was complete. The mixture was then quenched with $H_2O$ and extracted with ethyl acetate and the organic phase was dried over $MgSO_4$. Removal of solvent under vacuum yielded 0.077 g of a white solid. Purification by flash chromatography using SiO with 70% $CH_2Cl_2$/30% ethanol solvent, yielded 44 mg (78.7%) of clean product. ¹HNMR confirmed the structure.

EXAMPLE 36

Preparation of

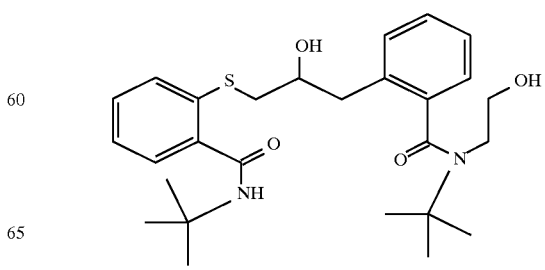

Step 36a

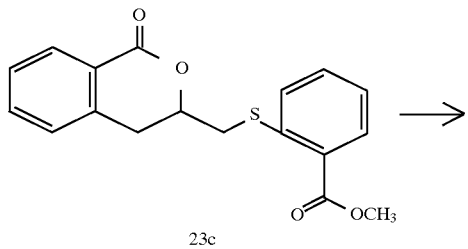
23c

→

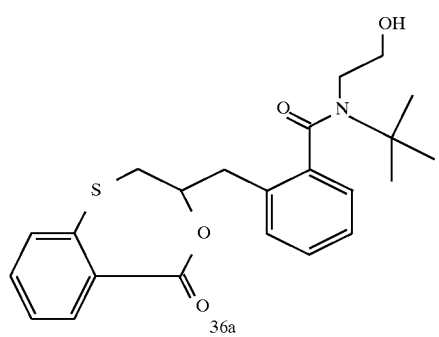
36a

To a solution of 0.86 g (7.32 mmol) of N-t-butyl-ethanol amine in 30 ml of toluene was added 3.66 ml of a 2M solution of trimethylaluminum at 0° C. and the mixture was stirred at room temperature for 45 minutes. A solution of 0.40 g (1.22 mmol) of compound 23c in 5 ml CH$_2$Cl$_2$ was added and the mixture was heated to 90° C. for 18 hours. The reaction mixture was cooled and quenched with 20 ml of saturated NH$_4$Cl solution. The mixture was then extracted three times with 30 ml portions of ethyl acetate and the combined organic phase was dried over MgSO$_4$. The solution was filtered and concentrated under vacuum to a yellow viscous oil which was purified by flash chromatography (75 g silica gel, 5–10% ethyl acetate/CH$_2$Cl$_2$) to yield 0.16 g (32% yield) of the product as a white solid.

Step 36b

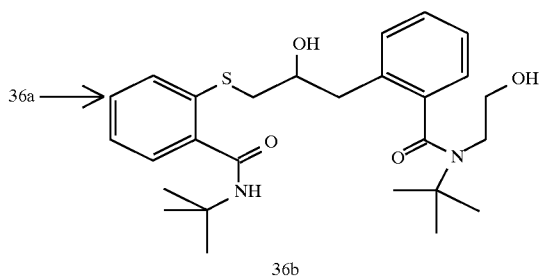
36b

To a solution of 170 mg (1.45 mmol) of t-butyl amine in 5 ml of toluene cooled to 0° C. was added, dropwise, 0.73 ml of 2M solution of trimethylaluminum in toluene. The mixture was stirred at room temperature for 45 minutes and 60 mg (0.5. mmol) of compound 23c in 1 ml of dichloroethane was added, dropwise. The mixture was heated for 5 hours at 110° C., cooled and quenched with 10 ml of saturated NH$_4$CL solution. The mixture was extracted three times with 15 ml portions of ethyl acetate and the combined organic phases were dried over Na$_2$SO$_4$. The solution was filtered and concentrated to a viscous yellow oil, which was purified by flash chromatography using 15–30% ethyl acetate/methylene chloride and 20 gm of silica gel to yield to 45 mg (76%) of product as a viscous oil.

EXAMPLE 37

Preparation of

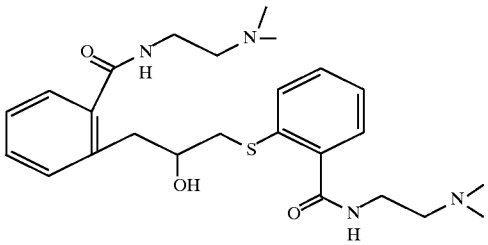

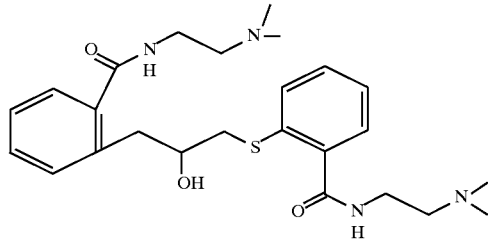
23c

→

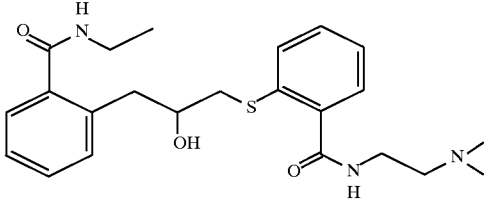

To a solution of 0.12 ml (1.09 mmol) of TMEDA in benzene at 0° C. was added 0.53 ml (1.06 mmol) of trimethyl aluminum and the solution was heated to room temperature for 1 hour. A solution of 0.07 g of compound 23c in 1 ml of benzene was added. The mixture was heated to reflux for about 40 minutes, allowed to cool slowly to room temperature and was then stirred overnight. Reflux was then continued for 2 more hours at which time TLC indicated that the reaction was complete. The reaction mixture was poured into 20 ml of water, extracted twice with 100 ml portions of ethyl acetate, dried over MgSO$_4$ and concentrated under vacuum. Yield was 0.84 g of material which was purified by flash chromatography (8% NH$_3$-methanol/methylene chloride) yielding 0.65 g (65%) of product. The structure was confirmed by NMR.

EXAMPLE 38

Preparation of

93

-continued
Step 38a

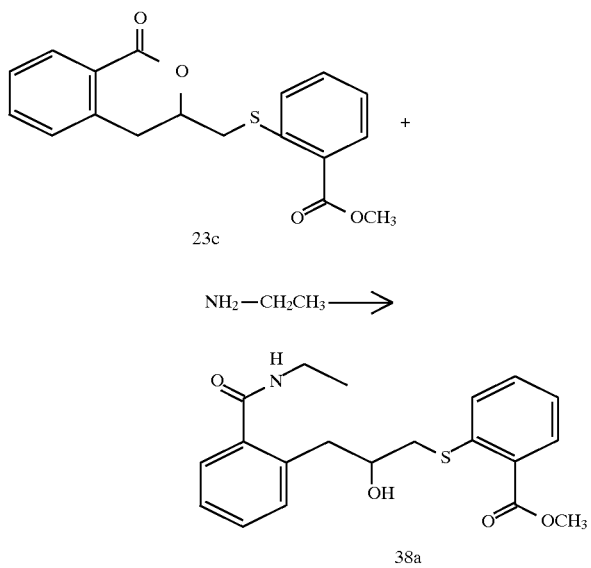

A suspension of 0.075 g (0.918 mmol) of ethylamine hydrochloride in 2 ml of benzene was cooled to 0° C. and 0.46 ml (0.92 mmol) of trimethyl aluminum was added. The solution was warmed to room temperature and stirred for 1 hour. It was then cooled in an ice bath and a solution of 0.15 g (0.461 mmol) of compound 23c in 2 ml of benzene was added. The solution was then warmed to room temperature and the reaction was allowed to continue overnight. The reaction was complete in the morning. It was poured into 0.5N HCl, extracted twice with ethyl acetate, washed with brine, dried over $Na_2SO_4$ and concentrated under vacuum. Yield was 0.166 g. The product was purified by flash chromatography (10% ethyl acetate/methylene chloride) yielding 0.133 g (77%) of an oil. NMR confirmed the structure of the product.

Step 38b

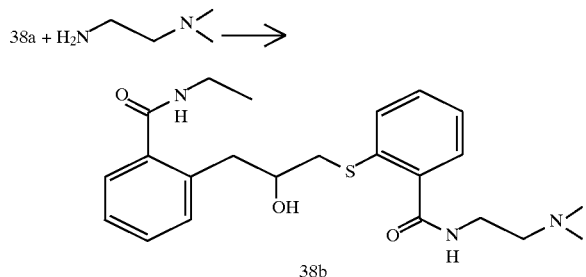

A solution of 0.4 ml (0.364 mmol) of N-N-dimethylethylenediamine in 2 ml of benzene at 0° C. was added to 1.8 ml (0.36 mmol) of trimethyl aluminum. The mixture was warmed to room temperature and allowed to stir for 1 hour at which time 0.066 g (0.177 mmol) of compound 38a in 1 ml of benzene was added. The mixture was heated to reflux for 2 hours, at which time TLC indicated the reaction was complete. The mixture was then poured into 20 ml of water, extracted twice with 100 ml portions of ethyl acetate, dried over $MgSO_4$ and concentrated under vacuum, yielding 0.058 g of product which was then purified by flash chromatography (5% methanol/methylene chloride changing to 1% $NH_3$-methanol/50%

94 methanol/methylene chloride). The yield was 0.04 g (53% of a white solid). The structure was confirmed by NMR.

EXAMPLE 39

Preparation of

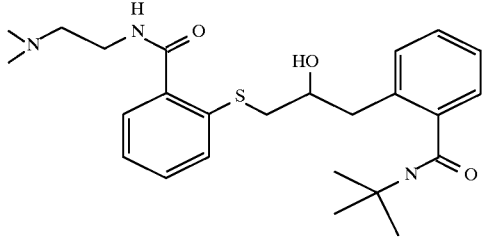

Step 39a

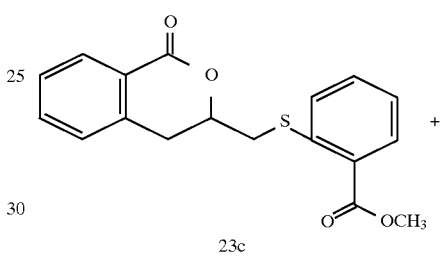

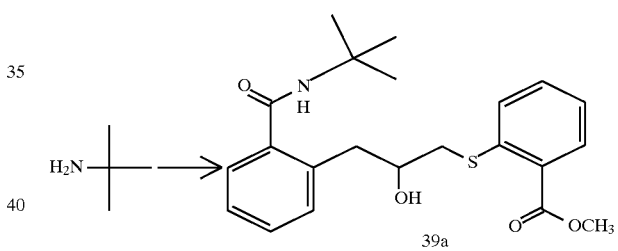

To a solution of 0.13 ml (1.237 mmol) of t-butylamine in 2 ml of benzene at 0° C. was added 0.6 ml (1.2 mmol) of trimethylaluminum. The solution was warmed to room temperature and stirred for 1 hour at which time 0.2 g (0.608 mmol) of compound 23c in 2 ml of benzene was added. After 4 hours, the reaction was warmed to 40° C.; after 2 more hours, TLC indicated the reaction about 90% complete. The reaction mixture was then allowed to cool to room temperature overnight and the reaction was complete by morning. The mixture was then poured into 0.5N HCl, extracted twice with ethyl acetate, dried over $MgSO_4$ and concentrated under vacuum. Purification by flash chromatography (10% ethyl acetate/methylene chloride) yielded 0.165 g (68%) of a yellow-white solid. Structure was confirmed by NMR.

Step 39b

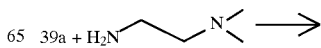

-continued
Step 39b

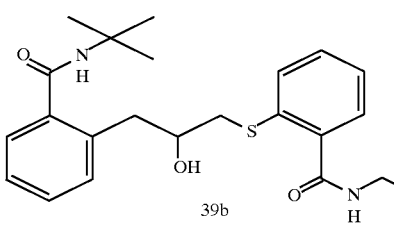

39b

To a solution of 0.05 gm (0.124 mmol) of compound 39a and 0.3 ml (0.273 mmol) of N-N-dimethylethylenediamine in 2 ml benzene at 0° C. was added 0.125 ml (0.25 mmol) of trimethylaluminum. The mixture was warmed to room temperature and stirred for 1 hour. A solution of 0.05 gm of compound 39a in 1 ml of benzene was added and the mixture was heated to reflux for about 2 hours. At this time, it was poured into 10 ml of water and extracted twice with 50 ml portions of ethyl acetate, then dried over MgSO$_4$, and concentrated under vacuum. Crude weight of product was 0.064 gm, which was purified by flash chromatography (10% methanol/methylene chloride) yielding 0.448 gm (78%) of a white solid. Structure of the product was confirmed by NMR.

EXAMPLE 40
Preparation of

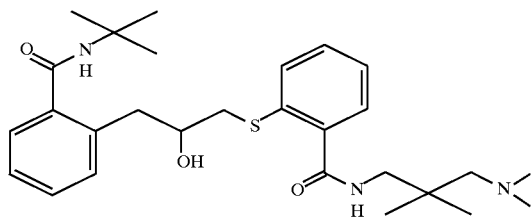

To a solution of 0.42 ml (0.251 mmol) of N-N-dimethylneopentyldiamine in 2 ml of benzene at 0° C. was added 0.125 ml (0.25 mmol) of trimethylaluminum. The solution was warmed to room temperature and stirred for 1 hour at which time 0.05 g (0.124 mmol) of compound 39a in 1 ml of benzene was added. The mixture was heated to reflux for about 1 hour and worked up as described for example 39, step b. Purification was effected by flash chromatography, using 8% methanol/methylene chloride. Yield was 0.058 gm (87%) of the product as an oil which solidified after pumping down. The structure was confirmed by NMR.

EXAMPLE 41
Preparation of

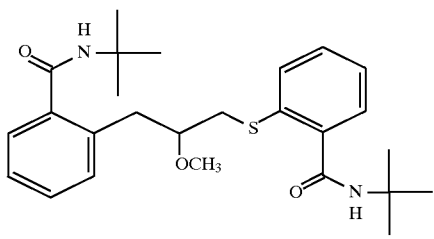

To a solution of 0.0366 g (0.083 mmol) of compound 23 in 0.5 ml of DMSO at room temperature was added 0.1 g (0.151 mmol) of 85% potassium hydroxide solution and 0.1 ml (1.61 mmol) of iodomethane. The reaction mixture was stirred for about 30 minutes then diluted with ethyl acetate, washed twice with water, dried over MgSO$_4$ and concentrated. Purification by flash chromatography (40% ethyl acetate/hexane) yielded 0.33 g (88%) of a white solid. Structure was confirmed by NMR.

EXAMPLE 42
Preparation of

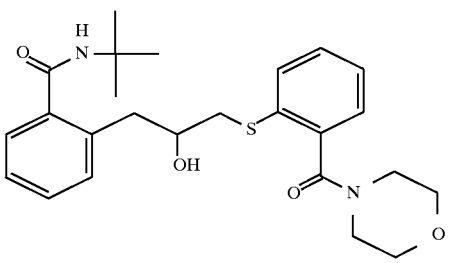

A solution was prepared of 0.56 ml (1.12 mmol) of trimethylaluminum and 0.1 ml (1.15 mmol) of morpholine in 2 ml of toluene at 0° C. The solution was warmed to room temperature and stirred for 1 hour at which point 0.091 g (0.0225 mmol) of compound 39a in 2 ml of toluene was added. The reaction mixture was heated to reflux for 45 minutes whereupon all starting material had been consumed. The mixture was cooled, poured into water, extracted three times with a total of 100 ml of ethyl acetate, dried over MgSO$_4$ and concentrated under vacuum. The yield was 0.118 g of crude material. Purification by flash chromatography (40% ethyl acetate/hexane) yielded 49 mg of a first product and 35 mg of a second product. Both were yellow-white foams. The products were vacuum pumped overnight and NMR confirmed that the second product was the desired compound.

EXAMPLE 43
Preparation of

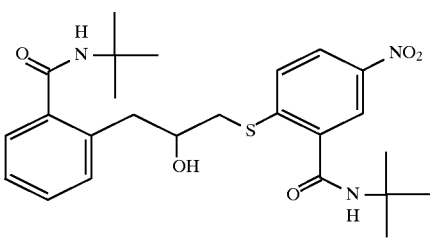

Step 43a

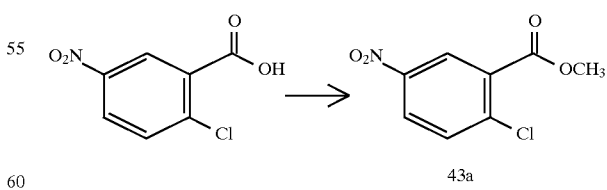

43a

A mixture of 1.0 g (50 mmol) of 1 chloro-4-nitrobenzoic acid in 100 ml of 3% HCl in methanol was stirred at room temperature for 1 hour then heated to reflux for a total of 5 hours. At this time the reaction was substantially complete. It was cooled and concentrated under vacuum to a yellow white solid which was dissolved in ethyl acetate, washed sequentially with saturated NaHCO$_3$, water and then brine. The extract was dried over MgSO$_4$, concentrated under vacuum to 9.2 g (45 mmol, 85%) of a white solid. Structure of the solid was confirmed by NMR.

Step 43b

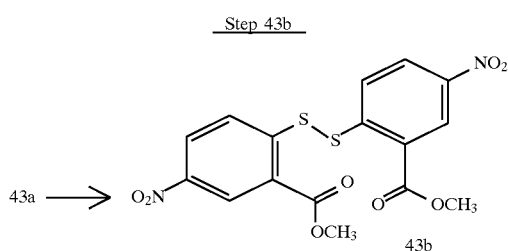

A solution of 5 g (23.2 mmol) of compound 43a in 50 ml of DMSO was reacted with NaSH at 50° C. A large quantity of solid formed. An additional 20 ml of DMSO was added and the reaction mixture was heated to 80° C. A dark brown mixture was formed and after 6 hours TLC indicated that all of the starting material had been consumed. The mixture was allowed to cool slowly and was stirred over a weekend. A brown sludge was poured slowly into water while stirring, yielding a yellow precipitate. The precipitate was filtered out, dissolved in hot ethyl acetate, reduced under vacuum to 400 ml volume, then purified by flash chromatography (10% ethyl acetate/40% hexane/methylene chloride). No separation occurred and the material was chromatographed once again using 20% hexane/methylene chloride. A yield of 1.75 g (36%) of the disulfide product was recovered. The structure was confirmed by NMR.

Step 43c

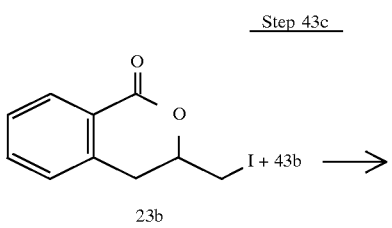

A solution was prepared of 1.54 g (3.63 mmol) of compound 43b in 40 ml of DMF with heating. The solution was then cooled in an ice bath. Sodium hydroxide was added, whereupon the solution turned dark red. It was stirred for one hour at room temperature. The solution was then cooled to 0° and 2.16 g (7.5 mmol) of compound 23b in 5 ml of ethanol was added and the reaction mixture was warmed to room temperature. After two hours of stirring, TLC showed all compound 43b had reacted. The mixture was poured into 1N HCL and extracted twice with ethyl acetate. The organic layers were washed sequentially with water and brine, dried over MgSO$_4$ and concentrated under vacuum. A crude weight of 4 g was recovered and purified by flash chromatography, in 33% yield, using methylene chloride. NMR confirmed the structure except that an ester interchange had taken place and the ester was now the ethyl ester.

Step 43d

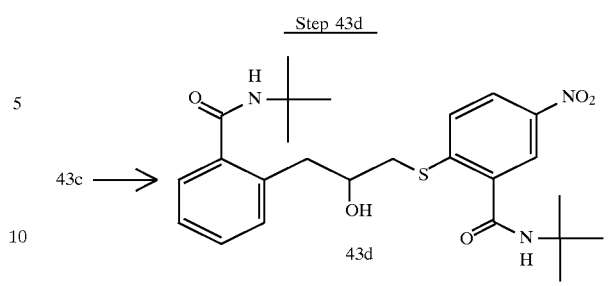

To a solution of 0.63 ml (1.26 mmol) of trimethylaluminum in 2 ml of toluene at 0° C. was added 0.13 ml (1.24 mmol) of t-butyl amine. The temperature was increased to room temperature and the mixture was stirred for 1 hour. Compound 43c (0.94 gm/0.225 mmol) in toluene was added and the mixture was heated to reflux. After 15 minutes, TLC indicated that all compound 43c had been consumed forming two products. After another 30 minutes of heating, the reaction was complete. The reaction mixture was poured into water, extracted twice with ethyl acetate, dried over MgSO$_4$ and concentrated under vacuum. Purification by flash chromatography (50% ethyl acetate/methylene chloride) yielded 0.63 gm (51%) of product. The structure was confirmed by 'HNMR.

EXAMPLE 44

Preparation of

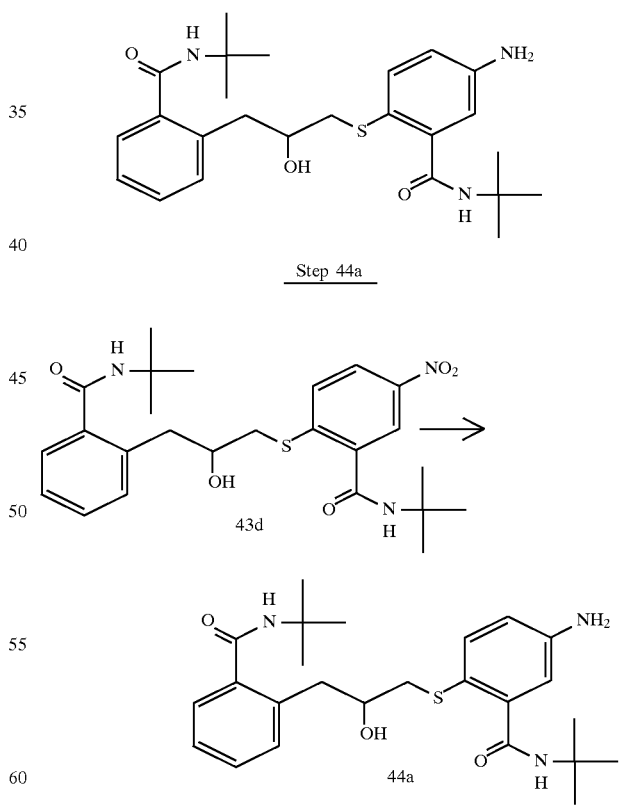

A solution of 0.03 g (0.061 mmol) of compound 43d in 2 ml of glacial acetic acid was treated with 20 mg of metallic zinc at room temperature. No reaction was noted after one hour so an additional 20 mg of zinc was added. The reaction was complete after 1.5 additional hours. The product was filtered through Celite, concentrated under vacuum, dissolved with ethyl acetate, washed with saturated NaHCO$_3$, dried over MgSO$_4$ and concentrated by vacuum. Purification by flash chromatography, using 50% ethyl acetate/hexane, yielded 7.6 mg of product. Structure was confirmed by NMR.

EXAMPLE 45

Preparation of

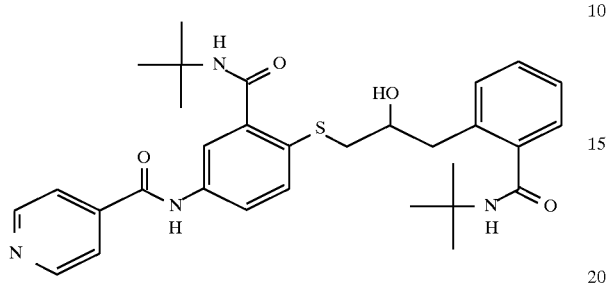

A solution of 0.37 g (0.082 mmol) of compound 44a and 17 microliters of pyridine in 0.5 ml of methylene chloride was cooled to −15° C. and reacted with 0.18 gm (0.103 mmol) of 3-pyridine carboxylic acid chloride hydrochloride salt. After 30 minutes, clean conversion to a more polar product had taken place. The reaction mixture was poured into water, extracted twice with ethyl acetate, washed with water, then brine and dried over MgSO$_4$. The extract was concentrated under vacuum to yield 30 mg of a yellow solid. The yellow solid was purified by flash chromatography (5% methanol/methylene chloride) yielding 0.27 gm (59%) of a yellow white solid. The structure was confirmed by NMR.

EXAMPLE 46

Preparation of

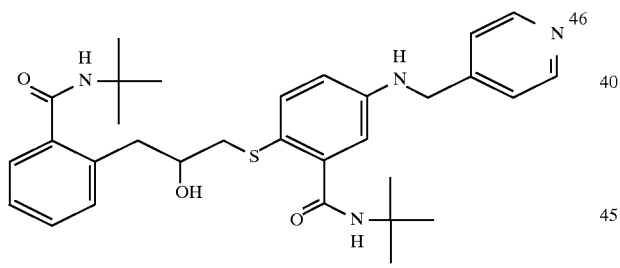

A solution of 0.5 g (0.108 mmol) of compound 44a, 10 μl of 4-pyridine-carboxaldehyde (0.105 mmol) in 1 ml of methanol and 0.5 ml of 6% hydrochloric acid in methanol was treated at room temperature with NaCNBH$_3$ and was allowed to stir overnight. By morning, a small amount of a polar compound had formed but the mixture was still mostly starting material. An additional 20 μl (2 equivalents) of the 4-pyridine-carboxaldehyde was added and the reaction was allowed to continue stirring at room temperature. After 4 additional hours, TLC indicated that all starting material had been consumed and 2 polar products had been formed. After one more hour of stirring, the reaction mixture was poured into 1N NaOH and extracted twice with ethyl acetate. The extract was dried over Na$_2$SO$_4$ and concentrated under vacuum. Flash chromatography using ethyl acetate yielded 29 mg of a first fraction and 14 mg of a second fraction. NMR confirmed the structure of the larger fraction to be the desired compound. This product was repurified by flash chromatography (3% methanol/methylene chloride) yielding 7 mg of the pure product. NMR confirmed the structure.

EXAMPLE 47

Preparation of

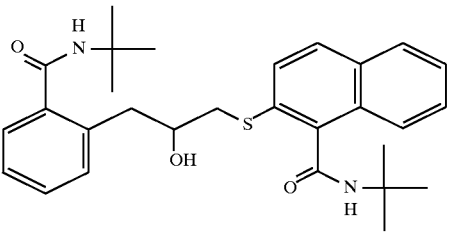

Step 47a

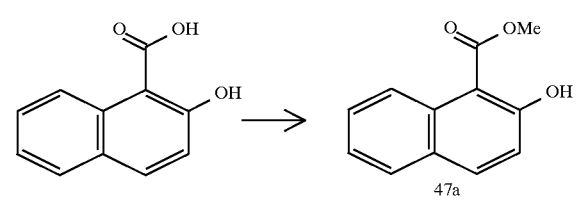

A solution of 10 g (53 mmol) of 2-hydroxy-naphthalene carboxylic acid in 200 ml of ethanol was added, dropwise, to a solution of excess diazomethane in ether at −5° C. Additional starting material (7.18 g) was added to kill the excess diazomethane. Acetic acid was added, the reaction mixture was diluted with ether and extracted with sodium hydroxide solution at a pH of about 8 to 9. The extract was washed with ether and brine, treated with charcoal and dried over MgSO$_4$. Concentration under vacuum yielded 18 g of crude light yellow solid. Structure of this material was confirmed by NMR. The product was then recrystallized from ether/hexane yielding a total of 14.94 g (82%).

Step 47b

47a + Cl–C(=S)–N(CH$_3$)$_2$ →

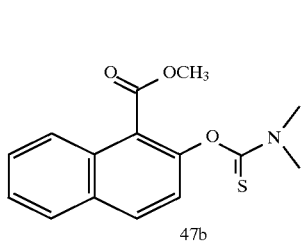

A solution of 2 g (9.915 mmol) of compound 47a in 15 ml of DMF was cooled to 0° C. and 0.40 g of sodium hydride was slowly added. Gas was evolved and the mixture was stirred for 5 minutes then warmed to room temperature. After ten minutes another 5 ml of DMF was added. The solution was then cooled to 0° C. and 1.61 gm of N,N-dimethyl-thio-carbamoyl chloride was added. The mixture was stirred 5 minutes and then warmed back to room temperature. After one hour, the reaction was indicated by TLC to be about 90% complete. The temperature was raised to 50° and the reaction was complete after one more hour. The reaction mixture was poured into ether, extracted with 1N NaOH then with brine. The aqueous layers were then extracted again. The extracts were washed with 1N HCl and dried over MgSO$_4$. The mass was then concentrated under vacuum to about 200 ml and 1.64 gm of a white solid was filtered off. The filtrate was also collected and concentrated under vacuum to 1.08 g of a yellow oil. The crude product was purified by flash chromatography (40% ethanol/hexane loaded on methylene chloride) yielding 0.23 g of a white solid. The 1.64 gms of white solid was also purified by flash chromatography yielding 1.55 gm. The two products were combined. NNR confirmed the structure.

Step 47c

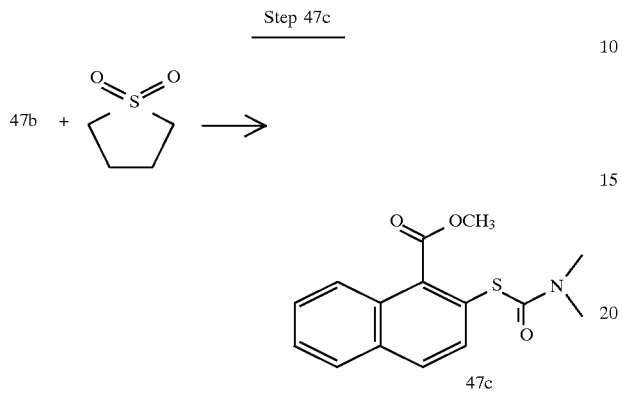

A mixture of 0.9 gm (3.11 mmol) of compound 47b in 25 ml of sulfolane was subjected to 2 freeze-pump-thaw cycles then heated to 180° C. After approximately 2 hours and 45 minutes of heating, TLC indicated that the reaction was complete and it was allowed to cool. The mixture was then poured into water, extracted twice with ether, washed twice with water, dried over MgSO₄ and concentrated under vacuum. The yield was 0.901 g which was purified by flash chromatography in a 1:1 ethyl acetate/hexane. Some impurity remained and the chromatography was repeated yielding a total of 0.46 g (51%). NMR confirmed the structure of the product.

Step 47d

47c →

<image of 47d>

A solution of 0.206 g (0.711 mmol) of compound 47c in 8 ml of methanol was treated at room temperature with 0.35 ml of 10% aqueous sodium hydroxide. When no reaction was observed after 20 minutes, the material was warmed to 40° C. for 30 minutes and stored cold overnight. Another ml of the 10% sodium hydroxide was added and the mixture was stirred at room temperature for one hour, at which time, the temperature was increased to 40° C. for 3 additional hours. The mixture was then washed with 1N HCl and extracted with ethyl acetate. The reaction was repeated and the products from the two runs were combined and purified by flash chromatography (30% ethyl acetate/hexane) yielding 0.262 g (83%). The structure was confirmed by NMR.

Step 47e

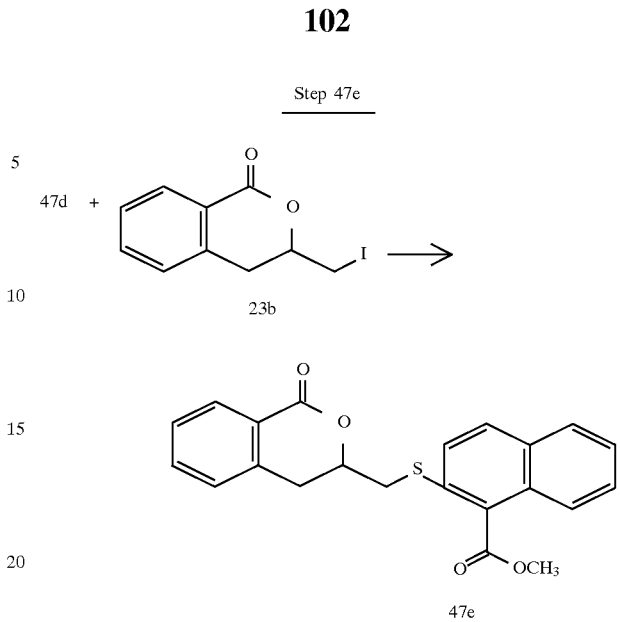

A solution of 0.08 g of potassium hydroxide in a mixture of 0.8 ml of water and 4 ml of ethanol was cooled to 0° C. and a solution of 0.253 g of compound 47d in 1 ml of ethanol was added. The mixture was stirred for 20 minutes and then 0.324 g (1.125 mmol) of compound 23b and 1 ml of ethanol was added. The mixture was allowed to warm overnight. The reaction mixture was then poured into water, extracted twice with ethyl acetate, then washed with brine and dried over MgSO₄. Concentration under vacuum yielded 0.381 g. The product was purified by flash chromatography (20% ethyl acetate/hexane) yielding 0.289 g (66%) of product. NMR confirmed the structure.

Step 47f

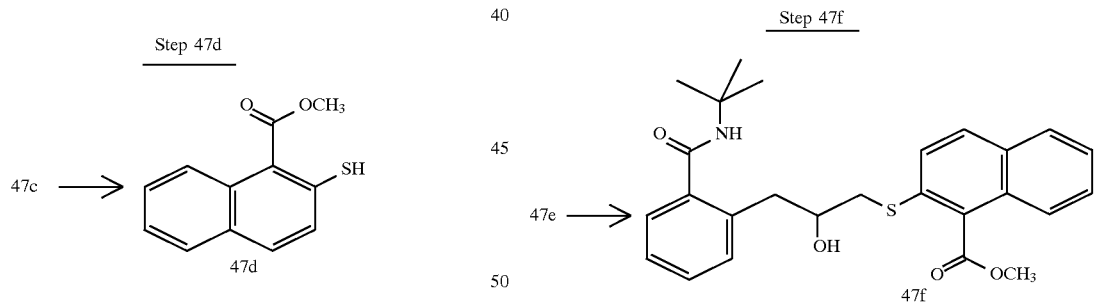

To a solution of 0.66 ml (1.32 mmol) of trimethylaluminum in toluene at 0° C. was added 0.14 ml (1.33 mmol) of t-butylamine. The mixture was warmed and stirred at room temperature for one hour, at which time a solution of 0.09 g (0.238 mmol) of compound 47e in 2 ml of toluene was added. The reaction mixture was heated to reflux for one hour, at which time, TLC showed complete conversion to a more polar product. The mass was cooled, poured into water, extracted twice with ethyl acetate and dried over MgSO₄, yielding a crude weight of 0.118 g. This was purified by flash chromatography (40% ethyl acetate/hexane) yielding 0.089 g (76%) of a white solid. NMR confirmed the structure.

Step 47g

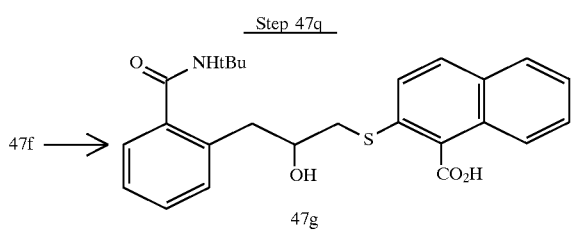

A solution of 2.35 gm (5.2 mmol) of compound 47f in a mixture 60 ml of methanol and 30 ml of 3N NaOH was heated to 60° C. and held at that temperature for about 2.5 hours. The reaction was allowed to cool and was then poured into water and extracted with ethyl acetate. The aqueous layer was acidified and extracted with ethyl acetate. The organic layers were dried over MgSO₄ and concentrated. The product was purified by flash chromatography using 50% methanol/methylene chloride, yielding 1.46 gm (64%) of compound 47g.

Step 47h

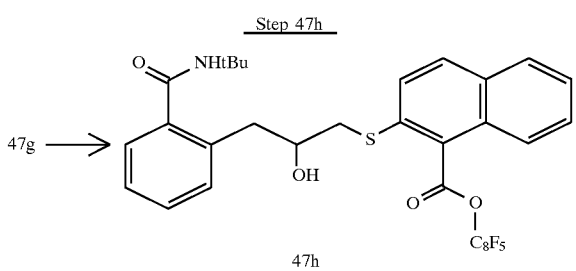

A solution of 0.0937 gm of dicyclohexyl carbodiimide (DCC) in 4 ml of ethyl acetate was cooled to 0° C. and 0.1979 gm of pentafluorophenol in 2 ml of ethyl acetate was added followed by 0.1254 gm of compound 47 g. The reaction progressed until about 80% of compound 47 g was esterified, at which time an additional 0.629 gm of the pentafluorophenol in 1 ml of ethyl acetate was added. After one hour, very little additional reaction had taken place. The mixture was filtered to remove DCC, washed 3 times with saturated Na₂HCO₃, dried over MgSO₄, concentrated under vacuum. Purification by flash chromatography using 40% ethyl acetate/hexane yielded 0.107 gm (59%) of the product as a white solid.

Step 47i

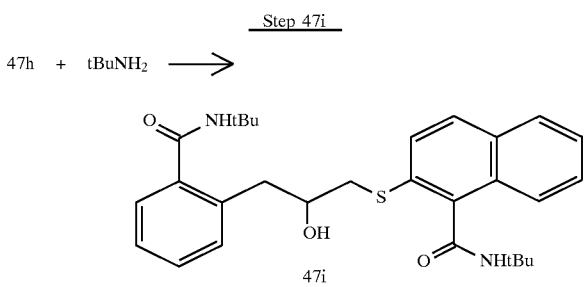

A solution of 0.10 gm (0.168 mmol) of compound 47h in 3 ml of THF was cooled to 0° C. and 50 μl (0.476 mmol) of t-butylamine was added. After ten minutes stirring, the mixture was warmed to room temperature for one hour, then heated to reflux for one hour, cooled to room temperature and stirred overnight. The mixture was reheated to reflux, 2 ml of DMF was added and stirring was continued for 24 hours. The mixture was then diluted in ethyl acetate, washed with H₂O, then with 1N HCl, then with brine, dried over MgSO₄ and concentrated under vacuum. The product was isolated by flash chromatography, yielding 8 mg (10%).

EXAMPLE 48

Preparation of

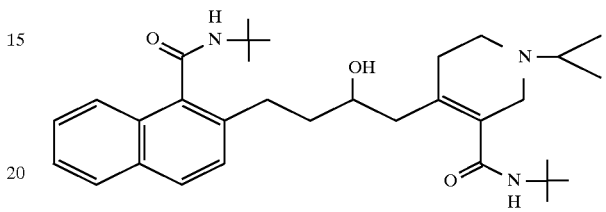

Step 48a

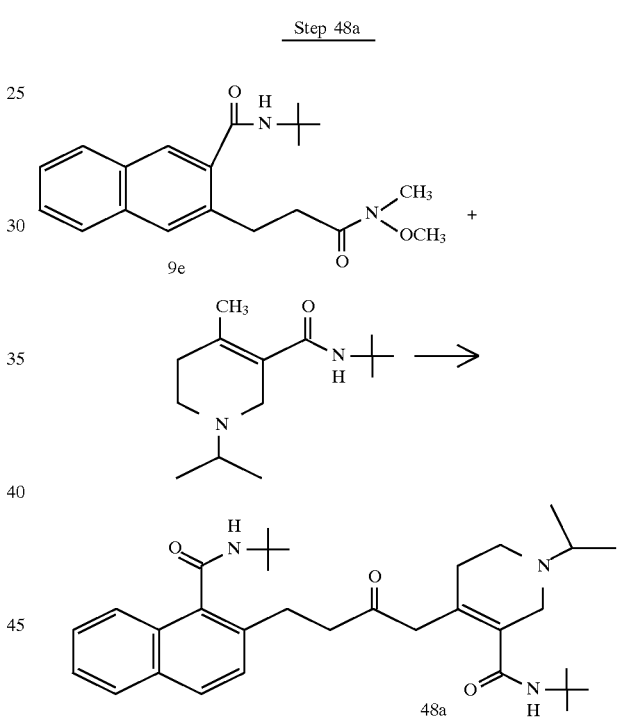

A solution of 6.31 g (1.3 mol) of the amidopyridine derivative in 5 ml of THF containing 0.3 ml of TMEDA was cooled to -78° C. and 2.6 mmol of s-butyl lithium was added. A yellow color resulted. The mixture was stirred for 1.5 hours at -78° C. At this time 0.247 gm (0.649 mmol) of compound 9e in 7 ml of THF was added. A red/brown solution resulted. This solution was stirred at -78° C. for one hour, then quenched with water, extracted with ethyl acetate and concentrated under vacuum. NMR confirmed the structure of the product contaminated with a small amount of residual amidopyridine derivative.

Step 48b

48a →

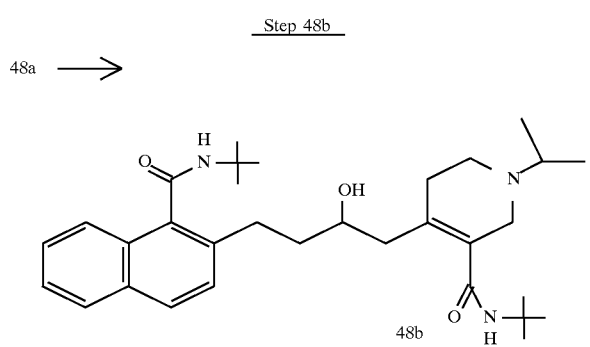

To a solution of 0.39 g (0.69 mmol) of compound 48a in 3 ml of methanol was added 30 mg of NaBH$_4$. The mixture was stirred at room temperature for two hours and methanol was stripped off under vacuum. The compound was dried over MgSO$_4$. Purification by flash chromatography (15% ethyl acetate/methylene chloride/1% methanol) followed by precipitation with ether yielded 0.02 gm of the product.

EXAMPLE 49

Preparation of

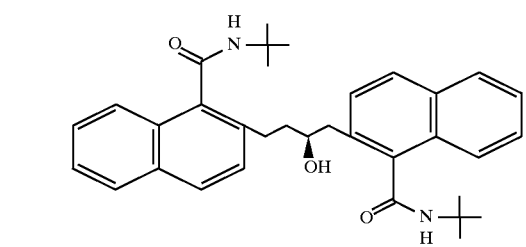

Step 49a

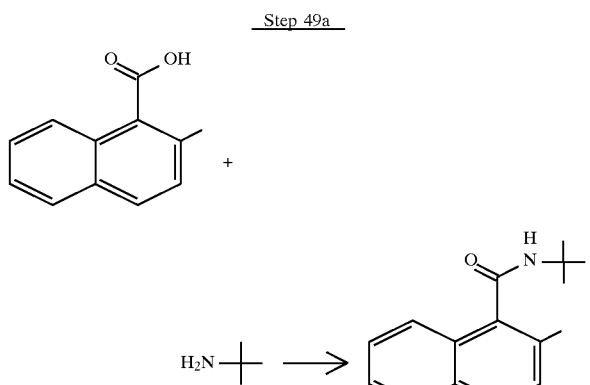

About 2.2 gm (11.82 mmol) of 2-methyl-1-naphthoic acid was partially dissolved in 30 ml of benzene and the solution was cooled to 0° C. To the cold solution was added 1.34 ml (15.37 mmol) of oxalyl chloride and one drop of DMF. Vigorous bubbling resulted when the solution was warmed to room temperature. Then the temperature was raised to near reflux for a total of 1 hour. TLC indicated fair amount of residual starting material remaining so another equivalent of oxalyl chloride and DMF was added. The temperature was raised back to reflux and allowed to reflux for 20 minutes. The reaction mixture was then concentrated under vacuum to an orange solid. The material was partially redissolved in 30 ml of methylene chloride and 2.73 ml of t-butyl amine was added. Reaction then proceeded cleanly but was allowed to continue overnight. The mass was washed with water and ethyl acetate and purified by flash chromatography using a 4:1 hexane/ether mixture. Yield was 2.6 gm (92%). Structure was confirmed by NMR.

Step 49b

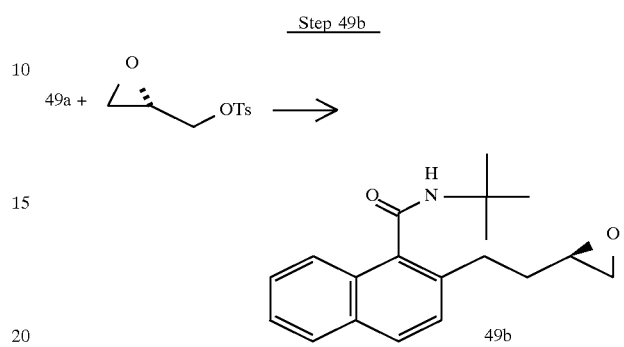

A solution of 1.2 g of compound 49a and 15 ml of THF was cooled to –78° C. and 11.7 ml of s-butyl lithium was added. The solution was stirred for 1.5 hours, at which time 1.14 g (4.97 mmol) of S-glycidyl tosylate was added. The reaction mix was stirred for one half hour at –78° C., then quenched with NH$_4$Cl, extracted with ethyl acetate and washed with water followed by brine and dried over MgSO$_4$. The extract was then concentrated on 7 ml of Florisil and purified by flash chromatography (20% THF/hexane). The yield was 0.75 g of product (51%). Structure was confirmed by NMR.

Step 49c

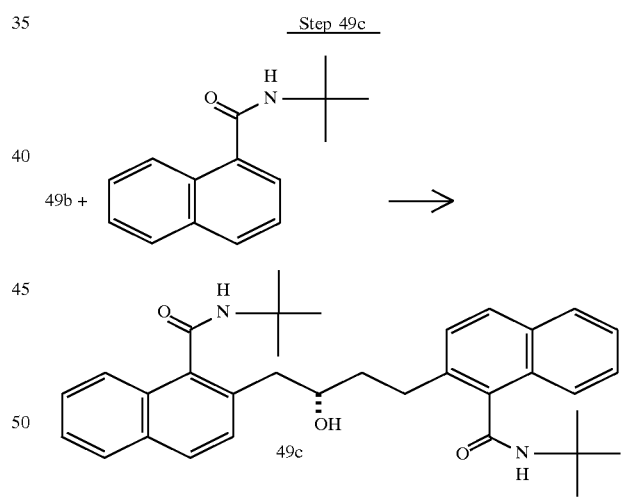

To 0.459 g (2.02 mmol) of N-(t-butyl)naphthamide at –12° C. was added 4 ml of s-butyl lithium, and the mix was warmed to 0° C. and stirred for 45 minutes. A solution of 0.3 g (1.01 mmol) of compound 49b in 10 ml of THF was added. The red solution turned to a milky yellow/brown. In about 18 minutes following addition of compound 49b, 80% of the compound had been consumed. The reaction was then quenched with saturated NH$_4$Cl and extracted with ethyl acetate. The material was purified by flash chromatography in a 1:1 hexane/ethyl acetate. The mass was then concentrated on 7 ml of Florisil, and subjected again to flash chromatography using THF/hexane. A total of about 0.16 g of product was recovered. NMR confirmed the structure.

EXAMPLE 50

Preparation of

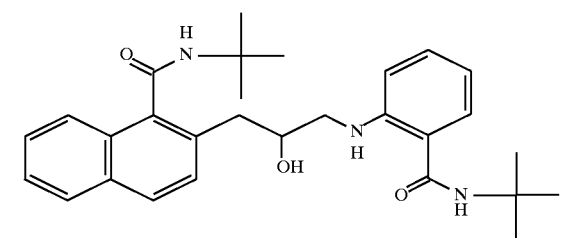

Step 50a

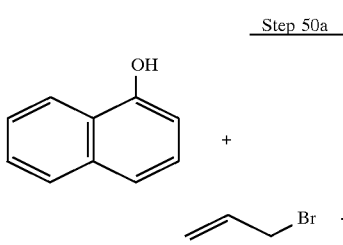

To a solution of 1 naphthol in 100 ml of acetone was added 13.7 g of $K_2CO_3$, then 6.6 ml (76.29 mmol) of allyl bromide. The solution was heated to reflux for four hours, at which time TLC indicated the reaction to be about 80% complete. Another 3.3 ml of allyl bromide was added and the solution was refluxed mildly overnight. The reaction mass was then filtered and concentrated under vacuum, yielding 13.7 g (98%) of product. Structure was confirmed by NMR.

Step 50b

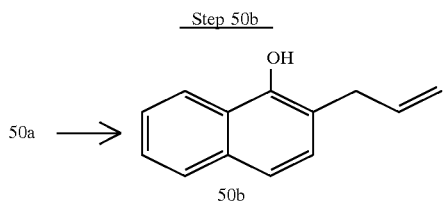

A solution of 16.32 g of compound 50a in 125 ml of N,N-dimethyl aniline was heated to reflux under an argon atmosphere. Reflux was continued for four hours, at which time TLC showed the reaction to be complete. The reaction mixture was allowed to sit overnight at room temperature, then poured into 100 ml of 3N HCl and then 200 ml of ether were added. The organic layer was separated, washed six times with 100 ml portions of 3N HCl and then four times with 200 ml of 1N HCl. The extract was then washed with four 200 ml portions of water and dried on $MgSO_4$. The dried product was distilled through a short path column at 130° C. under an atmosphere of argon. Yield was 15.58 gm of an orange oil which solidified upon standing.

Step 50c

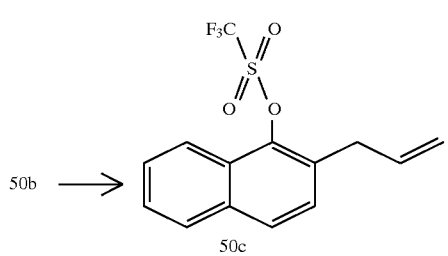

A solution of 4.1 gm (22.26 mmol) of compound 50b in 50 ml of methylene chloride was cooled to 0° C. and 1.89 ml of pyridine was added, followed by dropwise addition of 6.6 g (23.37 mmol) of triflic anhydride. The reaction mixture was stirred for 6 hours, while allowing the temperature to rise from 0° C. to room temperature. The mass was poured in 100 ml of 1N HCl and extracted with methylene chloride. The extracts were washed with saturated $NaHCO_3$, then concentrated on 20 ml of Florisil. Flash chromatography using a 20:1 hexane/ethyl acetate yielded 5.60 gm of product.

Step 50d

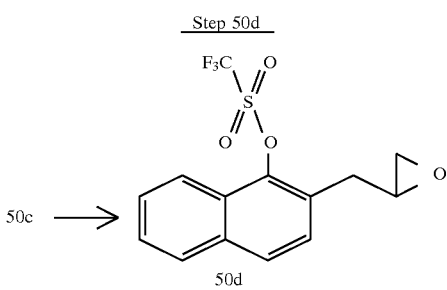

A solution of 5.6 gm (17.7 mmol) of compound 50c in 60 ml of methylene chloride was cooled to 0° C. and 6.11 g of m-chloro-perbenzoic acid (MCPBA) was added. The mixture was stirred for 30 minutes at 0° C., then at room temperature for 5 hours at which time another 1.3 g of MCPBA was added and the solution, warmed to 35° C. and allowed to stir overnight. The mixture was then poured into 0.5N NaOH, extracted with two 50 ml portions of methylene chloride, washed, dried and filtered through silica gel, then concentrated under vacuum. Flash chromatography in an 8:1 hexane ethyl acetate mixture yielded 5.4 g of product. The structure was confirmed by NMR.

Step 50e

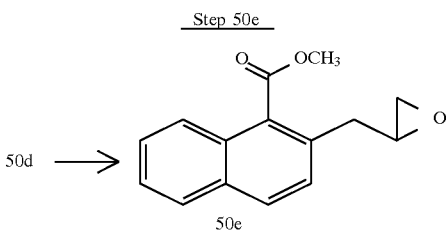

A mixture consisting of 1.41 gm (4.42 mmol) of compound 50d, 0.068 gm of palladium (II) acetate, 0.125 gm of 1,3-bis diphenylphosphino propane (DPPP), 1.4 ml of triethyl amine, 15 ml of DMSO and 10 ml of methanol was prepared and heated to 75° C. under a carbon monoxide atmosphere. Heating was continued for three hours at which time an additional 17 mg of the palladium acetate and 35 mg of DPPP was added. The mass was heated at 70° C.

overnight, at which time TLC indicated that the reaction was finished. The mass was poured into 50 ml of water, then into 50 ml of saturated NH₄Cl and extracted with ethyl acetate followed by washing with NaHCO₃ and brine. Flash chromatography in 4:1 hexane/ethyl acetate yielded 0.25 g (24.3%) of product. Structure was confirmed by NMR.

Step 50f

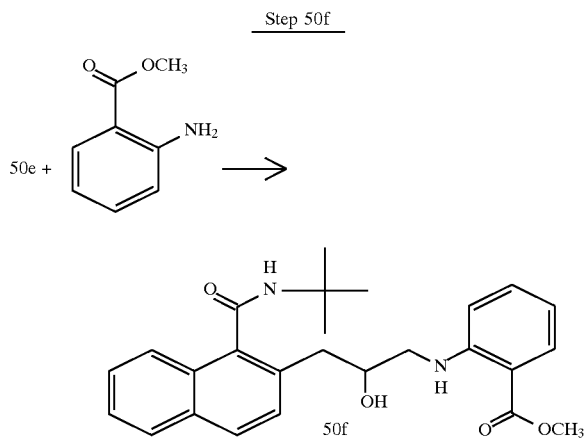

To a solution of 0.255 g (1.053 mmol) of compound 50e, 0.353 g of magnesium perchlorate in 3.5 ml of acetonitrile, was added 0.204 ml (1.58 mmol) of 2-amino methyl benzoate. The mixture was stirred overnight at room temperature, then poured into water, extracted with ethyl acetate, then concentrated in 3 ml of Florisil. Flash chromatography in 1:1 hexane/ether solution yielded 0.25 g of a white sticky foam.

Step 50g

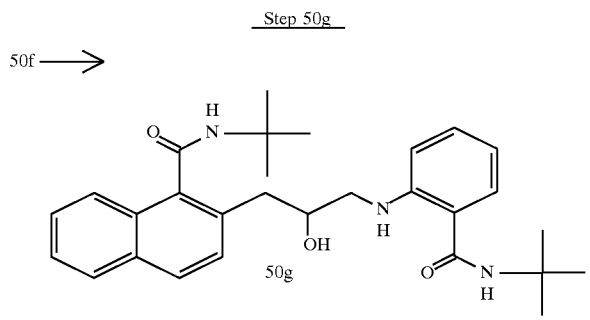

A solution of 2.34 ml of trimethyl aluminum in 4 ml of toluene was cooled to 0° C. and 0.504 ml (4 mmol) of t-butyl amine was added and the mixture was stirred for one hour at room temperature. After an hour, 0.23 g (0.0585 mmol) of compound 50f in 3 ml of toluene was added, dropwise, and the solution was heated to 95° C. for about 2.5 hours. Temperature was reduced to 65° C. and stirring was continued for 4 more hours at which point the heat was turned back up to 120° C. and continued at that temperature for a total of 22 hours. The reaction mixture was poured into 1N HCl and then extracted with ethyl acetate, washed with water and concentrated on 3 ml of Florisil. Flash chromatograph yielded 0.075 gm (80%) of product. Structure was confirmed by NMR.

EXAMPLE 51
Preparation of compound 50 by alternate route.

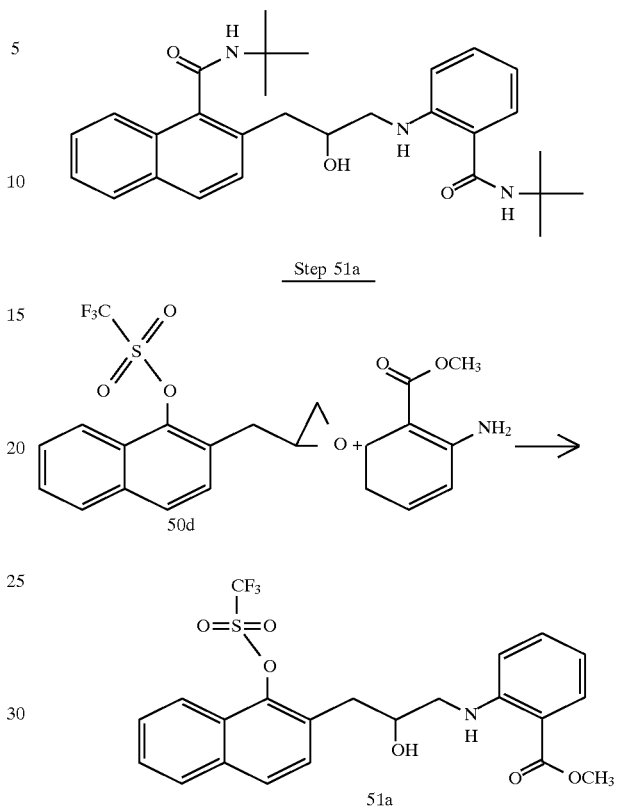

A solution of 0.068 g (0.205 mmol) of compound 50d and 0.046 g of magnesium perchlorate in 1 ml of acetonitrile was prepared. At room temperature, 26 microliters (0.205 mmol) of 2-amino-methyl benzoate was added. The mixture was stirred at room temperature for one hour at which time another 13 μl of the 2-amino-methyl benzoate was added and another 0.024 g of magnesium perchlorate. The reaction mixture was stirred overnight at room temperature, after which the solution was warmed to 45° C. and stirred for 4 more hours. The reaction mix was poured into water, extracted with ethyl acetate, then washed with brine. After concentration on 2 ml of Florisil, the mixture was purified by flash chromatography (hexane/ethyl acetate), yielding 0.068 g (68.7%) of product. NMR confirmed the structure.

Under a carbon monoxide atmosphere, a mixture consisting of 0.068 g of compound 51a, 3 mg of palladium (II) acetate, 4 mg of DPPP, 70 μl of triethyl amine, 1 ml of DMSO, 0.6 ml of methanol and 250 μl of 1,2-dichloroethane was heated under a carbon monoxide atmosphere to about 65° C. for three hours and then for one more hour at 70° C.

The reaction mixture was poured into dilute HCl and extracted with ethyl acetate, washed with NaHCO₃ and brine and dried over MgSO₄, then filtered through Celite and concentrated on 3 ml of Florisil. Flash chromatography in a 3:2 hexane/ether yielded about 0.06 g of a white solid product. NMR confirmed the structure.

Step 51c

51b ⟶

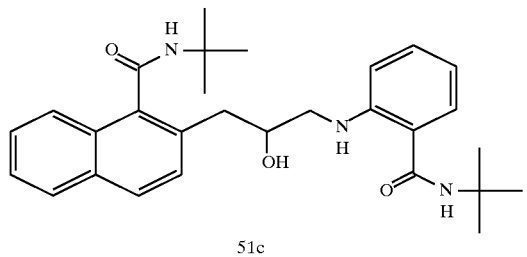

51c

To 0.44 ml of a 2.0M solution of trimethyl aluminum in toluene at 0° C. was added 95 microliters (0.904 mol) of t-butyl amine. The mixture was stirred for one hour at room temperature, at which time a solution of 0.04 g of compound 51b in 2 ml of toluene was slowly added. The mixture was heated at 95° C. for 45 minutes, at which time TLC indicated that the reaction was essentially complete. The solution was then refluxed mildly for three hours. Following reflux, the solution was poured into dilute HCl, extracted with ethyl acetate, and washed with water and brine. Following concentration on 2 ml of Florisil, the product was purified by flash chromatography in a 3:2 ethyl hexane solution. Structure was confirmed by NMR.

EXAMPLE 52

Preparation of

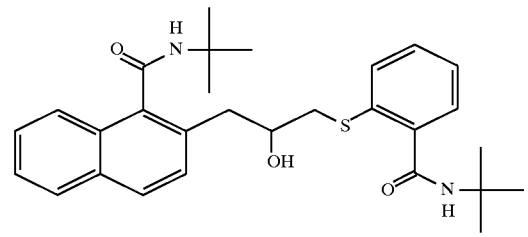

Step 52a

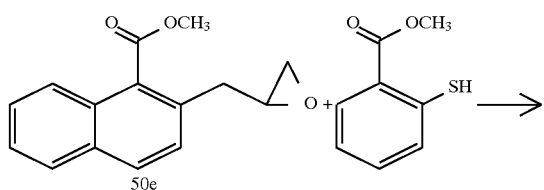

50e

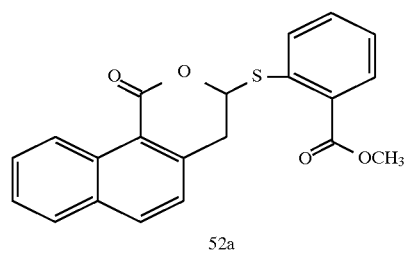

52a

To a solution of 107 μl (0.776 mmol) of 1-mercapto methylbenzoate in 2 ml of THF was added 23 mg of sodium hydride. Bubbling occurred and the reaction mixture turned yellow and was stirred at room temperature for 45 minutes. A solution of 0.188 g (0.776 mmol) of compound 50e in 1 ml of THF was added to the mass at room temperature. After one hour at 35° C., the mixture was warmed to 55° C. In about 20 minutes, reaction was complete. The reaction mass was worked up with 1N HCl and water and was combined with another portion of the same material derived in an earlier experiment using the same procedure. Flash chromatography in 3:1 hexane/ethyl acetate eluent yielded 0.19 gm of product. Structure was confirmed by NMR.

Step 52b

52a ⟶

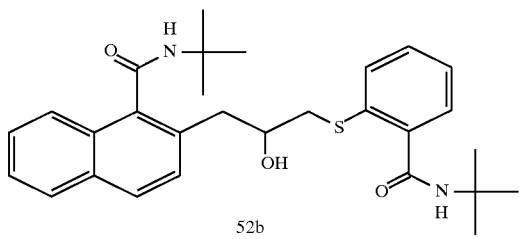

52b

To 3 ml of a 2.0M solution of trimethyl aluminum in toluene at 0° C., was added 0.293 μl (2.78 mmol) of t-butyl amine. The mix was left stirring for one hour at room temperature, at which time 0.17 g (0.449 mmol) of compound 52a in 2 ml of toluene was added, dropwise. The mixture was heated to mild reflux (75°–80° C.) for about 15 minutes at which time reflux was increased to 100° C. The mixture was then poured into 50 ml of water, extracted with ethyl acetate, dried under vacuum on 3 ml of Florisil, then purified by flash chromatography using a 1:1 hexane ethyl acetate. Structure of the product was confirmed by NMR.

EXAMPLE 53

Preparation of

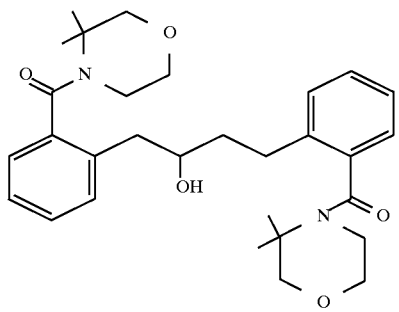

A 3 neck flask fitted with a septum and a stopper was flame dried in vacuum and purged with argon, after which 0.436 gm (3.78 mmol) of 2,2-dimethyl morpholine in 5 ml of benzene was charged into it. The flask and contents were cooled in an ice bath and 1.9 ml of a 2M solution of trimethyl aluminum was added over 2 minutes while maintaining the temperature between 5 and 8° C. The clear solution was warmed to room temperature and stirred for 45 minutes. In one portion, 0.195 gm (0.63 mmol) of compound 25e in one ml of benzene was added by syringe. The syringe was rinsed with 0.5 ml of benzene, which was also charged to the reaction flask. The mixture was stirred at 50° C. under argon for 5 hours at which time the temperature was increased to 70°–75° C. overnight. The reaction mass quenched with 2 ml of 0.5N $NH_{44}Cl$, poured into water and extracted twice with 20 ml portions of ethyl acetate. The organic layers were combined, dried and filtered. Solvent was removed under vacuum, yielding 212 mg of a yellow, oily mass. By flash chromatography using 30% hexane/ethyl acetate, 26.1 mg of a first product and 77 mg of a second product were isolated. Following solvent removal, these were identified as compound 53, the title compound, and compound 53a, an amide-ester.

EXAMPLE 54

Following substantially the identical procedure as was used in Example 53, 49.1 mg (0.125 mmol of) compound 53a was reacted with t-butylamine in toluene. Thirty (30) mg (52%) of product was recovered.

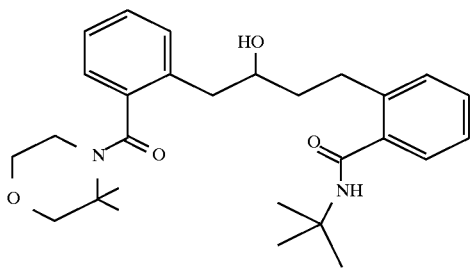

EXAMPLE 55

Preparation of

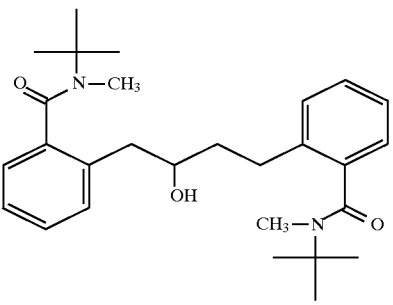

Following substantially the identical procedure as was used in Example 53, 0.197 gm (0.637 mmol) of compound 25e was reacted with N-methyl-t-butylamine in toluene medium. Yield was 44 mg (19.7%) of the desired product.

EXAMPLE 56

Preparation of

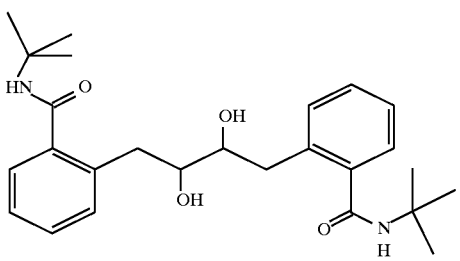

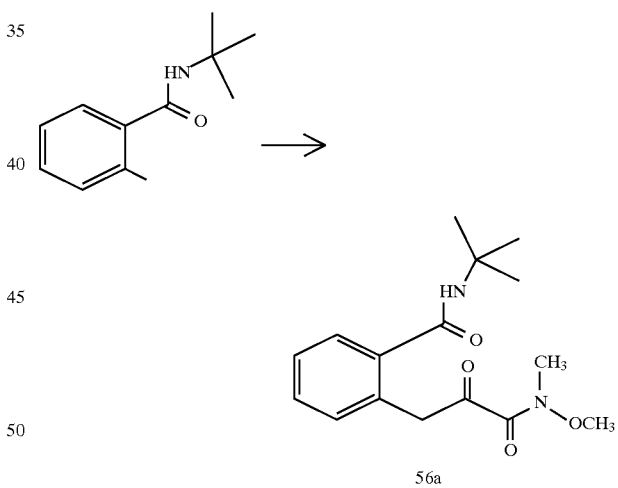

In a 50 ml 3-neck flask previously flame-dried and purged with argon, 1 gm (5.23 mmol) of N-t-butyl toluamide was dissolved in dry THF. The solution was stirred under argon then cooled to –78° C. in a dry ice/acetone bath. Dropwise 0.85 ml of s-butyl lithium was added by syringe over a 15 minute period. The temperature remained below –65° C. The mixture was stirred for one hour at –78° C. and 0.92 gm (5.23 mmol) of N,N', -dimethyl-dimethoxyoxalamide was added in one portion at –78° C. The mixture was stirred for one additional hour at –78° C., then was allowed to warm to room temperature over a two hour period. The resulting product was stirred at room temperature overnight, then poured into water and extracted with ethyl acetate. The extracts were washed with saturated $NaHCO_3$, water and brine, then dried over Na$_2$SO$_4$, filtered and concentrated under vacuum. The residue was purified by flash chromatography using a 10% ethyl acetate/hexane solution followed by a 25% ethyl acetate solution. The appropriate fractions were collected and concentrated yielding 1.1 gm of the product.

Step 56b

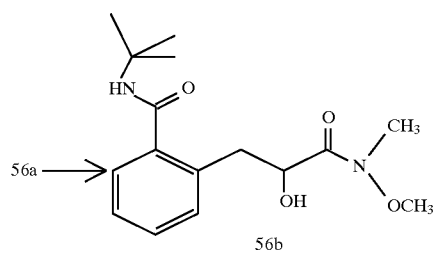

A solution of 0.7 gm (2.3 mmol) of compound 56a in 15 ml of alcohol was cooled to 0° C. in a 50 ml flask. In one portion, 0.086 gm of NaBH$_4$ was added and the mixture stirred for two hours. The reaction mixture was then poured into saturated NaHCO$_3$ and extracted with ethyl acetate. The extracts were washed with water, then with brine and the product was dried over MgSO$_4$, filtered and concentrated under vacuum yielding 0.51 gm of product.

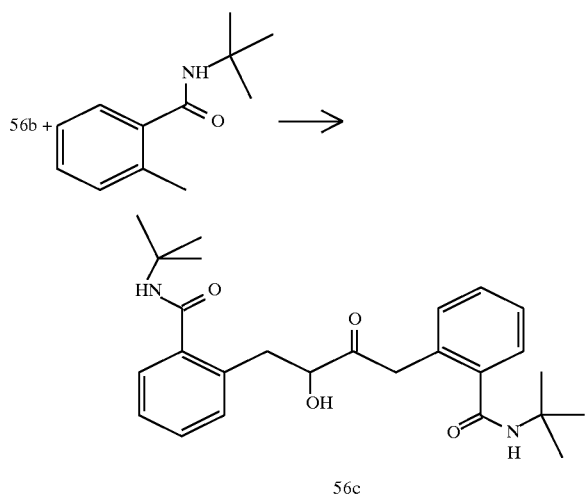

A solution of 1.55 gm (8.1 mmol) of N-t-butyl-toluamide in 30 ml of THF was stirred under an argon atmosphere and cooled to −78° C. Dropwise, over a ten minute time period, 13.11 ml (17 mmol) of s-butyl lithium was added and the reaction was stirred at −78° C. for one hour. After one hour of stirring 0.5 gm (1.6 mmol) of compound 56b in THF was added, dropwise, over a ten minute period. The reaction mixture was stirred at −78° C. for two hours, then allowed to warm slowly to room temperature and quenched with saturated NH$_4$Cl. The reaction mixture was then diluted with water and extracted with ethyl acetate. The extracts were washed with saturated brine, dried over MgSO$_4$, filtered and concentrated under vacuum. The product was purified by flash chromatography using a 10% ethyl acetate/hexane solution followed by a 20% solution then by a 30% solution. The appropriate fractions were collected and concentrated under vacuum yielding 0.193 mg of product.

Step 56d

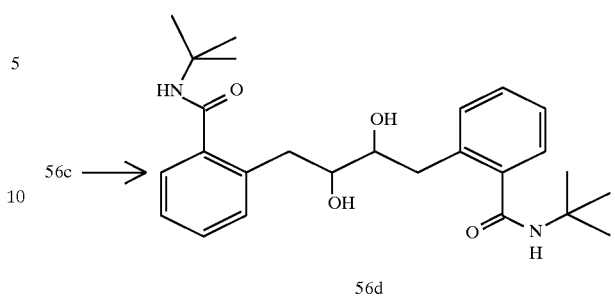

A solution of 150 mg (0.3425 mmol) of compound 56c in 3 ml of alcohol was cooled to 0° C. in a 10 ml round bottom flask and 0.013 gm of NaBH$_4$ is added in a single portion. The mixture was stirred at 0° C. for two hours then poured into saturated NaHCO$_3$ and extracted with ethyl acetate. The extracts were washed with water, dried over MgSO$_4$, filtered and concentrated under vacuum. The residue was purified using 1.5% methanol in methylene chloride yielding the product as a mixture of diastereomers.

EXAMPLE 57

Preparation of

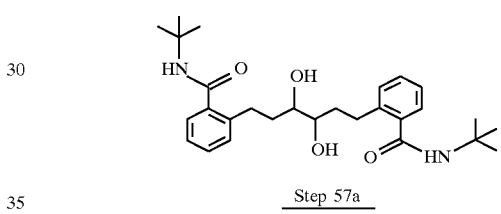

Step 57a

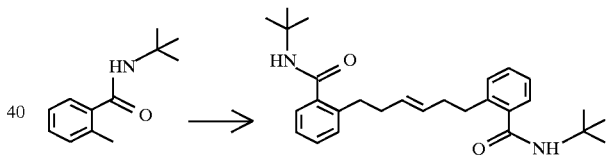

A solution of 500 mg (2.614 mmol) of N-t-butyl toluamide in 10 ml of THF was cooled to −78° C. and treated with 6.2 ml of s-butyl lithium dropwise from a syringe while maintaining temperature below −65° C. After one hour at the low temperature, a solution of 280 mg (1.307 mmol) of 1,4-dibromobut-2-ene and 5 ml of THF was added dropwise while not allowing the temperature to exceed −60° C. After one hour of stirring, the reaction mixture was quenched with saturated NH$_4$Cl solution, diluted with ethyl acetate and washed with water and brine, then dried and concentrated under vacuum yielding a yellow solid.

Step 57b

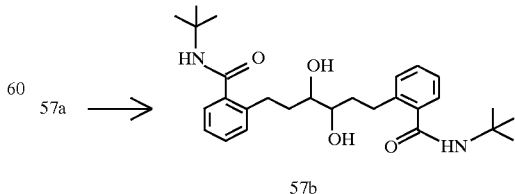

A solution of 9.3 mg of OsO$_4$ in t-butanol and 43 mg of N-methyl morpholine in a 2:1 acetone/water mixture were mixed. To this was added 160 mg (0.368 mmol) of compound 57a and the mixture was stirred overnight at room temperature. The reaction was then quenched with saturated NH₄Cl and extracted with ethyl acetate, washed with water and brine, then dried over MgSO₄ and concentrated under vacuum. The product was purified by flash chromatography using 50% ethyl alcohol/hexane, yielding 85 mg (50%) of an oily product.

EXAMPLE 58

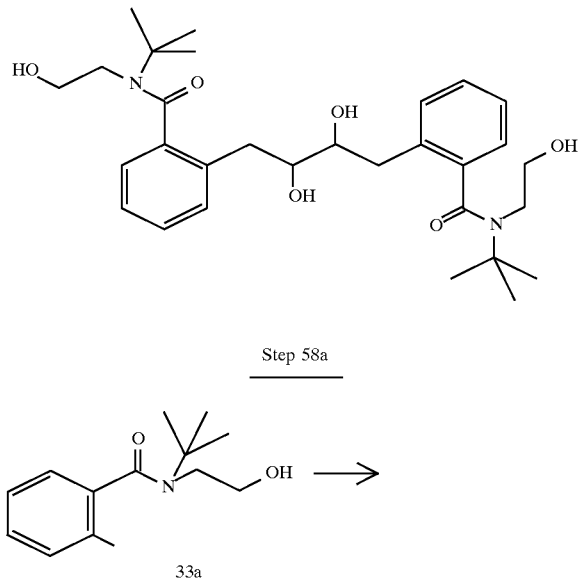

Step 58a

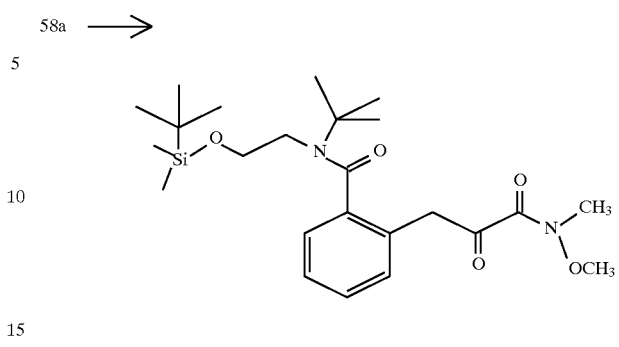

Step 58b

58a →

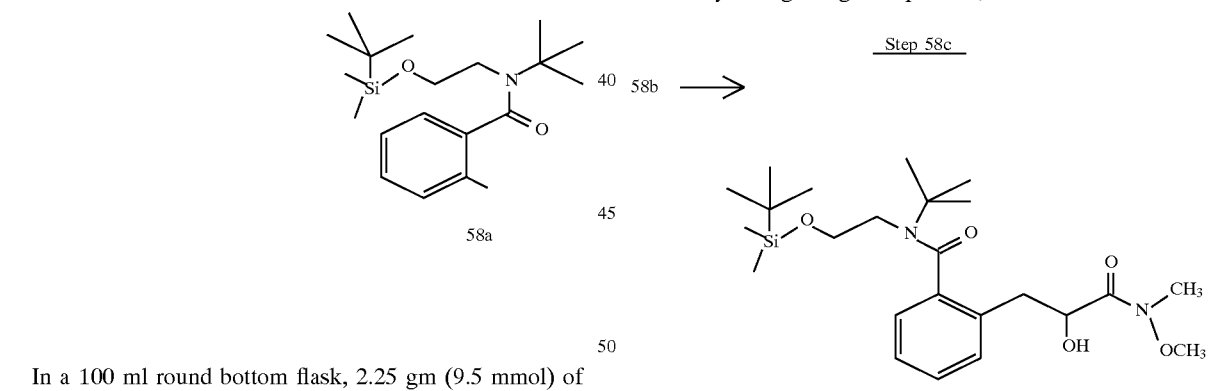

In a 100 ml round bottom flask, 2.25 gm (9.5 mmol) of compound 33a was dissolved in 22.5 ml of DMF. To this solution was added 4.32 gm (28.7 mmol) of t-butyldimethylsilyl chloride and 2.3 gm of imidazole. This reaction mixture was heated to 55° C. and stirred for 16 hours. At this time the reaction was completed and the reaction mixture was poured into water and extracted twice with ethyl acetate. The organic phases were washed with water and brine, dried over MgSO₄ and concentrated under vacuum. The residue was purified by flash chromatography using 10% ethyl acetate/hexane. The products were concentrated and pumped dry under vacuum yielding 1.6 gm of product.

A solution of 1 gm (2.9 mmol) of compound 58a was dissolved in 10 ml of dry THF, cooled under an argon blanket to −78° C. and stirred. In one portion, 43,mg of diisopropylamine was added followed by dropwise addition of 3.9 ml of s-butyl lithium at a rate such that the temperature remains below −65° C. The reaction mass was then stirred for 2 hours at −78° C. and a solution of N,N'-dimethyldimethoxyloxalylamide and 2 ml of THF was added dropwise again maintaining the temperature at no greater than −65° C. Stirring was continued for 2.5 hours at which time the reaction was quenched at −78° C. with saturated NH₄Cl. The quenched reaction mixture was then poured into water and extracted with ethyl acetate. The extracts were washed with water and brine, then concentrated under vacuum. The residue was purified by flash chromatography using 10% ethyl acetate/hexane. The appropriate fractions were combined and concentrated under vacuum yielding 0.5 gm of product, Step 58c 58b →

A solution of 0.5 gm (1.1 mmol) of compound 58b in 10 ml of ethyl alcohol was stirred and cooled to 0° C. In a single portion, 0.041 gm of NaBH₄ was added and stirring was continued for two hours. The reaction mixture was poured into an excess of saturated NaHCO₃ and extracted with ethyl acetate. The extracts were washed with water and brine, and dried over MgSO₄. The organic solution was filtered and concentrated under vacuum, yielding 0.45 gm of material suitable for use without further purification.

Step 58d

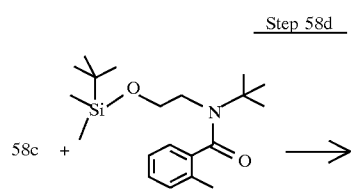

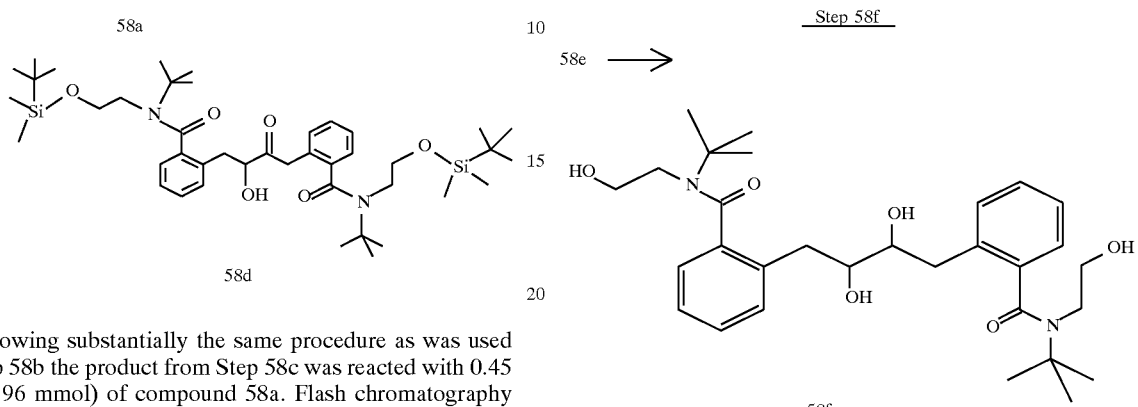

Following substantially the same procedure as was used in Step 58b the product from Step 58c was reacted with 0.45 gm (0.96 mmol) of compound 58a. Flash chromatography with a 15% ethyl acetate/hexane solution yielded 0.17 gm of product.

Step 58e

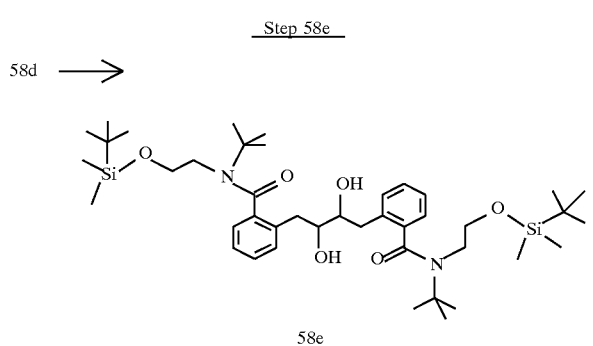

A solution of 0.17 gm of compound 58d was dissolved in 3.4 ml of ethanol, stirred and cooled to about 0° C. In one portion, 0.01 gm of $NaBH_4$ was added and the mixture was stirred for an additional two hours. The reaction mixture was then poured into saturated brine and extracted with ethyl acetate. The extract was dried over $MgSO_4$ yielding 0.15 gm of product suitable for use without further purification.

Step 58f

58e ⟶

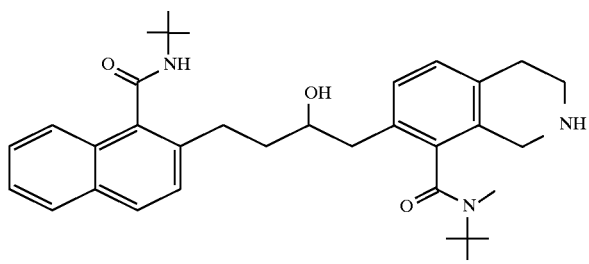

To a solution of 0.15 gm of compound 58e in 2 ml of THF was added 2 equivalents of tetrabutyl ammonium fluoride and the mixture was stirred at room temperature overnight, then poured into 0.5N HCl and extracted with ethyl acetate. The extract was washed with water and brine, then purified by flash chromatography using 5% ethyl acetate/hexane. The appropriate fractions were combined and concentrated under vacuum, yielding 0.022 gm of product.

EXAMPLES 59–115

Using essentially the same chemistry and the same reaction sequences described in Examples 1 through 58, the following compounds have also been synthesized:

| EXAMPLE # | STRUCTURE |
|---|---|
| 59 | 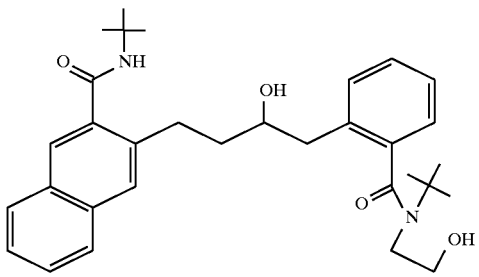 |
| 60 | 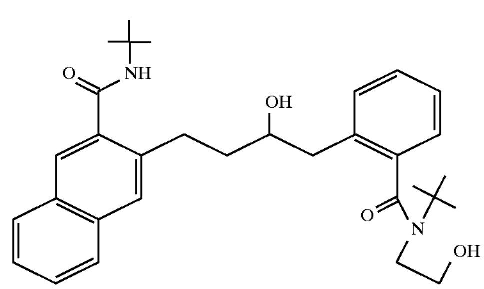 |

5,863,950
| EXAMPLE # | STRUCTURE |
|---|---|
| 61 | 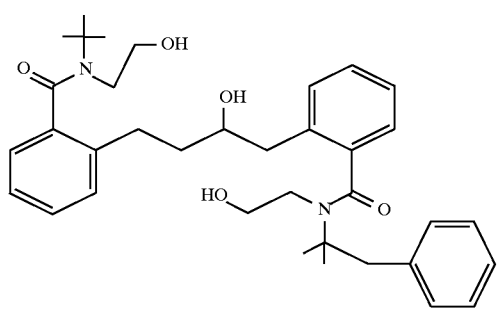 |
| 62 | 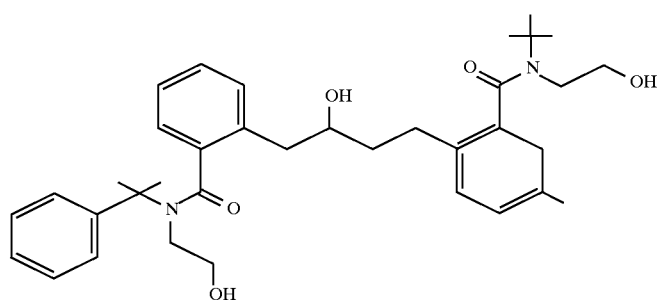 |
| 63 | 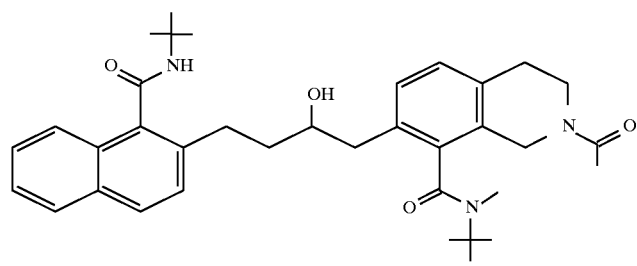 |
| 64 | 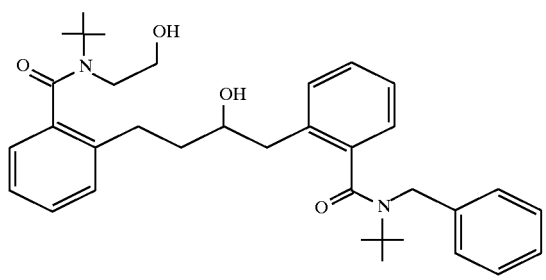 |
| 65 | 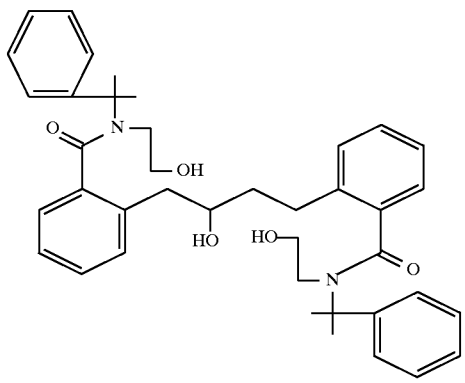 |

| EXAMPLE # | STRUCTURE |
|---|---|
| 66 | 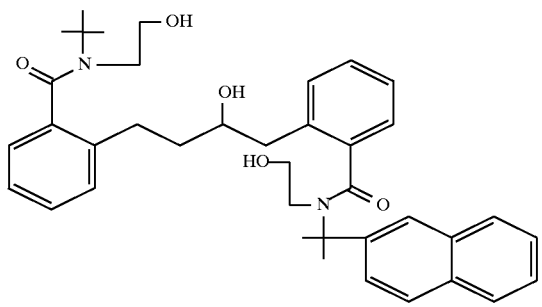 |
| 67 | 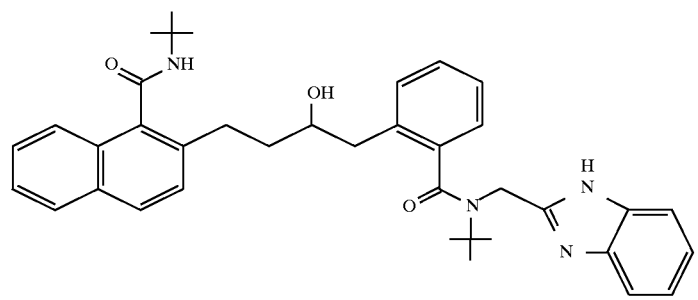 |
| 68 | 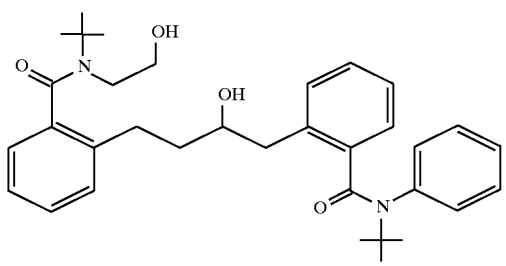 |
| 69 | 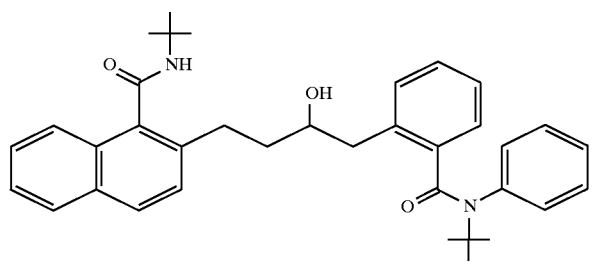 |
| 70 | 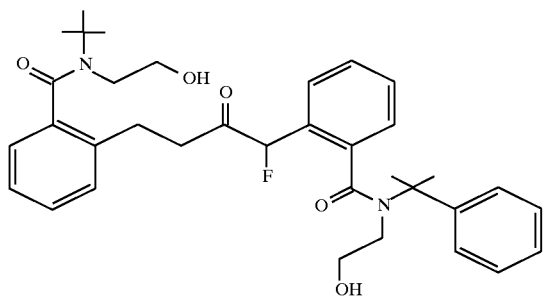 |

-continued
| EXAMPLE # | STRUCTURE |
|---|---|
| 71 | 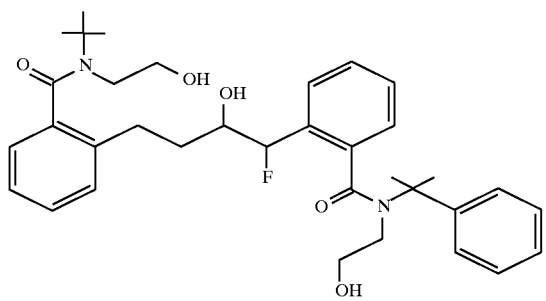 |
| 72 | 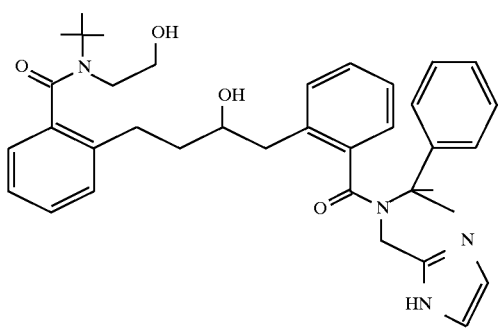 |
| 73 | 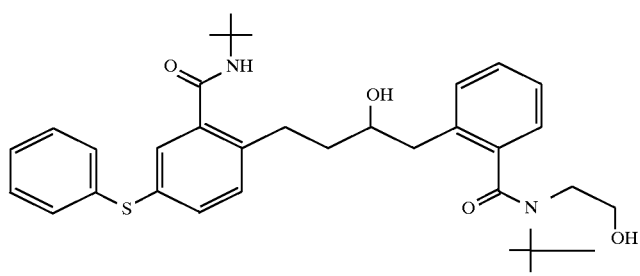 |
| 74 | 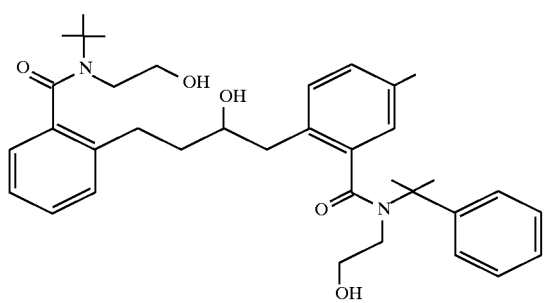 |
| 75 | 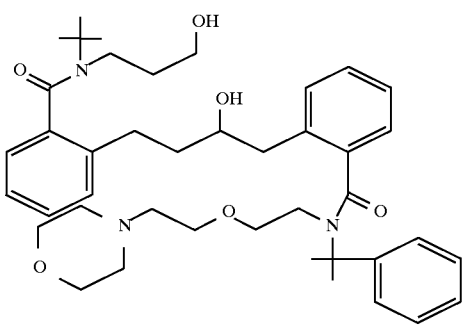 |

| EXAMPLE # | STRUCTURE |
|---|---|
| 76 | 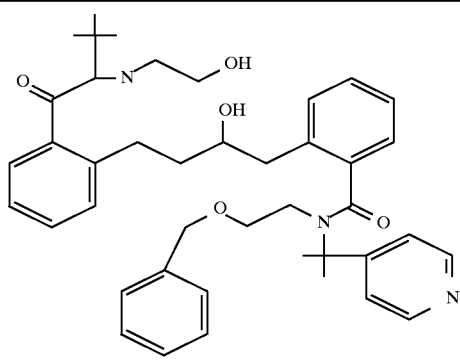 |
| 77 | 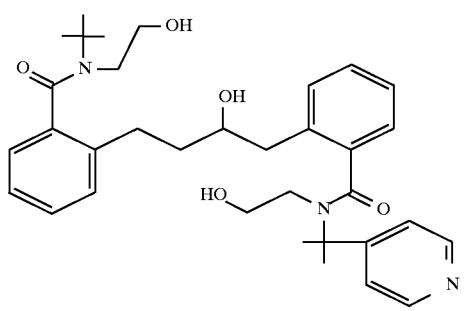 |
| 78 | 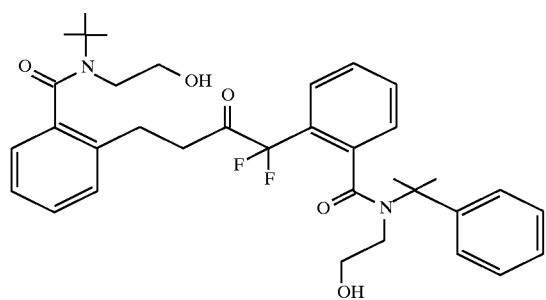 |
| 79 | 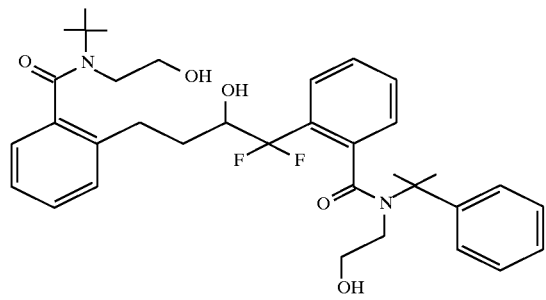 |
| 80 | 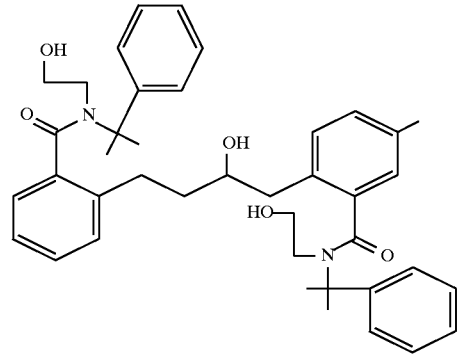 |

| EXAMPLE # | STRUCTURE |
|---|---|
| 81 | 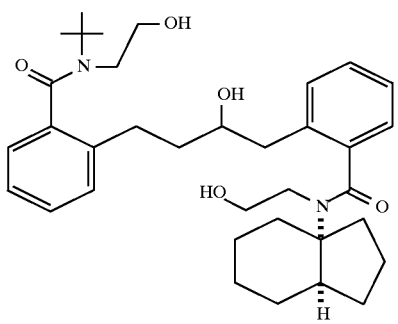 |
| 82 | 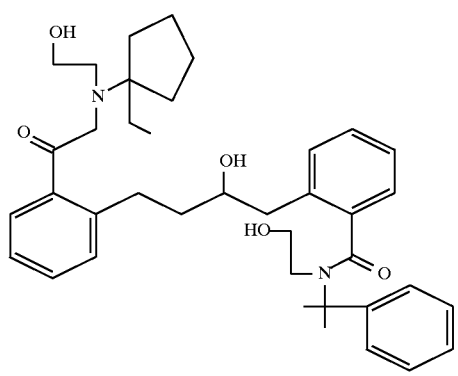 |
| 83 | 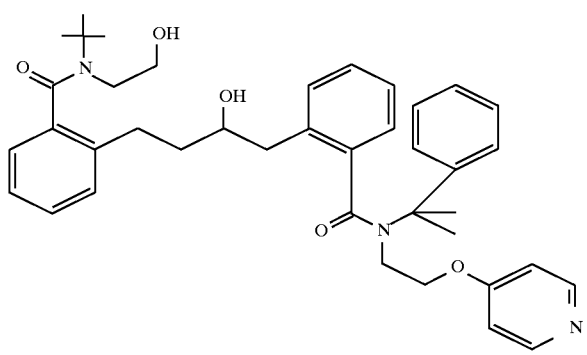 |
| 84 | 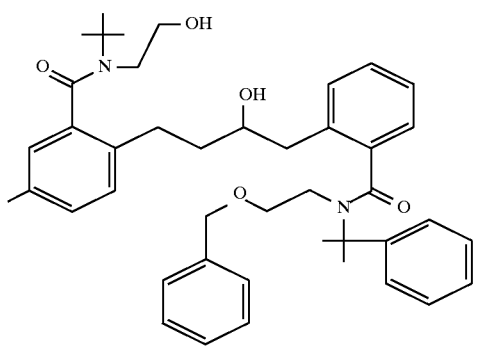 |

| EXAMPLE # | STRUCTURE |
|---|---|
| 85 | 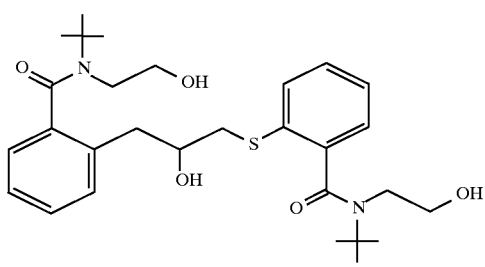 |
| 86 | 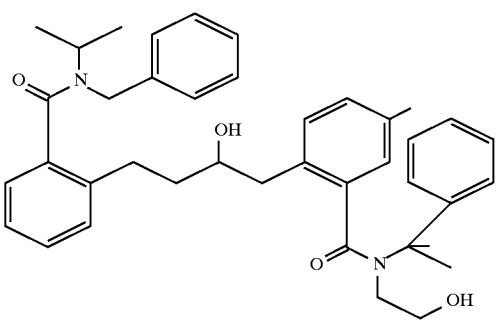 |
| 87 | 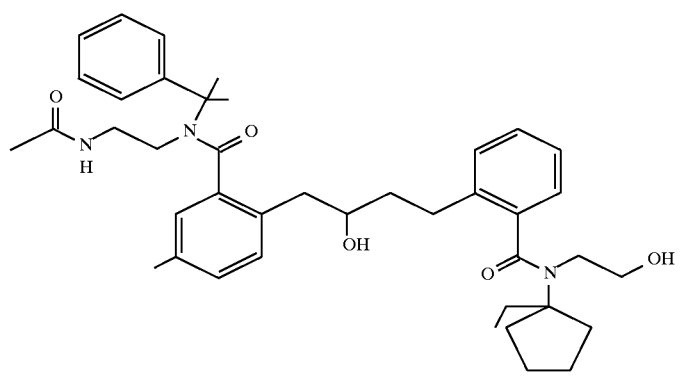 |
| 88 | 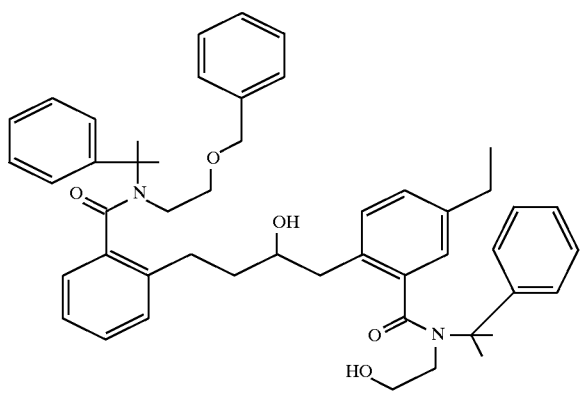 |

| EXAMPLE # | STRUCTURE |
|---|---|
| 89 | 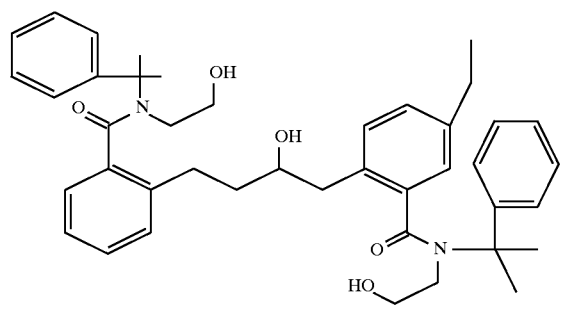 |
| 90 | 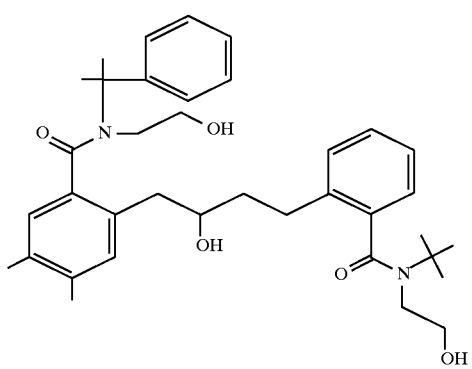 |
| 91 | 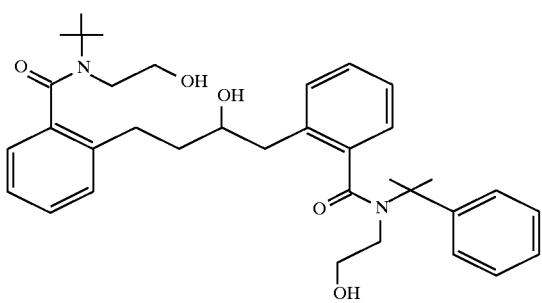 |
| 92 | 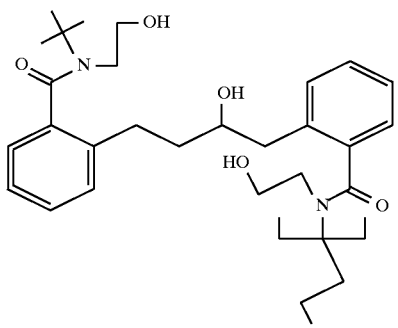 |

| EXAMPLE # | STRUCTURE |
|---|---|
| 93 | 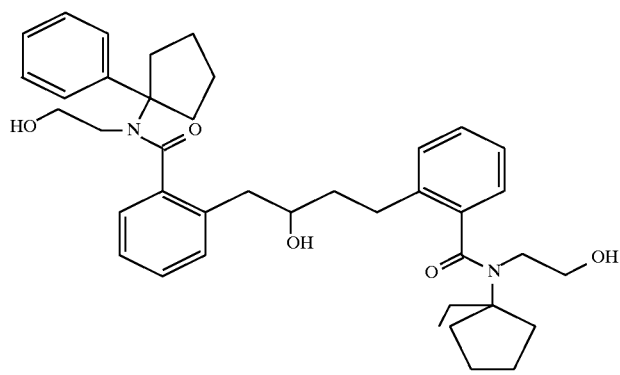 |
| 94 | 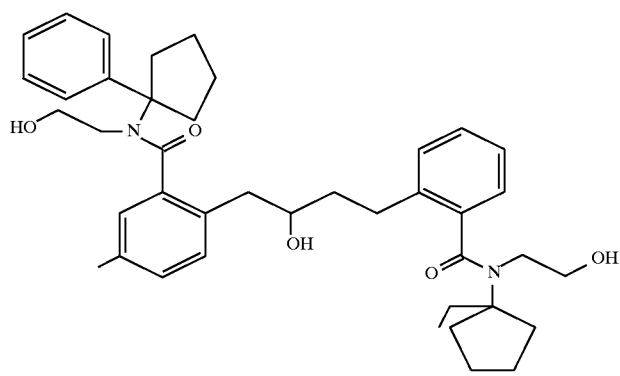 |
| 95 | 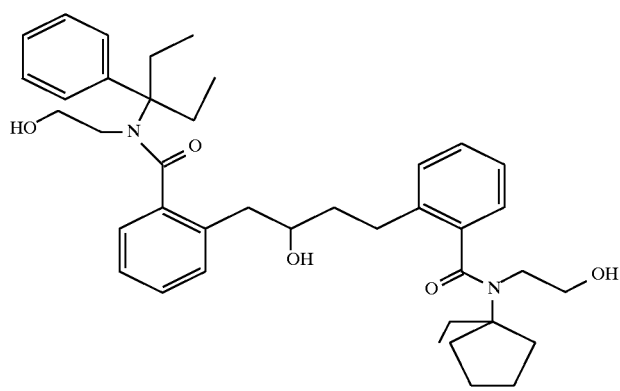 |
| 96 | 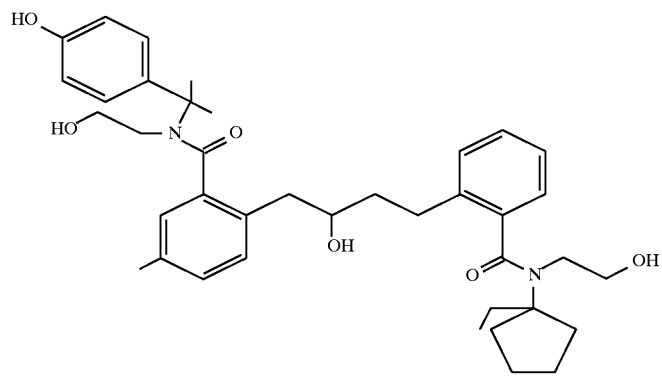 |

| EXAMPLE # | STRUCTURE |
|---|---|
| 97 | 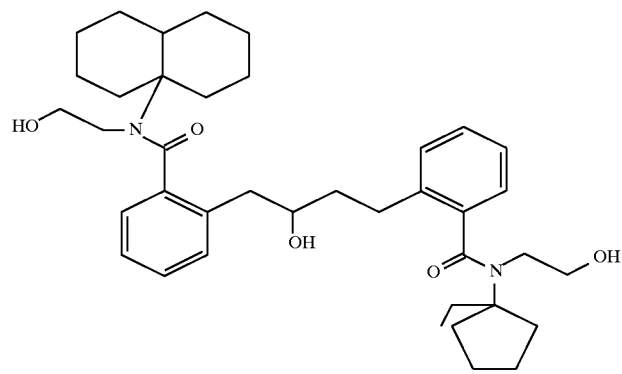 |
| 98 | 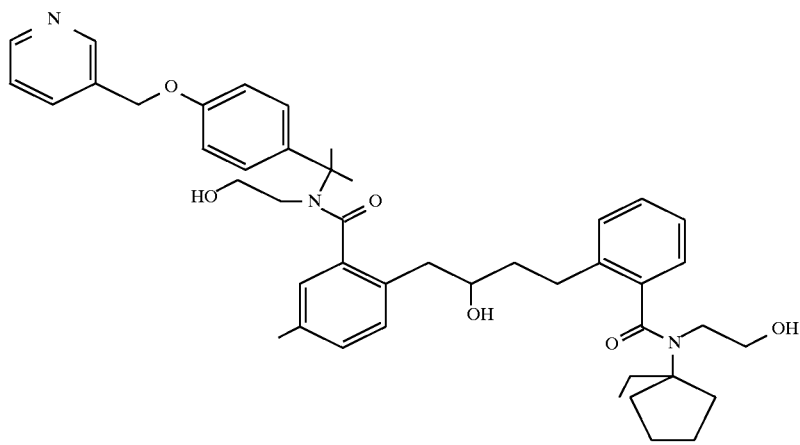 |
| 99 | 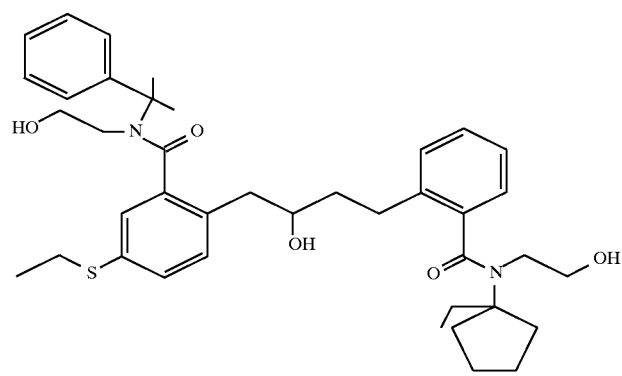 |
| 100 | 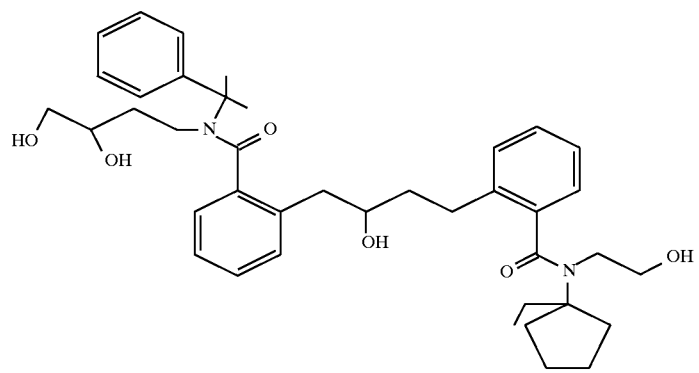 |

| EXAMPLE # | STRUCTURE |
|---|---|
| 101 | 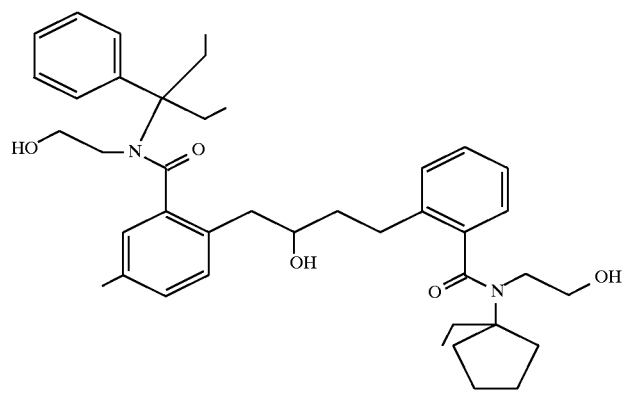 |
| 102 | 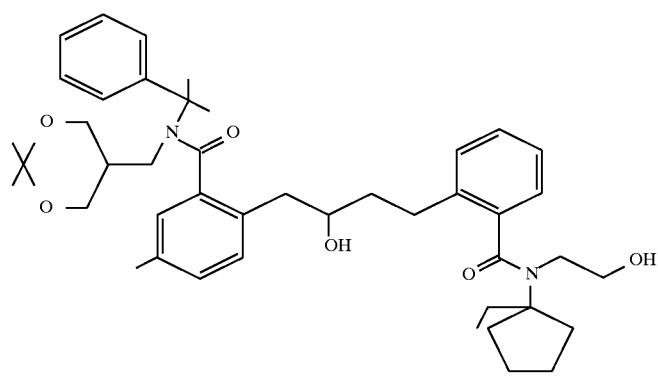 |
| 103 | 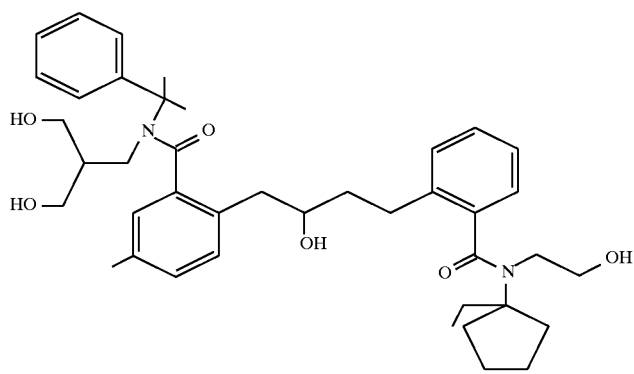 |
| 104 | 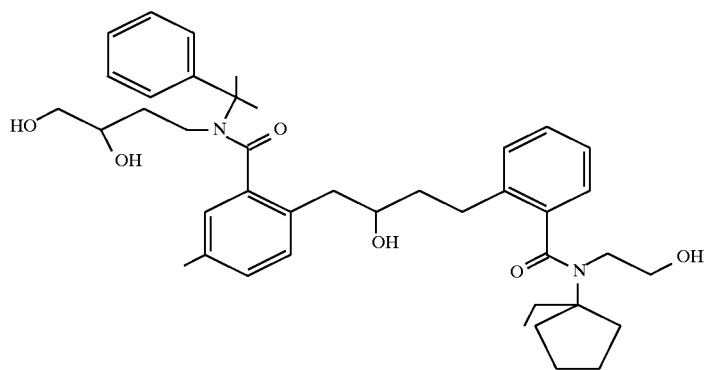 |

| EXAMPLE # | STRUCTURE |
|---|---|
| 105 | 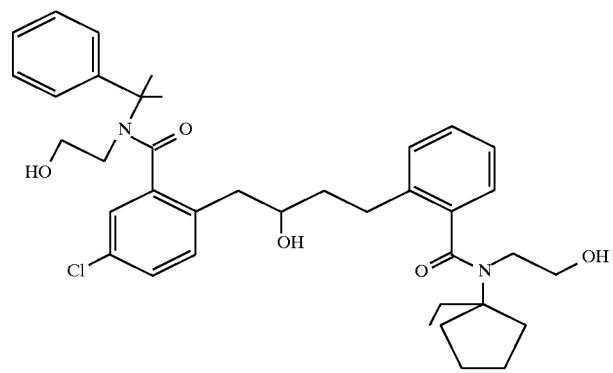 |
| 106 | 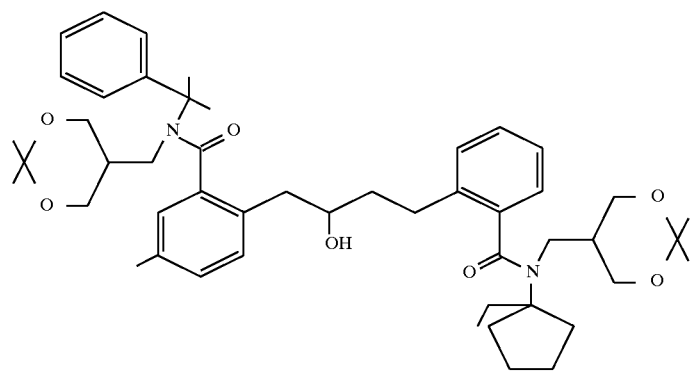 |
| 107 | 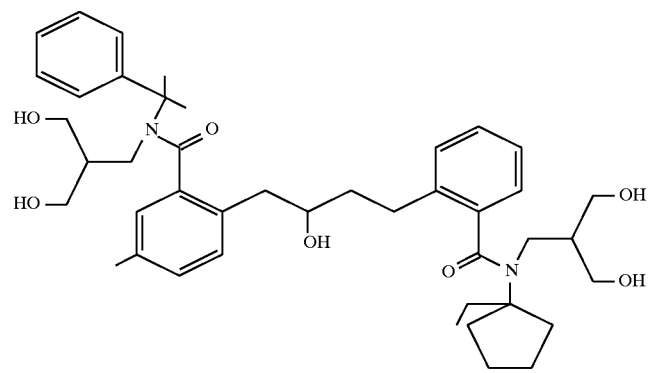 |
| 108 | 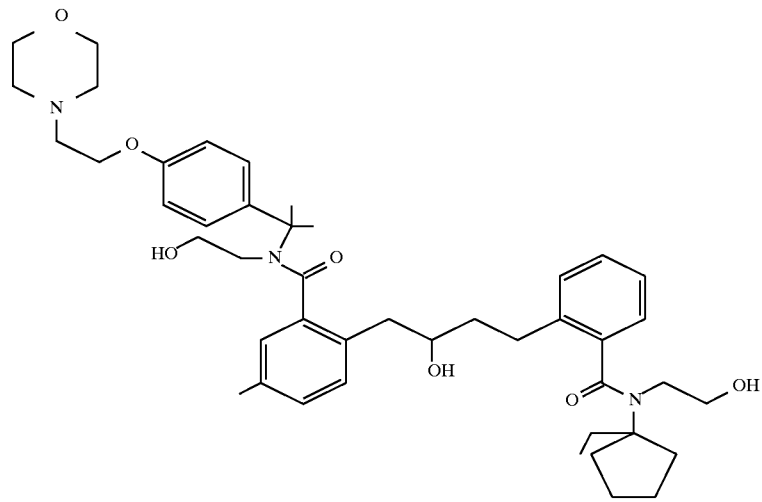 |

| EXAMPLE # | STRUCTURE |
|---|---|
| 109 | 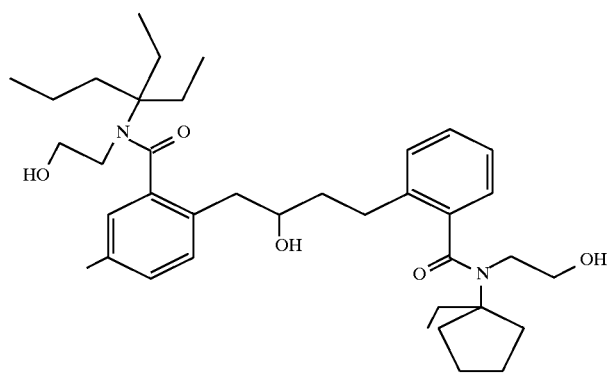 |
| 110 | 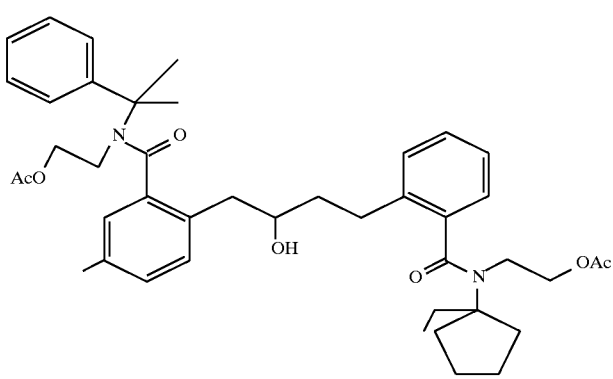 |
| 111 | 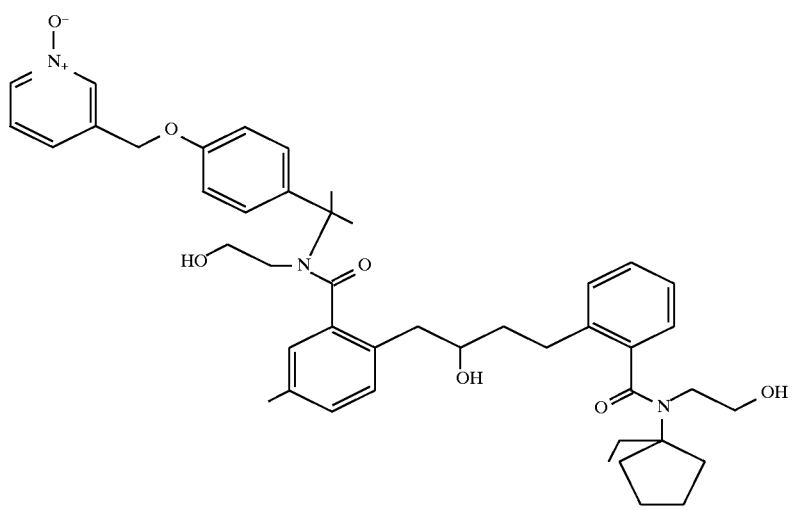 |

| EXAMPLE # | STRUCTURE |
|---|---|
| 112 | 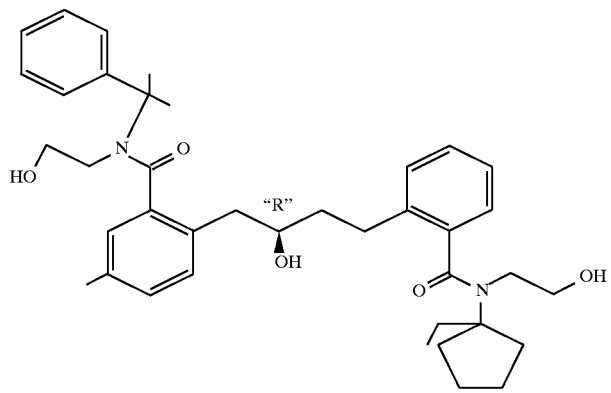 |
| 113 | 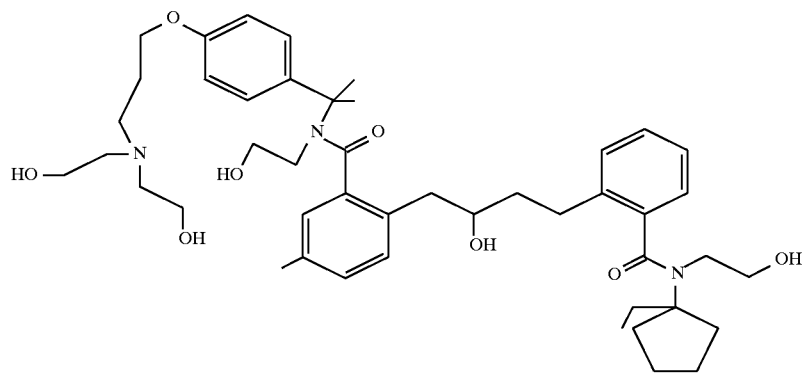 |
| 114 | 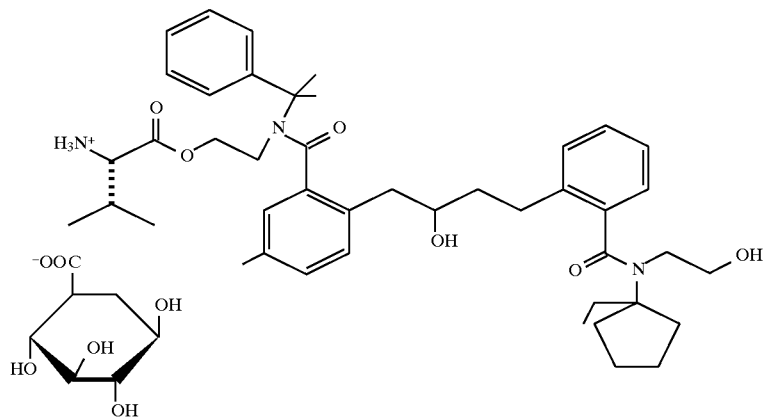 |
| 115 | 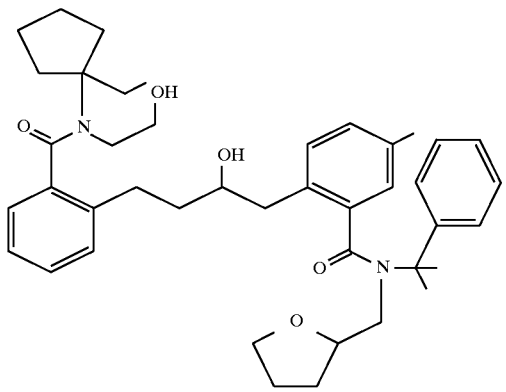 |

EXAMPLE 116

Using a Chiralcel OD HPLC column (J. T. Baker) and a mobile phase of 90/10 hexane-ethanol and a flow rate of 1 mL/min, racemic 18m was separated into individual pure enantiomers, the more polar compound (HPLC retention= 15.79 min) designated example 116a. This enantiomer was the more active against the HIV protease enzyme and in the antiviral assay (see table 1) relative to example 116b (the less polar, and less active enantiomer, HPLC retention time=11.26 min).

Optical Rotation:

116a $\alpha_D$=+9.1° C. [CHCl$_3$]

116b $\alpha_D$=10.9° [CHCL$_3$]

The structure of the compound of Example 116a is shown in Example 112.

The terms "essentially enantiomerically pure" or "essentially diastereomerically pure" mean that a compound so described is essentially free of either its enantiomer or of other diastereomers. Thus, such a compound has a significantly lower Ki than a compound that is not essentially free of its enantiomer or of other diastereomers.

The compounds of the subject invention also include prodrugs, i.e. Examples 110 and 114.

As a further embodiment, the present invention also includes a method for preparing a compound of the formula XII

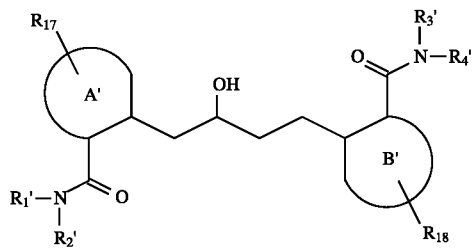

wherein:

A' and B' are individually selected from carbocyclic or heterocyclic, aromatic, saturated or partially saturated 5, 6 or 7 member rings which can be further substituted;

R'$_1$, R'$_2$, R'$_3$ and R'$_4$ are individually selected from alkyl, cycloalkyl, aryl, and substituted alkyl, cycloalkyl or aryl, and R'$_1$ and R'$_2$ or R'$_3$ and R'$_4$ can form a ring with the nitrogen atom to which they are attached;

R$_{17}$ and R$_{18}$ are individually selected from hydrogen, halogen, hydroxyl, substituted or unsubstituted alkoxy, mercapto, thioether, —NR'$_1$R'$_2$, nitro, alkyl, aryl and substituted alkyl or aryl, wherein R$_{17}$ can form a fused ring structure with A' and R$_{18}$ can form a fused ring structure with B';

which method comprises carrying out the following reactions:

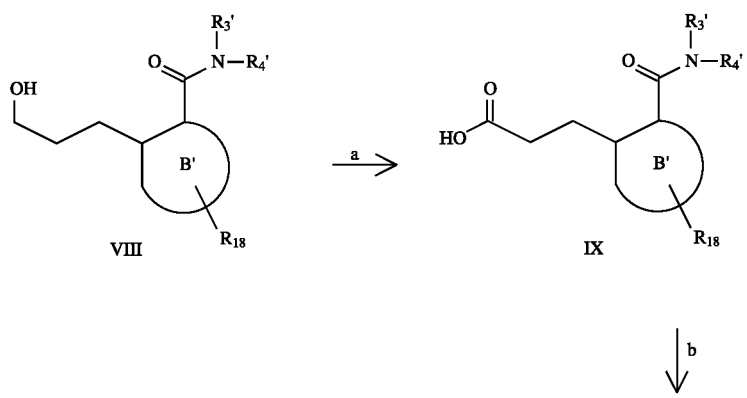

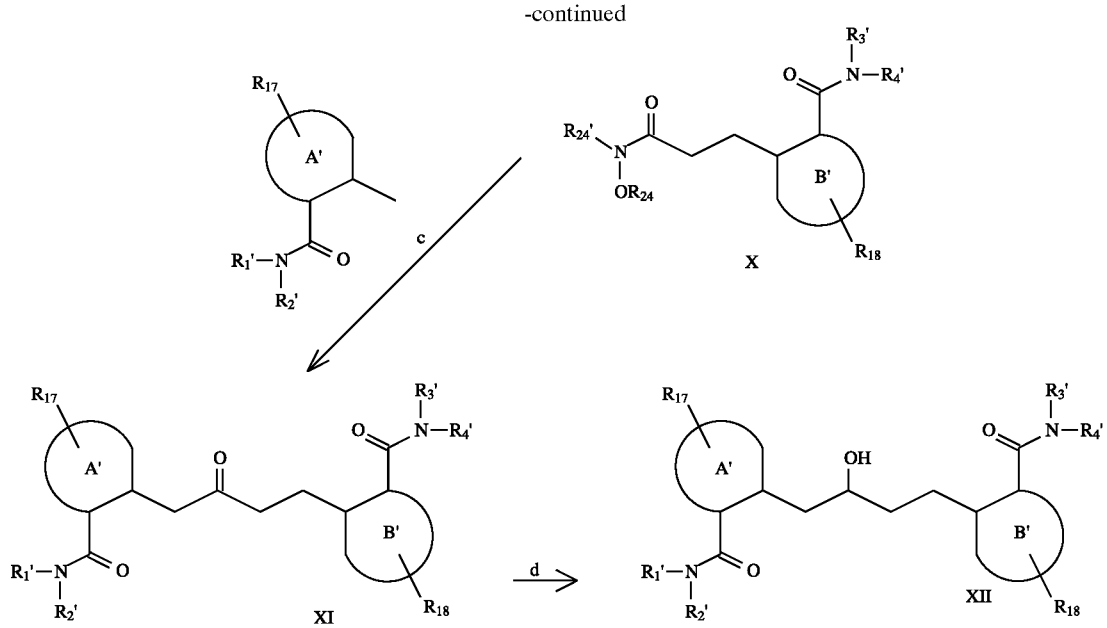

wherein:

a) the compound of the formula VIII is oxidized under conditions sufficient to obtain the compound of the formula IX;

b) the compound of the formula IX is reacted with the compound $HN(OR_{24})R'_{24}$ under conditions sufficient to obtain the compound of the formula X, wherein $R_{24}$ and $R'_{24}$ are individually selected from alkyl groups;

c) the compound of the formula X is reacted with the compound of the formula Xa under conditions sufficient to obtain the compound of the formula XI; and d) the compound of the formula XI is reduced under conditions sufficient to obtain the compound of the formula XII.

The HIV-protease inhibitory compounds were screened by a variety of assays to determine their biological utility. Among the tests performed were the proteolytic inhibition rates and antiviral effect on HIV-infected cell lines. The procedures for each experiment are described in detail below. the IC50 and Ki data were generated by Agouron scientists, whereas the protease activity with the cell cultures was measured by independent, outside laboratories. The results from these assays for Examples 1–115 are summarized in Table I, which is set forth following the descriptions below of the experimental procedures.

IC50 and Ki Determination of HIV Protease Inhibitors

1. Proteolytic activity of purified HIV-1 protease was routinely measured using the chromogenic assay developed by Richards et al. (J. Biol. Chem. 265: 7733 (1990)). Synthetic peptide His-Lys-Ala-Arg-Val-Leu-Phe (pNO2)-Glu-Ala-Nle-Ser-NH2 (American Peptide Company) was used as the substrate.

2. The assay was carried out in 0.5M NaCl, 50 mM MES pH 5.6, 2% DMSO (dimethylsulfoxide) at 37° C. Cleavage of the scissile bond between leucine and paranitro-phenylalanine (Phe(pNO2)) was assayed by spectrophotometric monitoring of the decrease in absorbance at 305 nm. Initial velocity was determined as the rate of decline of absorbance during the first 100 seconds of reaction. Under standard conditions, the Michaelis constant (Km) for this substrate is 52±16 μM.

3. For determination of inhibition rates of HIV-1 protease inhibitors, saturated concentration of substrate (200μM) was used. Between 15–25 concentrations of inhibitor were added and velocity of reaction was measured at each of the concentrations, as described above.

4. Inhibition constants were calculated using the method of Jackson et al. (Adv. in Enzyme Regulation 22: 187 (1984)). In the above described assay, Pepstatin A-a standard inhibitor of aspartic proteases has a Ki app= 3.1±0.1 μM and $IC_{50}$=3.8±0.7 μM.

Primary Drug Screening of Anti-HIV Compounds at Southern Research Institute (SRI)

1. Principle of MTT Assay:

SRI has an established program for the primary antiviral analysis of compounds in microtiter assays which measure the ability of a selected compound to inhibit HIV-induced cell killing. This assay involves the conversion of the tetrazolium dye MTT to a colored formazan product by mitochondrial enzymes in metabolically active cells. This assay system is presently used at SRI to screen over 30,000 compounds per year. Briefly, the assay involves the infection of CEM or MT2 cells in round bottom 96-well plates. The compound of interest is added just prior to infection. Following 6 days of incubation at 37° C. the plates are stained with MTT. The results of the assay are quantitated spectrophotometrically on a Molecular Devices Vmax plate reader. The data is analyzed by linear regression utilizing an in-house software program to calculate antiviral activity. ($IC_{25}$, $IC_{50}$, $IC_{95}$) and toxicity ($TC_{25}$, $TC_{50}$, $TC_{95}$) as well as other values.

Primary antiviral assays are routinely performed in CEM or MT-2 cells. SRI has found that all active compounds have been identified in CEM cells while experiments performed in the MT-2 cell line miss a small proportion of the active compounds.

2. Standard Screening Assays in CEM and MT-2 Cells a. Compound dilution and delivery to the plates Drugs will be solubilized in the appropriate vehicle such as distilled water or DMSO if necessary. Latex gloves, lab coats and masks are used during all phases of the handling process to prevent exposure to potentially harmful agents. The drug is prepared at the appropriate concentration and stored at −20° C. until used by the screening laboratory. The first dilution of each compound is made in a dilution tube with medium to yield a concentration two-fold that of the highest test concentration. Sterile titer tubes are then used to make serial one half-log dilutions of each compound. Following drug dilution, the diluted compound is added to the appropriate well of a 96-well microtiter plate. Up to 12 dilutions can be assayed conveniently in triplicate on a single plate with all appropriate controls including cell control, virus control, toxicity control, drug color control, medium control and plastic (background) control. When testing includes only six dilutions, two drugs can be assayed on a single microtiter plate. The drugs are added to the plate in a final volume of 100 microliters.

b. Cells and virus

During the time the drug dilutions are prepared, cells are washed and counted. Viability is monitored by trypan blue dye exclusion and assays are not performed if the viability falls below 90%. Cells are maintained in an exponential growth phase and are split 1:2 on the day prior to assay to assure exponential growth rate.

For the primary screen, the cell lines utilized are CEM and MT-2. Unless otherwise indicated, the medium used is RPMI 1640 with 10% heat-inactivated fetal calf serum (FBS), glutamine and antibiotics.

Cells are propagated at 37° C. in an atmosphere of 5% $CO_2$ in air. The virus employed for this work is HIV-1 isolates IIIB and/or RF, which are prepared by an acute infection process.

Briefly, virus-infected cells are pelleted on a daily basis beginning at three days post-infection until the virus has killed all of the cells in the culture. Reverse transcriptase activity and p24 ELISA are used to identify pools with the greatest amount of virus.

These 24-hour harvests are pooled, filtered and frozen at −90° C. Prior to use in the assay, the infectious pool of virus is titered on all available cell lines in order to determine the amount of virus required in the antiviral assay.

In general, pools produced by the acute infection method require the addition of one microliter of infectious virus per well resulting in the screening of drugs at a multiplicity of infection of 0.01. In this manner enough virus is prepared and frozen to complete over one thousand microtiter plates, allowing the testing of up to two thousand compounds from a single stock of infectious virus. The use of a single stock of virus for a long period of testing has very favorable effects on the repeatability of the assay systems.

Virus infection of the CEM and MT-2 cells for the antiviral assay is carried out in a bulk infection process. The appropriate number of cells required to complete the assay is mixed with infectious virus in a conical centrifuge tube in a small total volume of 1–2 milliliters.

Following a 4-hour incubation the infected cells are brought to the appropriate final concentration of $5\times10^4$ cells per milliliter with fresh tissue culture medium and 100 microliters are added to the appropriate experimental and virus control wells. Uninfected cells at the same concentration are plated for the toxicity controls and for the cell controls. Assays can also be performed using an in-well infection method. In this case, drug, cells and virus are added to the well individually. In each case the MOI is adjusted to give complete cell killing in the virus control wells by Day 6.

c. Evaluation of CPE-inhibition

Following the addition of cells and drugs to the microtiter plate the plate is incubated for 6 days at 37° C. Experience has determined that incubation for longer periods of time (7–8 days) or the use of higher input cell numbers ($1\times10^4$) results in significant decreases in cell control viability and a narrowing in the differential in optical density between cell and virus controls upon staining with MTT.

The method of evaluating the antiviral assay involves the addition of 20 microliters of the tetrazolium salt MTT at 5mg/ml to each well of the plate for 4–8 hours. After this incubation period the cells are disrupted by the addition of 50 $\mu$l of 20% SDS in 0.01N HCl.

The metabolic activity of the viable cells in the culture result in a colored reaction product which is measured spectropotometrically in a Molecular Devices Vmax plate reader at 570 nm. The optical density (O.D.) value is a function of the amount of formazan product which is proportional to the number of viable cells.

The plate reader is on-line to the screening laboratory microcomputer which evaluates the plate data and calculates plate data. The plate report provides a rundown of all pertinent information including the raw O.D. values, the calculated mean O.D.'s and the percent reduction in viral CPE as well as calculations including $TC_{50}$, $IC_{50}$ and antiviral and specificity indices. Finally, the results include a plot which visually depicts the effect of the compound on uninfected cells (toxicity) and the protective or nonprotective effect of the compound on the infected cells.

Table I

Notes about the table:

(1) If $IC_{50}$ or Ki values are not indicated, the test was performed for the particular compound.

(2) The anti-viral data are given for 2 cell lines, representing testing done at Southern Research Institute. The first position of each line represents data obtained for the CEM cell line and the second position indicates the viral inhibition of MT-2 cells. If no data are listed, then the compound has not been tested for its anti-viral effects.

| Ex | IC50 ($\mu$M) | Ki ($\mu$M) | Viral CEM/MT-2 ($\mu$g/ml) |
|---|---|---|---|
| 1 | 1.03 | 0.835 | 18.6/23 |
| 2 | 5.7 | 2.2 | −/− |
| 3 | 2.38 | 1.31 | −/− |
| 4 | 0.72 | 0.42 | −/− |
| 5 | 0.95 | 0.84 | 17.4/32 |
| 6 | 30 | — | −/− |
| 7 | 1.02 | 1.01 | −/− |
| 8 | ~20 | — | −/− |
| 9 | 40% at 20 | — | −/− |
| 10 | 15 | — | −/− |
| 11 | 18 | — | −/− |
| 12 | 0.82 | 0.79 | 29.5/− |
| 13 | 40% at 10 | — | −/− |
| 14 | 5.6 | 5.4 | −/− |
| 15 | 1.42 | 0.99 | 6.01/− |
| 16 | 20% at 50 | — | −/− |
| 17 | >200 | — | −/− |
| 18 | 0.089 | 0.0016 | 0.49/0.53 |
| 19 | — | — | −/− |
| 20 | — | — | −/− |

| Ex | IC50 (μM) | Ki (μM) | Viral CEM/MT-2 (μg/ml) |
|---|---|---|---|
| 21 | 10% at 200 | — | -/- |
| 22 | 60 | — | -/- |
| 23 | 75–100 | — | -/- |
| 24 | >200 5 | — | -/- |
| 25 | 18 | — | -/- |
| 26 | >200 | — | -/- |
| 27 | 40% at 200 | — | -/- |
| 28 | 40% at 200 | — | -/- |
| 29 | 55 | — | -/- |
| 30 | 38 | — | -/- |
| 31 | 20% at 100 35% at 100 | — | -/- |
| 32 | 7 | — | -/- |
| 33 | 6 | — | -/- |
| 34 | 40% at 100 | — | -/- |
| 35 | 1.19 | 0.84 | -/- |
| 36 | 25 | — | -/- |
| 37 | >500 | — | -/- |
| 38 | >500 | — | -/- |
| 39 | >500 | — | -/- |
| 40 | >500 | — | -/- |
| 41 | >500 | — | -/- |
| 42 | 150–200 | — | -/- |
| 43 | 20% at 200 | — | -/- |
| 44 | 20% at 200 | — | -/- |
| 45 | 60 | — | -/- |
| 46 | 200 | — | -/- |
| 47 | 50 | — | -/- |
| 48 | 70 | — | -/- |
| 49 | 0.88 | 0.48 | -/- |
| 50 | 120 | — | -/- |
| 51 | 120 | — | -/- |
| 52 | 25 | — | -/- |
| 53 | 42 | — | -/- |
| 54 | 9 | — | -/- |
| 55 | 6.3 | — | -/- |
| 56 | 64 | 56 | -/- |
| 57 | 93% at 200 | — | -/- |
| 58 | 9.6 | 7.7 | -/- |
| 59 | 20% at 100 | — | -/- |
| 60 | 4.1 | 2.7 | -/- |
| 61 | 1.33 | 1.27 | -/- |
| 62 | 0.169 | 0.152 | 2.86/4.98 |
| 63 | 40% at 200 | — | -/- |
| 64 | 8.3 | 7.9 | -/- |
| 65 | 0.082 | 0.031 | 0.89/1.76 |
| 66 | 0.250 | 0.145 | 4.53/12.71 |
| 67 | 40% at 10 | — | -/- |
| 68 | 11.9 | 5.8 | -/- |
| 69 | 40% at 10 | — | -/- |
| 70 | 9 | — | -/- |
| 71 | 1.3 | 0.879 | -/- |
| 72 | 0.326 | 0.100 | 5.54/17.9 |
| 73 | 0.68 | 0.717 | >10/>10 |
| 74 | 0.180 | 0.021 | 3.69/5.54 |
| 75 | 8.0 | — | -/- |
| 76 | 1.74 | 0.92 | -/- |
| 77 | 1.23 | 1.01 | 7.57/16.4 |
| 78 | 0.42 | 0.32 | >10/6.64 |
| 79 | 3.5 | 3.2 | -/- |
| 80 | 0.089 | 0.012 | 0.53/0.68 |
| 81 | 0.23 | 0.064 | 4.39/5.58 |
| 82 | 0.104 | 0.017 | 0.75/0.64 |
| 83 | 2.5 | 0.735 | >100/>100 |
| 84 | 0.351 | 0.315 | >100/>100 |
| 85 | 36 | 18.4 | -/- |
| 86 | 0.448 | 0.379 | -/- |
| 87 | 0.0076 | 0.085 | -/- |
| 88 | 0.230 | 0.075 | -/- |
| 89 | 0.144 | 0.017 | 1.0/1.79 |
| 90 | 0.200 | 0.176 | -/- |
| 91 | 0.274 | 0.172 | 1.95/5.28 |
| 92 | 0.183 | 0.088 | 2.12/5.06 |
| 93 | 0.104 | 0.0023 | 1.35/1.67 |
| 94 | 0.141 | 0.00055 | 0.52/1.47 |
| 95 | 0.090 | 0.0015 | 0.60/1.46 |
| 96 | 0.063 | 0.004 | 0.57/1.18 |
| 97 | 0.225 | 0.038 | 1.58/>10 |
| 98 | 0.103 | 0.002 | 0.48/1.94 |
| 99 | 0.196 | 0.015 | 1.62/5.75 |
| 100 | 0.110 | 0.007 | 0.48/1.94 |
| 101 | 0.102 | 0.004 | 4.16/1.67 |
| 102 | 0.133 | 0.0023 | 0.42/0.47 |
| 103 | 0.106 | 0.010 | 0.64/1.15 |
| 104 | 0.081 | 0.0096 | 0.58/0.55 |
| 105 | 0.086 | 0.001 | 0.47/0.49 |
| 106 | 0.067 | 0.0039 | 3.91/1.7 |
| 107 | 0.092 | 0.032 | 1.44/1.34 |
| 108 | 0.108 | 0.0098 | 0.64/0.56 |
| 109 | 0.059 | 0.0136 | 0.79/0.59 |
| 110 | 0.068 | 0.0054 | 0.69/1.72 |
| 111 | 0.052 | 0.0080 | 1.03/1.81 |
| 112 | 0.076 | 0.0025 | 0.54/1.47 |
| 113 | 0.103 | 0.010 | 1.73/1.58 |
| 114 | 0.398 | 0.230 | 2.11/1.75 |
| 115 | 0.290 | 0.017 | 4.16/6.34 |

With respect to all compounds of formula I described both in the specification and the claims, there is a proviso to exclude certain compounds otherwise falling within the scope of formula I. In other words, compounds of the formula

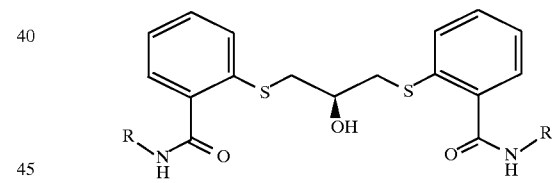

wherein R is independently alkyl or substituted alkyl are not included within the scope of formula I.

What is claimed is:

1. A compound having the formula II

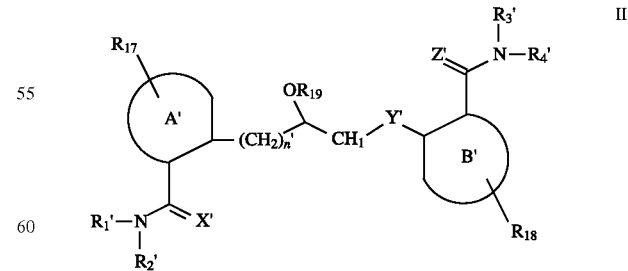

wherein:

f is 0, 1, or 2;

A' and B' are individually selected from carbocyclic or heterocyclic, aromatic, saturated or partially saturated 5, 6 or 7 member rings which can be further substituted;

n' is 0, 1 or 2;

X' and Z' are individually selected from oxygen and sulphur;

when f is 2, Y' is a substituted or unsubstituted amino group, oxygen, sulphur, or —$CH_2$—;

when f is 1, Y' is —CH=;

when f is 0, Y' is C≡;

$R'_1$, $R'_2$, $R'_3$ and $R'_4$ are individually selected from hydrogen, alkyl, cycloalkyl, aryl, substituted alkyl, cycloalkyl or aryl, substituted oxygen, hydroxyl, substituted or unsubstituted non-cyclic amino and substituted or unsubstituted non-aryl heterocycle, wherein $R'_1$ and $R'_2$ or $R'_3$ and $R'_4$ can form a ring with the nitrogen atom to which they are attached;

$R_{17}$ and $R_{18}$ are individually selected from hydrogen, halogen, hydroxyl, substituted or unsubstituted alkoxy, mercapto, thioether, —$NR'_1R'_2$, nitro, alkyl, aryl and substituted alkyl or aryl, wherein $R_{17}$ can form a fused ring structure with A' and $R_{18}$ can form a fused ring structure with B'; and $R_{19}$ is hydrogen or a 1 to 3 carbon substituted or unsubstituted alkyl group;

or a pharmaceutically acceptable salt thereof.

2. A compound according to claim 1, wherein further substituents on the A' and B' are individually selected from halogen, hydroxyl, substituted or unsubstituted alkoxy, mercapto, thioether, —$NR'_1R'_2$, nitro, alkyl, aryl and substituted alkyl or aryl.

3. A compound according to claim 1, wherein substituents on the Y' amino group are individually selected from those recited for $R'_1$, $R'_2$, $R'_3$, and $R'_4$.

4. A compound according to claim 1 wherein X' and Z' are oxygen.

5. A compound according to claim 4 wherein $R_{19}$ is hydrogen.

6. A compound according to claim 6 wherein one of $R'_1$ and $R'_2$ is hydrogen and one is an alkyl or substituted alkyl group and one of $R'_3$ and $R'_4$ is hydrogen and one is an alkyl or substituted alkyl group.

7. A compound according to claim 5 wherein $R'_3$ and $R'_4$ are joined to form a ring with the nitrogen atom to which they are attached and $R'_1$ and $R'_2$ are individually selected from hydrogen and alkyl groups or substituted alkyl groups.

8. A compound according to claim 5 wherein $R_{17}$ and $R_{18}$ are both hydrogen.

9. A compound according to claim 5 wherein one of $R_{17}$ and $R_{18}$ forms a fused ring structure with the ring to which it is attached.

10. A compound according to claim 5 wherein each of $R_{17}$ and $R_{18}$ forms a fused ring structure with the ring to which it is attached.

11. A compound according to claim 5, wherein $R'_1$, $R'_2$, $R'_3$ and $R'_4$ are independently selected from alkyl or substituted alkyl groups.

12. A compound according to claim 5, wherein each of $R_{17}$ and $R_{18}$ is independently selected from alkyl, substituted alkyl, mercapto and thioether groups.

13. A compound according to claim 12, wherein said thioether group is of the formula S—R, wherein R is substituted or unsubstituted alkyl, aryl, or non-aryl heterocycle and wherein said substituted alkyl is of the formula $CH_2R$.

14. A compound according to claim 5 wherein Y' is sulphur.

15. A compound according to claim 14 wherein $R'_1$, $R'_2$, $R'_3$ and $R'_4$ are independently selected from alkyl or substituted alkyl groups.

16. A compound according to claim 14, wherein one of $R'_1$ and $R'_2$ is hydrogen and one is an alkyl or substituted alkyl group and one of $R'_3$ and $R'_4$ is hydrogen and one is an alkyl or substituted alkyl group.

17. A compound according to claim 14 wherein $R'_3$ and $R'_4$ are joined to form a ring with the nitrogen atom to which they are attached and $R'_1$ and $R'_2$ are individually selected from hydrogen and alkyl groups or substituted alkyl groups.

18. A compound according to claim 14 wherein $R_{17}$ and $R_{18}$ are both hydrogen.

19. A compound according to claim 14 wherein one of $R_{17}$ and $R_{18}$ forms a fused ring structure with the ring to which it is attached.

20. A compound according to claim 14 wherein each of $R_{17}$ and $R_{18}$ forms a fused ring structure with the ring to which it is attached.

21. A compound according to claim 14, wherein each of $R_{17}$ and $R_{18}$ is independently selected from alkyl, substituted alkyl, mercapto and thioether groups.

22. A compound according to claim 21, wherein said thioether group is of the formula S—R, wherein R is substituted or unsubstituted alkyl, aryl, or non-aryl heterocycle and wherein said substituted alkyl is of the formula $CH_2R$.

23. A compound according to claim 5 wherein Y' is an amino group.

24. A compound according to claim 23 wherein $R'_1$, $R'_2$, $R'_3$ and $R'_4$ are independently selected from alkyl or substituted alkyl groups.

25. A compound according to claim 23 wherein one of $R'_1$ and $R'_2$ is hydrogen and one is an alkyl or substituted alkyl group and one of $R'_3$ and $R'_4$ is hydrogen and one is an alkyl or substituted alkyl group.

26. A compound according to claim 23 wherein $R'_3$ and $R'_4$ are joined to form a ring with the nitrogen atom to which they are attached and $R'_1$ and $R'_2$ are individually selected from hydrogen and alkyl or substituted alkyl groups.

27. A compound according to claim 23 wherein $R_{17}$ and $R_{18}$ are both hydrogen.

28. A compound according to claim 23 wherein one of $R_{17}$ and $R_{18}$ forms a fused ring structure with the ring to which it is attached.

29. A compound according to claim 23, wherein each of $R_{17}$ and $R_{18}$ is independently selected from alkyl, substituted alkyl, mercapto and thioether groups.

30. A compound according to claim 29, wherein said thioether group is of the formula S—R, wherein R is substituted or unsubstituted alkyl, aryl, or non-aryl heterocycle and wherein said substituted alkyl is of the formula $CH_2R$.

31. A compound according to claim 23 wherein each of $R_{17}$ and $R_{18}$ forms a fused ring structure with the ring to which it is attached.

32. A compound according to claim 5 wherein Y' is —$CH_2$—, —CH=, or —C≡.

33. A compound according to claim 32 wherein $R'_1$, $R'_2$, $R'_3$ and $R'_4$ are independently selected from alkyl or substituted alkyl groups.

34. A compound according to claim 32 wherein one of $R'_1$ and $R'_2$ is hydrogen and one is an alkyl or substituted alkyl group and one of $R'_3$ and $R'_4$ is hydrogen and one is an alkyl or substituted alkyl group.

35. A compound according to claim 32 wherein $R'_3$ and $R'_4$ are joined to form a ring with the nitrogen atom to which they are attached and $R'_1$ and $R'_2$ are individually selected from hydrogen and alkyl or substituted alkyl groups.

36. A compound according to claim 32 wherein $R_{17}$ and $R_{18}$ are both hydrogen.

37. A compound according to claim 32 wherein one of $R_{17}$ and $R_{18}$ forms a fused ring structure with the ring to which it is attached.

38. A compound according to claim 32 wherein each of $R_{17}$ and $R_{18}$ forms a fused ring structure with the ring to which it is attached.

39. A compound according to claim 32, wherein each of $R_{17}$ and $R_{18}$ is independently selected from alkyl, substituted alkyl, mercapto and thioether groups.

40. A compound according to claim 39, wherein said thioether group is of the formula S—R, wherein R is substituted or unsubstituted alkyl, aryl, or non-aryl heterocycle and wherein said substituted alkyl is of the formula $CH_2R$.

41. A compound having the formula

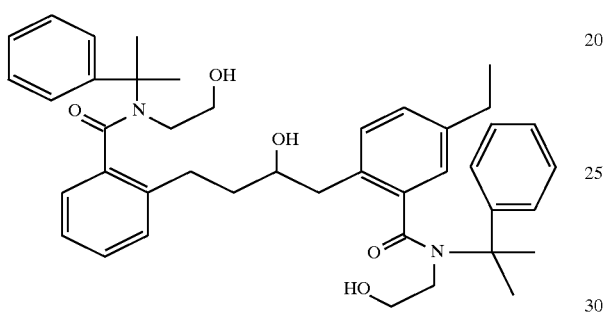

42. A compound having the formula

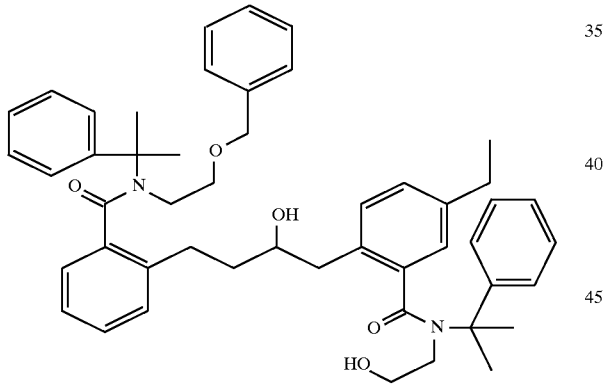

43. A compound having the formula

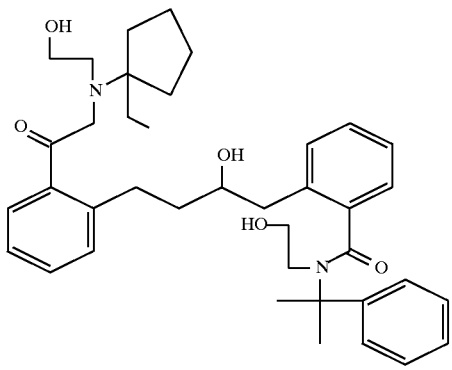

44. A compound having the formula

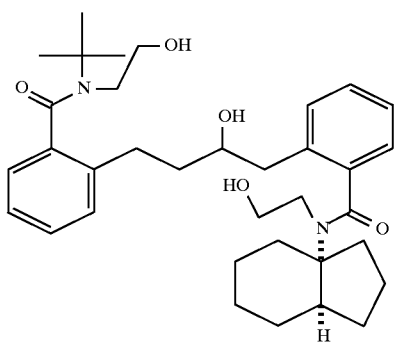

45. A compound having the formula

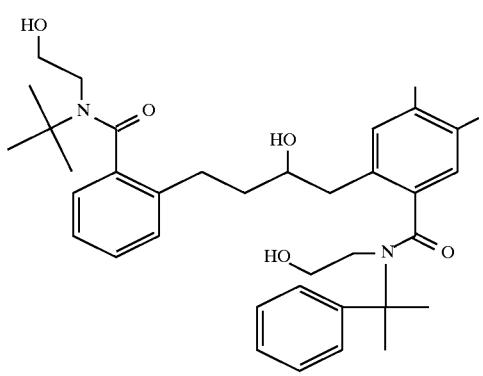

46. A compound having the formula

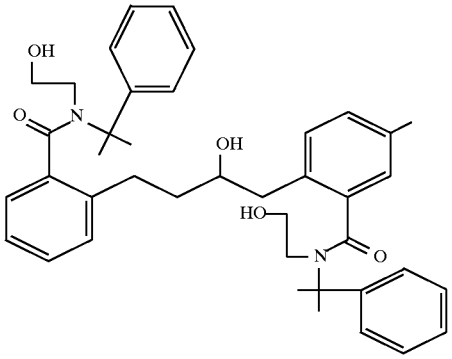

47. A compound having the formula

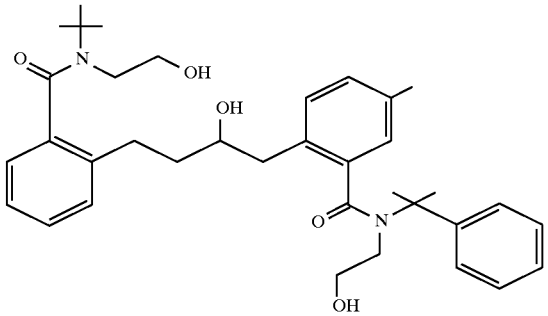

48. A compound having the formula

49. A compound having the formula

50. A compound having the formula

51. A composition useful for inhibiting HIV protease which comprises
(1) a compound having the formula II wherein:
f is 0, 1, or 2;
A' and B' are individually selected from carbocyclic or heterocyclic, aromatic, saturated or partially saturated 5, 6 or 7 member rings which can be further substituted;

n' is 0, 1 or 2;
X' and Z' are individually selected from oxygen and sulphur;
when f is 2, Y' is a substituted or unsubstituted amino group, oxygen, sulphur, or —$CH_2$—;
when f is 1, Y' is —CH═;
when f is 0, Y' is —C≡;
$R'_1$, $R'_2$, $R'_3$ and $R'_4$ are individually selected from hydrogen, alkyl, cycloalkyl, aryl, substituted alkyl, cycloalkyl or aryl, substituted oxygen, hydroxyl, substituted or unsubstituted non-cyclic amino and substituted or unsubstituted non-aryl heterocycle, wherein $R'_1$ and $R'_2$ or $R'_3$ and $R'_4$ can form a ring with the nitrogen atom to which they are attached;
$R_{17}$ and $R_{18}$ are individually selected from hydrogen, halogen, hydroxyl, substituted or unsubstituted alkoxy, mercapto, thioether, —$NR'_1R'_2$, nitro, alkyl, aryl and substituted alkyl or aryl, wherein $R_{17}$ can form a fused ring structure with A' and $R_{18}$ can form a fused ring structure with B'; and
$R_{19}$ is hydrogen or a 1 to 3 carbon substituted or unsubstituted alkyl group;
or a pharmaceutically acceptable salt thereof; and
(2) a pharmaceutically acceptable carrier.

52. A composition according to claim 51 wherein X' and Z' are oxygen.

53. A composition according to claim 51 wherein $R_{19}$ is hydrogen.

54. A composition according to claim 53 wherein one of $R'_1$ and $R'_2$ is hydrogen and one is an alkyl or substituted alkyl group and one of $R'_3$ and $R'_4$ is hydrogen and one is an alkyl or substituted alkyl group.

55. A composition according to claim 53 wherein $R'_3$ and $R'_4$ are joined to form a ring with the nitrogen atom to which they are attached and $R'_1$ and $R'_2$ are individually selected from hydrogen and alkyl groups or substituted alkyl groups.

56. A composition according to claim 53 wherein $R_{17}$ and $R_{18}$ are both hydrogen.

57. A composition according to claim 53 wherein one of $R_{17}$ and $R_{18}$ forms a fused ring structure with the ring to which it is attached.

58. A composition according to claim 53 wherein each of $R_{17}$ and $R_{18}$ forms a fused ring structure with the ring to which it is attached.

59. A composition according to claim 53 wherein $R'_1$, $R'_2$, $R'_3$ and $R'_4$ are independently selected from alkyl or substituted alkyl groups.

60. A composition according to claim 53, wherein each of $R_{17}$ and $R_{18}$ is independently selected from alkyl, substituted alkyl, mercapto and thioether groups.

61. A composition according to claim 60, wherein said thioether group is of the formula S—R, wherein R is substituted or unsubstituted alkyl, aryl, or non-aryl heterocycle and wherein said substituted alkyl is of the formula $CH_2R$.

62. A composition according to claim 53 wherein Y' is sulphur.

63. A composition according to claim 62 wherein $R'_1$, $R'_2$, $R'_3$ and $R'_4$ are independently selected from alkyl or substituted alkyl groups.

64. A composition according to claim 62, wherein each of $R_{17}$ and $R_{18}$ is independently selected from alkyl, substituted alkyl, mercapto and thioether groups.

65. A composition according to claim 64, wherein said thioether group is of the formula S—R, wherein R is substituted or unsubstituted alkyl, aryl, or non-aryl heterocycle and wherein said substituted alkyl is of the formula $CH_2R$.

66. A composition according to claim 62 wherein one of R'$_1$ and R'$_2$ is hydrogen and one is an alkyl or substituted alkyl group and one of R'$_3$ and R'$_4$ is hydrogen and one is an alkyl or substituted alkyl group.

67. A composition according to claim 62 wherein R'$_3$ and R'$_4$ are joined to form a ring with the nitrogen atom to which they are attached and R'$_1$ and R'$_2$ are individually selected from hydrogen and alkyl groups or substituted alkyl groups.

68. A composition according to claim 62 wherein R$_{17}$ and R$_{18}$ are both hydrogen.

69. A composition according to claim 62 wherein one of R$_{17}$ and R$_{18}$ forms a fused ring structure with the ring to which it is attached.

70. A composition according to claim 62 wherein each of R$_{17}$ and R$_{18}$ forms a fused ring structure with the ring to which it is attached.

71. A composition according to claim 53 wherein Y' is an amino group.

72. A composition according to claim 71 wherein R'$_1$, R'$_2$, R'$_3$ and R'$_4$ are independently selected from alkyl or substituted alkyl groups.

73. A composition according to claim 71, wherein each of R$_{17}$ and R$_{18}$ is independently selected from alkyl, substituted alkyl, mercapto and thioether groups.

74. A composition according to claim 73, wherein said thioether group is of the formula S—R, wherein R is substituted or unsubstituted alkyl, aryl, or non-aryl heterocycle and wherein said substituted alkyl is of the formula CH$_2$R.

75. A composition according to claim 71 wherein one of R'$_1$ and R'$_2$ is hydrogen and one is an alkyl or substituted alkyl group and one of R'$_3$ and R'$_4$ is hydrogen and one is an alkyl or substituted alkyl group.

76. A composition according to claim 71 wherein R'$_3$ and R'$_4$ are joined to form a ring with the nitrogen atom to which they are attached and R'$_1$ and R'$_2$ are individually selected from hydrogen and alkyl or substituted alkyl groups.

77. A composition according to claim 71 wherein R$_{17}$ and R$_{18}$ are both hydrogen.

78. A composition according to claim 71 wherein one of R$_{17}$ and R$_{18}$ forms a fused ring structure with the ring to which it is attached.

79. A composition according to claim 71 wherein each of R$_{17}$ and R$_{18}$ forms a fused ring structure with the ring to which it is attached.

80. A composition according to claim 53 wherein Y' is —CH$_2$—, —CH=, or —C≡.

81. A composition according to claim 80 wherein R'$_1$, R'$_2$, R'$_3$ and R'$_4$ are independently selected from alkyl or substituted alkyl groups.

82. A composition according to claim 80, wherein each of R$_{17}$ and R$_{18}$ is independently selected from alkyl, substituted alkyl, mercapto and thioether groups.

83. A composition according to claim 82, wherein said thioether group is of the formula S—R, wherein R is substituted or unsubstituted alkyl, aryl, or non-aryl heterocycle and wherein said substituted alkyl is of the formula CH$_2$R.

84. A composition according to claim 80 wherein one of R'$_1$ and R'$_2$ is hydrogen and one is an alkyl or substituted alkyl group and one R'$_3$ and R'$_4$ is hydrogen and one is an alkyl or substituted alkyl group.

85. A composition according to claim 80 wherein R'$_3$ and R'$_4$ are joined to form a ring with the nitrogen atom to which they are attached and R'$_1$ and R'$_2$ are individually selected from hydrogen and alkyl or substituted alkyl groups.

86. A composition according to claim 80 wherein R$_{17}$ and R$_{18}$ are both hydrogen.

87. A composition according to claim 80 wherein one of R$_{17}$ and R$_{18}$ forms a fused ring structure with the ring to which it is attached.

88. A composition according to claim 80 wherein each of R$_{17}$ and R$_{18}$ forms a fused ring structure with the ring to which it is attached.

89. A process for inhibiting the action of the HIV virus which process comprises administering to a host in recognized need of such treatment an effective amount of a compound of the formula II

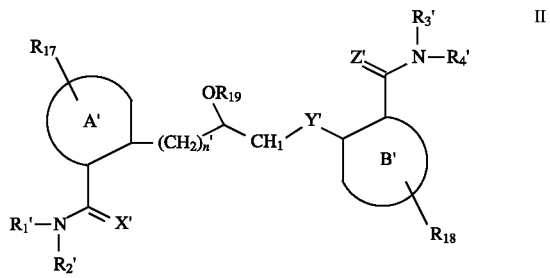

wherein:

f is 0, 1, or 2;

A' and B' are individually selected from carbocyclic or heterocyclic, aromatic, saturated or partially saturated 5, 6 or 7 member rings which can be further substituted;

n' is 0, 1 or 2;

X' and Z' are individually selected from oxygen and sulphur;

when f is 2, Y' is a substituted or unsubstituted amino group, oxygen, sulphur, or —CH$_2$—;

when f is 1, Y' is —CH=;

when f is 0, Y' is —C≡;

R'$_1$, R'$_2$, R'$_3$ and R'$_4$ are individually selected from hydrogen, alkyl, cycloalkyl, aryl, substituted alkyl, cycloalkyl or aryl, substituted oxygen, hydroxyl, substituted or unsubstituted non-cyclic amino and substituted or unsubstituted non-aryl heterocycle, wherein R'$_1$ and R'$_2$ or R'$_3$ and R'$_4$ can form a ring with the nitrogen atom to which they are attached;

R$_{17}$ and R$_{18}$ are individually selected from hydrogen, halogen, hydroxyl, substituted or unsubstituted alkoxy, mercapto, thioether, —NR'$_1$R'$_2$, nitro, alkyl, aryl and substituted alkyl or aryl, wherein R$_{17}$ can form a fused ring structure with A' and R$_{18}$ can form a fused ring structure with B'; and R$_{19}$ is hydrogen or a 1 to 3 carbon substituted or unsubstituted alkyl group;

or a pharmaceutically acceptable salt thereof.

90. A process according to claim 89 wherein X' and Z' are oxygen.

91. A process according to claim 90 wherein R$_{19}$ is hydrogen.

92. A process according to claim 91 wherein one of R'$_1$ and R'$_2$ is hydrogen and one is an alkyl or substituted alkyl group and one of R'$_3$ and R'$_4$ is hydrogen and one is an alkyl or substituted alkyl group.

93. A process according to claim 91 wherein R'$_3$ and R'$_4$ are joined to form a ring with the nitrogen atom to which they are attached and R'$_1$ and R'$_2$ are individually selected from hydrogen and alkyl groups or substituted alkyl groups.

94. A process according to claim 91 wherein R$_{17}$ and R$_{18}$ are both hydrogen.

95. A process according to claim 91 wherein one of R$_{17}$ and R$_{18}$ forms a fused ring structure with the ring to which it is attached.

96. A process according to claim 91 wherein each of $R_{17}$ and $R_{18}$ forms a fused ring structure with the ring to which it is attached.

97. A process according to claim 91, wherein $R'_1$, $R'_2$, $R'_3$ and $R'_4$ are independently selected from alkyl or substituted alkyl groups.

98. A process according to claim 91, wherein each of $R_{17}$ and $R_{18}$ is independently selected from alkyl, substituted alkyl, mercapto and thioether groups.

99. A process according to claim 91, wherein said thioether group is of the formula S—R, wherein R is substituted or unsubstituted alkyl, aryl, or non-aryl heterocycle and wherein said substituted alkyl is of the formula $CH_2R$.

100. A process according to claim 91 wherein Y' is sulphur.

101. A process according to claim 100 wherein $R'_1$, $R'_2$, $R'_3$ and $R'_4$ are independently selected from alkyl or substituted alkyl groups.

102. A process according to claim 100, wherein each of $R_{17}$ and $R_{18}$ is independently selected from alkyl, substituted alkyl, mercapto and thioether groups.

103. A process according to claim 102, wherein said thioether group is of the formula S—R, wherein R is substituted or unsubstituted alkyl, aryl, or non-aryl heterocycle and wherein said substituted alkyl is of the formula $CH_2R$.

104. A process according to claim 100 wherein one of $R'_1$ and $R'_2$ is hydrogen and one is an alkyl or unsubstituted alkyl group and one of $R'_3$ and $R'_4$ is hydrogen and one is an alkyl or substituted alkyl group.

105. A process according to claim 100 wherein $R'_3$ and $R'_4$ are joined to form a ring with the nitrogen atom to which they are attached and $R'_1$ and $R'_2$ are individually selected from hydrogen and alkyl groups or substituted alkyl groups.

106. A process according to claim 100 wherein $R_{17}$ and $R_{18}$ are both hydrogen.

107. A process according to claim 100 wherein one of $R_{17}$ and $R_{18}$ forms a fused ring structure with the ring to which it is attached.

108. A process according to claim 100 wherein each of $R_{17}$ and $R_{18}$ forms a fused ring structure with the ring to which it is attached.

109. A process according to claim 91 wherein Y' is an amino group.

110. A process according to claim 109 wherein $R'_1$, $R'_2$, $R'_3$ and $R'_4$ are independently selected from alkyl or substituted alkyl groups.

111. A process according to claim 109 wherein each of $R_{17}$ and $R_{18}$ is independently selected from alkyl, substituted alkyl, mercapto and thioether groups.

112. A process according to claim 111, wherein said thioether group is of the formula S—R, wherein R is substituted or unsubstituted alkyl, aryl, or non-aryl heterocycle and wherein said substituted alkyl is of the formula $CH_2R$.

113. A process according to claim 109 wherein one of $R'_1$ and $R'_2$ is hydrogen and one is an alkyl or substituted alkyl group and one of $R'_3$ and $R'_4$ is hydrogen and one is an alkyl or substituted alkyl group.

114. A process according to claim 109 wherein $R'_3$ and $R'_4$ are joined to form a ring with the nitrogen atom to which they are attached and $R'_1$ and $R'_2$ are individually selected from hydrogen and alkyl or substituted alkyl groups.

115. A process according to 109 wherein $R_{17}$ and $R_{18}$ are both hydrogen.

116. A process according to claim 109 wherein one of $R_{17}$ and $R_{18}$ forms a fused ring structure with the ring to which it is attached.

117. A process according to claim 109 wherein each of $R_{17}$ and $R_{18}$ forms a fused ring structure with the ring to which it is attached.

118. A process according to claim 91 wherein Y' is —$CH_2$—, —CH=, or —C≡.

119. A process according to claim 118 wherein $R'_1$, $R'_2$, $R'_3$ and $R'_4$ are independently selected from alkyl or substituted alkyl groups.

120. A process according to claim 118, wherein each of $R_{17}$ and $R_{18}$ is independently selected from alkyl, substituted alkyl, mercapto and thioether groups.

121. A process according to claim 120, wherein said thioether group is of the formula S—R, wherein R is substituted or unsubstituted alkyl, aryl, or non-aryl heterocycle and wherein said substituted alkyl is of the formula $CH_2R$.

122. A process according to claim 118 wherein one of $R'_1$ and $R'_2$ is hydrogen and one is an alkyl or substituted alkyl group and one $R'_3$ and $R'_4$ is hydrogen and one is an alkyl or substituted alkyl group.

123. A process according to claim 118 wherein $R'_3$ and $R'_4$ are joined to form a ring with the nitrogen atom to which they are attached and $R'_1$ and $R'_2$ are individually selected from hydrogen and alkyl or substituted alkyl groups.

124. A process according to claim 118 wherein $R_{17}$ and $R_{18}$ are both hydrogen.

125. A process according to claim 118 wherein one of $R_{17}$ and $R_{18}$ forms a fused ring structure with the ring to which it is attached.

126. A process according to claim 118 wherein each of $R_{17}$ and $R_{18}$ forms a fused ring structure with the ring to which it is attached.

127. A method for preparing a compound of the formula XVI

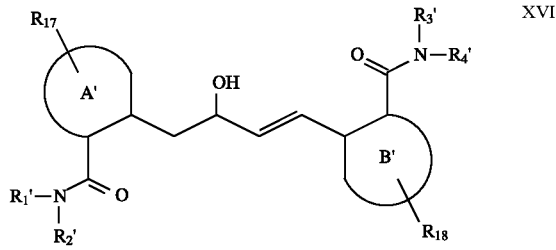

wherein:

A' and B' are individually selected from carbocyclic or heterocyclic, aromatic, saturated or partially saturated 5, 6 or 7 member rings which can be further substituted;

$R'_1$, $R'_2$, $R'_3$ and $R'_4$ are individually selected from hydrogen, alkyl, cycloalkyl, aryl, substituted alkyl, cycloalkyl or aryl, substituted oxygen, hydroxyl, substituted or unsubstituted non-cyclic amino and substituted or unsubstituted non-aryl heterocycle, wherein $R'_1$ and $R'_2$ or $R'_3$ and $R'_4$ can form a ring with the nitrogen atom to which they are attached;

$R_{17}$ and $R_{18}$ are individually selected from hydrogen, halogen, hydroxyl, substituted or unsubstituted alkoxy, mercapto, thioether, —$NR'_1R'_2$, nitro, alkyl, aryl and substituted alkyl or aryl, wherein $R_{17}$ can form a fused ring structure with A' and $R_{18}$ can form a fused ring structure with B';

which method comprises carrying out the following reactions:

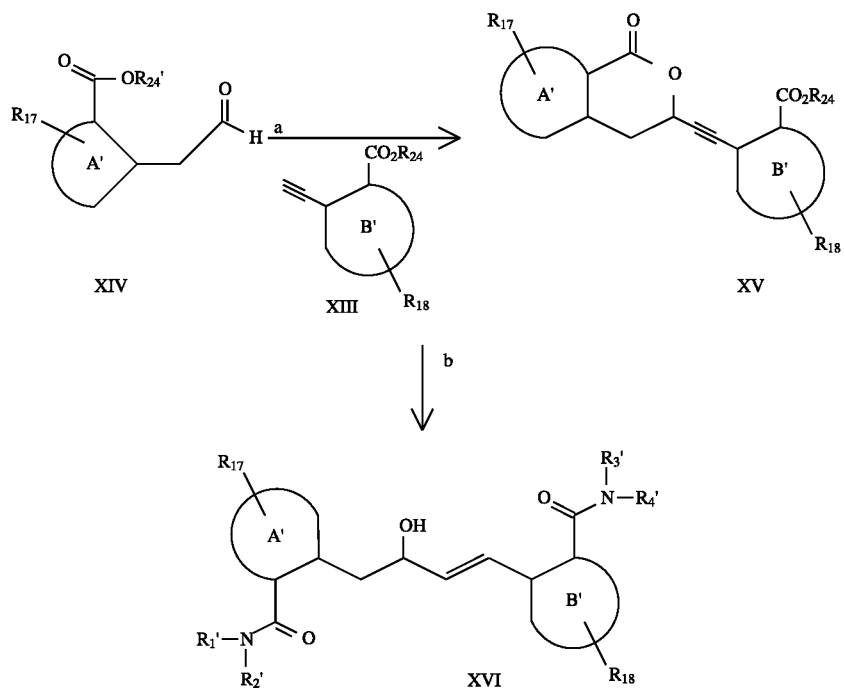

wherein:

a) the compound of the formula XIII, wherein $R_{24}$ and $R'_{24}$ are individually selected from alkyl groups, is reacted with a compound of the formula XIV under conditions sufficient to form a compound of the formula XV; and b) the compound of the formula XV is sequentially reduced, followed by reaction of the reduced compound with at least one amine selected from $R'_1 R'_2 NH$ and $R'_3 R'_4 NH$ under conditions sufficient to form a compound of the formula XVI.

128. The method of claim 127, further comprising the step of converting the compound of formula XVI to a pharmaceutically acceptable salt thereof.

129. The method of claim 127, wherein in step b), the reduction is carried out before the reaction of compound XV with said at least one amine to form compound XVI.

130. The method of claim 127, wherein in step b), the reaction of compound XV with said at least one amine to form compound XVI is carried out before the reduction.

131. The method according to claim 127, wherein in step b), the reduction is continued to form a compound of the formula XVII

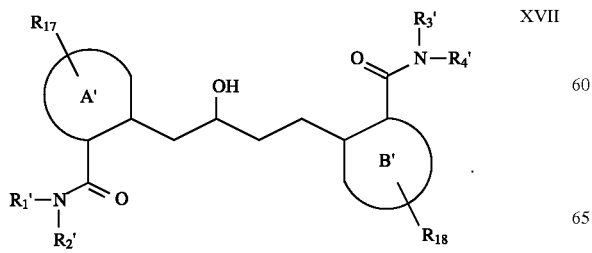

132. A compound having the formula

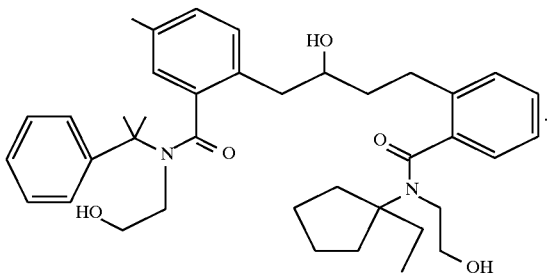

133. A compound having the formula

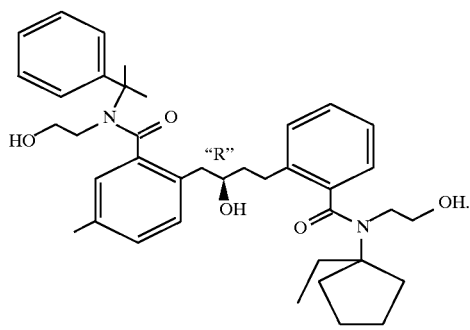

134. A composition according to claim 51, further comprising at least one other compound that inhibits HIV.

135. A composition according to claim 134, wherein said other compound inhibits HIV protease.

136. A composition according to claim 51, further comprising at least one other compound that performs a pharmaceutically desirable function different from inhibiting HIV.

137. A composition according to claim 135, wherein the compound having the formula II is

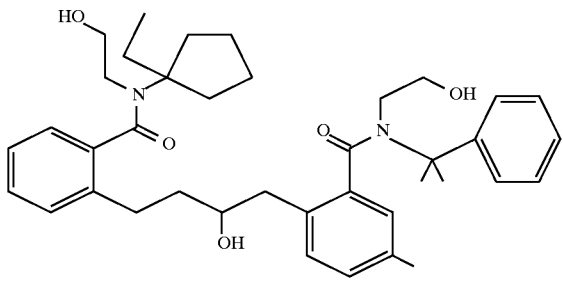

138. A composition according to claim 136, wherein the compound having the compound formula II is

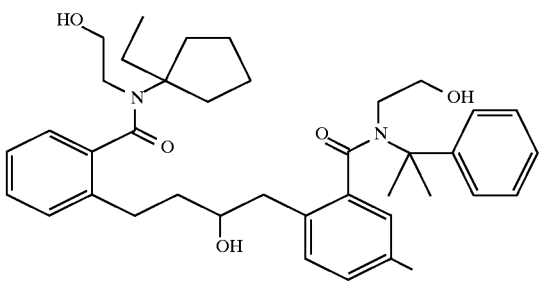

139. A process according to claim 89, further comprising at least one other compound that inhibits HIV.

140. A process according to claim 139, wherein the compound that inhibits HIV is a protease inhibitor.

141. A process according to claim 89, further comprising at least one other compound that performs a pharmaceutically desirable function different from inhibiting HIV.

* * * * *